(12) United States Patent
Olland et al.

(10) Patent No.: US 7,496,489 B2
(45) Date of Patent: Feb. 24, 2009

(54) DESIGN OF PROGESTERONE RECEPTOR LIGANDS

(75) Inventors: Andrea M. Olland, Arlington, MA (US); James M. Wilhelm, Boston, MA (US); Karl Malakian, Boxborough, MA (US); Rayomand J. Unwalla, Eagleville, PA (US)

(73) Assignee: Wyeth, Madison, NJ (US)

( * ) Notice: Subject to any disclaimer, the term of this patent is extended or adjusted under 35 U.S.C. 154(b) by 346 days.

(21) Appl. No.: 11/208,303

(22) Filed: Aug. 19, 2005

(65) Prior Publication Data

US 2006/0074081 A1     Apr. 6, 2006

Related U.S. Application Data

(60) Provisional application No. 60/603,242, filed on Aug. 20, 2004.

(51) Int. Cl.
*G06G 7/48* (2006.01)
*G01N 33/50* (2006.01)
*G06F 19/00* (2006.01)

(52) U.S. Cl. ............................. 703/11; 702/19; 702/27

(58) Field of Classification Search .................... 703/11
See application file for complete search history.

(56) References Cited

U.S. PATENT DOCUMENTS

| | | | |
|---|---|---|---|
| 5,834,228 A | 11/1998 | Becker et al. | |
| 5,856,116 A | 1/1999 | Wilson et al. | |
| 5,939,528 A | 8/1999 | Clardy et al. | |
| 6,562,857 B2 | 5/2003 | Collins et al. | |

FOREIGN PATENT DOCUMENTS

| | | |
|---|---|---|
| WO | WO 99/09148 | 2/1999 |
| WO | WO00/66570 | 11/2000 |
| WO | WO00/66581 | 11/2000 |
| WO | WO2004/000230 | 12/2003 |
| WO | WO2004/000801 | 12/2003 |

OTHER PUBLICATIONS

McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Cudney R. Protein Crystallization and Dumb Luck. The Rigaku Journal. 1999. vol. 16, No. 1, pp. 1-7.*
Ginalski et al., Comparative Modeling for Protein Structure Prediction. Current Opinion in Structural Biololgy, 2006. vol. 16, pp. 172-177.*
Zhi et al. Journal of Medicinal Chemistry, 1998, vol. 41, pp. 291-302.*
Böhm et al., Journal of Computer-Aided Molecular Design, 1992, vol. 6, pp. 61-78.*
Goodsell et al., Journal of Molecular Recognition, 1996, vol. 9, pp. 1-5.*
Appendix A -Resuls from DaliLite pairwise comparison of 1ZUC (instant Table 2) with Williams et al. 1A28. No date.*
Structural Coordinates of 1A28. No date.*
Branden & Tooze, "Introduction to Protein Structure", Garland Publishing, Inc. New York and London, 1991; p. 249.*
International Preliminary Report on Patentability for PCT Application No. PCT/US2005/029711, dated Mar. 1, 2007.
Madauss et al., "Progesterone Receptor Ligand Binding Pocket Flexibility: Crystal Structures of the Norethindrone and Mometasone Furoate Complexes," J. Med. Chem., vol. 47, No. 13, pp. 3381-3387, Jun. 17, 2004.
Zhang et al., "Novel 6-aryl-1, 4-dihydrobenzo[d][1,3]oxazine-2-thiones as Potent, Selective, and Orally Active Nonsteroidal Progesterone Receptor Agonists," Bioorganic & Medicinal Chemistry Letters, vol. 13, No. 7, pp. 1313-1316, Apr. 7, 2003.
Klebe, "Recent developments in structure-based drug design," Journal of Molecular Medicine,Springer Verlag, DE, vol. 78, No. 5, pp. 269-281, Feb. 26, 2000.
Zhang et al., "Molecular and pharmacological properties of a potent and selective novel nonsteroidal progesterone receptor agonist tanaproget," Journal of Biological Chemistry, vol. 280, No. 31, pp. 28468-28475, Aug. 5, 2005.
Fensome et al., "Synthesis and structure-activity relationship of novel 6-aryl-1, 4-dihydrobenzo[d][1,3]oxazine-2-t hiones as progesterone receptor modulators leading to the potent and selective nonsteroidal progesterone receptor agonist tanaproget," Journal of Medicinal Chemistry, vol. 48, No. 16, pp. 5092-5095, Aug. 2005.
GenBank Accession No. NM_000926 (Dec. 22, 2003).
Matias et al., "Structural Evidence for Ligand Specificity in the Binding Domain of the Human Androgen Receptor" *J. Biol. Chem.* 275:26164-26171 (2000).
Tanenbaum et al., "Crystallographic comparison of the estrogen and progesterone receptor's ligand binding domains" *Proc. Natl. Acad. Sci. USA*95:5998-6003 (1998).
Williams et al., "Atomic structure of progesterone complexed with its receptor" *Nature*393:392-396 (1998).

* cited by examiner

*Primary Examiner*—Suzanne M. Noakes
(74) *Attorney, Agent, or Firm*—Lowrie, Lando & Anastasi, LLP

(57) ABSTRACT

This invention relates to progesterone receptor/ligand complex, and related methods and software systems. Methods for designing and/or selecting ligands of the progesterone receptor using the three-dimensional structural coordinates of the progesterone receptor and/or nonsteroidal ligands are disclosed.

18 Claims, 3 Drawing Sheets

GST:PR-LBD fusion protein

MSPILGYWKI KGLVQPTRLL LEYLEEKYEE HLYERDEGDK WRNKKFELGL EFPNLPYYID
GDVKLTQSMA IIRYIADKHN MLGGCPKERA EISMLEGAVL DIRYGVSRIA YSKDFETLKV
DFLSKLPEML KMFEDRLCHK TYLNGDHVTH PDFMLYDALD VVLYMDPMCL DAFPKLVCFK
KRIEAIPQID KYLKSSKYIA WPLQGWQATF GGGDHPPKSD LVPRGSPGQD IQLIPPLINL
LMSIEPDVIY AGHDNTKPDT SSSLLTSLNQ LGERQLLSVV KWSKSLPGFR NLHIDDQITL
IQYSWMSLMV FGLGWRSYKH VSGQMLYFAP DLILNEQRMK ESSFYSLCLT MWQIPQEFVK
LQVSQEEFLC MKVLLLLNTI PLEGLRSQTQ FEEMRSSYIR ELIKAIGLRQ KGVVSSSQRF
YQLTKLLDNL HDLVKQLHLY CLNTFIQSRA LSVEFPEMMS EVIAAQLPKI LAGMVKPLLF
HKK            (SEQ ID NO:1)

FIG. 2A

PR-LBD (PR numbering)

671 ----GSPGQD IQLIPPLINL LMSIEPDVIY AGHDNTKPDT SSSLLTSLNQ LGERQLLSVV
731 KWSKSLPGFR NLHIDDQITL IQYSWMSLMV FGLGWRSYKH VSGQMLYFAP DLILNEQRMK
791 ESSFYSLCLT MWQIPQEFVK LQVSQEEFLC MKVLLLLNTI PLEGLRSQTQ FEEMRSSYIR
851 ELIKAIGLRQ KGVVSSSQRF YQLTKLLDNL HDLVKQLHLY CLNTFIQSRA LSVEFPEMMS
911 EVIAAQLPKI LAGMVKPLLF HKK       (SEQ ID NO:2)

FIG. 2B

MTELKAKGPRAPHVAGGPPSPEVGSPLLCRPAAGPFPGSQTSDTLPEVSAIPISLDGLLFPR
PCQGQDPSDEKTQDQQSLSDVEGAYSRAEATRGAGGSSSSPPEKDSGLLDSVLDTLLAPSGP
GQSQPSPPACEVTSSWCLFGPELPEDPPAAPATQRVLSPLMSRSGCKVGDSSGTAAAHKVLP
RGLSPARQLLLPASESPHWSGAPVKPSPQAAAVEVEEEDSSESEESAGPLLKGKPRALGGAA
AGGGAAACPPGAAAGGVALVPKEDSRFSAPRVALVEQDAPMAPGRSPLATTVMDFIHVPILP
LNHALLAARTRQLLEDESYDGGAGAASAFAPPRTSPCASSTPVAVGDFPDCAYPPDAEPKDD
AYPLYSDFQPPALKIKEEEEGAEASARSPRSYLVAGANPAAFPDFPLGPPPPLPPRATPSRP
GEAAVTAAPASASVSSASSSGSTLECILYKAEGAPPQQGPFAPPPCKAPGASGCLLPRDGLP
STSASAAAAGAAPALYPALGLNGLPQLGYQAAVLKEGLPQVYPPYLNYLRPDSEASQSPQYS
FESLPQKICLICGDEASGCHYGVLTCGSCKVFFKRAMEGQHNYLCAGRNDCIVDKIRRKNCP
ACRLRKCCQAGMVLGGRKFKKFNKVRVVRALDAVALPQPLGVPNESQALSQRFTF<u>SPGQDIQ</u>
<u>LIPPLINLLMSIEPDVIYAGHDNTKPDTSSSLLTSLNQLGERQLLSVVKWSKSLPGFRNLHI</u>
<u>DDQITLIQYSWMSLMVFGLGWRSYKHVSGQMLYFAPDLILNEQRMKESSFYSLCLTMWQIPQ</u>
<u>EFVKLQVSQEEFLCMKVLLLLNTIPLEGLRSQTQFEEMRSSYIRELIKAIGLRQKGVVSSSQ</u>
<u>RFYQLTKLLDNLHDLVKQLHLYCLNTFIQSRALSVEFPEMMSEVIAAQLPKILAGMVKPLLF</u>
<u>HKK</u>                (SEQ ID NO:4)

FIG. 2C

DESIGN OF PROGESTERONE RECEPTOR LIGANDS

RELATED APPLICATIONS

This application claims the benefit of U.S. Provisional Application No. 60/603,242, filed Aug. 20, 2004, which is incorporated herein by reference in its entirety

TECHNICAL FIELD

This invention relates to progesterone receptor/ligand complexes, and related methods and software systems.

BACKGROUND

Progesterone is a steroidal hormone that regulates many biological processes. Many of the physiological effects of progesterone are mediated by progesterone receptors (PRs). Interaction of progesterone with progesterone receptor can cause activation of the receptor. This can cause the progesterone receptor to be transported from the cytoplasm into the nucleus. In the nucleus, the progesterone receptor can function as a transcriptional activator, which can cause increased expression of specific gene targets.

SUMMARY

In general, the invention relates to crystalline protein/ligand complexes that include a PR polypeptide bound to a non-steroidal ligand. The PR polypeptide can include the ligand binding domain of the PR, and the non-steroidal ligand can be an agonist or antagonist of the receptor. The invention also relates to methods of using a three-dimensional model of a PR polypeptide/non-steroidal ligand complex to design an agent, such as an agonist or antagonist, that can interact with a PR polypeptide. The invention also features related software methods.

In one aspect, the invention features a crystallized protein-ligand complex that includes a progesterone receptor polypeptide and a non-steroidal ligand. The non-steroidal ligand is an agonist or antagonist of the progesterone receptor polypeptide.

In another aspect, the invention features a crystallized protein-ligand complex that includes a progesterone receptor polypeptide, which includes the amino acid sequence of SEQ ID NO:2, and a non-steroidal ligand. The crystallized protein-ligand complex diffracts X-rays to a resolution of at least about 3.5 Å. The non-steroidal ligand is an agonist or antagonist of the progesterone receptor polypeptide.

In another aspect, the invention features a composition that includes a crystal, which includes a progesterone receptor polypeptide and a non-steroidal ligand. The non-steroidal ligand is an agonist or antagonist of the progesterone receptor polypeptide.

In yet another aspect, the invention features a method that includes using a three-dimensional model to design an agent that interacts with a progesterone receptor polypeptide. The three-dimensional model includes the progesterone receptor polypeptide bound to a non-steroidal ligand that is an agonist or antagonist of the receptor polypeptide.

Another aspect of the invention features a method that includes selecting an agent by performing rational drug design with a three-dimensional structure of a crystalline complex. The complex includes a progesterone receptor polypeptide bound to a non-steroidal ligand that is an agonist or antagonist of the receptor polypeptide, and the method includes contacting the agent with a receptor polypeptide and detecting the ability of the agent to bind the polypeptide.

In another aspect, the invention features a method of growing a crystal that includes a progesterone receptor polypeptide and a non-steroidal ligand that is an agonist or antagonist of the polypeptide. The method includes contacting the receptor polypeptide with the non-steroidal ligand, and the resulting crystal can diffract X-rays to a resolution of at least about 3.5 Å.

Another aspect of the invention features a software system for determining binding characteristics of a candidate agent to a progesterone receptor polypeptide. The software system includes instructions for causing a computer system to accept information relating to the structure of a progesterone receptor polypeptide bound to a non-steroidal ligand that is an agonist or antagonist of the progesterone receptor polypeptide, and to accept information relating to a candidate agent. The determination of binding characteristics is based on the information relating to the structure of the receptor polypeptide and the information relating to the candidate agent.

Another aspect of the invention features a computer program for determining the binding characteristics of a candidate agent to a progesterone receptor polypeptide. The computer program resides on a computer readable medium that includes a plurality of instructions. When executed by one or more processors, the plurality of instructions causes the one or more processors to accept information relating to the structure of a progesterone receptor polypeptide bound to a non-steroidal ligand that is an agonist or antagonist of the progesterone receptor polypeptide, and to accept information relating to a candidate agent. The determination of binding characteristics is based on the information relating to the structure of the receptor polypeptide and the information relating to the candidate agent.

In another aspect, the invention features a method for modeling the binding characteristics of a progesterone receptor polypeptide with a candidate agent. The method includes a software system that models the binding characteristics by accepting information relating to the structure of a progesterone receptor polypeptide bound to a non-steroidal ligand that is an agonist or antagonist of the progesterone receptor polypeptide.

In yet another aspect, the invention features a computer program for modeling the binding characteristics of a progesterone receptor polypeptide with a candidate agent. The computer program resides on a computer readable medium on which is stored a plurality of instructions. When the instructions are executed by one or more processors, the processors accept information relating to the structure of a progesterone receptor polypeptide bound to a non-steroidal ligand that is an agonist or antagonist of the progesterone receptor polypeptide and the processors model the binding characteristics of the receptor polypeptide with the candidate agent.

In another aspect, the invention features a software system for modeling the binding characteristics of a progesterone receptor polypeptide with a candidate agent. The software system includes instructions for causing a computer system to accept information relating to the structure of a progesterone receptor polypeptide bound to a non-steroidal ligand that is an agonist or antagonist of the progesterone receptor polypeptide and to model the binding characteristics of the receptor polypeptide with a candidate agent.

Structural information of a polypeptide can lead to a greater understanding of how the polypeptide functions in vivo. For example, knowledge of the structure of a protein can reveal properties that facilitate the interaction of the protein with its ligands, including other proteins, effector molecules (e.g., hormones), and nucleic acids. In the case of a progesterone receptor, an understanding of such interactions can facilitate the design or selection of ligands (e.g., drugs) that can be useful for modulating the activity of the progesterone receptor in vivo, and can therefore be useful for treating a human. Structure based modeling can be used to identify ligands capable of interacting with a PR polypeptide, thus eliminating the need for screening assays, which can be expensive and time-consuming. Structural information can also be used to direct the modification of a ligand known to interact with a PR polypeptide to generate an alternative ligand with more desirable properties, such as tighter binding or greater specificity.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, useful methods and materials are described below. The materials, methods, and examples are illustrative only and not intended to be limiting. Other features and advantages of the invention will be apparent from the accompanying drawings and description, and from the claims. The contents of all references, pending patent applications and published patents, cited throughout this application are hereby expressly incorporated by reference. In case of conflict, the present specification, including definitions, will control.

DESCRIPTION OF DRAWINGS

FIG. 2A shows the amino acid sequence of the human progesterone receptor ligand binding domain (human PR-LBD) (sequence underlined) fused to glutathione-S-transferase (GST) (sequence not underlined) (SEQ ID NO:1). A thrombin cleavage site (LVPRG (SEQ ID NO:3), marked in bold) occurs at the junction between the GST and PR-LBD sequences.

FIG. 2B shows the amino acid sequence (SEQ ID NO:2) of the human PR-LBD. Amino acids are numbered according to the amino acid sequence of the full-length human progesterone receptor (see FIG. 2C).

FIG. 2C is the full-length sequence of human progesterone receptor (GenBank Accession Number NM_000926; SEQ ID NO:4). Amino acids of the human PR-LBD are underlined.

DETAILED DESCRIPTION

Figure 1A:
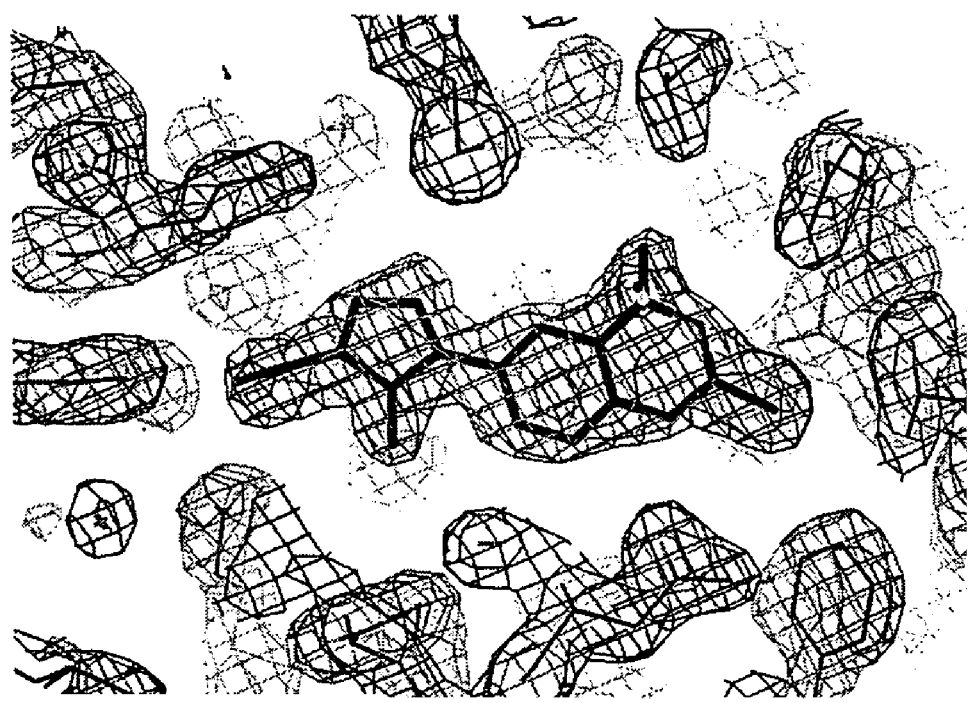
FIG. 1A is an electron density map showing tanaproget bound to the human PR-LBD. The A, B, and C rings of tanaproget are as designated. The benzoxazine moiety of tanaproget is formed of rings B and C.
Figure 1B:
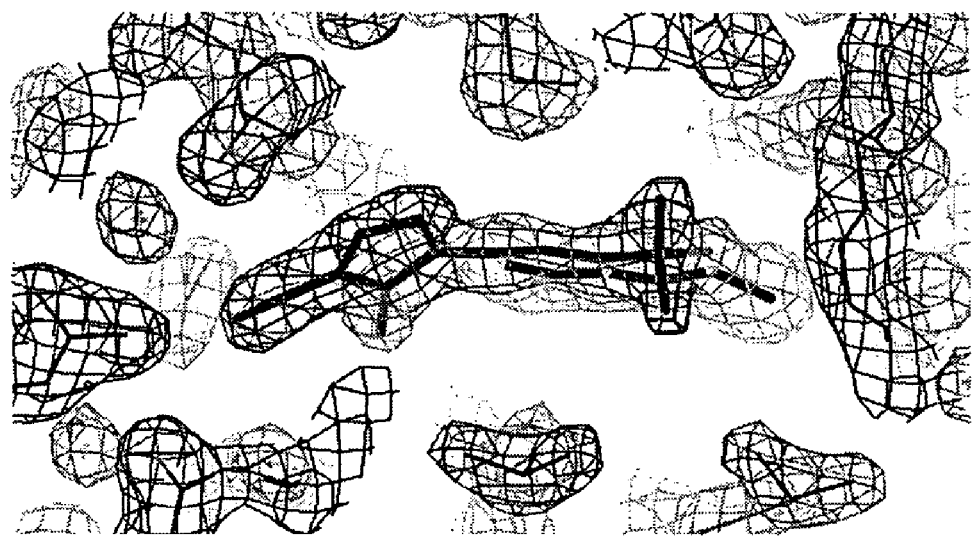
FIG. 1B is an electron density map showing tanaproget bound to the human PR-LBD.

The structure of the human progesterone receptor ligand binding domain (PR-LBD) bound to the non-steroidal hormone tanaproget (IUPAC name: 5-(4,4-dimethyl-2-thioxo-1,4-dihydro-2H-3,1-benzoxazin-6-yl)-1-methyl-1H-pyrrole-2-carbonitrile; tanaproget is the United States Adopted Name (USAN)) was determined by X-ray crystallography and is described herein. FIGS. 1A and 1B are electron density maps illustrating the structure of the PR-LBD/tanaproget complex. The electron density maps provide evidence indicating that the tertiary structure of the human PR-LBD bound to tanaproget is very similar to that of the human PR-LBD bound to its natural ligand, progesterone. It is therefore believed that the crystal structure of the human PR-LBD/tanaproget complex (see Table 2 below) can be useful for designing or identifying other ligands, such as, for example, non-steroidal ligands, that can also interact with a PR-LBD.

FIGS. 2A and 2B provide information regarding the amino acid sequence of the human PR-LBD, and FIG. 2C provides information regarding the full length sequence of human PR.

The chemical structure of tanaproget is shown below:

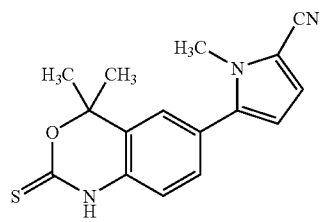

In general, a complex of the human PR-LBD bound to tanaproget can be prepared as desired. In some embodiments, such a complex can be prepared as follows. The human PR-LBD is expressed from a DNA plasmid. The expression can be driven by a promoter, such as an inducible promoter. The human PR-LBD can be expressed as a fusion protein with a suitable tag, such as a glutathione-S-transferase (GST), myc, HA, hexahistidine (SEQ ID NO:5), or FLAG tag. The tag can facilitate isolation of the human PR-LBD from cells. A fusion protein can be cleaved at a protease site engineered into the fusion protein, such as at or near the site of fusion between the polypeptide and the tag. Following cleavage and purification, the human PR-LBD can be contacted with tanaproget. For example, the human PR-LBD can be mixed with tanaproget prior to purification (e.g., prior to cleavage of a polypeptide tag), or the human PR-LBD can be mixed with tanaproget after purification. In some embodiments, tanaproget can be mixed with the human PR-LBD prior to purification and again following purification.

The human PR-LBD and tanaproget can be combined in a solution for collecting spectral data for the human PR-LBD/tanaproget complex, NMR data for the human PR-LBD/tanaproget complex, or for growing a crystal of the human PR-LBD/tanaproget complex. For example, the human PR-LBD/tanaproget complex can be crystallized in the presence of a salt (e.g., a sodium salt), a polymer (e.g., polyethylene glycol (PEG)), and/or an organic solvent. Crystals can be grown by various methods, such as, for example, sitting or hanging drop vapor diffusion. In general, crystallization can be performed at a temperature of from about 4° C. to about 60° C. (e.g., from about 4° C. to about 45° C., such as at about 4° C., about 15° C., about 18° C., about 20° C., about 25° C., about 30° C., about 32° C., about 35° C., about 37° C.).

In general, a crystal of the human PR-LBD bound to tanaproget can diffract X-rays to a resolution of about 3.5 Å or less (e.g., about 3.2 Å or less, about 3.0 Å or less, about 2.5 Å or less, about 2.4 Å or less, about 2.3 Å or less, about 2.2 Å or less, about 2.1 Å or less, about 2.0 Å or less, about 1.9 Å or less, about 1.8 Å or less, about 1.7 Å or less, about 1.6 Å or less, about 1.5 Å or less, or about 1.4 Å or less). In some embodiments, a crystal of the human PR-LBD bound to tanaproget can diffract X-rays to a resolution of from about 1.6 Å to about 2.5 Å (e.g., from about 1.8 Å to about 2.2 Å).

In some embodiments, a crystal of the human PR-LBD bound to tanaproget belongs to space group $P2_1$ with unit cell parameters a=57.52 Å, b=64.50 Å, c=70.41 Å, and b=95.76°.

In certain embodiments, a crystal of the human PR-LBD bound to tanaproget can further contain two molecules of the human PR-LBD in the asymmetric unit.

Structural data describing a crystal can be obtained, for example, by X-ray diffraction. X-ray diffraction data can be collected by a variety of sources, X-ray wavelengths and detectors. In some embodiments, rotating anodes and synchrotron sources (e.g., Advanced Light Source (ALS), Berkeley, Calif.; or Advanced Photon Source (APS), Argonne, Ill.) can be used as the source(s) of X-rays. In certain embodiments, X-rays for generating diffraction data can have a wavelength of from about 0.5 Å to about 1.6 Å (e.g., about 0.7 Å, about 0.9 Å, about 1.1 Å, about 1.3 Å, about 1.4 Å, about 1.5 Å, or about 1.6 Å). In some embodiments, area detectors and/or charge-couple devices (CCDs) can be used as the detector(s).

X-ray diffraction data of a crystal of a complex of the human PR-LBD bound to tanaproget can be used to obtain the structural coordinates of the atoms in the complex. The structural coordinates are Cartesian coordinates that describe the location of atoms in three-dimensional space in relation to other atoms in the complex. For example, the structural coordinates listed in Table 2 are the structural coordinates of a crystalline complex of the human PR-LBD bound to tanaproget. These structural coordinates describe the location of atoms of the human PR-LBD in relation to each other, the location of atoms in the human PR-LBD in relation to the atoms in tanaproget, and the location of atoms in tanaproget in relation to each other. The structural coordinates of the complex can be modified by mathematical manipulation, such as by inversion or integer additions or subtractions. As such, structural coordinates are relative coordinates. For example, structural coordinates describing the location of atoms in a PR-LBD bound to tanaproget are not specifically limited by the actual x, y, and z coordinates of Table 2.

The structural coordinates of a complex of the human PR-LBD bound to tanaproget can be used to derive a representation (e.g., a two dimensional representation or three dimensional representation) of the complex, a fragment of the complex, the PR-LBD or a fragment of the PR-LBD. Such a representation can be useful for a number of applications, including, for example, the visualization, identification and characterization of an active site of the polypeptide. In certain embodiments, a three-dimensional representation can include the structural coordinates of the human PR-LBD according to Table 2 ± a root mean square deviation from the alpha carbon atoms of amino acids of not more than about 1.5 Å (e.g., not more than about 1.0 Å, not more than about 0.5 Å). Root mean square deviation is the square root of the arithmetic mean of the squares of the deviations from the mean, and is a way of expressing deviation or variation from structural coordinates. Conservative substitutions (see discussion below) of amino acids can result in a molecular representation having structural coordinates within the stated root mean square deviation. For example, two molecular models of polypeptides that differ from one another by conservative amino acid substitutions can have coordinates of backbone atoms within a stated rms deviation, such as less than about 1.5 Å (e.g., less than about 1.0 Å, less than about 0.5 Å). Backbone atoms of a polypeptide include the alpha carbon ($C_\alpha$ or CA) atoms, carbonyl carbon (C) atoms, and amide nitrogen (N) atoms.

Various software programs allow for the graphical representation of a set of structural coordinates to obtain a representation of a complex of the human PR-LBD bound to tanaproget or a fragment thereof. In general, such a representation should accurately reflect (relatively and/or absolutely) structural coordinates, or information derived from structural coordinates, such as distances or angles between features. In some embodiments, the representation is a two-dimensional figure, such as a stereoscopic two-dimensional figure. In certain embodiments, the representation is an interactive two-dimensional display, such as an interactive stereoscopic two-dimensional display. An interactive two-dimensional display can be, for example, a computer display that can be rotated to show different faces of a polypeptide, a fragment of a polypeptide, a complex and/or a fragment of a complex. In some embodiments, the representation is a three-dimensional representation. As an example, a three-dimensional model can be a physical model of a molecular structure (e.g., a ball-and-stick model). As another example, a three dimensional representation can be a graphical representation of a molecular structure (e.g., a drawing or a figure presented on a computer display). A two-dimensional graphical representation (e.g., a drawing) can correspond to a three-dimensional representation when the two-dimensional representation reflects three-dimensional information, for example, through the use of perspective, shading, or the obstruction of features more distant from the viewer by features closer to the viewer. In some embodiments, a representation can be modeled at more than one level. As an example, when the three-dimensional representation includes a polypeptide, such as a complex of the human PR-LBD bound to tanaproget, the polypeptide can be represented at one or more different levels of structure, such as primary (amino acid sequence), secondary (e.g., α-helices and β-sheets), tertiary (overall fold), and quaternary (oligomerization state) structure.

A representation can include different levels of detail. For example, the representation can include the relative locations of secondary structural features of a protein without specifying the positions of atoms. A more detailed representation could, for example, include the positions of atoms.

In some embodiments, a representation can include information in addition to the structural coordinates of the atoms in a complex of the human PR-LBD bound to tanaproget. For example, a representation can provide information regarding the shape of a solvent accessible surface, the van der Waals radii of the atoms of the model, and the van der Waals radius of a solvent (e.g., water). Other features that can be derived from a representation include, for example, electrostatic potential, the location of voids or pockets within a macromolecular structure, and the location of hydrogen bonds and salt bridges.

An agent that interacts with a human PR-LBD can be identified or designed by a method that includes using a representation of the human PR-LBD or a fragment thereof, or a complex of human PR-LBD bound to tanaproget or a fragment thereof. Exemplary types of representations include the representations discussed above. In some embodiments, the representation can be of an analog polypeptide, polypeptide fragment, complex or fragment of a complex. A candidate agent that interacts with the representation can be designed or identified by performing computer fitting analysis of the candidate agent with the representation. In general, an agent is a molecule. Examples of agents include polypeptides, nucleic acids (including DNA or RNA), steroids and non-steroidal organic compounds. An agent can be a ligand, and can act as an agonist or antagonist. An agent that interacts with a polypeptide (e.g., a PR polypeptide) can interact transiently or stably with the polypeptide. The interaction can be mediated by any of the forces noted herein, including, for example, hydrogen bonding, electrostatic forces, hydrophobic interactions, and van der Waals interactions.

As noted above, X-ray crystallography can be used to obtain structural coordinates of a complex of human PR-LBD bound to tanaproget. However, such structural coordinates can be obtained using other techniques including NMR techniques. Additional structural information can be obtained from spectral techniques (e.g., optical rotary dispersion (ORD), circular dichroism (CD)), homology modeling, and computational methods (e.g., computational methods that can include data from molecular mechanics, computational methods that include data from dynamics assays).

In some embodiments, the X-ray diffraction data can be used to construct an electron density map of a complex of human PR-LBD bound to tanaproget or a fragment thereof, and the electron density map can be used to derive a representation (e.g., a two dimensional representation, a three dimensional representation) of human PR-LBD bound to tanaproget or a fragment thereof. Creation of an electron density map typically involves using information regarding the phase of the X-ray scatter. Phase information can be extracted, for example, either from the diffraction data or from supplementing diffraction experiments to complete the construction of the electron density map. Methods for calculating phase from X-ray diffraction data include, for example, multiwavelength anomalous dispersion (MAD), multiple isomorphous replacement (MIR), multiple isomorphous replacement with anomalous scattering (MIRAS), single isomorphous replacement with anomalous scattering (SIRAS), reciprocal space solvent flattening, molecular replacement, or a combination thereof. These methods generate phase information by making isomorphous structural modifications to the native protein, such as by including a heavy atom or changing the scattering strength of a heavy atom already present, and then measuring the diffraction amplitudes for the native protein and each of the modified cases. If the position of the additional heavy atom or the change in its scattering strength is known, then the phase of each diffracted X-ray can be determined by solving a set of simultaneous phase equations. The location of heavy atom sites can be identified using a computer program, such as SHELXS (Sheldrick, Institut Anorg. Chemie, Gottingen, Germany), and diffraction data can be processed using computer programs such as MOSFLM, SCALA, SOLOMON, and SHARP ("The CCP4 Suite: Programs for Protein Crystallography," *Acta Crystallogr. Sect. D*, 54:905-921, 1997; deLa Fortelle and Brigogne, *Meth. Enzym.* 276:472-494, 1997). Upon determination of the phase, an electron density map of the polypeptide or the complex can be constructed.

The electron density map can be used to derive a representation of a polypeptide or a complex, or a fragment of a polypeptide or complex, by aligning a three-dimensional model of a previously known polypeptide or a previously known complex (e.g., a complex containing a polypeptide bound to a ligand) with the electron density map. This process results in a comparative model that shows the degree to which the calculated electron density map varies from the model of the previously known polypeptide or the previously known complex. The comparative model is then refined over one or more cycles (e.g., two cycles, three cycles, four cycles, five cycles, six cycles, seven cycles, eight cycles, nine cycles, 10 cycles) to generate a better fit with the electron density map. A software program such as CNS (Brunger et al., *Acta Crystallogr. D*54:905-921, 1998) can be used to refine the model. The quality of fit in the comparative model can be measured by, for example, an $R_{work}$ or $R_{free}$ value. A smaller value of $R_{work}$ or $R_{free}$ generally indicates a better fit. Misalignments in the comparative model can be adjusted to provide a modified comparative model and a lower $R_{work}$ or $R_{free}$ value. The adjustments can be based on information (e.g., sequence information) relating to human PR-LBD, tanaproget, the previously known polypeptide and/or the previously known complex. As an example, in embodiments in which a model of a previously known complex of a polypeptide bound to a ligand is used, an adjustment can include replacing the ligand in the previously known complex with tanaproget. As another example, in certain embodiments, an adjustment can include replacing an amino acid in the previously known polypeptide with the amino acid in the corresponding site of human PR-LBD. When adjustments to the modified comparative model satisfy a best fit to the electron density map, the resulting model is that which is determined to describe the polypeptide or complex from which the X-ray data was derived (e.g., the PR-LBD/tanaproget complex). Methods of such processes are disclosed, for example, in Carter and Sweet, eds., "Macromolecular Crystallography" in *Methods in Enzymology*, Vol. 277, Part B, New York: Academic Press, 1997, and articles therein, e.g., Jones and Kjeldgaard, "Electron-Density Map Interpretation," p. 173, and Kleywegt and Jones, "Model Building and Refinement Practice," p. 208.

In some embodiments, a representation of human PR-LBD bound to tanaproget can be derived by aligning a previously determined structural model of progesterone bound to human PR-LBD (e.g., Protein Databank Identification No. 1a28) with the electron density map of human PR-LBD bound to tanaproget derived from X-ray diffraction data. One adjustment that can be used in the modeling process can include replacing progesterone with tanaproget.

A machine, such as a computer, can be programmed in memory with the structural coordinates of a complex of the human PR-LBD bound to tanaproget, together with a program capable of generating a graphical representation of the structural coordinates on a display connected to the machine. Alternatively or additionally, a software system can be designed and/or utilized to accept and store the structural coordinates. The software system can be capable of generating a graphical representation of the structural coordinates. The software system can also be capable of accessing external databases to identify compounds (e.g., polypeptides) with similar structural features as human PR-LBD, and/or to identify one or more candidate agents with characteristics that may render the candidate agent(s) likely to interact with human PR-LBD.

A machine having a memory containing structure data or a software system containing such data can aid in the rational design or selection of PR agonists and/or PR antagonists. For example, such a machine or software system can aid in the evaluation of the ability of an agent to associate with a complex of the human PR-LBD bound to tanaproget, or can aid in the modeling of compounds or proteins related by structural or sequence homology to a PR-LBD.

The machine can produce a representation (e.g., a two dimensional representation, a three dimensional representation) of a complex of the human PR-LBD bound to tanaproget or a fragment thereof. A software system, for example, can cause the machine to produce such information. The machine can include a machine-readable data storage medium including a data storage material encoded with machine-readable data. The machine-readable data can include structural coordinates of atoms of a complex of the human PR-LBD bound to tanaproget or a fragment thereof. Machine-readable storage media (e.g., data storage material) include, for example, conventional computer hard drives, floppy disks, DAT tape, CD-ROM, DVD, and other magnetic, magneto-optical, optical, and other media which may be adapted for use with a machine (e.g., a computer). The machine can also have a working memory for storing instructions for processing the machine-readable data, as well as a central processing unit (CPU) coupled to the working memory and to the machine-readable data storage medium for the purpose of processing the machine-readable data into the desired three-dimensional representation. A display can be connected to the CPU so that the three-dimensional representation can be visualized by the user. Accordingly, when used with a machine programmed with instructions for using the data (e.g., a computer loaded with one or more programs of the sort described herein) the machine is capable of displaying a graphical representation (e.g., a two dimensional graphical representation, a three-dimensional graphical representation) of any of the polypeptides, polypeptide fragments, complexes, or complex fragments described herein.

A display (e.g., a computer display) can show a representation of a complex of human PR-LBD bound to tanaproget or a fragment thereof. The user can inspect the representation and, using information gained from the representation, generate a model of a complex or fragment thereof that includes an agent other than tanaproget. The model can be generated, for example, by altering a previously existing representation of a human PR-LBD/tanaproget complex. Optionally, the user can superimpose a three-dimensional model of an agent on the representation of human PR-LBD bound to tanaproget. The agent can be an agonist (e.g., a candidate agonist) of human PR-LBD or an antagonist (e.g., a candidate antagonist) of human PR-LBD. In some embodiments, the agent can be a known compound or fragment of a compound. In certain embodiments, the agent can be a previously unknown compound, or a fragment of a previously unknown compound.

It can be desirable for the agent to have a shape that complements the shape of the active site. There can be a preferred distance, or range of distances, between atoms of the agent and atoms of the PR polypeptide. Distances longer than a preferred distance may be associated with a weak interaction between the agent and active site (e.g., human PR-LBD). Distances shorter than a preferred distance may be associated with repulsive forces that can weaken the interaction between the agent and the polypeptide. A steric clash can occur when distances between atoms are too short. A steric clash occurs when the locations of two atoms are unreasonably close together, for example, when two atoms are separated by a distance less than the sum of their van der Waals radii. If a steric clash exists, the user can adjust the position of the agent relative to the PR polypeptide (e.g., a rigid body translation or rotation of the agent), until the steric clash is relieved. The user can adjust the conformation of the agent or of the PR polypeptide in the vicinity of the agent in order to relieve a steric clash. Steric clashes can also be removed by altering the structure of the agent, for example, by changing a "bulky group," such as an aromatic ring, to a smaller group, such as to a methyl or hydroxyl group, or by changing a rigid group to a flexible group that can accommodate a conformation that does not produce a steric clash. Electrostatic forces can also influence an interaction between an agent and a ligand-binding domain. For example, electrostatic properties can be associated with repulsive forces that can weaken the interaction between the agent and the PR polypeptide. Electrostatic repulsion can be relieved by altering the charge of the agent, e.g., by replacing a positively charged group with a neutral group.

Forces that influence binding strength between tanaproget and human PR-LBD can be evaluated in the polypeptide/agent model. These can include, for example, hydrogen bonding, electrostatic forces, hydrophobic interactions, van der Waals interactions, dipole-dipole interactions, $\pi$-stacking forces, and cation-$\pi$ interactions. The user can evaluate these forces visually, for example by noting a hydrogen bond donor/acceptor pair arranged with a distance and angle suitable for a hydrogen bond. Based on the evaluation, the user can alter the model to find a more favorable interaction between the PR polypeptide and the agent. Altering the model can include changing the three-dimensional structure of the polypeptide without altering its chemical structure, for example by altering the conformation of amino acid side chains or backbone dihedral angles. Altering the model can include altering the position or conformation of the agent, as described above. Altering the model can also include altering the chemical structure of the agent, for example by substituting, adding, or removing groups. For example, if a hydrogen bond donor on the PR polypeptide is located near a hydrogen bond donor on the agent, the user can replace the hydrogen bond donor on the agent with a hydrogen bond acceptor.

The relative locations of an agent and the PR polypeptide, or their conformations, can be adjusted to find an optimized binding geometry for a particular agent to the PR polypeptide. An optimized binding geometry is characterized by, for example, favorable hydrogen bond distances and angles, maximal electrostatic attractions, minimal electrostatic repulsions, the sequestration of hydrophobic moieties away from an aqueous environment, and the absence of steric clashes. The optimized geometry can have the lowest calculated energy of a family of possible geometries for a PR polypeptide/agent complex. An optimized geometry can be determined, for example, through molecular mechanics or molecular dynamics calculations.

A series of representations of complexes of human PR-LBD bound to tanaproget, where tanaproget is replaced or overlaid with different agents, can be generated. A score can be calculated for each representation. The score can describe, for example, an expected strength of interaction between human PR-LBD and the agent. The score can reflect one of the factors described above that influence binding strength. The score can be an aggregate score that reflects more than one of the factors. The different agents can be ranked according to their scores.

Steps in the design of the agent can be carried out in an automated fashion by a machine. For example, a representation of PR-LBD can be programmed in the machine, along with representations of candidate agents. The machine can find an optimized binding geometry for each of the candidate agents to the active site, and calculate a score to determine which of the agents in the series is likely to interact most strongly with human PR-LBD.

A software system can be designed and/or implemented to facilitate these steps. Software systems (e.g., computer programs) used to generate such three-dimensional models or perform the necessary fitting analyses include, but are not limited to: MCSS, Ludi, QUANTA, Insight II, Cerius2, CHARMm, and Modeler from Accelrys, Inc. (San Diego, Calif.); SYBYL, Unity, FleXX, and LEAPFROG from TRIPOS, Inc. (St. Louis, Mo.); AUTODOCK (Scripps Research Institute, La Jolla, Calif.); GRID (Oxford University, Oxford, UK); DOCK (University of California, San Francisco, Calif.); and Flo+ and Flo99 (Thistlesoft, Morris Township, N.J.). Other useful programs include ROCS, ZAP, FRED, Vida, and Szybki from Openeye Scientific Software (Santa Fe, N. Mex.); Maestro, Macromodel, and Glide from Schrodinger, LLC (Portland, Oreg.); MOE (Chemical Computing Group, Montreal, Quebec), Allegrow (Boston De Novo, Boston, Mass.), CNS (Brunger, et al., *Acta Crystall. Sect. D* 54:905-921, 1997) and GOLD (Jones et al., *J. Mol. Biol.* 245:43-53, 1995). The structural coordinates can also be used to visualize the three-dimensional structure of PKCθ using MOLSCRIPT, RASTER3D, or PYMOL (Kraulis, *J. Appl. Crystallogr.* 24: 946-950, 1991; Bacon and Anderson, *J. Mol. Graph.* 6: 219-220, 1998; DeLano, The PYMOL Molecular Graphics System (2002) DeLano Scientific, San Carlos, Calif.).

The agent, whether an agonist or antagonist, can, for example, be selected by screening an appropriate database, can be designed de novo by analyzing the steric configurations and charge potentials of unbound human PR-LBD in conjunction with the appropriate software systems, and/or can be designed using characteristics of known agonists or antagonists of progesterone receptors or other hormone receptors. The method can be used to design or select agonists or antagonists of human PR-LBD. A software system can be designed and/or implemented to facilitate database searching, and/or agent selection and design.

Once an agent has been designed or identified, it can be obtained or synthesized and further evaluated for its effect on human PR-LBD activity. For example, the agent can be evaluated by contacting it with human PR-LBD and measuring the effect of the agent on polypeptide activity. A method for evaluating the agent can include an activity assay performed in vitro or in vivo. An activity assay can be a cell-based assay, for example. Depending upon the action of the agent on human PR-LBD, the agent can act either as an agonist or antagonist of human PR-LBD activity. The agent also can be contacted with the polypeptide in the presence of progesterone in order to determine whether or not the agent inhibits binding of progesterone to the polypeptide. A crystal containing human PR-LBD bound to the identified agent can be grown and the structure determined by X-ray crystallography. A second agent can be designed or identified based on the interaction of the first agent with human PR-LBD.

Various molecular analysis and rational drug design techniques are further disclosed in, for example, U.S. Pat. Nos. 5,834,228, 5,939,528 and 5,856,116, as well as in PCT Application No. PCT/US98/16879, published as WO 99/09148.

While certain embodiments have been described, other embodiments are also contemplated.

As an example, while embodiments involving the human PR-LBD and tanaproget have been described, the description herein is more generally directed to any PR polypeptide and any non-steroidal ligand.

A PR polypeptide can be a full-length, mature polypeptide, including the full-length amino acid sequence of any isoform of a PR polypeptide. An isoform is any of several multiple forms of a protein that differ in their primary structure. For example, human progesterone receptor exists in at least two isoforms, Pr-B (full-length PR) and Pr-A (N-terminally truncated PR). The two isoforms are transcribed from a single gene, but have different translation start sites. Thus the isoforms are identical except that Pr-B contains an additional 164 N-terminal amino acids. The isoforms have an identical centrally located DNA binding domain, which is flanked at the N-terminus by a transcriptional activation function-1 (AF-1) domain, and at the C-terminus by a hinge region containing nuclear localization signals and a ligand binding domain (PR-LBD). A second transcriptional activation function domain (AF-2) is located in the PR-LBD.

A PR polypeptide can be a fragment of a PR, such as a ligand binding domain, a DNA-binding domain, a protein-interaction domain (e.g., an activation domain), or a combination thereof.

A PR polypeptide can have an active site. In general, an active site can include a site of ligand binding, or a site of phosphorylation, glycosylation, alkylation, acylation, or other covalent modification. A ligand binding site can include accessory binding sites adjacent or proximal to the actual site of binding that may affect activity upon interaction with the ligand. An active site of a PR polypeptide can include amino acids of SEQ ID NO:2. For example, an active site of a PR-polypeptide can include one or more of amino acids Ile699, Ala701, Leu714, Leu715, Leu718, Asn719, Leu721, Gln725, Trp755, Met756, Met759, Val760, Leu763, Arg766, Ser767, Tyr777, Phe778, Ala779, Leu782, Phe794, Leu797, Lys798, Met801, Ile804, Leu887, His888, Tyr890, Cys891, Asn893, Thr894, Phe895, Ser898, Leu901, Val903, Phe905, Met909, Ile913, and Leu917 as defined by SEQ ID NO:2.

The numbering of the amino acids of a PR polypeptide may be different than that set forth herein, and the sequence of the PR polypeptide may contain certain conservative amino acid substitutions that yield the same three-dimensional structure. For example, the numbering of a PR-LBD may be different than that set forth in FIG. 2B, and the sequence of the PR-LBD may contain conservative amino acid substitutions but yield the same structure as that defined by the coordinates of Table 2 and illustrated in FIGS. 1A and 1B. Corresponding amino acids and conservative substitutions in other isoforms or analogs are easily identified by visual inspection of the relevant amino acid sequences or by using commercially available homology software programs (e.g., MODELLAR, MSI, San Diego, Calif.).

An analog is a polypeptide having conservative amino acid substitutions. A conservative substitution can include switching one amino acid for another with similar polarity, steric arrangement, or of the same class (e.g., hydrophobic, acidic or basic), and includes substitutions having an inconsequential effect on the three-dimensional structure of the PR polypeptide with respect to identification and design of agents that interact with the polypeptide (e.g., a PR-LBD), as well as for molecular replacement analyses and/or for homology modeling.

A PR polypeptide can originate from a nonmammalian or mammalian species. A mammalian PR polypeptide can originate from a human, for example. Exemplary nonhuman mammals include, a nonhuman primate (such as a monkey or ape), a mouse, rat, goat, cow, bull, pig, horse, sheep, wild boar, sea otter, cat, and dog. Exemplary nonmammalian species include chicken, turkey, shrimp, alligator, and fish.

As another example, while embodiments have been described in which tanaproget is a ligand, more generally other non-steroidal compounds may also be used as ligands. For example, based on a representation of the human PR-LBD bound to tanaproget derived from the structure of the crystalline complex, without wishing to be bound by theory it is believed that: the carbonitrilo nitrogen of tanaproget forms hydrogen bonds with the side chains of Gln725 and Arg766 of the human PR-LBD; the benzoxazine nitrogen of tanaproget forms hydrogen bonds with the side chain oxygen of Asn719 of the human PR-LBD; hydrophobic interactions occur between Leu797 of the human PR-LBD and the hydrophobic region of the benzoxazine moiety (which includes the pair of methyl substituents in the 4 position) of tanaproget; and an electrostatic interaction occurs between Thr894 of the human PR-LBD and the sulfur of tanaproget.

Based on this information, without wishing to be bound by theory, it is believed that other non-steroidal compounds capable of having one or more similar interactions with the human PR-LBD may also be capable of acting as ligands (e.g., agonists, antagonists) for the human PR-LBD. Such non-steroidal compounds may have the structure:

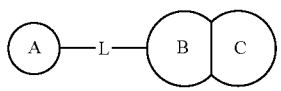

where A, B and C represent ring systems, B and C are fused rings, and L is a linker moiety.

In general, rings A, B and C are each independently formed of at least four atoms (e.g., five atoms, six atoms, seven atoms, eight atoms, nine atoms, 10 atoms, 11 atoms, 12 atoms, 13 atoms, 14 atoms). One or more atoms (e.g., one atom, two atoms, three atoms, four atoms) in rings A, B and/or C can independently be heteroatoms (e.g., N, S, O). In some embodiments, rings B and C form an indole, an oxindole, a thioindole, a benzothiophene, a benzofuran, a benzothiazole, a benzimidazole, a benzoxazine or a benzthiazine. In one embodiment rings B and C can form a benzoxazine ring that can have at least one hydrophobic substituent at the 4 position. In another embodiment the benzoxazine ring can have at least one hydrophobic substituent near the 4 position e.g. at the 5 position. Benzoxazine derivatives are described, for example, in U.S. Pat. No. 6,562,857, which is hereby incorporated by reference. Ring A can be, for example, a pyrrole, a furan, a thiophene, an imidazole, an oxazole, or a phenyl. In some embodiments, rings A, B and/or C can each independently include one or more (e.g., one, two, three, four) substituents (e.g., one or more substituents that provide favorable interaction with the human PR-LBD, such as, for example, through hydrogen bonding, hydrophobic interaction and/or electrostatic interaction). Examples of substituents include hydroxy substituents, amino substituents, cyano substituents, nitro substituents, oxime substituents, thiol substituents, amido substituents, oxo substituents, alkyl substituents e.g. having 1-6 carbon atoms, alkenyl substituents e.g. having 2-6 carbon atoms, alkynyl substituents e.g. having 2-6 carbon atoms, aryl substituents e.g. an aromatic carbocyclic mono- or polycyclic ring system having from 6-20 ring carbon atoms, cyclyl substituents e.g. a saturated or partially saturated mono- or polycyclic carbocyclic ring system having from 3-14 ring atoms, heteroaryl substituents e.g. an aromatic heterocyclic mono- or polycyclic ring system having from 5-14 ring atoms wherein 1, 2, 3 or 4 of the ring atoms are selected from N, O or S, heterocyclyl substituents e.g. a saturated or partially saturated mono- or polycyclic heterocyclic ring system having from 3-14 ring atoms wherein 1, 2, 3 or 4 of the ring atoms are selected from N, O or S, and halogens (e.g., fluorine, chlorine, bromine, iodine). While in some embodiments, a substituent itself may be a hydrogen bond donor or acceptor with the human PR-LBD, in other embodiments, the substituent may form a hydrogen bond with a portion of the human PR-LBD through one or more solvent molecules such as water.

In general, L can be a direct chemical bond, or L can be formed of a chemical moiety, such as, for example, an alkyl moiety e.g. having 1-6 carbon atoms, an alkenyl moiety e.g. having 2-6 carbon atoms, an alkynyl moiety e.g. having 2-6 carbon atoms, an ether moiety, a thioether moiety, an amido moiety, a carbonyl moiety or a sulfonyl moiety. In some embodiments, L can be formed of multiple moieties (e.g., a sulfonyl moiety bonded to an alkyl moiety).

Although embodiments have been described in which the non-steroidal compound includes rings B and C fused together, in some embodiments, rings B and C can be joined by a chemical linker. Examples of linkers are noted above. In certain embodiments, ring B is not present. For example, ring B can be replaced with a linker moiety that connects ring C with ring A. The linker moiety can, for example, be of sufficient length to allow favorable interactions between ring A and one or both of Glu725 or Arg766 of the human PR-LBD, and between ring C and one or more of Asn719, Thr894, or Cys891 of the human PR-LBD. For example, ring B can be replaced with an alkenyl linker such as a branched alkene, which can provide sufficient length, structural rigidity, and, where desired, bulk (e.g., the linker moiety can include a branched alkenyl moiety).

The following example is illustrative and not intended as limiting.

EXAMPLE

Human progesterone ligand binding domain (PR-LBD) was expressed as an amino terminal glutathione-S-transferase (GST) fusion protein from *Escherichia coli* BL21 (Stratagene). The PR-LBD domain coding sequence was cloned into the pGEX plasmid (Amersham Pharmacia Biotech) under tac transcriptional control. A thrombin cleavage site (LVPRG, SEQ ID NO:3) R and the G). The sequence of this fusion protein is shown in FIG. 2A. The sequence of the PR-LBD polypeptide following thrombin cleavage is shown in FIG. 2B.

Bacterial growth and protein expression were performed in a Biostat 10 liter fermenter (B. Braun Biotech). A 100 mL preculture was used to inoculate 10 liters of media (fermenter salts, glucose, ampicillin, trace metals and yeast extract media) and expanded overnight at 25° C. Fifteen minutes prior to induction, the vessel temperature was lowered to 15° C. and 5 mls of 66 mM progesterone (Sigma-Aldrich, St. Louis, Mo.) in 100% ethanol was added. The culture was induced at a density of 5.4 OD600 absorbance units with addition of isopropyl-beta-D-thiogalactopyranoside (IPTG, Fisher) to a final concentration of 1.0 mM. Progesterone was again added in 5 ml aliquots of 66 mM at the time of induction and every fifteen minutes thereafter, for the duration of expression (4 hours total, 660 μM final concentration of progesterone). After 4 hours of induction, the culture was harvested yielding 158.76 g of wet cell weight. The protein of interest represented 5-7% of total cell protein, as estimated by SDS-PAGE. Successful isolation of PR-LBD depended strongly on inclusion of a PR ligand during expression (possibly to ensure proper protein folding) and purification. See, for example, Williams and Sigler, *Nature* 393:392-396, 1998; Tanenbaum et al., *Proc. Natl. Acad. Sci. USA* 95:5998-6003, 1998; and Matias et al., *J. Biol. Chem.* 275: 26164-26171, 2000. Tanaproget was exchanged for progesterone during purification.

20 g of frozen cells were suspended in 300 mL of 50 mM HEPES pH 7.3, 150 mM NaCl, 5 mM EDTA, 10% glycerol, 5 mM dithiothreitol (DTT) with 0.33 mM of the protease inhibitor aminoethylbenzenesulfonyl fluoride (AEBSF, Sigma-Aldrich), 0.3 mL of protease inhibitor cocktail (Sigma-Aldrich catalog number 8849) and 5 μM progesterone (Progesterone was stored as a 50 mM stock solution in dimethylsulfoxide). Cells were broken by passage through a microfluidizer (Midrofluidics, Newton, Mass.). Cell debris and aggregated GST/PR-LBD were removed by centrifugation for 2.5 hrs at approximately 40,000 g. CHAPS (Sigma) was added to 1.5% and the solution was passed through a 0.45 micron cellulose nitrate filter and stored overnight.

An initial purification of GST/PR-LBD fusion protein was carried out by affinity chromatography. The filtered solution was passed over two 5 mL columns (in tandem) of GSTrap FF glutathione-Sepharose chromatography media (Amersham Bioscience) at flow rate of about 1 mL/min. Resin was washed with 50 mL of 50 mM HEPES pH 7.3, 150 mM NaCl, 5 mM EDTA, 10% glycerol, then with 50 mL of same solution containing 50 µM tanaproget. GST/PR-LBD was eluted with 12 mM reduced glutathione (Sigma) in 50 mM HEPES pH 7.3, 100 mM NaCl, 10% glycerol, 0.1% octyl-β-glucoside, and 50 µM tanaproget. Fractions of 5 mL were collected. Those fractions containing GST/PR-LBD were identified by SDS-PAGE and pooled. Typically the pooled fractions had a total volume of 30-40 mL. Thrombin was added to 25,000 NIH units/mL. The solution was incubated overnight for specific proteolysis.

The solution was diluted with 4 volumes of 10 mM HEPES pH 7.3, 10% glycerol, 5 mM DTT, 0.1% octyl-β-glucoside, and 50 µM tanaproget. The solution was passed over a 1 mL column of HiTrap SP FF sulfopropyl-Sepharose (Amersham Bioscience) at a flow rate of 1 mL/min. The column was washed with 5 mL of 10 mM HEPES pH 7.3, 20 mM NaCl, 10% glycerol, 0.1% octyl-β-glucoside, and 1 µM tanaproget (tanaproget was stored as a 50 mM stock solution in dimethylsulfoxide). PR-LBD was eluted from the column with a 15 mL gradient of sodium chloride, running from 20 mM to 220 mM (other components as above). Fractions of 1 mL were collected, PR-LBD was located by SDS-PAGE and those fractions containing PR/LBD at a concentration of 1 to 2 mg/mL were used directly for crystallization.

Prior to crystallization, the PR-LBD/tanaproget complex was determined to be homogeneous by SDS-PAGE. The protein had the expected mass as determined by MALDI mass spectrometry (~29,800 Da). The protein behaved as a single species during size-exclusion chromatography. The retention volume, as compared with reference proteins, was consistent with a dimer of PR-LBD. Only those preparations of the PR-LBD/tanaproget complex without any detectable progesterone were used for crystallization. Bound ligand was analyzed by reverse-phase chromatography following protein denaturation in the presence of guanidine-HCl.

Crystals were grown by hanging drop vapor diffusion at 18° C. The drops contained 2.0 µL protein stock solution (5 mg/mL protein, 10 mM HEPES pH 7.3, 10% glycerol, 5 mM DTT, ~100 mM NaCl, 0.1% octyl-β-glucoside, 1 µM tanaproget) mixed with 1.0 µL well solution (8% PEG 3350 (Hampton Research), 300 mM MgSO$_4$, 50 mM PIPES pH 6.5, 10% glycerol) and 0.5 µL, 1,3-propanediol (40% v/v, Hampton Research) and equilibrated against a 1 mL well solution. Diamond shaped crystals grew in 2-6 weeks, measuring ~50 µm across.

Showers of small crystals grew in the conditions described above with a variety of sulfate salts. The number of nucleation events was reduced by the addition of 1,3-propanediol (40% v/v) to drops, enabling the growth of fewer, larger, single crystals. The crystals belonged to space group P2$_1$ with unit cell parameters a=57.52 Å, b=64.50 Å, c=70.41 Å, and β=95.76°, and contained two molecules of PR-LBD in the asymmetric unit, implying a solvent content of 44%. Crystals were drawn through a cryoprotectant solution of 20% ethylene glycol and 80% well solution, and cooled rapidly in liquid nitrogen. Diffraction data were recorded on an R-axis 4 detector. Intensities were integrated and scaled using the programs Denzo and Scalepack (Otwinowski and Minor, *Methods Enzymol.* 276: 307-326, 1997).

The structure was solved by molecular replacement using the protein model of the PR-LBD/progesterone structure (Williams and Sigler, *Nature* 393:392-396, 1998) as the search model. After several iterative cycles of refinement using CNS (Brunger et al., *Acta Crystallogr.* D54:905-921, 1998) and model improvement, tanaproget was placed and refined. The final values of R$_{work}$ and R$_{free}$ were 19.62% and 23.74%, respectively. Table 1 summarizes the data collection parameters and results.

TABLE 1

Statistics of X-Ray Diffraction Data Collection

| Data Collection | |
|---|---|
| Crystal System | monoclinic |
| Space Group | P2$_1$ |
| Unit Cell Dimensions | A = 57.52 Å, b = 64.50 Å, c = 70.41 Å, β = 95.76° |
| Data Collection Temperature | −180° C. |
| Number of crystals | 1 |
| Radiation Source | Rigaku rotating anode X-ray generator |
| X-ray wavelength | 1.54179 Å |
| Resolution range of data | 30.0-2.0 Å |
| Maximum Resolution | 2.0 Å |
| R$_{merge}$$^a$ | 4.9% (17.6%) |
| Completeness | 100.0% (99.9%) |
| Total reflections | 147,224 |
| Unique reflections | 34,825 |
| I/σ(I) | 26.9 (8.3) |
| Phasing and Refinement | |
| Model for molecular refinement | 1a28.pdb (PR-LBD/progesterone) |
| Construct (aa) | PR-LBD (675-933) |
| Compound (ligand) | tanaproget |
| PR-LBD molecules per asymmetric unit | 2 |
| Resolution range of refinement | 20.0-2.0 Å |
| R$_{work}$ | 19.62% |
| R$_{free}$ | 23.74% |
| Number of non-hydrogen protein atoms | 4072 |
| Number of water molecules | 179 |
| RMS deviations from ideal bond lengths | 0.0057 Å |
| RMS deviations from ideal bond angles | 1.132° |

$^a$R$_{merge}$ = |I$_h$ − <I$_h$>|/I$_h$, where <I$_h$> is the average intensity over symmetry equivalents.
Numbers in parentheses reflect statistics for the last shell.
$^b$R$_{work}$ = ||F$_{obs}$| − |F$_{calc}$||/|F$_{obs}$|
$^c$R$_{free}$ is equivalent to R$_{work}$, but calculated for a randomly chosen 5% of reflections omitted from the refinement process.

The refined model included two PR-LBD molecules in the asymmetric unit of the crystal, each bound to one agonist. Tanaproget fit into the buried hydrophobic ligand binding pocket, occupying roughly the same area as progesterone.

The principle features of nuclear receptor ligand binding domains were conserved in the PR-LBD. There were ten helices (following standard steroid receptor nomenclature, helix 2 is missing, and helices 10 and 11 are contiguous), of which helices 3, 5, 7, 11 and 12 contributed to the ligand binding pocket. The two PR-LBD molecules in the crystal formed a dimer centered around interactions between helix 11 of one subunit with helix 12 of the other.

The tertiary structure of PR-LBD/tanaproget was very similar to that of PR-LBD/progesterone. Tanaproget occupied the same binding pocket as progesterone. See FIGS. 1A and 1B, which present views of a 3F$_{obs}$-2F$_{calc}$ experimental map of tanaproget bound to PR-LBD unbiased by ligand phases and contoured at 1.2 σ. Superposition of the structures of the PR-LBD/tanaproget complex and the PR-LBD/progesterone complex revealed that the 1-methyl-1H-pyrrole-2-carbonitrile ring lay roughly between the A and B rings of progesterone, and the 1,4-dihydro-3,1-benzoxazine-2-thione moiety ("benzoxazine") lay just above the C and D rings of progesterone in the direction of the protruding methyl groups of progesterone.

Tanaproget mimicked the interaction of progesterone with the ligand binding pocket of PR-LBD in many ways. The nitrile group, positioned approximately 0.6 Å from the 3-keto substituent of the progesterone A ring, formed hydrogen bonds with the side chains of Gln725 and Arg766. Similarly, the progesterone 3-keto group interacted with the side chains of Gln725 and Arg766, and maintained the hydrogen bonding network that provides specificity for steroids with an oxygen atom at the 3-position of the A ring. The benzoxazine moiety occupied approximately the same space as rings C and D of progesterone with similar hydrophobic interactions. The sulfur of the benzoxazine appeared to extend beyond the methylketone substituent at C17 of progesterone. Tanaproget had an additional favorable interaction with the protein in the hydrogen bond formed between the benzoxazine nitrogen and the side chain oxygen of Asn719. The loop between helix 6 and helix 7, including amino acids 788-794, was rearranged with respect to the PR-LBD/progesterone structure. This rearrangement did not appear to be directly due to the different ligand, however, as the shortest distance between tanaproget and PR-LBD in this region is 5 Å, from one tanaproget methyl substituent of the benzoxazine to the side chain of Phe794. The structure indicated that the sulfur atom of tanaproget may form a weak interaction with Thr894 of the PR-LBD, and a hydrophobic region on the benzoxazine molecule forms a favorable hydrophobic interaction with Leu797 of the receptor LBD.

Several side chains were well defined by the experimental electron density in one molecule of the asymmetric unit (molecule "A"), but not in the other (molecule "B"). These side chains include: Met908, Phe794, Trp755, and Leu714. Met908 is somewhat disordered in molecule "A", with more than one rotamer represented in the electron density.

TABLE 2

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1 | CB | GLN | A | 682 | −7.348 | 13.179 | 57.749 | 1.00 | 59.37 | A |
| ATOM | 2 | CG | GLN | A | 682 | −6.839 | 14.229 | 58.725 | 1.00 | 62.50 | A |
| ATOM | 3 | CD | GLN | A | 682 | −6.509 | 13.648 | 60.089 | 1.00 | 64.16 | A |
| ATOM | 4 | OE1 | GLN | A | 682 | −7.383 | 13.129 | 60.785 | 1.00 | 65.34 | A |
| ATOM | 5 | NE2 | GLN | A | 682 | −5.240 | 13.732 | 60.476 | 1.00 | 64.49 | A |
| ATOM | 6 | C | GLN | A | 682 | −6.989 | 11.007 | 56.577 | 1.00 | 54.95 | A |
| ATOM | 7 | O | GLN | A | 682 | −6.920 | 9.824 | 56.915 | 1.00 | 55.50 | A |
| ATOM | 8 | N | GLN | A | 682 | −5.169 | 12.697 | 56.667 | 1.00 | 58.18 | A |
| ATOM | 9 | CA | GLN | A | 682 | −6.321 | 12.097 | 57.404 | 1.00 | 57.18 | A |
| ATOM | 10 | N | LEU | A | 683 | −7.640 | 11.412 | 55.493 | 1.00 | 51.76 | A |
| ATOM | 11 | CA | LEU | A | 683 | −8.315 | 10.464 | 54.618 | 1.00 | 48.27 | A |
| ATOM | 12 | CB | LEU | A | 683 | −9.448 | 11.156 | 53.851 | 1.00 | 50.10 | A |
| ATOM | 13 | CG | LEU | A | 683 | −10.757 | 11.418 | 54.603 | 1.00 | 52.21 | A |
| ATOM | 14 | CD1 | LEU | A | 683 | −11.685 | 12.275 | 53.749 | 1.00 | 52.58 | A |
| ATOM | 15 | CD2 | LEU | A | 683 | −11.420 | 10.091 | 54.945 | 1.00 | 51.94 | A |
| ATOM | 16 | C | LEU | A | 683 | −7.338 | 9.846 | 53.627 | 1.00 | 43.82 | A |
| ATOM | 17 | O | LEU | A | 683 | −7.630 | 8.815 | 53.027 | 1.00 | 43.05 | A |
| ATOM | 18 | N | ILE | A | 684 | −6.175 | 10.471 | 53.470 | 1.00 | 39.89 | A |
| ATOM | 19 | CA | ILE | A | 684 | −5.173 | 9.983 | 52.526 | 1.00 | 35.45 | A |
| ATOM | 20 | CB | ILE | A | 684 | −4.119 | 11.060 | 52.215 | 1.00 | 35.60 | A |
| ATOM | 21 | CG2 | ILE | A | 684 | −3.298 | 10.633 | 51.014 | 1.00 | 34.67 | A |
| ATOM | 22 | CG1 | ILE | A | 684 | −4.798 | 12.400 | 51.921 | 1.00 | 34.80 | A |
| ATOM | 23 | CD1 | ILE | A | 684 | −5.754 | 12.361 | 50.761 | 1.00 | 35.65 | A |
| ATOM | 24 | C | ILE | A | 684 | −4.435 | 8.732 | 52.996 | 1.00 | 33.40 | A |
| ATOM | 25 | O | ILE | A | 684 | −3.823 | 8.724 | 54.063 | 1.00 | 32.14 | A |
| ATOM | 26 | N | PRO | A | 685 | −4.482 | 7.657 | 52.190 | 1.00 | 31.08 | A |
| ATOM | 27 | CD | PRO | A | 685 | −5.212 | 7.563 | 50.914 | 1.00 | 29.47 | A |
| ATOM | 28 | CA | PRO | A | 685 | −3.823 | 6.386 | 52.497 | 1.00 | 29.34 | A |
| ATOM | 29 | CB | PRO | A | 685 | −4.051 | 5.566 | 51.230 | 1.00 | 28.42 | A |
| ATOM | 30 | CG | PRO | A | 685 | −5.360 | 6.071 | 50.745 | 1.00 | 29.55 | A |
| ATOM | 31 | C | PRO | A | 685 | −2.341 | 6.604 | 52.777 | 1.00 | 28.94 | A |
| ATOM | 32 | O | PRO | A | 685 | −1.685 | 7.395 | 52.099 | 1.00 | 27.20 | A |
| ATOM | 33 | N | PRO | A | 686 | −1.795 | 5.892 | 53.776 | 1.00 | 28.63 | A |
| ATOM | 34 | CD | PRO | A | 686 | −2.499 | 4.881 | 54.583 | 1.00 | 30.74 | A |
| ATOM | 35 | CA | PRO | A | 686 | −0.388 | 5.983 | 54.178 | 1.00 | 28.46 | A |
| ATOM | 36 | CB | PRO | A | 686 | −0.225 | 4.796 | 55.122 | 1.00 | 29.48 | A |
| ATOM | 37 | CG | PRO | A | 686 | −1.565 | 4.697 | 55.750 | 1.00 | 30.51 | A |
| ATOM | 38 | C | PRO | A | 686 | 0.615 | 5.941 | 53.026 | 1.00 | 26.34 | A |
| ATOM | 39 | O | PRO | A | 686 | 1.448 | 6.836 | 52.897 | 1.00 | 27.12 | A |
| ATOM | 40 | N | LEU | A | 687 | 0.538 | 4.907 | 52.192 | 1.00 | 23.00 | A |
| ATOM | 41 | CA | LEU | A | 687 | 1.474 | 4.782 | 51.077 | 1.00 | 21.26 | A |
| ATOM | 42 | CB | LEU | A | 687 | 1.145 | 3.552 | 50.228 | 1.00 | 19.41 | A |
| ATOM | 43 | CG | LEU | A | 687 | 2.091 | 3.305 | 49.047 | 1.00 | 18.40 | A |
| ATOM | 44 | CD1 | LEU | A | 687 | 3.537 | 3.370 | 49.521 | 1.00 | 17.99 | A |
| ATOM | 45 | CD2 | LEU | A | 687 | 1.788 | 1.944 | 48.420 | 1.00 | 17.48 | A |
| ATOM | 46 | C | LEU | A | 687 | 1.484 | 6.022 | 50.194 | 1.00 | 21.24 | A |
| ATOM | 47 | O | LEU | A | 687 | 2.535 | 6.432 | 49.700 | 1.00 | 21.10 | A |
| ATOM | 48 | N | ILE | A | 688 | 0.317 | 6.623 | 49.994 | 1.00 | 20.14 | A |
| ATOM | 49 | CA | ILE | A | 688 | 0.234 | 7.818 | 49.168 | 1.00 | 20.01 | A |
| ATOM | 50 | CB | ILE | A | 688 | −1.243 | 8.179 | 48.845 | 1.00 | 20.19 | A |
| ATOM | 51 | CG2 | ILE | A | 688 | −1.321 | 9.546 | 48.196 | 1.00 | 19.71 | A |
| ATOM | 52 | CG1 | ILE | A | 688 | −1.833 | 7.114 | 47.907 | 1.00 | 20.43 | A |
| ATOM | 53 | CD1 | ILE | A | 688 | −3.294 | 7.332 | 47.534 | 1.00 | 20.19 | A |
| ATOM | 54 | C | ILE | A | 688 | 0.938 | 8.983 | 49.862 | 1.00 | 20.11 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 55 | O | ILE | A | 688 | 1.686 | 9.725 | 49.225 | 1.00 | 20.42 | A |
| ATOM | 56 | N | ASN | A | 689 | 0.712 | 9.146 | 51.164 | 1.00 | 21.73 | A |
| ATOM | 57 | CA | ASN | A | 689 | 1.370 | 10.227 | 51.901 | 1.00 | 22.53 | A |
| ATOM | 58 | CB | ASN | A | 689 | 0.967 | 10.200 | 53.380 | 1.00 | 28.18 | A |
| ATOM | 59 | CG | ASN | A | 689 | −0.417 | 10.782 | 53.627 | 1.00 | 32.46 | A |
| ATOM | 60 | OD1 | ASN | A | 689 | −1.037 | 10.513 | 54.659 | 1.00 | 37.47 | A |
| ATOM | 61 | ND2 | ASN | A | 689 | −0.901 | 11.594 | 52.693 | 1.00 | 35.14 | A |
| ATOM | 62 | C | ASN | A | 689 | 2.884 | 10.040 | 51.790 | 1.00 | 22.06 | A |
| ATOM | 63 | O | ASN | A | 689 | 3.634 | 10.997 | 51.609 | 1.00 | 20.86 | A |
| ATOM | 64 | N | LEU | A | 690 | 3.325 | 8.793 | 51.888 | 1.00 | 20.88 | A |
| ATOM | 65 | CA | LEU | A | 690 | 4.746 | 8.497 | 51.794 | 1.00 | 21.42 | A |
| ATOM | 66 | CB | LEU | A | 690 | 4.982 | 7.013 | 52.057 | 1.00 | 21.51 | A |
| ATOM | 67 | CG | LEU | A | 690 | 6.427 | 6.547 | 52.240 | 1.00 | 22.35 | A |
| ATOM | 68 | CD1 | LEU | A | 690 | 6.409 | 5.229 | 52.969 | 1.00 | 26.08 | A |
| ATOM | 69 | CD2 | LEU | A | 690 | 7.129 | 6.416 | 50.897 | 1.00 | 23.08 | A |
| ATOM | 70 | C | LEU | A | 690 | 5.259 | 8.895 | 50.411 | 1.00 | 20.43 | A |
| ATOM | 71 | O | LEU | A | 690 | 6.299 | 9.545 | 50.293 | 1.00 | 20.25 | A |
| ATOM | 72 | N | LEU | A | 691 | 4.523 | 8.524 | 49.366 | 1.00 | 19.54 | A |
| ATOM | 73 | CA | LEU | A | 691 | 4.931 | 8.873 | 48.008 | 1.00 | 18.70 | A |
| ATOM | 74 | CB | LEU | A | 691 | 3.908 | 8.357 | 46.989 | 1.00 | 16.88 | A |
| ATOM | 75 | CG | LEU | A | 691 | 3.852 | 6.840 | 46.763 | 1.00 | 16.04 | A |
| ATOM | 76 | CD1 | LEU | A | 691 | 2.834 | 6.533 | 45.671 | 1.00 | 15.95 | A |
| ATOM | 77 | CD2 | LEU | A | 691 | 5.230 | 6.311 | 46.355 | 1.00 | 16.73 | A |
| ATOM | 78 | C | LEU | A | 691 | 5.088 | 10.385 | 47.868 | 1.00 | 19.45 | A |
| ATOM | 79 | O | LEU | A | 691 | 6.028 | 10.870 | 47.238 | 1.00 | 18.17 | A |
| ATOM | 80 | N | MET | A | 692 | 4.166 | 11.136 | 48.459 | 1.00 | 20.70 | A |
| ATOM | 81 | CA | MET | A | 692 | 4.243 | 12.588 | 48.380 | 1.00 | 23.63 | A |
| ATOM | 82 | CB | MET | A | 692 | 2.998 | 13.232 | 49.000 | 1.00 | 25.77 | A |
| ATOM | 83 | CG | MET | A | 692 | 2.988 | 14.751 | 48.917 | 1.00 | 29.26 | A |
| ATOM | 84 | SD | MET | A | 692 | 3.036 | 15.361 | 47.206 | 1.00 | 35.42 | A |
| ATOM | 85 | CE | MET | A | 692 | 4.716 | 16.016 | 47.096 | 1.00 | 34.93 | A |
| ATOM | 86 | C | MET | A | 692 | 5.484 | 13.105 | 49.104 | 1.00 | 23.94 | A |
| ATOM | 87 | O | MET | A | 692 | 6.139 | 14.033 | 48.636 | 1.00 | 22.01 | A |
| ATOM | 88 | N | SER | A | 693 | 5.804 | 12.496 | 50.243 | 1.00 | 23.84 | A |
| ATOM | 89 | CA | SER | A | 693 | 6.953 | 12.925 | 51.036 | 1.00 | 25.43 | A |
| ATOM | 90 | CB | SER | A | 693 | 6.960 | 12.218 | 52.397 | 1.00 | 26.51 | A |
| ATOM | 91 | OG | SER | A | 693 | 7.373 | 10.868 | 52.268 | 1.00 | 30.46 | A |
| ATOM | 92 | C | SER | A | 693 | 8.310 | 12.716 | 50.370 | 1.00 | 23.96 | A |
| ATOM | 93 | O | SER | A | 693 | 9.257 | 13.432 | 50.677 | 1.00 | 22.54 | A |
| ATOM | 94 | N | ILE | A | 694 | 8.415 | 11.745 | 49.465 | 1.00 | 22.45 | A |
| ATOM | 95 | CA | ILE | A | 694 | 9.694 | 11.492 | 48.814 | 1.00 | 21.42 | A |
| ATOM | 96 | CB | ILE | A | 694 | 10.001 | 9.976 | 48.740 | 1.00 | 20.54 | A |
| ATOM | 97 | CG2 | ILE | A | 694 | 10.052 | 9.393 | 50.153 | 1.00 | 18.76 | A |
| ATOM | 98 | CG1 | ILE | A | 694 | 8.947 | 9.261 | 47.896 | 1.00 | 20.09 | A |
| ATOM | 99 | CD1 | ILE | A | 694 | 9.257 | 7.790 | 47.648 | 1.00 | 19.61 | A |
| ATOM | 100 | C | ILE | A | 694 | 9.828 | 12.100 | 47.422 | 1.00 | 23.09 | A |
| ATOM | 101 | O | ILE | A | 694 | 10.756 | 11.767 | 46.677 | 1.00 | 23.23 | A |
| ATOM | 102 | N | GLU | A | 695 | 8.904 | 12.989 | 47.069 | 1.00 | 23.79 | A |
| ATOM | 103 | CA | GLU | A | 695 | 8.956 | 13.658 | 45.773 | 1.00 | 24.75 | A |
| ATOM | 104 | CB | GLU | A | 695 | 7.691 | 14.489 | 45.544 | 1.00 | 23.00 | A |
| ATOM | 105 | CG | GLU | A | 695 | 6.538 | 13.671 | 45.009 | 1.00 | 22.30 | A |
| ATOM | 106 | CD | GLU | A | 695 | 6.766 | 13.243 | 43.574 | 1.00 | 22.70 | A |
| ATOM | 107 | OE1 | GLU | A | 695 | 6.637 | 14.100 | 42.679 | 1.00 | 24.09 | A |
| ATOM | 108 | OE2 | GLU | A | 695 | 7.082 | 12.060 | 43.339 | 1.00 | 20.49 | A |
| ATOM | 109 | C | GLU | A | 695 | 10.181 | 14.563 | 45.739 | 1.00 | 26.09 | A |
| ATOM | 110 | O | GLU | A | 695 | 10.596 | 15.097 | 46.762 | 1.00 | 24.44 | A |
| ATOM | 111 | N | PRO | A | 696 | 10.775 | 14.746 | 44.554 | 1.00 | 27.98 | A |
| ATOM | 112 | CD | PRO | A | 696 | 10.513 | 13.991 | 43.318 | 1.00 | 30.08 | A |
| ATOM | 113 | CA | PRO | A | 696 | 11.964 | 15.589 | 44.402 | 1.00 | 29.41 | A |
| ATOM | 114 | CB | PRO | A | 696 | 12.419 | 15.286 | 42.974 | 1.00 | 30.04 | A |
| ATOM | 115 | CG | PRO | A | 696 | 11.895 | 13.887 | 42.729 | 1.00 | 31.56 | A |
| ATOM | 116 | C | PRO | A | 696 | 11.692 | 17.072 | 44.592 | 1.00 | 30.11 | A |
| ATOM | 117 | O | PRO | A | 696 | 10.561 | 17.527 | 44.436 | 1.00 | 28.96 | A |
| ATOM | 118 | N | ASP | A | 697 | 12.737 | 17.819 | 44.941 | 1.00 | 31.22 | A |
| ATOM | 119 | CA | ASP | A | 697 | 12.624 | 19.264 | 45.093 | 1.00 | 32.61 | A |
| ATOM | 120 | CB | ASP | A | 697 | 13.829 | 19.834 | 45.852 | 1.00 | 36.05 | A |
| ATOM | 121 | CG | ASP | A | 697 | 13.550 | 20.037 | 47.328 | 1.00 | 39.53 | A |
| ATOM | 122 | OD1 | ASP | A | 697 | 12.602 | 20.786 | 47.654 | 1.00 | 40.51 | A |
| ATOM | 123 | OD2 | ASP | A | 697 | 14.281 | 19.458 | 48.160 | 1.00 | 40.91 | A |
| ATOM | 124 | C | ASP | A | 697 | 12.641 | 19.794 | 43.661 | 1.00 | 32.25 | A |
| ATOM | 125 | O | ASP | A | 697 | 12.689 | 19.012 | 42.712 | 1.00 | 29.97 | A |
| ATOM | 126 | N | VAL | A | 698 | 12.609 | 21.114 | 43.506 | 1.00 | 32.44 | A |
| ATOM | 127 | CA | VAL | A | 698 | 12.640 | 21.722 | 42.180 | 1.00 | 32.25 | A |
| ATOM | 128 | CB | VAL | A | 698 | 12.444 | 23.260 | 42.257 | 1.00 | 34.46 | A |
| ATOM | 129 | CG1 | VAL | A | 698 | 12.766 | 23.896 | 40.918 | 1.00 | 36.09 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 130 | CG2 | VAL | A | 698 | 11.014 | 23.587 | 42.653 | 1.00 | 35.95 | A |
| ATOM | 131 | C | VAL | A | 698 | 13.995 | 21.435 | 41.543 | 1.00 | 30.21 | A |
| ATOM | 132 | O | VAL | A | 698 | 15.025 | 21.495 | 42.217 | 1.00 | 30.12 | A |
| ATOM | 133 | N | ILE | A | 699 | 13.990 | 21.114 | 40.253 | 1.00 | 27.42 | A |
| ATOM | 134 | CA | ILE | A | 699 | 15.226 | 20.835 | 39.526 | 1.00 | 25.67 | A |
| ATOM | 135 | CB | ILE | A | 699 | 15.239 | 19.399 | 38.956 | 1.00 | 25.17 | A |
| ATOM | 136 | CG2 | ILE | A | 699 | 16.491 | 19.190 | 38.091 | 1.00 | 23.70 | A |
| ATOM | 137 | CG1 | ILE | A | 699 | 15.196 | 18.387 | 40.102 | 1.00 | 23.56 | A |
| ATOM | 138 | CD1 | ILE | A | 699 | 14.904 | 16.973 | 39.652 | 1.00 | 24.85 | A |
| ATOM | 139 | C | ILE | A | 699 | 15.384 | 21.810 | 38.366 | 1.00 | 25.34 | A |
| ATOM | 140 | O | ILE | A | 699 | 14.507 | 21.912 | 37.503 | 1.00 | 22.56 | A |
| ATOM | 141 | N | TYR | A | 700 | 16.504 | 22.526 | 38.349 | 1.00 | 25.69 | A |
| ATOM | 142 | CA | TYR | A | 700 | 16.769 | 23.486 | 37.286 | 1.00 | 26.30 | A |
| ATOM | 143 | CB | TYR | A | 700 | 17.538 | 24.689 | 37.830 | 1.00 | 29.84 | A |
| ATOM | 144 | CG | TYR | A | 700 | 16.802 | 25.473 | 38.890 | 1.00 | 33.46 | A |
| ATOM | 145 | CD1 | TYR | A | 700 | 16.630 | 24.956 | 40.173 | 1.00 | 35.57 | A |
| ATOM | 146 | CE1 | TYR | A | 700 | 15.977 | 25.685 | 41.161 | 1.00 | 36.93 | A |
| ATOM | 147 | CD2 | TYR | A | 700 | 16.296 | 26.744 | 38.617 | 1.00 | 35.62 | A |
| ATOM | 148 | CE2 | TYR | A | 700 | 15.640 | 27.484 | 39.600 | 1.00 | 37.08 | A |
| ATOM | 149 | CZ | TYR | A | 700 | 15.487 | 26.947 | 40.868 | 1.00 | 37.98 | A |
| ATOM | 150 | OH | TYR | A | 700 | 14.857 | 27.677 | 41.849 | 1.00 | 42.60 | A |
| ATOM | 151 | C | TYR | A | 700 | 17.573 | 22.845 | 36.165 | 1.00 | 26.05 | A |
| ATOM | 152 | O | TYR | A | 700 | 18.347 | 21.911 | 36.395 | 1.00 | 25.35 | A |
| ATOM | 153 | N | ALA | A | 701 | 17.384 | 23.352 | 34.949 | 1.00 | 25.26 | A |
| ATOM | 154 | CA | ALA | A | 701 | 18.092 | 22.845 | 33.781 | 1.00 | 24.29 | A |
| ATOM | 155 | CB | ALA | A | 701 | 17.270 | 23.101 | 32.518 | 1.00 | 24.28 | A |
| ATOM | 156 | C | ALA | A | 701 | 19.457 | 23.510 | 33.650 | 1.00 | 25.20 | A |
| ATOM | 157 | O | ALA | A | 701 | 20.378 | 22.947 | 33.053 | 1.00 | 23.68 | A |
| ATOM | 158 | N | GLY | A | 702 | 19.576 | 24.711 | 34.212 | 1.00 | 26.21 | A |
| ATOM | 159 | CA | GLY | A | 702 | 20.824 | 25.453 | 34.141 | 1.00 | 26.56 | A |
| ATOM | 160 | C | GLY | A | 702 | 20.991 | 26.136 | 32.794 | 1.00 | 27.49 | A |
| ATOM | 161 | O | GLY | A | 702 | 22.113 | 26.367 | 32.342 | 1.00 | 25.92 | A |
| ATOM | 162 | N | HIS | A | 703 | 19.875 | 26.456 | 32.147 | 1.00 | 25.65 | A |
| ATOM | 163 | CA | HIS | A | 703 | 19.911 | 27.106 | 30.841 | 1.00 | 28.02 | A |
| ATOM | 164 | CB | HIS | A | 703 | 18.604 | 26.829 | 30.090 | 1.00 | 26.86 | A |
| ATOM | 165 | CG | HIS | A | 703 | 18.596 | 27.332 | 28.681 | 1.00 | 28.60 | A |
| ATOM | 166 | CD2 | HIS | A | 703 | 18.915 | 26.723 | 27.515 | 1.00 | 27.33 | A |
| ATOM | 167 | ND1 | HIS | A | 703 | 18.233 | 28.621 | 28.354 | 1.00 | 28.67 | A |
| ATOM | 168 | CE1 | HIS | A | 703 | 18.325 | 28.782 | 27.046 | 1.00 | 29.35 | A |
| ATOM | 169 | NE2 | HIS | A | 703 | 18.738 | 27.646 | 26.513 | 1.00 | 29.47 | A |
| ATOM | 170 | C | HIS | A | 703 | 20.155 | 28.615 | 30.961 | 1.00 | 29.77 | A |
| ATOM | 171 | O | HIS | A | 703 | 19.651 | 29.265 | 31.873 | 1.00 | 27.82 | A |
| ATOM | 172 | N | ASP | A | 704 | 20.931 | 29.159 | 30.027 | 1.00 | 32.72 | A |
| ATOM | 173 | CA | ASP | A | 704 | 21.275 | 30.579 | 30.019 | 1.00 | 37.35 | A |
| ATOM | 174 | CB | ASP | A | 704 | 22.110 | 30.896 | 28.767 | 1.00 | 40.24 | A |
| ATOM | 175 | CG | ASP | A | 704 | 21.321 | 30.733 | 27.468 | 1.00 | 42.83 | A |
| ATOM | 176 | OD1 | ASP | A | 704 | 20.357 | 31.498 | 27.263 | 1.00 | 41.93 | A |
| ATOM | 177 | OD2 | ASP | A | 704 | 21.664 | 29.847 | 26.646 | 1.00 | 42.26 | A |
| ATOM | 178 | C | ASP | A | 704 | 20.082 | 31.542 | 30.110 | 1.00 | 39.25 | A |
| ATOM | 179 | O | ASP | A | 704 | 19.964 | 32.310 | 31.070 | 1.00 | 42.51 | A |
| ATOM | 180 | N | ASN | A | 705 | 19.204 | 31.487 | 29.115 | 1.00 | 40.19 | A |
| ATOM | 181 | CA | ASN | A | 705 | 18.023 | 32.347 | 29.018 | 1.00 | 39.83 | A |
| ATOM | 182 | CB | ASN | A | 705 | 17.213 | 32.328 | 30.318 | 1.00 | 39.65 | A |
| ATOM | 183 | CG | ASN | A | 705 | 16.404 | 31.052 | 30.482 | 1.00 | 39.53 | A |
| ATOM | 184 | OD1 | ASN | A | 705 | 15.623 | 30.677 | 29.602 | 1.00 | 38.94 | A |
| ATOM | 185 | ND2 | ASN | A | 705 | 16.582 | 30.382 | 31.614 | 1.00 | 37.25 | A |
| ATOM | 186 | C | ASN | A | 705 | 18.358 | 33.791 | 28.637 | 1.00 | 40.65 | A |
| ATOM | 187 | O | ASN | A | 705 | 17.479 | 34.540 | 28.206 | 1.00 | 40.21 | A |
| ATOM | 188 | N | THR | A | 706 | 19.619 | 34.186 | 28.792 | 1.00 | 40.22 | A |
| ATOM | 189 | CA | THR | A | 706 | 20.024 | 35.542 | 28.429 | 1.00 | 41.37 | A |
| ATOM | 190 | CB | THR | A | 706 | 21.211 | 36.046 | 29.276 | 1.00 | 41.45 | A |
| ATOM | 191 | OG1 | THR | A | 706 | 22.376 | 35.273 | 28.974 | 1.00 | 42.94 | A |
| ATOM | 192 | CG2 | THR | A | 706 | 20.899 | 35.930 | 30.760 | 1.00 | 42.56 | A |
| ATOM | 193 | C | THR | A | 706 | 20.449 | 35.555 | 26.963 | 1.00 | 41.48 | A |
| ATOM | 194 | O | THR | A | 706 | 20.735 | 36.609 | 26.398 | 1.00 | 42.00 | A |
| ATOM | 195 | N | LYS | A | 707 | 20.493 | 34.373 | 26.355 | 1.00 | 39.94 | A |
| ATOM | 196 | CA | LYS | A | 707 | 20.882 | 34.246 | 24.957 | 1.00 | 39.25 | A |
| ATOM | 197 | CB | LYS | A | 707 | 22.080 | 33.303 | 24.805 | 1.00 | 40.35 | A |
| ATOM | 198 | CG | LYS | A | 707 | 23.378 | 33.794 | 25.420 | 1.00 | 43.83 | A |
| ATOM | 199 | CD | LYS | A | 707 | 24.534 | 32.911 | 24.963 | 1.00 | 45.58 | A |
| ATOM | 200 | CE | LYS | A | 707 | 25.874 | 33.379 | 25.514 | 1.00 | 48.00 | A |
| ATOM | 201 | NZ | LYS | A | 707 | 25.993 | 33.156 | 26.982 | 1.00 | 50.15 | A |
| ATOM | 202 | C | LYS | A | 707 | 19.727 | 33.690 | 24.146 | 1.00 | 36.97 | A |
| ATOM | 203 | O | LYS | A | 707 | 18.858 | 33.009 | 24.684 | 1.00 | 37.69 | A |
| ATOM | 204 | N | PRO | A | 708 | 19.703 | 33.978 | 22.838 | 1.00 | 35.45 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 205 | CD | PRO | A | 708 | 20.543 | 34.966 | 22.141 | 1.00 | 36.01 | A |
| ATOM | 206 | CA | PRO | A | 708 | 18.640 | 33.487 | 21.954 | 1.00 | 33.79 | A |
| ATOM | 207 | CB | PRO | A | 708 | 18.937 | 34.194 | 20.632 | 1.00 | 33.78 | A |
| ATOM | 208 | CG | PRO | A | 708 | 19.611 | 35.460 | 21.065 | 1.00 | 35.82 | A |
| ATOM | 209 | C | PRO | A | 708 | 18.745 | 31.966 | 21.824 | 1.00 | 32.66 | A |
| ATOM | 210 | O | PRO | A | 708 | 19.848 | 31.420 | 21.802 | 1.00 | 31.44 | A |
| ATOM | 211 | N | ASP | A | 709 | 17.605 | 31.289 | 21.738 | 1.00 | 30.13 | A |
| ATOM | 212 | CA | ASP | A | 709 | 17.596 | 29.835 | 21.613 | 1.00 | 27.78 | A |
| ATOM | 213 | CB | ASP | A | 709 | 16.164 | 29.288 | 21.594 | 1.00 | 26.98 | A |
| ATOM | 214 | CG | ASP | A | 709 | 15.494 | 29.335 | 22.941 | 1.00 | 26.45 | A |
| ATOM | 215 | OD1 | ASP | A | 709 | 16.180 | 29.603 | 23.947 | 1.00 | 27.85 | A |
| ATOM | 216 | OD2 | ASP | A | 709 | 14.271 | 29.086 | 22.989 | 1.00 | 27.12 | A |
| ATOM | 217 | C | ASP | A | 709 | 18.257 | 29.357 | 20.337 | 1.00 | 27.24 | A |
| ATOM | 218 | O | ASP | A | 709 | 18.204 | 30.026 | 19.310 | 1.00 | 25.71 | A |
| ATOM | 219 | N | THR | A | 710 | 18.877 | 28.187 | 20.413 | 1.00 | 25.67 | A |
| ATOM | 220 | CA | THR | A | 710 | 19.480 | 27.565 | 19.245 | 1.00 | 26.35 | A |
| ATOM | 221 | CB | THR | A | 710 | 21.025 | 27.716 | 19.195 | 1.00 | 26.29 | A |
| ATOM | 222 | OG1 | THR | A | 710 | 21.616 | 26.958 | 20.255 | 1.00 | 24.75 | A |
| ATOM | 223 | CG2 | THR | A | 710 | 21.433 | 29.182 | 19.329 | 1.00 | 25.04 | A |
| ATOM | 224 | C | THR | A | 710 | 19.129 | 26.097 | 19.428 | 1.00 | 27.11 | A |
| ATOM | 225 | O | THR | A | 710 | 18.912 | 25.640 | 20.555 | 1.00 | 26.86 | A |
| ATOM | 226 | N | SER | A | 711 | 19.052 | 25.364 | 18.328 | 1.00 | 26.94 | A |
| ATOM | 227 | CA | SER | A | 711 | 18.725 | 23.950 | 18.395 | 1.00 | 30.05 | A |
| ATOM | 228 | CB | SER | A | 711 | 18.857 | 23.323 | 17.004 | 1.00 | 30.48 | A |
| ATOM | 229 | OG | SER | A | 711 | 18.600 | 21.934 | 17.046 | 1.00 | 35.04 | A |
| ATOM | 230 | C | SER | A | 711 | 19.644 | 23.227 | 19.382 | 1.00 | 29.29 | A |
| ATOM | 231 | O | SER | A | 711 | 19.187 | 22.424 | 20.197 | 1.00 | 30.34 | A |
| ATOM | 232 | N | SER | A | 712 | 20.937 | 23.529 | 19.326 | 1.00 | 27.88 | A |
| ATOM | 233 | CA | SER | A | 712 | 21.891 | 22.870 | 20.207 | 1.00 | 27.73 | A |
| ATOM | 234 | CB | SER | A | 712 | 23.322 | 23.089 | 19.706 | 1.00 | 30.70 | A |
| ATOM | 235 | OG | SER | A | 712 | 23.692 | 24.451 | 19.784 | 1.00 | 37.15 | A |
| ATOM | 236 | C | SER | A | 712 | 21.803 | 23.264 | 21.678 | 1.00 | 25.40 | A |
| ATOM | 237 | O | SER | A | 712 | 21.922 | 22.401 | 22.544 | 1.00 | 23.44 | A |
| ATOM | 238 | N | SER | A | 713 | 21.593 | 24.547 | 21.970 | 1.00 | 23.22 | A |
| ATOM | 239 | CA | SER | A | 713 | 21.519 | 24.983 | 23.363 | 1.00 | 23.17 | A |
| ATOM | 240 | CB | SER | A | 713 | 21.554 | 26.516 | 23.466 | 1.00 | 23.10 | A |
| ATOM | 241 | OG | SER | A | 713 | 20.364 | 27.104 | 22.976 | 1.00 | 27.55 | A |
| ATOM | 242 | C | SER | A | 713 | 20.277 | 24.442 | 24.068 | 1.00 | 21.24 | A |
| ATOM | 243 | O | SER | A | 713 | 20.332 | 24.077 | 25.246 | 1.00 | 20.24 | A |
| ATOM | 244 | N | LEU | A | 714 | 19.159 | 24.391 | 23.351 | 1.00 | 20.03 | A |
| ATOM | 245 | CA | LEU | A | 714 | 17.922 | 23.871 | 23.924 | 1.00 | 18.97 | A |
| ATOM | 246 | CB | LEU | A | 714 | 16.734 | 24.100 | 22.978 | 1.00 | 17.28 | A |
| ATOM | 247 | CG | LEU | A | 714 | 16.139 | 25.503 | 22.873 | 1.00 | 20.44 | A |
| ATOM | 248 | CD1 | LEU | A | 714 | 14.961 | 25.473 | 21.901 | 1.00 | 16.61 | A |
| ATOM | 249 | CD2 | LEU | A | 714 | 15.682 | 25.978 | 24.245 | 1.00 | 21.04 | A |
| ATOM | 250 | C | LEU | A | 714 | 18.039 | 22.378 | 24.215 | 1.00 | 17.72 | A |
| ATOM | 251 | O | LEU | A | 714 | 17.733 | 21.927 | 25.322 | 1.00 | 19.37 | A |
| ATOM | 252 | N | LEU | A | 715 | 18.476 | 21.610 | 23.222 | 1.00 | 16.17 | A |
| ATOM | 253 | CA | LEU | A | 715 | 18.611 | 20.163 | 23.396 | 1.00 | 16.51 | A |
| ATOM | 254 | CB | LEU | A | 715 | 18.941 | 19.497 | 22.054 | 1.00 | 15.83 | A |
| ATOM | 255 | CG | LEU | A | 715 | 17.839 | 19.637 | 20.990 | 1.00 | 17.05 | A |
| ATOM | 256 | CD1 | LEU | A | 715 | 18.291 | 19.026 | 19.668 | 1.00 | 17.78 | A |
| ATOM | 257 | CD2 | LEU | A | 715 | 16.566 | 18.953 | 21.489 | 1.00 | 17.52 | A |
| ATOM | 258 | C | LEU | A | 715 | 19.676 | 19.842 | 24.444 | 1.00 | 17.19 | A |
| ATOM | 259 | O | LEU | A | 715 | 19.526 | 18.905 | 25.233 | 1.00 | 15.94 | A |
| ATOM | 260 | N | THR | A | 716 | 20.755 | 20.618 | 24.456 | 1.00 | 16.23 | A |
| ATOM | 261 | CA | THR | A | 716 | 21.807 | 20.405 | 25.444 | 1.00 | 16.41 | A |
| ATOM | 262 | CB | THR | A | 716 | 23.002 | 21.353 | 25.192 | 1.00 | 17.33 | A |
| ATOM | 263 | OG1 | THR | A | 716 | 23.719 | 20.901 | 24.039 | 1.00 | 18.63 | A |
| ATOM | 264 | CG2 | THR | A | 716 | 23.946 | 21.383 | 26.393 | 1.00 | 18.48 | A |
| ATOM | 265 | C | THR | A | 716 | 21.254 | 20.625 | 26.855 | 1.00 | 17.19 | A |
| ATOM | 266 | O | THR | A | 716 | 21.569 | 19.873 | 27.777 | 1.00 | 17.56 | A |
| ATOM | 267 | N | SER | A | 717 | 20.422 | 21.649 | 27.025 | 1.00 | 17.82 | A |
| ATOM | 268 | CA | SER | A | 717 | 19.836 | 21.917 | 28.334 | 1.00 | 17.93 | A |
| ATOM | 269 | CB | SER | A | 717 | 19.142 | 23.282 | 28.349 | 1.00 | 18.40 | A |
| ATOM | 270 | OG | SER | A | 717 | 20.099 | 24.315 | 28.459 | 1.00 | 20.04 | A |
| ATOM | 271 | C | SER | A | 717 | 18.840 | 20.826 | 28.699 | 1.00 | 17.68 | A |
| ATOM | 272 | O | SER | A | 717 | 18.774 | 20.399 | 29.849 | 1.00 | 17.99 | A |
| ATOM | 273 | N | LEU | A | 718 | 18.060 | 20.372 | 27.723 | 1.00 | 18.63 | A |
| ATOM | 274 | CA | LEU | A | 718 | 17.092 | 19.312 | 27.987 | 1.00 | 18.40 | A |
| ATOM | 275 | CB | LEU | A | 718 | 16.256 | 19.022 | 26.733 | 1.00 | 18.14 | A |
| ATOM | 276 | CG | LEU | A | 718 | 15.122 | 20.027 | 26.496 | 1.00 | 17.83 | A |
| ATOM | 277 | CD1 | LEU | A | 718 | 14.466 | 19.780 | 25.139 | 1.00 | 18.47 | A |
| ATOM | 278 | CD2 | LEU | A | 718 | 14.096 | 19.894 | 27.626 | 1.00 | 19.81 | A |
| ATOM | 279 | C | LEU | A | 718 | 17.835 | 18.057 | 28.447 | 1.00 | 19.24 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 280 | O | LEU | A | 718 | 17.357 | 17.320 | 29.317 | 1.00 | 18.56 | A |
| ATOM | 281 | N | ASN | A | 719 | 19.012 | 17.821 | 27.872 | 1.00 | 17.74 | A |
| ATOM | 282 | CA | ASN | A | 719 | 19.811 | 16.664 | 28.259 | 1.00 | 18.99 | A |
| ATOM | 283 | CB | ASN | A | 719 | 20.880 | 16.359 | 27.207 | 1.00 | 19.92 | A |
| ATOM | 284 | CG | ASN | A | 719 | 20.300 | 15.715 | 25.964 | 1.00 | 21.70 | A |
| ATOM | 285 | OD1 | ASN | A | 719 | 19.264 | 15.051 | 26.023 | 1.00 | 22.14 | A |
| ATOM | 286 | ND2 | ASN | A | 719 | 20.975 | 15.888 | 24.834 | 1.00 | 21.49 | A |
| ATOM | 287 | C | ASN | A | 719 | 20.464 | 16.870 | 29.625 | 1.00 | 19.54 | A |
| ATOM | 288 | O | ASN | A | 719 | 20.631 | 15.915 | 30.383 | 1.00 | 18.51 | A |
| ATOM | 289 | N | GLN | A | 720 | 20.833 | 18.111 | 29.946 | 1.00 | 20.24 | A |
| ATOM | 290 | CA | GLN | A | 720 | 21.438 | 18.383 | 31.248 | 1.00 | 20.89 | A |
| ATOM | 291 | CB | GLN | A | 720 | 22.024 | 19.804 | 31.299 | 1.00 | 24.62 | A |
| ATOM | 292 | CG | GLN | A | 720 | 22.851 | 20.080 | 32.562 | 1.00 | 29.69 | A |
| ATOM | 293 | CD | GLN | A | 720 | 23.710 | 21.344 | 32.462 | 1.00 | 34.45 | A |
| ATOM | 294 | OE1 | GLN | A | 720 | 23.197 | 22.465 | 32.431 | 1.00 | 36.61 | A |
| ATOM | 295 | NE2 | GLN | A | 720 | 25.024 | 21.159 | 32.409 | 1.00 | 34.00 | A |
| ATOM | 296 | C | GLN | A | 720 | 20.345 | 18.211 | 32.303 | 1.00 | 20.76 | A |
| ATOM | 297 | O | GLN | A | 720 | 20.571 | 17.608 | 33.355 | 1.00 | 18.85 | A |
| ATOM | 298 | N | LEU | A | 721 | 19.156 | 18.736 | 32.007 | 1.00 | 18.88 | A |
| ATOM | 299 | CA | LEU | A | 721 | 18.018 | 18.611 | 32.909 | 1.00 | 19.76 | A |
| ATOM | 300 | CB | LEU | A | 721 | 16.783 | 19.313 | 32.317 | 1.00 | 20.61 | A |
| ATOM | 301 | CG | LEU | A | 721 | 15.529 | 19.375 | 33.197 | 1.00 | 21.89 | A |
| ATOM | 302 | CD1 | LEU | A | 721 | 15.845 | 20.126 | 34.491 | 1.00 | 17.83 | A |
| ATOM | 303 | CD2 | LEU | A | 721 | 14.389 | 20.058 | 32.435 | 1.00 | 17.08 | A |
| ATOM | 304 | C | LEU | A | 721 | 17.743 | 17.115 | 33.063 | 1.00 | 18.66 | A |
| ATOM | 305 | O | LEU | A | 721 | 17.457 | 16.626 | 34.157 | 1.00 | 18.65 | A |
| ATOM | 306 | N | GLY | A | 722 | 17.839 | 16.392 | 31.953 | 1.00 | 18.59 | A |
| ATOM | 307 | CA | GLY | A | 722 | 17.623 | 14.959 | 31.981 | 1.00 | 18.69 | A |
| ATOM | 308 | C | GLY | A | 722 | 18.591 | 14.261 | 32.922 | 1.00 | 19.59 | A |
| ATOM | 309 | O | GLY | A | 722 | 18.184 | 13.426 | 33.735 | 1.00 | 21.70 | A |
| ATOM | 310 | N | GLU | A | 723 | 19.874 | 14.598 | 32.817 | 1.00 | 18.22 | A |
| ATOM | 311 | CA | GLU | A | 723 | 20.898 | 13.998 | 33.674 | 1.00 | 18.14 | A |
| ATOM | 312 | CB | GLU | A | 723 | 22.271 | 14.631 | 33.400 | 1.00 | 18.39 | A |
| ATOM | 313 | CG | GLU | A | 723 | 23.409 | 14.008 | 34.198 | 1.00 | 19.11 | A |
| ATOM | 314 | CD | GLU | A | 723 | 23.922 | 12.713 | 33.588 | 1.00 | 22.52 | A |
| ATOM | 315 | OE1 | GLU | A | 723 | 23.277 | 12.184 | 32.655 | 1.00 | 22.75 | A |
| ATOM | 316 | OE2 | GLU | A | 723 | 24.979 | 12.220 | 34.040 | 1.00 | 22.45 | A |
| ATOM | 317 | C | GLU | A | 723 | 20.549 | 14.209 | 35.145 | 1.00 | 18.01 | A |
| ATOM | 318 | O | GLU | A | 723 | 20.691 | 13.296 | 35.967 | 1.00 | 16.59 | A |
| ATOM | 319 | N | ARG | A | 724 | 20.110 | 15.422 | 35.474 | 1.00 | 17.42 | A |
| ATOM | 320 | CA | ARG | A | 724 | 19.742 | 15.756 | 36.850 | 1.00 | 19.72 | A |
| ATOM | 321 | CB | ARG | A | 724 | 19.551 | 17.266 | 36.987 | 1.00 | 20.72 | A |
| ATOM | 322 | CG | ARG | A | 724 | 20.820 | 18.047 | 36.693 | 1.00 | 21.86 | A |
| ATOM | 323 | CD | ARG | A | 724 | 20.602 | 19.549 | 36.744 | 1.00 | 23.18 | A |
| ATOM | 324 | NE | ARG | A | 724 | 21.855 | 20.245 | 36.465 | 1.00 | 23.39 | A |
| ATOM | 325 | CZ | ARG | A | 724 | 22.021 | 21.563 | 36.505 | 1.00 | 25.86 | A |
| ATOM | 326 | NH1 | ARG | A | 724 | 21.008 | 22.362 | 36.813 | 1.00 | 24.78 | A |
| ATOM | 327 | NH2 | ARG | A | 724 | 23.217 | 22.079 | 36.252 | 1.00 | 23.92 | A |
| ATOM | 328 | C | ARG | A | 724 | 18.476 | 15.029 | 37.292 | 1.00 | 20.26 | A |
| ATOM | 329 | O | ARG | A | 724 | 18.383 | 14.546 | 38.422 | 1.00 | 18.14 | A |
| ATOM | 330 | N | GLN | A | 725 | 17.493 | 14.947 | 36.405 | 1.00 | 19.29 | A |
| ATOM | 331 | CA | GLN | A | 725 | 16.271 | 14.256 | 36.762 | 1.00 | 21.28 | A |
| ATOM | 332 | CB | GLN | A | 725 | 15.191 | 14.504 | 35.705 | 1.00 | 23.07 | A |
| ATOM | 333 | CG | GLN | A | 725 | 14.691 | 15.955 | 35.716 | 1.00 | 27.51 | A |
| ATOM | 334 | CD | GLN | A | 725 | 13.556 | 16.210 | 34.743 | 1.00 | 30.36 | A |
| ATOM | 335 | OE1 | GLN | A | 725 | 13.084 | 17.341 | 34.600 | 1.00 | 33.13 | A |
| ATOM | 336 | NE2 | GLN | A | 725 | 13.111 | 15.161 | 34.068 | 1.00 | 31.54 | A |
| ATOM | 337 | C | GLN | A | 725 | 16.570 | 12.769 | 36.918 | 1.00 | 21.14 | A |
| ATOM | 338 | O | GLN | A | 725 | 15.952 | 12.087 | 37.731 | 1.00 | 21.59 | A |
| ATOM | 339 | N | LEU | A | 726 | 17.542 | 12.276 | 36.156 | 1.00 | 20.47 | A |
| ATOM | 340 | CA | LEU | A | 726 | 17.919 | 10.870 | 36.232 | 1.00 | 20.31 | A |
| ATOM | 341 | CB | LEU | A | 726 | 18.928 | 10.547 | 35.126 | 1.00 | 21.56 | A |
| ATOM | 342 | CG | LEU | A | 726 | 19.070 | 9.108 | 34.622 | 1.00 | 22.31 | A |
| ATOM | 343 | CD1 | LEU | A | 726 | 17.705 | 8.482 | 34.346 | 1.00 | 20.98 | A |
| ATOM | 344 | CD2 | LEU | A | 726 | 19.908 | 9.127 | 33.346 | 1.00 | 22.17 | A |
| ATOM | 345 | C | LEU | A | 726 | 18.512 | 10.607 | 37.621 | 1.00 | 21.15 | A |
| ATOM | 346 | O | LEU | A | 726 | 18.190 | 9.611 | 38.272 | 1.00 | 19.58 | A |
| ATOM | 347 | N | LEU | A | 727 | 19.375 | 11.509 | 38.077 | 1.00 | 19.81 | A |
| ATOM | 348 | CA | LEU | A | 727 | 19.972 | 11.376 | 39.400 | 1.00 | 20.36 | A |
| ATOM | 349 | CB | LEU | A | 727 | 20.927 | 12.535 | 39.662 | 1.00 | 23.93 | A |
| ATOM | 350 | CG | LEU | A | 727 | 22.304 | 12.433 | 39.009 | 1.00 | 26.70 | A |
| ATOM | 351 | CD1 | LEU | A | 727 | 23.092 | 13.712 | 39.259 | 1.00 | 30.45 | A |
| ATOM | 352 | CD2 | LEU | A | 727 | 23.037 | 11.231 | 39.586 | 1.00 | 27.44 | A |
| ATOM | 353 | C | LEU | A | 727 | 18.862 | 11.384 | 40.455 | 1.00 | 18.86 | A |
| ATOM | 354 | O | LEU | A | 727 | 18.910 | 10.637 | 41.437 | 1.00 | 17.62 | A |

TABLE 2-continued

Structure coordinates (Table discloses SEQ ID NO: 6 twice)

| | # | Name | Res. | Chain | Res # | X | Y | Z | occ | B | SegID |
|---|---|---|---|---|---|---|---|---|---|---|---|
| ATOM | 355 | N | SER | A | 728 | 17.863 | 12.229 | 40.223 | 1.00 | 17.97 | A |
| ATOM | 356 | CA | SER | A | 728 | 16.724 | 12.376 | 41.115 | 1.00 | 19.31 | A |
| ATOM | 357 | CB | SER | A | 728 | 15.836 | 13.523 | 40.625 | 1.00 | 21.26 | A |
| ATOM | 358 | OG | SER | A | 728 | 14.794 | 13.788 | 41.542 | 1.00 | 24.60 | A |
| ATOM | 359 | C | SER | A | 728 | 15.916 | 11.083 | 41.180 | 1.00 | 19.09 | A |
| ATOM | 360 | O | SER | A | 728 | 15.465 | 10.675 | 42.251 | 1.00 | 18.25 | A |
| ATOM | 361 | N | VAL | A | 729 | 15.730 | 10.445 | 40.027 | 1.00 | 18.98 | A |
| ATOM | 362 | CA | VAL | A | 729 | 14.990 | 9.190 | 39.962 | 1.00 | 17.54 | A |
| ATOM | 363 | CB | VAL | A | 729 | 14.814 | 8.720 | 38.498 | 1.00 | 17.32 | A |
| ATOM | 364 | CG1 | VAL | A | 729 | 14.261 | 7.312 | 38.460 | 1.00 | 17.30 | A |
| ATOM | 365 | CG2 | VAL | A | 729 | 13.875 | 9.676 | 37.770 | 1.00 | 19.41 | A |
| ATOM | 366 | C | VAL | A | 729 | 15.718 | 8.112 | 40.765 | 1.00 | 17.34 | A |
| ATOM | 367 | O | VAL | A | 729 | 15.095 | 7.382 | 41.537 | 1.00 | 16.18 | A |
| ATOM | 368 | N | VAL | A | 730 | 17.033 | 8.015 | 40.590 | 1.00 | 15.92 | A |
| ATOM | 369 | CA | VAL | A | 730 | 17.812 | 7.024 | 41.330 | 1.00 | 16.21 | A |
| ATOM | 370 | CB | VAL | A | 730 | 19.321 | 7.098 | 40.957 | 1.00 | 17.70 | A |
| ATOM | 371 | CG1 | VAL | A | 730 | 20.151 | 6.236 | 41.909 | 1.00 | 17.59 | A |
| ATOM | 372 | CG2 | VAL | A | 730 | 19.518 | 6.592 | 39.533 | 1.00 | 19.79 | A |
| ATOM | 373 | C | VAL | A | 730 | 17.628 | 7.234 | 42.840 | 1.00 | 18.41 | A |
| ATOM | 374 | O | VAL | A | 730 | 17.364 | 6.282 | 43.582 | 1.00 | 20.77 | A |
| ATOM | 375 | N | LYS | A | 731 | 17.747 | 8.480 | 43.290 | 1.00 | 18.40 | A |
| ATOM | 376 | CA | LYS | A | 731 | 17.571 | 8.809 | 44.707 | 1.00 | 19.11 | A |
| ATOM | 377 | CB | LYS | A | 731 | 17.806 | 10.307 | 44.915 | 1.00 | 22.06 | A |
| ATOM | 378 | CG | LYS | A | 731 | 17.424 | 10.842 | 46.297 | 1.00 | 26.05 | A |
| ATOM | 379 | CD | LYS | A | 731 | 18.409 | 10.437 | 47.379 | 1.00 | 30.61 | A |
| ATOM | 380 | CE | LYS | A | 731 | 18.029 | 11.072 | 48.717 | 1.00 | 32.42 | A |
| ATOM | 381 | NZ | LYS | A | 731 | 19.059 | 10.845 | 49.766 | 1.00 | 35.26 | A |
| ATOM | 382 | C | LYS | A | 731 | 16.158 | 8.435 | 45.179 | 1.00 | 19.62 | A |
| ATOM | 383 | O | LYS | A | 731 | 15.973 | 7.778 | 46.209 | 1.00 | 19.40 | A |
| ATOM | 384 | N | TRP | A | 732 | 15.164 | 8.873 | 44.417 | 1.00 | 18.65 | A |
| ATOM | 385 | CA | TRP | A | 732 | 13.767 | 8.595 | 44.714 | 1.00 | 16.92 | A |
| ATOM | 386 | CB | TRP | A | 732 | 12.905 | 9.226 | 43.617 | 1.00 | 18.08 | A |
| ATOM | 387 | CG | TRP | A | 732 | 11.453 | 8.863 | 43.602 | 1.00 | 16.59 | A |
| ATOM | 388 | CD2 | TRP | A | 732 | 10.791 | 8.069 | 42.612 | 1.00 | 18.88 | A |
| ATOM | 389 | CE2 | TRP | A | 732 | 9.412 | 8.062 | 42.931 | 1.00 | 19.08 | A |
| ATOM | 390 | CE3 | TRP | A | 732 | 11.228 | 7.366 | 41.478 | 1.00 | 16.99 | A |
| ATOM | 391 | CD1 | TRP | A | 732 | 10.481 | 9.286 | 44.469 | 1.00 | 19.57 | A |
| ATOM | 392 | NE1 | TRP | A | 732 | 9.250 | 8.810 | 44.069 | 1.00 | 18.44 | A |
| ATOM | 393 | CZ2 | TRP | A | 732 | 8.467 | 7.375 | 42.157 | 1.00 | 19.26 | A |
| ATOM | 394 | CZ3 | TRP | A | 732 | 10.289 | 6.685 | 40.710 | 1.00 | 17.20 | A |
| ATOM | 395 | CH2 | TRP | A | 732 | 8.923 | 6.697 | 41.054 | 1.00 | 18.84 | A |
| ATOM | 396 | C | TRP | A | 732 | 13.508 | 7.090 | 44.808 | 1.00 | 16.34 | A |
| ATOM | 397 | O | TRP | A | 732 | 12.876 | 6.611 | 45.754 | 1.00 | 17.11 | A |
| ATOM | 398 | N | SER | A | 733 | 14.016 | 6.341 | 43.838 | 1.00 | 16.51 | A |
| ATOM | 399 | CA | SER | A | 733 | 13.803 | 4.901 | 43.813 | 1.00 | 18.54 | A |
| ATOM | 400 | CB | SER | A | 733 | 14.448 | 4.287 | 42.561 | 1.00 | 18.74 | A |
| ATOM | 401 | OG | SER | A | 733 | 15.861 | 4.291 | 42.643 | 1.00 | 18.35 | A |
| ATOM | 402 | C | SER | A | 733 | 14.319 | 4.202 | 45.072 | 1.00 | 19.10 | A |
| ATOM | 403 | O | SER | A | 733 | 13.749 | 3.196 | 45.508 | 1.00 | 18.34 | A |
| ATOM | 404 | N | LYS | A | 734 | 15.385 | 4.741 | 45.658 | 1.00 | 18.85 | A |
| ATOM | 405 | CA | LYS | A | 734 | 15.958 | 4.160 | 46.865 | 1.00 | 19.80 | A |
| ATOM | 406 | CB | LYS | A | 734 | 17.295 | 4.831 | 47.200 | 1.00 | 22.02 | A |
| ATOM | 407 | CG | LYS | A | 734 | 18.381 | 4.547 | 46.178 | 1.00 | 24.28 | A |
| ATOM | 408 | CD | LYS | A | 734 | 19.678 | 5.259 | 46.517 | 1.00 | 29.24 | A |
| ATOM | 409 | CE | LYS | A | 734 | 20.717 | 5.021 | 45.429 | 1.00 | 30.96 | A |
| ATOM | 410 | NZ | LYS | A | 734 | 21.974 | 5.767 | 45.688 | 1.00 | 34.40 | A |
| ATOM | 411 | C | LYS | A | 734 | 15.012 | 4.275 | 48.054 | 1.00 | 19.01 | A |
| ATOM | 412 | O | LYS | A | 734 | 15.107 | 3.500 | 49.000 | 1.00 | 18.14 | A |
| ATOM | 413 | N | SER | A | 735 | 14.099 | 5.240 | 47.998 | 1.00 | 19.77 | A |
| ATOM | 414 | CA | SER | A | 735 | 13.131 | 5.445 | 49.075 | 1.00 | 20.89 | A |
| ATOM | 415 | CB | SER | A | 735 | 13.032 | 6.931 | 49.418 | 1.00 | 21.77 | A |
| ATOM | 416 | OG | SER | A | 735 | 14.270 | 7.412 | 49.899 | 1.00 | 26.19 | A |
| ATOM | 417 | C | SER | A | 735 | 11.741 | 4.928 | 48.735 | 1.00 | 18.31 | A |
| ATOM | 418 | O | SER | A | 735 | 10.864 | 4.888 | 49.594 | 1.00 | 17.33 | A |
| ATOM | 419 | N | LEU | A | 736 | 11.544 | 4.544 | 47.480 | 1.00 | 18.55 | A |
| ATOM | 420 | CA | LEU | A | 736 | 10.258 | 4.036 | 47.007 | 1.00 | 16.70 | A |
| ATOM | 421 | CB | LEU | A | 736 | 10.280 | 3.936 | 45.478 | 1.00 | 16.07 | A |
| ATOM | 422 | CG | LEU | A | 736 | 9.049 | 3.372 | 44.766 | 1.00 | 17.19 | A |
| ATOM | 423 | CD1 | LEU | A | 736 | 7.807 | 4.227 | 45.062 | 1.00 | 16.11 | A |
| ATOM | 424 | CD2 | LEU | A | 736 | 9.328 | 3.338 | 43.270 | 1.00 | 12.10 | A |
| ATOM | 425 | C | LEU | A | 736 | 9.954 | 2.670 | 47.622 | 1.00 | 16.59 | A |
| ATOM | 426 | O | LEU | A | 736 | 10.643 | 1.686 | 47.341 | 1.00 | 14.96 | A |
| ATOM | 427 | N | PRO | A | 737 | 8.906 | 2.588 | 48.461 | 1.00 | 16.50 | A |
| ATOM | 428 | CD | PRO | A | 737 | 7.985 | 3.652 | 48.900 | 1.00 | 15.57 | A |
| ATOM | 429 | CA | PRO | A | 737 | 8.564 | 1.306 | 49.092 | 1.00 | 18.45 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 430 | CB | PRO | A | 737 | 7.215 | 1.593 | 49.753 | 1.00 | 18.84 | A |
| ATOM | 431 | CG | PRO | A | 737 | 7.356 | 3.040 | 50.154 | 1.00 | 16.58 | A |
| ATOM | 432 | C | PRO | A | 737 | 8.510 | 0.127 | 48.126 | 1.00 | 20.18 | A |
| ATOM | 433 | O | PRO | A | 737 | 7.839 | 0.181 | 47.090 | 1.00 | 18.72 | A |
| ATOM | 434 | N | GLY | A | 738 | 9.244 | −0.928 | 48.468 | 1.00 | 19.99 | A |
| ATOM | 435 | CA | GLY | A | 738 | 9.269 | −2.122 | 47.643 | 1.00 | 20.37 | A |
| ATOM | 436 | C | GLY | A | 738 | 10.379 | −2.222 | 46.609 | 1.00 | 21.67 | A |
| ATOM | 437 | O | GLY | A | 738 | 10.883 | −3.314 | 46.344 | 1.00 | 22.52 | A |
| ATOM | 438 | N | PHE | A | 739 | 10.784 | −1.094 | 46.033 | 1.00 | 20.61 | A |
| ATOM | 439 | CA | PHE | A | 739 | 11.807 | −1.113 | 44.988 | 1.00 | 19.83 | A |
| ATOM | 440 | CB | PHE | A | 739 | 12.028 | 0.300 | 44.431 | 1.00 | 19.10 | A |
| ATOM | 441 | CG | PHE | A | 739 | 12.605 | 0.322 | 43.035 | 1.00 | 19.43 | A |
| ATOM | 442 | CD1 | PHE | A | 739 | 11.907 | −0.252 | 41.972 | 1.00 | 20.73 | A |
| ATOM | 443 | CD2 | PHE | A | 739 | 13.835 | 0.925 | 42.782 | 1.00 | 21.00 | A |
| ATOM | 444 | CE1 | PHE | A | 739 | 12.426 | −0.225 | 40.669 | 1.00 | 20.34 | A |
| ATOM | 445 | CE2 | PHE | A | 739 | 14.366 | 0.961 | 41.482 | 1.00 | 20.08 | A |
| ATOM | 446 | CZ | PHE | A | 739 | 13.653 | 0.381 | 40.424 | 1.00 | 18.50 | A |
| ATOM | 447 | C | PHE | A | 739 | 13.154 | −1.703 | 45.404 | 1.00 | 20.67 | A |
| ATOM | 448 | O | PHE | A | 739 | 13.695 | −2.555 | 44.708 | 1.00 | 19.78 | A |
| ATOM | 449 | N | ARG | A | 740 | 13.690 | −1.248 | 46.532 | 1.00 | 21.77 | A |
| ATOM | 450 | CA | ARG | A | 740 | 14.990 | −1.716 | 47.010 | 1.00 | 22.39 | A |
| ATOM | 451 | CB | ARG | A | 740 | 15.355 | −1.009 | 48.321 | 1.00 | 21.37 | A |
| ATOM | 452 | CG | ARG | A | 740 | 14.409 | −1.304 | 49.480 | 1.00 | 21.34 | A |
| ATOM | 453 | CD | ARG | A | 740 | 14.946 | −0.719 | 50.780 | 1.00 | 19.50 | A |
| ATOM | 454 | NE | ARG | A | 740 | 14.050 | −0.960 | 51.908 | 1.00 | 20.23 | A |
| ATOM | 455 | CZ | ARG | A | 740 | 14.351 | −0.652 | 53.165 | 1.00 | 20.17 | A |
| ATOM | 456 | NH1 | ARG | A | 740 | 15.520 | −0.095 | 53.442 | 1.00 | 18.30 | A |
| ATOM | 457 | NH2 | ARG | A | 740 | 13.488 | −0.900 | 54.144 | 1.00 | 19.12 | A |
| ATOM | 458 | C | ARG | A | 740 | 15.092 | −3.225 | 47.213 | 1.00 | 24.06 | A |
| ATOM | 459 | O | ARG | A | 740 | 16.195 | −3.776 | 47.272 | 1.00 | 24.88 | A |
| ATOM | 460 | N | ASN | A | 741 | 13.953 | −3.899 | 47.308 | 1.00 | 24.13 | A |
| ATOM | 461 | CA | ASN | A | 741 | 13.962 | −5.340 | 47.531 | 1.00 | 26.03 | A |
| ATOM | 462 | CB | ASN | A | 741 | 12.744 | −5.736 | 48.373 | 1.00 | 27.83 | A |
| ATOM | 463 | CG | ASN | A | 741 | 12.650 | −4.931 | 49.660 | 1.00 | 29.37 | A |
| ATOM | 464 | OD1 | ASN | A | 741 | 13.637 | −4.780 | 50.381 | 1.00 | 29.40 | A |
| ATOM | 465 | ND2 | ASN | A | 741 | 11.464 | −4.409 | 49.952 | 1.00 | 30.58 | A |
| ATOM | 466 | C | ASN | A | 741 | 14.042 | −6.172 | 46.253 | 1.00 | 25.13 | A |
| ATOM | 467 | O | ASN | A | 741 | 14.128 | −7.401 | 46.305 | 1.00 | 24.44 | A |
| ATOM | 468 | N | LEU | A | 742 | 14.012 | −5.504 | 45.104 | 1.00 | 22.83 | A |
| ATOM | 469 | CA | LEU | A | 742 | 14.135 | −6.197 | 43.831 | 1.00 | 21.37 | A |
| ATOM | 470 | CB | LEU | A | 742 | 13.496 | −5.384 | 42.698 | 1.00 | 21.88 | A |
| ATOM | 471 | CG | LEU | A | 742 | 12.009 | −5.019 | 42.812 | 1.00 | 21.52 | A |
| ATOM | 472 | CD1 | LEU | A | 742 | 11.613 | −4.138 | 41.624 | 1.00 | 21.95 | A |
| ATOM | 473 | CD2 | LEU | A | 742 | 11.159 | −6.284 | 42.840 | 1.00 | 19.89 | A |
| ATOM | 474 | C | LEU | A | 742 | 15.637 | −6.311 | 43.597 | 1.00 | 21.92 | A |
| ATOM | 475 | O | LEU | A | 742 | 16.406 | −5.514 | 44.130 | 1.00 | 21.09 | A |
| ATOM | 476 | N | HIS | A | 743 | 16.057 | −7.302 | 42.818 | 1.00 | 23.00 | A |
| ATOM | 477 | CA | HIS | A | 743 | 17.477 | −7.485 | 42.527 | 1.00 | 23.50 | A |
| ATOM | 478 | CB | HIS | A | 743 | 17.652 | −8.612 | 41.507 | 1.00 | 25.73 | A |
| ATOM | 479 | CG | HIS | A | 743 | 19.071 | −9.056 | 41.328 | 1.00 | 29.22 | A |
| ATOM | 480 | CD2 | HIS | A | 743 | 19.697 | −10.202 | 41.690 | 1.00 | 29.68 | A |
| ATOM | 481 | ND1 | HIS | A | 743 | 20.025 | −8.277 | 40.708 | 1.00 | 28.89 | A |
| ATOM | 482 | CE1 | HIS | A | 743 | 21.177 | −8.925 | 40.694 | 1.00 | 31.58 | A |
| ATOM | 483 | NE2 | HIS | A | 743 | 21.005 | −10.096 | 41.283 | 1.00 | 31.35 | A |
| ATOM | 484 | C | HIS | A | 743 | 18.011 | −6.170 | 41.961 | 1.00 | 24.00 | A |
| ATOM | 485 | O | HIS | A | 743 | 17.290 | −5.459 | 41.252 | 1.00 | 22.58 | A |
| ATOM | 486 | N | ILE | A | 744 | 19.260 | −5.840 | 42.276 | 1.00 | 22.45 | A |
| ATOM | 487 | CA | ILE | A | 744 | 19.854 | −4.598 | 41.791 | 1.00 | 23.13 | A |
| ATOM | 488 | CB | ILE | A | 744 | 21.316 | −4.437 | 42.286 | 1.00 | 24.13 | A |
| ATOM | 489 | CG2 | ILE | A | 744 | 22.158 | −5.623 | 41.829 | 1.00 | 23.77 | A |
| ATOM | 490 | CG1 | ILE | A | 744 | 21.908 | −3.128 | 41.751 | 1.00 | 25.51 | A |
| ATOM | 491 | CD1 | ILE | A | 744 | 21.194 | −1.865 | 42.234 | 1.00 | 27.84 | A |
| ATOM | 492 | C | ILE | A | 744 | 19.819 | −4.496 | 40.263 | 1.00 | 21.80 | A |
| ATOM | 493 | O | ILE | A | 744 | 19.639 | −3.406 | 39.715 | 1.00 | 19.60 | A |
| ATOM | 494 | N | ASP | A | 745 | 19.990 | −5.622 | 39.574 | 1.00 | 21.91 | A |
| ATOM | 495 | CA | ASP | A | 745 | 19.945 | −5.609 | 38.112 | 1.00 | 21.89 | A |
| ATOM | 496 | CB | ASP | A | 745 | 20.271 | −6.987 | 37.526 | 1.00 | 25.03 | A |
| ATOM | 497 | CG | ASP | A | 745 | 21.706 | −7.415 | 37.776 | 1.00 | 27.05 | A |
| ATOM | 498 | OD1 | ASP | A | 745 | 22.562 | −6.546 | 38.028 | 1.00 | 28.56 | A |
| ATOM | 499 | OD2 | ASP | A | 745 | 21.973 | −8.632 | 37.703 | 1.00 | 31.09 | A |
| ATOM | 500 | C | ASP | A | 745 | 18.545 | −5.210 | 37.653 | 1.00 | 20.59 | A |
| ATOM | 501 | O | ASP | A | 745 | 18.386 | −4.530 | 36.637 | 1.00 | 19.07 | A |
| ATOM | 502 | N | ASP | A | 746 | 17.530 | −5.656 | 38.391 | 1.00 | 19.31 | A |
| ATOM | 503 | CA | ASP | A | 746 | 16.154 | −5.332 | 38.043 | 1.00 | 18.60 | A |
| ATOM | 504 | CB | ASP | A | 746 | 15.160 | −6.124 | 38.903 | 1.00 | 19.50 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 505 | CG | ASP | A | 746 | 15.187 | −7.620 | 38.620 | 1.00 | 20.87 | A |
| ATOM | 506 | OD1 | ASP | A | 746 | 15.631 | −8.029 | 37.530 | 1.00 | 24.46 | A |
| ATOM | 507 | OD2 | ASP | A | 746 | 14.743 | −8.391 | 39.493 | 1.00 | 22.73 | A |
| ATOM | 508 | C | ASP | A | 746 | 15.901 | −3.842 | 38.232 | 1.00 | 18.23 | A |
| ATOM | 509 | O | ASP | A | 746 | 15.283 | −3.201 | 37.383 | 1.00 | 16.68 | A |
| ATOM | 510 | N | GLN | A | 747 | 16.379 | −3.294 | 39.347 | 1.00 | 16.31 | A |
| ATOM | 511 | CA | GLN | A | 747 | 16.196 | −1.877 | 39.635 | 1.00 | 16.33 | A |
| ATOM | 512 | CB | GLN | A | 747 | 16.870 | −1.505 | 40.965 | 1.00 | 17.68 | A |
| ATOM | 513 | CG | GLN | A | 747 | 16.402 | −2.330 | 42.158 | 1.00 | 16.41 | A |
| ATOM | 514 | CD | GLN | A | 747 | 17.039 | −1.894 | 43.471 | 1.00 | 19.86 | A |
| ATOM | 515 | OE1 | GLN | A | 747 | 17.270 | −2.714 | 44.361 | 1.00 | 21.96 | A |
| ATOM | 516 | NE2 | GLN | A | 747 | 17.307 | −0.601 | 43.605 | 1.00 | 13.08 | A |
| ATOM | 517 | C | GLN | A | 747 | 16.790 | −1.025 | 38.519 | 1.00 | 16.94 | A |
| ATOM | 518 | O | GLN | A | 747 | 16.158 | −0.083 | 38.032 | 1.00 | 16.26 | A |
| ATOM | 519 | N | ILE | A | 748 | 18.011 | −1.360 | 38.119 | 1.00 | 17.19 | A |
| ATOM | 520 | CA | ILE | A | 748 | 18.694 | −0.621 | 37.067 | 1.00 | 17.75 | A |
| ATOM | 521 | CB | ILE | A | 748 | 20.133 | −1.136 | 36.867 | 1.00 | 18.93 | A |
| ATOM | 522 | CG2 | ILE | A | 748 | 20.736 | −0.537 | 35.591 | 1.00 | 19.15 | A |
| ATOM | 523 | CG1 | ILE | A | 748 | 20.979 | −0.780 | 38.094 | 1.00 | 19.91 | A |
| ATOM | 524 | CD1 | ILE | A | 748 | 22.419 | −1.268 | 38.003 | 1.00 | 26.17 | A |
| ATOM | 525 | C | ILE | A | 748 | 17.951 | −0.726 | 35.745 | 1.00 | 16.60 | A |
| ATOM | 526 | O | ILE | A | 748 | 17.801 | 0.263 | 35.035 | 1.00 | 17.71 | A |
| ATOM | 527 | N | THR | A | 749 | 17.490 | −1.926 | 35.415 | 1.00 | 16.86 | A |
| ATOM | 528 | CA | THR | A | 749 | 16.772 | −2.128 | 34.166 | 1.00 | 17.95 | A |
| ATOM | 529 | CB | THR | A | 749 | 16.441 | −3.618 | 33.942 | 1.00 | 18.55 | A |
| ATOM | 530 | OG1 | THR | A | 749 | 17.657 | −4.358 | 33.776 | 1.00 | 19.19 | A |
| ATOM | 531 | CG2 | THR | A | 749 | 15.589 | −3.794 | 32.695 | 1.00 | 19.51 | A |
| ATOM | 532 | C | THR | A | 749 | 15.479 | −1.317 | 34.114 | 1.00 | 17.38 | A |
| ATOM | 533 | O | THR | A | 749 | 15.178 | −0.690 | 33.099 | 1.00 | 17.28 | A |
| ATOM | 534 | N | LEU | A | 750 | 14.720 | −1.327 | 35.206 | 1.00 | 16.72 | A |
| ATOM | 535 | CA | LEU | A | 750 | 13.455 | −0.591 | 35.259 | 1.00 | 16.64 | A |
| ATOM | 536 | CB | LEU | A | 750 | 12.727 | −0.887 | 36.576 | 1.00 | 15.87 | A |
| ATOM | 537 | CG | LEU | A | 750 | 12.229 | −2.334 | 36.712 | 1.00 | 17.09 | A |
| ATOM | 538 | CD1 | LEU | A | 750 | 11.660 | −2.569 | 38.111 | 1.00 | 13.60 | A |
| ATOM | 539 | CD2 | LEU | A | 750 | 11.166 | −2.604 | 35.642 | 1.00 | 15.56 | A |
| ATOM | 540 | C | LEU | A | 750 | 13.675 | 0.911 | 35.097 | 1.00 | 17.48 | A |
| ATOM | 541 | O | LEU | A | 750 | 12.894 | 1.599 | 34.423 | 1.00 | 16.71 | A |
| ATOM | 542 | N | ILE | A | 751 | 14.737 | 1.427 | 35.706 | 1.00 | 16.32 | A |
| ATOM | 543 | CA | ILE | A | 751 | 15.026 | 2.850 | 35.581 | 1.00 | 17.20 | A |
| ATOM | 544 | CB | ILE | A | 751 | 16.123 | 3.289 | 36.576 | 1.00 | 18.58 | A |
| ATOM | 545 | CG2 | ILE | A | 751 | 16.583 | 4.694 | 36.251 | 1.00 | 17.18 | A |
| ATOM | 546 | CG1 | ILE | A | 751 | 15.581 | 3.223 | 38.010 | 1.00 | 17.86 | A |
| ATOM | 547 | CD1 | ILE | A | 751 | 16.642 | 3.467 | 39.092 | 1.00 | 20.51 | A |
| ATOM | 548 | C | ILE | A | 751 | 15.464 | 3.190 | 34.151 | 1.00 | 17.20 | A |
| ATOM | 549 | O | ILE | A | 751 | 15.093 | 4.234 | 33.613 | 1.00 | 16.21 | A |
| ATOM | 550 | N | GLN | A | 752 | 16.241 | 2.306 | 33.534 | 1.00 | 17.94 | A |
| ATOM | 551 | CA | GLN | A | 752 | 16.714 | 2.543 | 32.169 | 1.00 | 18.41 | A |
| ATOM | 552 | CB | GLN | A | 752 | 17.844 | 1.571 | 31.824 | 1.00 | 19.20 | A |
| ATOM | 553 | CG | GLN | A | 752 | 19.052 | 1.687 | 32.760 | 1.00 | 21.33 | A |
| ATOM | 554 | CD | GLN | A | 752 | 20.237 | 0.850 | 32.311 | 1.00 | 22.26 | A |
| ATOM | 555 | OE1 | GLN | A | 752 | 20.075 | −0.214 | 31.717 | 1.00 | 21.77 | A |
| ATOM | 556 | NE2 | GLN | A | 752 | 21.439 | 1.323 | 32.614 | 1.00 | 22.92 | A |
| ATOM | 557 | C | GLN | A | 752 | 15.600 | 2.435 | 31.128 | 1.00 | 19.31 | A |
| ATOM | 558 | O | GLN | A | 752 | 15.657 | 3.088 | 30.082 | 1.00 | 19.71 | A |
| ATOM | 559 | N | TYR | A | 753 | 14.594 | 1.609 | 31.408 | 1.00 | 16.40 | A |
| ATOM | 560 | CA | TYR | A | 753 | 13.468 | 1.445 | 30.488 | 1.00 | 17.45 | A |
| ATOM | 561 | CB | TYR | A | 753 | 12.649 | 0.189 | 30.812 | 1.00 | 16.91 | A |
| ATOM | 562 | CG | TYR | A | 753 | 13.220 | −1.160 | 30.420 | 1.00 | 18.88 | A |
| ATOM | 563 | CD1 | TYR | A | 753 | 14.312 | −1.280 | 29.560 | 1.00 | 19.37 | A |
| ATOM | 564 | CE1 | TYR | A | 753 | 14.775 | −2.542 | 29.158 | 1.00 | 19.99 | A |
| ATOM | 565 | CD2 | TYR | A | 753 | 12.609 | −2.329 | 30.874 | 1.00 | 20.86 | A |
| ATOM | 566 | CE2 | TYR | A | 753 | 13.058 | −3.579 | 30.483 | 1.00 | 19.71 | A |
| ATOM | 567 | CZ | TYR | A | 753 | 14.134 | −3.685 | 29.628 | 1.00 | 21.49 | A |
| ATOM | 568 | OH | TYR | A | 753 | 14.546 | −4.944 | 29.251 | 1.00 | 22.20 | A |
| ATOM | 569 | C | TYR | A | 753 | 12.480 | 2.606 | 30.583 | 1.00 | 18.38 | A |
| ATOM | 570 | O | TYR | A | 753 | 11.925 | 3.053 | 29.578 | 1.00 | 20.69 | A |
| ATOM | 571 | N | SER | A | 754 | 12.263 | 3.080 | 31.804 | 1.00 | 16.00 | A |
| ATOM | 572 | CA | SER | A | 754 | 11.259 | 4.108 | 32.070 | 1.00 | 17.01 | A |
| ATOM | 573 | CB | SER | A | 754 | 10.514 | 3.731 | 33.349 | 1.00 | 16.69 | A |
| ATOM | 574 | OG | SER | A | 754 | 11.362 | 3.939 | 34.477 | 1.00 | 14.48 | A |
| ATOM | 575 | C | SER | A | 754 | 11.651 | 5.574 | 32.195 | 1.00 | 16.37 | A |
| ATOM | 576 | O | SER | A | 754 | 10.774 | 6.425 | 32.338 | 1.00 | 15.97 | A |
| ATOM | 577 | N | TRP | A | 755 | 12.934 | 5.896 | 32.141 | 1.00 | 16.30 | A |
| ATOM | 578 | CA | TRP | A | 755 | 13.310 | 7.289 | 32.333 | 1.00 | 16.48 | A |
| ATOM | 579 | CB | TRP | A | 755 | 14.828 | 7.468 | 32.235 | 1.00 | 17.08 | A |

TABLE 2-continued

Structure coordinates (Table discloses SEQ ID NO: 6 twice)

|  | # | Name | Res. | Chain | Res # | X | Y | Z | occ | B | SegID |
|---|---|---|---|---|---|---|---|---|---|---|---|
| ATOM | 580 | CG | TRP | A | 755 | 15.389 | 7.268 | 30.884 | 1.00 | 19.06 | A |
| ATOM | 581 | CD2 | TRP | A | 755 | 15.593 | 8.276 | 29.890 | 1.00 | 18.43 | A |
| ATOM | 582 | CE2 | TRP | A | 755 | 16.138 | 7.640 | 28.757 | 1.00 | 18.03 | A |
| ATOM | 583 | CE3 | TRP | A | 755 | 15.364 | 9.657 | 29.848 | 1.00 | 20.60 | A |
| ATOM | 584 | CD1 | TRP | A | 755 | 15.807 | 6.093 | 30.333 | 1.00 | 21.01 | A |
| ATOM | 585 | NE1 | TRP | A | 755 | 16.260 | 6.308 | 29.053 | 1.00 | 21.00 | A |
| ATOM | 586 | CZ2 | TRP | A | 755 | 16.462 | 8.336 | 27.590 | 1.00 | 20.14 | A |
| ATOM | 587 | CZ3 | TRP | A | 755 | 15.686 | 10.351 | 28.687 | 1.00 | 23.49 | A |
| ATOM | 588 | CH2 | TRP | A | 755 | 16.229 | 9.686 | 27.572 | 1.00 | 20.73 | A |
| ATOM | 589 | C | TRP | A | 755 | 12.608 | 8.330 | 31.461 | 1.00 | 16.13 | A |
| ATOM | 590 | O | TRP | A | 755 | 12.208 | 9.372 | 31.970 | 1.00 | 15.92 | A |
| ATOM | 591 | N | MET | A | 756 | 12.450 | 8.073 | 30.165 | 1.00 | 15.54 | A |
| ATOM | 592 | CA | MET | A | 756 | 11.791 | 9.066 | 29.314 | 1.00 | 15.68 | A |
| ATOM | 593 | CB | MET | A | 756 | 11.881 | 8.677 | 27.832 | 1.00 | 15.94 | A |
| ATOM | 594 | CG | MET | A | 756 | 11.294 | 9.720 | 26.872 | 1.00 | 15.93 | A |
| ATOM | 595 | SD | MET | A | 756 | 12.195 | 11.300 | 26.820 | 1.00 | 20.03 | A |
| ATOM | 596 | CE | MET | A | 756 | 13.530 | 10.864 | 25.738 | 1.00 | 18.29 | A |
| ATOM | 597 | C | MET | A | 756 | 10.327 | 9.249 | 29.710 | 1.00 | 15.47 | A |
| ATOM | 598 | O | MET | A | 756 | 9.837 | 10.379 | 29.778 | 1.00 | 15.06 | A |
| ATOM | 599 | N | SER | A | 757 | 9.627 | 8.150 | 29.983 | 1.00 | 16.31 | A |
| ATOM | 600 | CA | SER | A | 757 | 8.226 | 8.258 | 30.371 | 1.00 | 17.31 | A |
| ATOM | 601 | CB | SER | A | 757 | 7.569 | 6.872 | 30.481 | 1.00 | 19.17 | A |
| ATOM | 602 | OG | SER | A | 757 | 8.121 | 6.111 | 31.537 | 1.00 | 23.52 | A |
| ATOM | 603 | C | SER | A | 757 | 8.087 | 9.005 | 31.690 | 1.00 | 16.83 | A |
| ATOM | 604 | O | SER | A | 757 | 7.166 | 9.798 | 31.855 | 1.00 | 16.08 | A |
| ATOM | 605 | N | LEU | A | 758 | 8.998 | 8.765 | 32.632 | 1.00 | 16.85 | A |
| ATOM | 606 | CA | LEU | A | 758 | 8.918 | 9.456 | 33.915 | 1.00 | 15.97 | A |
| ATOM | 607 | CB | LEU | A | 758 | 9.940 | 8.899 | 34.911 | 1.00 | 17.47 | A |
| ATOM | 608 | CG | LEU | A | 758 | 9.748 | 7.461 | 35.401 | 1.00 | 18.97 | A |
| ATOM | 609 | CD1 | LEU | A | 758 | 10.879 | 7.100 | 36.362 | 1.00 | 19.01 | A |
| ATOM | 610 | CD2 | LEU | A | 758 | 8.408 | 7.324 | 36.094 | 1.00 | 18.02 | A |
| ATOM | 611 | C | LEU | A | 758 | 9.156 | 10.950 | 33.730 | 1.00 | 15.21 | A |
| ATOM | 612 | O | LEU | A | 758 | 8.469 | 11.774 | 34.333 | 1.00 | 14.38 | A |
| ATOM | 613 | N | MET | A | 759 | 10.131 | 11.301 | 32.895 | 1.00 | 15.87 | A |
| ATOM | 614 | CA | MET | A | 759 | 10.424 | 12.707 | 32.650 | 1.00 | 15.98 | A |
| ATOM | 615 | CB | MET | A | 759 | 11.675 | 12.855 | 31.784 | 1.00 | 18.16 | A |
| ATOM | 616 | CG | MET | A | 759 | 12.968 | 12.528 | 32.506 | 1.00 | 20.79 | A |
| ATOM | 617 | SD | MET | A | 759 | 14.388 | 12.785 | 31.431 | 1.00 | 26.08 | A |
| ATOM | 618 | CE | MET | A | 759 | 15.672 | 11.980 | 32.416 | 1.00 | 25.95 | A |
| ATOM | 619 | C | MET | A | 759 | 9.266 | 13.441 | 31.981 | 1.00 | 16.81 | A |
| ATOM | 620 | O | MET | A | 759 | 8.900 | 14.542 | 32.392 | 1.00 | 18.56 | A |
| ATOM | 621 | N | VAL | A | 760 | 8.688 | 12.837 | 30.949 | 1.00 | 17.28 | A |
| ATOM | 622 | CA | VAL | A | 760 | 7.590 | 13.483 | 30.241 | 1.00 | 17.08 | A |
| ATOM | 623 | CB | VAL | A | 760 | 7.290 | 12.761 | 28.897 | 1.00 | 18.35 | A |
| ATOM | 624 | CG1 | VAL | A | 760 | 6.511 | 11.486 | 29.137 | 1.00 | 19.74 | A |
| ATOM | 625 | CG2 | VAL | A | 760 | 6.545 | 13.699 | 27.964 | 1.00 | 20.50 | A |
| ATOM | 626 | C | VAL | A | 760 | 6.330 | 13.548 | 31.111 | 1.00 | 18.39 | A |
| ATOM | 627 | O | VAL | A | 760 | 5.547 | 14.499 | 31.017 | 1.00 | 19.10 | A |
| ATOM | 628 | N | PHE | A | 761 | 6.140 | 12.545 | 31.963 | 1.00 | 16.68 | A |
| ATOM | 629 | CA | PHE | A | 761 | 4.986 | 12.523 | 32.857 | 1.00 | 16.45 | A |
| ATOM | 630 | CB | PHE | A | 761 | 4.897 | 11.174 | 33.575 | 1.00 | 16.18 | A |
| ATOM | 631 | CG | PHE | A | 761 | 3.529 | 10.861 | 34.130 | 1.00 | 15.95 | A |
| ATOM | 632 | CD1 | PHE | A | 761 | 2.420 | 10.794 | 33.290 | 1.00 | 13.24 | A |
| ATOM | 633 | CD2 | PHE | A | 761 | 3.359 | 10.588 | 35.485 | 1.00 | 15.65 | A |
| ATOM | 634 | CE1 | PHE | A | 761 | 1.164 | 10.457 | 33.791 | 1.00 | 14.74 | A |
| ATOM | 635 | CE2 | PHE | A | 761 | 2.104 | 10.248 | 35.997 | 1.00 | 16.67 | A |
| ATOM | 636 | CZ | PHE | A | 761 | 1.007 | 10.183 | 35.148 | 1.00 | 16.46 | A |
| ATOM | 637 | C | PHE | A | 761 | 5.155 | 13.651 | 33.876 | 1.00 | 16.84 | A |
| ATOM | 638 | O | PHE | A | 761 | 4.205 | 14.377 | 34.175 | 1.00 | 17.63 | A |
| ATOM | 639 | N | GLY | A | 762 | 6.372 | 13.798 | 34.400 | 1.00 | 15.02 | A |
| ATOM | 640 | CA | GLY | A | 762 | 6.644 | 14.853 | 35.363 | 1.00 | 15.08 | A |
| ATOM | 641 | C | GLY | A | 762 | 6.480 | 16.213 | 34.706 | 1.00 | 15.77 | A |
| ATOM | 642 | O | GLY | A | 762 | 5.978 | 17.158 | 35.316 | 1.00 | 16.20 | A |
| ATOM | 643 | N | LEU | A | 763 | 6.920 | 16.317 | 33.457 | 1.00 | 15.32 | A |
| ATOM | 644 | CA | LEU | A | 763 | 6.796 | 17.559 | 32.706 | 1.00 | 17.12 | A |
| ATOM | 645 | CB | LEU | A | 763 | 7.346 | 17.373 | 31.294 | 1.00 | 17.85 | A |
| ATOM | 646 | CG | LEU | A | 763 | 6.960 | 18.409 | 30.236 | 1.00 | 18.06 | A |
| ATOM | 647 | CD1 | LEU | A | 763 | 7.544 | 19.779 | 30.588 | 1.00 | 17.06 | A |
| ATOM | 648 | CD2 | LEU | A | 763 | 7.473 | 17.931 | 28.878 | 1.00 | 16.76 | A |
| ATOM | 649 | C | LEU | A | 763 | 5.316 | 17.906 | 32.627 | 1.00 | 17.25 | A |
| ATOM | 650 | O | LEU | A | 763 | 4.920 | 19.064 | 32.795 | 1.00 | 16.63 | A |
| ATOM | 651 | N | GLY | A | 764 | 4.511 | 16.883 | 32.365 | 1.00 | 17.94 | A |
| ATOM | 652 | CA | GLY | A | 764 | 3.077 | 17.067 | 32.265 | 1.00 | 19.00 | A |
| ATOM | 653 | C | GLY | A | 764 | 2.510 | 17.652 | 33.540 | 1.00 | 19.54 | A |
| ATOM | 654 | O | GLY | A | 764 | 1.750 | 18.621 | 33.497 | 1.00 | 18.93 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 655 | N | TRP | A | 765 | 2.890 | 17.073 | 34.677 | 1.00 | 19.11 | A |
| ATOM | 656 | CA | TRP | A | 765 | 2.408 | 17.539 | 35.971 | 1.00 | 20.62 | A |
| ATOM | 657 | CB | TRP | A | 765 | 2.930 | 16.632 | 37.092 | 1.00 | 21.33 | A |
| ATOM | 658 | CG | TRP | A | 765 | 2.414 | 17.012 | 38.449 | 1.00 | 23.29 | A |
| ATOM | 659 | CD2 | TRP | A | 765 | 1.078 | 16.833 | 38.937 | 1.00 | 23.57 | A |
| ATOM | 660 | CE2 | TRP | A | 765 | 1.034 | 17.368 | 40.242 | 1.00 | 25.22 | A |
| ATOM | 661 | CE3 | TRP | A | 765 | −0.088 | 16.272 | 38.396 | 1.00 | 25.69 | A |
| ATOM | 662 | CD1 | TRP | A | 765 | 3.107 | 17.630 | 39.449 | 1.00 | 24.56 | A |
| ATOM | 663 | NE1 | TRP | A | 765 | 2.284 | 17.848 | 40.532 | 1.00 | 25.99 | A |
| ATOM | 664 | CZ2 | TRP | A | 765 | −0.132 | 17.362 | 41.016 | 1.00 | 27.48 | A |
| ATOM | 665 | CZ3 | TRP | A | 765 | −1.248 | 16.266 | 39.166 | 1.00 | 24.65 | A |
| ATOM | 666 | CH2 | TRP | A | 765 | −1.259 | 16.808 | 40.460 | 1.00 | 25.43 | A |
| ATOM | 667 | C | TRP | A | 765 | 2.794 | 18.988 | 36.255 | 1.00 | 19.81 | A |
| ATOM | 668 | O | TRP | A | 765 | 1.928 | 19.812 | 36.546 | 1.00 | 19.54 | A |
| ATOM | 669 | N | ARG | A | 766 | 4.087 | 19.299 | 36.174 | 1.00 | 19.47 | A |
| ATOM | 670 | CA | ARG | A | 766 | 4.556 | 20.666 | 36.421 | 1.00 | 19.40 | A |
| ATOM | 671 | CB | ARG | A | 766 | 6.080 | 20.763 | 36.247 | 1.00 | 18.97 | A |
| ATOM | 672 | CG | ARG | A | 766 | 6.882 | 20.041 | 37.320 | 1.00 | 19.48 | A |
| ATOM | 673 | CD | ARG | A | 766 | 8.363 | 20.419 | 37.252 | 1.00 | 17.56 | A |
| ATOM | 674 | NE | ARG | A | 766 | 8.984 | 20.012 | 35.994 | 1.00 | 18.67 | A |
| ATOM | 675 | CZ | ARG | A | 766 | 9.269 | 18.755 | 35.666 | 1.00 | 20.53 | A |
| ATOM | 676 | NH1 | ARG | A | 766 | 8.996 | 17.761 | 36.502 | 1.00 | 19.81 | A |
| ATOM | 677 | NH2 | ARG | A | 766 | 9.822 | 18.488 | 34.492 | 1.00 | 17.68 | A |
| ATOM | 678 | C | ARG | A | 766 | 3.884 | 21.687 | 35.505 | 1.00 | 19.03 | A |
| ATOM | 679 | O | ARG | A | 766 | 3.505 | 22.774 | 35.944 | 1.00 | 19.25 | A |
| ATOM | 680 | N | SER | A | 767 | 3.741 | 21.348 | 34.229 | 1.00 | 18.79 | A |
| ATOM | 681 | CA | SER | A | 767 | 3.108 | 22.265 | 33.281 | 1.00 | 18.18 | A |
| ATOM | 682 | CB | SER | A | 767 | 3.140 | 21.671 | 31.875 | 1.00 | 19.63 | A |
| ATOM | 683 | OG | SER | A | 767 | 4.472 | 21.475 | 31.433 | 1.00 | 20.37 | A |
| ATOM | 684 | C | SER | A | 767 | 1.662 | 22.507 | 33.708 | 1.00 | 20.50 | A |
| ATOM | 685 | O | SER | A | 767 | 1.156 | 23.638 | 33.670 | 1.00 | 17.64 | A |
| ATOM | 686 | N | TYR | A | 768 | 1.008 | 21.427 | 34.123 | 1.00 | 21.00 | A |
| ATOM | 687 | CA | TYR | A | 768 | −0.375 | 21.465 | 34.579 | 1.00 | 22.52 | A |
| ATOM | 688 | CB | TYR | A | 768 | −0.845 | 20.027 | 34.853 | 1.00 | 24.84 | A |
| ATOM | 689 | CG | TYR | A | 768 | −2.213 | 19.874 | 35.490 | 1.00 | 26.80 | A |
| ATOM | 690 | CD1 | TYR | A | 768 | −3.330 | 20.524 | 34.968 | 1.00 | 27.94 | A |
| ATOM | 691 | CE1 | TYR | A | 768 | −4.601 | 20.319 | 35.505 | 1.00 | 28.43 | A |
| ATOM | 692 | CD2 | TYR | A | 768 | −2.401 | 19.012 | 36.577 | 1.00 | 28.57 | A |
| ATOM | 693 | CE2 | TYR | A | 768 | −3.672 | 18.799 | 37.119 | 1.00 | 29.44 | A |
| ATOM | 694 | CZ | TYR | A | 768 | −4.765 | 19.455 | 36.575 | 1.00 | 30.55 | A |
| ATOM | 695 | OH | TYR | A | 768 | −6.024 | 19.238 | 37.092 | 1.00 | 32.27 | A |
| ATOM | 696 | C | TYR | A | 768 | −0.545 | 22.328 | 35.834 | 1.00 | 23.30 | A |
| ATOM | 697 | O | TYR | A | 768 | −1.411 | 23.202 | 35.884 | 1.00 | 23.03 | A |
| ATOM | 698 | N | LYS | A | 769 | 0.296 | 22.100 | 36.836 | 1.00 | 24.38 | A |
| ATOM | 699 | CA | LYS | A | 769 | 0.195 | 22.834 | 38.097 | 1.00 | 25.93 | A |
| ATOM | 700 | CB | LYS | A | 769 | 0.828 | 22.013 | 39.228 | 1.00 | 29.02 | A |
| ATOM | 701 | CG | LYS | A | 769 | 0.293 | 20.591 | 39.364 | 1.00 | 33.47 | A |
| ATOM | 702 | CD | LYS | A | 769 | −1.225 | 20.546 | 39.541 | 1.00 | 36.41 | A |
| ATOM | 703 | CE | LYS | A | 769 | −1.671 | 21.179 | 40.850 | 1.00 | 37.62 | A |
| ATOM | 704 | NZ | LYS | A | 769 | −3.160 | 21.214 | 40.952 | 1.00 | 38.42 | A |
| ATOM | 705 | C | LYS | A | 769 | 0.759 | 24.255 | 38.155 | 1.00 | 25.94 | A |
| ATOM | 706 | O | LYS | A | 769 | 0.248 | 25.085 | 38.908 | 1.00 | 25.87 | A |
| ATOM | 707 | N | HIS | A | 770 | 1.799 | 24.549 | 37.380 | 1.00 | 25.10 | A |
| ATOM | 708 | CA | HIS | A | 770 | 2.405 | 25.881 | 37.425 | 1.00 | 25.51 | A |
| ATOM | 709 | CB | HIS | A | 770 | 3.928 | 25.770 | 37.294 | 1.00 | 28.44 | A |
| ATOM | 710 | CG | HIS | A | 770 | 4.572 | 24.979 | 38.389 | 1.00 | 32.15 | A |
| ATOM | 711 | CD2 | HIS | A | 770 | 5.154 | 23.755 | 38.383 | 1.00 | 33.76 | A |
| ATOM | 712 | ND1 | HIS | A | 770 | 4.641 | 25.427 | 39.691 | 1.00 | 36.27 | A |
| ATOM | 713 | CE1 | HIS | A | 770 | 5.236 | 24.515 | 40.439 | 1.00 | 35.37 | A |
| ATOM | 714 | NE2 | HIS | A | 770 | 5.557 | 23.490 | 39.670 | 1.00 | 34.58 | A |
| ATOM | 715 | C | HIS | A | 770 | 1.893 | 26.879 | 36.390 | 1.00 | 25.25 | A |
| ATOM | 716 | O | HIS | A | 770 | 1.779 | 28.073 | 36.679 | 1.00 | 25.06 | A |
| ATOM | 717 | N | VAL | A | 771 | 1.601 | 26.404 | 35.185 | 1.00 | 22.32 | A |
| ATOM | 718 | CA | VAL | A | 771 | 1.132 | 27.300 | 34.134 | 1.00 | 22.97 | A |
| ATOM | 719 | CB | VAL | A | 771 | 2.213 | 27.486 | 33.043 | 1.00 | 23.19 | A |
| ATOM | 720 | CG1 | VAL | A | 771 | 3.326 | 28.385 | 33.575 | 1.00 | 23.98 | A |
| ATOM | 721 | CG2 | VAL | A | 771 | 2.786 | 26.134 | 32.630 | 1.00 | 23.30 | A |
| ATOM | 722 | C | VAL | A | 771 | −0.179 | 26.869 | 33.491 | 1.00 | 21.91 | A |
| ATOM | 723 | O | VAL | A | 771 | −0.411 | 27.101 | 32.305 | 1.00 | 23.10 | A |
| ATOM | 724 | N | SER | A | 772 | −1.036 | 26.247 | 34.291 | 1.00 | 20.67 | A |
| ATOM | 725 | CA | SER | A | 772 | −2.340 | 25.796 | 33.825 | 1.00 | 22.11 | A |
| ATOM | 726 | CB | SER | A | 772 | −3.226 | 27.012 | 33.532 | 1.00 | 23.44 | A |
| ATOM | 727 | OG | SER | A | 772 | −3.245 | 27.902 | 34.643 | 1.00 | 22.81 | A |
| ATOM | 728 | C | SER | A | 772 | −2.222 | 24.923 | 32.583 | 1.00 | 21.42 | A |
| ATOM | 729 | O | SER | A | 772 | −3.157 | 24.830 | 31.781 | 1.00 | 21.19 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 730 | N | GLY | A | 773 | −1.060 | 24.292 | 32.426 | 1.00 | 21.10 | A |
| ATOM | 731 | CA | GLY | A | 773 | −0.820 | 23.415 | 31.292 | 1.00 | 19.40 | A |
| ATOM | 732 | C | GLY | A | 773 | −0.654 | 24.099 | 29.944 | 1.00 | 20.22 | A |
| ATOM | 733 | O | GLY | A | 773 | −0.603 | 23.426 | 28.911 | 1.00 | 21.05 | A |
| ATOM | 734 | N | GLN | A | 774 | −0.541 | 25.423 | 29.935 | 1.00 | 19.35 | A |
| ATOM | 735 | CA | GLN | A | 774 | −0.422 | 26.144 | 28.669 | 1.00 | 19.19 | A |
| ATOM | 736 | CB | GLN | A | 774 | −1.335 | 27.372 | 28.703 | 1.00 | 19.43 | A |
| ATOM | 737 | CG | GLN | A | 774 | −2.793 | 26.987 | 28.931 | 1.00 | 19.08 | A |
| ATOM | 738 | CD | GLN | A | 774 | −3.187 | 25.750 | 28.136 | 1.00 | 18.95 | A |
| ATOM | 739 | OE1 | GLN | A | 774 | −3.122 | 25.739 | 26.904 | 1.00 | 18.16 | A |
| ATOM | 740 | NE2 | GLN | A | 774 | −3.590 | 24.697 | 28.842 | 1.00 | 18.81 | A |
| ATOM | 741 | C | GLN | A | 774 | 0.992 | 26.527 | 28.224 | 1.00 | 18.56 | A |
| ATOM | 742 | O | GLN | A | 774 | 1.178 | 27.356 | 27.337 | 1.00 | 18.81 | A |
| ATOM | 743 | N | MET | A | 775 | 1.981 | 25.911 | 28.855 | 1.00 | 19.20 | A |
| ATOM | 744 | CA | MET | A | 775 | 3.385 | 26.105 | 28.520 | 1.00 | 19.64 | A |
| ATOM | 745 | CB | MET | A | 775 | 4.009 | 27.253 | 29.323 | 1.00 | 20.86 | A |
| ATOM | 746 | CG | MET | A | 775 | 3.522 | 28.652 | 28.959 | 1.00 | 21.16 | A |
| ATOM | 747 | SD | MET | A | 775 | 4.507 | 29.907 | 29.799 | 1.00 | 25.84 | A |
| ATOM | 748 | CE | MET | A | 775 | 3.216 | 30.919 | 30.610 | 1.00 | 25.72 | A |
| ATOM | 749 | C | MET | A | 775 | 4.061 | 24.803 | 28.921 | 1.00 | 18.35 | A |
| ATOM | 750 | O | MET | A | 775 | 3.516 | 24.050 | 29.727 | 1.00 | 20.32 | A |
| ATOM | 751 | N | LEU | A | 776 | 5.224 | 24.521 | 28.349 | 1.00 | 17.82 | A |
| ATOM | 752 | CA | LEU | A | 776 | 5.955 | 23.317 | 28.721 | 1.00 | 18.54 | A |
| ATOM | 753 | CB | LEU | A | 776 | 6.723 | 22.741 | 27.526 | 1.00 | 18.50 | A |
| ATOM | 754 | CG | LEU | A | 776 | 5.844 | 22.027 | 26.490 | 1.00 | 19.83 | A |
| ATOM | 755 | CD1 | LEU | A | 776 | 6.711 | 21.491 | 25.367 | 1.00 | 19.70 | A |
| ATOM | 756 | CD2 | LEU | A | 776 | 5.068 | 20.890 | 27.149 | 1.00 | 18.31 | A |
| ATOM | 757 | C | LEU | A | 776 | 6.912 | 23.762 | 29.813 | 1.00 | 18.66 | A |
| ATOM | 758 | O | LEU | A | 776 | 7.886 | 24.471 | 29.551 | 1.00 | 19.30 | A |
| ATOM | 759 | N | TYR | A | 777 | 6.611 | 23.354 | 31.040 | 1.00 | 16.71 | A |
| ATOM | 760 | CA | TYR | A | 777 | 7.401 | 23.719 | 32.203 | 1.00 | 17.38 | A |
| ATOM | 761 | CB | TYR | A | 777 | 6.459 | 23.907 | 33.405 | 1.00 | 18.98 | A |
| ATOM | 762 | CG | TYR | A | 777 | 7.056 | 24.636 | 34.591 | 1.00 | 22.23 | A |
| ATOM | 763 | CD1 | TYR | A | 777 | 7.970 | 24.008 | 35.439 | 1.00 | 23.96 | A |
| ATOM | 764 | CE1 | TYR | A | 777 | 8.500 | 24.670 | 36.550 | 1.00 | 25.16 | A |
| ATOM | 765 | CD2 | TYR | A | 777 | 6.689 | 25.954 | 34.878 | 1.00 | 22.47 | A |
| ATOM | 766 | CE2 | TYR | A | 777 | 7.216 | 26.626 | 35.984 | 1.00 | 24.25 | A |
| ATOM | 767 | CZ | TYR | A | 777 | 8.118 | 25.978 | 36.816 | 1.00 | 25.97 | A |
| ATOM | 768 | OH | TYR | A | 777 | 8.632 | 26.629 | 37.918 | 1.00 | 25.81 | A |
| ATOM | 769 | C | TYR | A | 777 | 8.440 | 22.641 | 32.500 | 1.00 | 16.79 | A |
| ATOM | 770 | O | TYR | A | 777 | 8.290 | 21.867 | 33.443 | 1.00 | 16.14 | A |
| ATOM | 771 | N | PHE | A | 778 | 9.479 | 22.575 | 31.675 | 1.00 | 17.41 | A |
| ATOM | 772 | CA | PHE | A | 778 | 10.533 | 21.590 | 31.890 | 1.00 | 18.04 | A |
| ATOM | 773 | CB | PHE | A | 778 | 11.592 | 21.668 | 30.780 | 1.00 | 17.18 | A |
| ATOM | 774 | CG | PHE | A | 778 | 11.076 | 21.299 | 29.414 | 1.00 | 19.92 | A |
| ATOM | 775 | CD1 | PHE | A | 778 | 10.664 | 22.284 | 28.520 | 1.00 | 19.96 | A |
| ATOM | 776 | CD2 | PHE | A | 778 | 11.017 | 19.967 | 29.016 | 1.00 | 18.19 | A |
| ATOM | 777 | CE1 | PHE | A | 778 | 10.206 | 21.946 | 27.244 | 1.00 | 20.84 | A |
| ATOM | 778 | CE2 | PHE | A | 778 | 10.561 | 19.620 | 27.745 | 1.00 | 20.50 | A |
| ATOM | 779 | CZ | PHE | A | 778 | 10.155 | 20.611 | 26.855 | 1.00 | 19.47 | A |
| ATOM | 780 | C | PHE | A | 778 | 11.178 | 21.873 | 33.245 | 1.00 | 17.23 | A |
| ATOM | 781 | O | PHE | A | 778 | 11.393 | 20.961 | 34.049 | 1.00 | 15.16 | A |
| ATOM | 782 | N | ALA | A | 779 | 11.479 | 23.149 | 33.486 | 1.00 | 17.50 | A |
| ATOM | 783 | CA | ALA | A | 779 | 12.091 | 23.588 | 34.738 | 1.00 | 18.81 | A |
| ATOM | 784 | CB | ALA | A | 779 | 13.599 | 23.329 | 34.708 | 1.00 | 16.57 | A |
| ATOM | 785 | C | ALA | A | 779 | 11.816 | 25.083 | 34.940 | 1.00 | 20.23 | A |
| ATOM | 786 | O | ALA | A | 779 | 11.372 | 25.771 | 34.021 | 1.00 | 18.79 | A |
| ATOM | 787 | N | PRO | A | 780 | 12.068 | 25.603 | 36.151 | 1.00 | 22.34 | A |
| ATOM | 788 | CD | PRO | A | 780 | 12.432 | 24.933 | 37.411 | 1.00 | 22.01 | A |
| ATOM | 789 | CA | PRO | A | 780 | 11.815 | 27.031 | 36.373 | 1.00 | 23.57 | A |
| ATOM | 790 | CB | PRO | A | 780 | 12.236 | 27.232 | 37.825 | 1.00 | 25.03 | A |
| ATOM | 791 | CG | PRO | A | 780 | 11.911 | 25.906 | 38.448 | 1.00 | 23.19 | A |
| ATOM | 792 | C | PRO | A | 780 | 12.610 | 27.911 | 35.406 | 1.00 | 23.67 | A |
| ATOM | 793 | O | PRO | A | 780 | 12.154 | 28.982 | 35.018 | 1.00 | 22.71 | A |
| ATOM | 794 | N | ASP | A | 781 | 13.795 | 27.442 | 35.017 | 1.00 | 23.34 | A |
| ATOM | 795 | CA | ASP | A | 781 | 14.657 | 28.182 | 34.098 | 1.00 | 21.94 | A |
| ATOM | 796 | CB | ASP | A | 781 | 16.107 | 28.136 | 34.594 | 1.00 | 21.93 | A |
| ATOM | 797 | CG | ASP | A | 781 | 16.646 | 26.718 | 34.718 | 1.00 | 23.63 | A |
| ATOM | 798 | OD1 | ASP | A | 781 | 15.843 | 25.769 | 34.856 | 1.00 | 22.19 | A |
| ATOM | 799 | OD2 | ASP | A | 781 | 17.883 | 26.554 | 34.693 | 1.00 | 24.73 | A |
| ATOM | 800 | C | ASP | A | 781 | 14.569 | 27.676 | 32.653 | 1.00 | 21.19 | A |
| ATOM | 801 | O | ASP | A | 781 | 15.390 | 28.032 | 31.806 | 1.00 | 20.19 | A |
| ATOM | 802 | N | LEU | A | 782 | 13.572 | 26.847 | 32.369 | 1.00 | 19.89 | A |
| ATOM | 803 | CA | LEU | A | 782 | 13.385 | 26.343 | 31.013 | 1.00 | 20.33 | A |
| ATOM | 804 | CB | LEU | A | 782 | 14.151 | 25.028 | 30.802 | 1.00 | 18.43 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 805 | CG | LEU | A | 782 | 14.176 | 24.494 | 29.361 | 1.00 | 19.40 | A |
| ATOM | 806 | CD1 | LEU | A | 782 | 14.784 | 25.536 | 28.434 | 1.00 | 20.75 | A |
| ATOM | 807 | CD2 | LEU | A | 782 | 14.981 | 23.203 | 29.300 | 1.00 | 19.07 | A |
| ATOM | 808 | C | LEU | A | 782 | 11.895 | 26.139 | 30.768 | 1.00 | 19.43 | A |
| ATOM | 809 | O | LEU | A | 782 | 11.377 | 25.027 | 30.848 | 1.00 | 18.09 | A |
| ATOM | 810 | N | ILE | A | 783 | 11.211 | 27.240 | 30.486 | 1.00 | 19.42 | A |
| ATOM | 811 | CA | ILE | A | 783 | 9.779 | 27.208 | 30.233 | 1.00 | 20.01 | A |
| ATOM | 812 | CB | ILE | A | 783 | 9.036 | 28.186 | 31.172 | 1.00 | 20.25 | A |
| ATOM | 813 | CG2 | ILE | A | 783 | 7.536 | 28.162 | 30.877 | 1.00 | 23.95 | A |
| ATOM | 814 | CG1 | ILE | A | 783 | 9.298 | 27.803 | 32.632 | 1.00 | 20.97 | A |
| ATOM | 815 | CD1 | ILE | A | 783 | 8.914 | 28.885 | 33.646 | 1.00 | 21.41 | A |
| ATOM | 816 | C | ILE | A | 783 | 9.531 | 27.614 | 28.786 | 1.00 | 19.86 | A |
| ATOM | 817 | O | ILE | A | 783 | 9.954 | 28.686 | 28.352 | 1.00 | 18.73 | A |
| ATOM | 818 | N | LEU | A | 784 | 8.861 | 26.752 | 28.032 | 1.00 | 18.35 | A |
| ATOM | 819 | CA | LEU | A | 784 | 8.577 | 27.073 | 26.642 | 1.00 | 18.52 | A |
| ATOM | 820 | CB | LEU | A | 784 | 9.040 | 25.946 | 25.709 | 1.00 | 18.59 | A |
| ATOM | 821 | CG | LEU | A | 784 | 10.420 | 25.291 | 25.813 | 1.00 | 20.62 | A |
| ATOM | 822 | CD1 | LEU | A | 784 | 10.716 | 24.600 | 24.479 | 1.00 | 19.63 | A |
| ATOM | 823 | CD2 | LEU | A | 784 | 11.496 | 26.306 | 26.120 | 1.00 | 21.85 | A |
| ATOM | 824 | C | LEU | A | 784 | 7.090 | 27.303 | 26.389 | 1.00 | 18.16 | A |
| ATOM | 825 | O | LEU | A | 784 | 6.290 | 26.373 | 26.513 | 1.00 | 17.61 | A |
| ATOM | 826 | N | ASN | A | 785 | 6.714 | 28.536 | 26.058 | 1.00 | 18.24 | A |
| ATOM | 827 | CA | ASN | A | 785 | 5.323 | 28.809 | 25.708 | 1.00 | 18.38 | A |
| ATOM | 828 | CB | ASN | A | 785 | 4.970 | 30.302 | 25.866 | 1.00 | 19.86 | A |
| ATOM | 829 | CG | ASN | A | 785 | 5.922 | 31.220 | 25.127 | 1.00 | 21.17 | A |
| ATOM | 830 | OD1 | ASN | A | 785 | 6.473 | 30.861 | 24.091 | 1.00 | 22.33 | A |
| ATOM | 831 | ND2 | ASN | A | 785 | 6.104 | 32.428 | 25.654 | 1.00 | 21.27 | A |
| ATOM | 832 | C | ASN | A | 785 | 5.257 | 28.377 | 24.242 | 1.00 | 18.94 | A |
| ATOM | 833 | O | ASN | A | 785 | 6.286 | 28.051 | 23.655 | 1.00 | 19.11 | A |
| ATOM | 834 | N | GLU | A | 786 | 4.077 | 28.376 | 23.637 | 1.00 | 20.82 | A |
| ATOM | 835 | CA | GLU | A | 786 | 3.974 | 27.919 | 22.256 | 1.00 | 20.94 | A |
| ATOM | 836 | CB | GLU | A | 786 | 2.513 | 27.923 | 21.792 | 1.00 | 23.70 | A |
| ATOM | 837 | CG | GLU | A | 786 | 2.345 | 27.424 | 20.366 | 1.00 | 24.17 | A |
| ATOM | 838 | CD | GLU | A | 786 | 0.935 | 26.968 | 20.058 | 1.00 | 26.71 | A |
| ATOM | 839 | OE1 | GLU | A | 786 | −0.012 | 27.549 | 20.630 | 1.00 | 20.59 | A |
| ATOM | 840 | OE2 | GLU | A | 786 | 0.781 | 26.037 | 19.235 | 1.00 | 23.53 | A |
| ATOM | 841 | C | GLU | A | 786 | 4.839 | 28.649 | 21.239 | 1.00 | 22.11 | A |
| ATOM | 842 | O | GLU | A | 786 | 5.375 | 28.023 | 20.330 | 1.00 | 21.62 | A |
| ATOM | 843 | N | GLN | A | 787 | 4.978 | 29.963 | 21.370 | 1.00 | 22.98 | A |
| ATOM | 844 | CA | GLN | A | 787 | 5.799 | 30.702 | 20.417 | 1.00 | 24.73 | A |
| ATOM | 845 | CB | GLN | A | 787 | 5.738 | 32.207 | 20.698 | 1.00 | 26.16 | A |
| ATOM | 846 | CG | GLN | A | 787 | 6.457 | 33.064 | 19.652 | 1.00 | 29.65 | A |
| ATOM | 847 | CD | GLN | A | 787 | 5.977 | 32.785 | 18.233 | 1.00 | 34.00 | A |
| ATOM | 848 | OE1 | GLN | A | 787 | 4.771 | 32.732 | 17.967 | 1.00 | 35.14 | A |
| ATOM | 849 | NE2 | GLN | A | 787 | 6.920 | 32.613 | 17.313 | 1.00 | 35.97 | A |
| ATOM | 850 | C | GLN | A | 787 | 7.251 | 30.218 | 20.487 | 1.00 | 25.27 | A |
| ATOM | 851 | O | GLN | A | 787 | 7.916 | 30.078 | 19.457 | 1.00 | 23.55 | A |
| ATOM | 852 | N | ARG | A | 788 | 7.740 | 29.957 | 21.696 | 1.00 | 24.46 | A |
| ATOM | 853 | CA | ARG | A | 788 | 9.113 | 29.488 | 21.856 | 1.00 | 23.62 | A |
| ATOM | 854 | CB | ARG | A | 788 | 9.512 | 29.486 | 23.332 | 1.00 | 23.38 | A |
| ATOM | 855 | CG | ARG | A | 788 | 11.013 | 29.406 | 23.555 | 1.00 | 22.19 | A |
| ATOM | 856 | CD | ARG | A | 788 | 11.371 | 29.462 | 25.035 | 1.00 | 22.56 | A |
| ATOM | 857 | NE | ARG | A | 788 | 12.817 | 29.466 | 25.241 | 1.00 | 21.14 | A |
| ATOM | 858 | CZ | ARG | A | 788 | 13.410 | 29.478 | 26.433 | 1.00 | 25.92 | A |
| ATOM | 859 | NH1 | ARG | A | 788 | 14.737 | 29.481 | 26.514 | 1.00 | 26.50 | A |
| ATOM | 860 | NH2 | ARG | A | 788 | 12.682 | 29.482 | 27.546 | 1.00 | 26.08 | A |
| ATOM | 861 | C | ARG | A | 788 | 9.224 | 28.081 | 21.270 | 1.00 | 23.70 | A |
| ATOM | 862 | O | ARG | A | 788 | 10.282 | 27.683 | 20.769 | 1.00 | 23.15 | A |
| ATOM | 863 | N | MET | A | 789 | 8.122 | 27.335 | 21.331 | 1.00 | 23.02 | A |
| ATOM | 864 | CA | MET | A | 789 | 8.072 | 25.987 | 20.776 | 1.00 | 23.37 | A |
| ATOM | 865 | CB | MET | A | 789 | 6.746 | 25.298 | 21.124 | 1.00 | 23.06 | A |
| ATOM | 866 | CG | MET | A | 789 | 6.543 | 24.933 | 22.592 | 1.00 | 21.04 | A |
| ATOM | 867 | SD | MET | A | 789 | 4.957 | 24.068 | 22.811 | 1.00 | 21.30 | A |
| ATOM | 868 | CE | MET | A | 789 | 4.293 | 24.917 | 24.247 | 1.00 | 21.48 | A |
| ATOM | 869 | C | MET | A | 789 | 8.185 | 26.074 | 19.255 | 1.00 | 25.50 | A |
| ATOM | 870 | O | MET | A | 789 | 8.940 | 25.325 | 18.636 | 1.00 | 25.04 | A |
| ATOM | 871 | N | LYS | A | 790 | 7.423 | 26.992 | 18.664 | 1.00 | 27.11 | A |
| ATOM | 872 | CA | LYS | A | 790 | 7.408 | 27.190 | 17.214 | 1.00 | 29.59 | A |
| ATOM | 873 | CB | LYS | A | 790 | 6.447 | 28.322 | 16.833 | 1.00 | 32.00 | A |
| ATOM | 874 | CG | LYS | A | 790 | 4.976 | 27.980 | 16.967 | 1.00 | 37.02 | A |
| ATOM | 875 | CD | LYS | A | 790 | 4.103 | 29.124 | 16.456 | 1.00 | 38.59 | A |
| ATOM | 876 | CE | LYS | A | 790 | 2.628 | 28.840 | 16.698 | 1.00 | 41.04 | A |
| ATOM | 877 | NZ | LYS | A | 790 | 1.753 | 29.958 | 16.236 | 1.00 | 42.99 | A |
| ATOM | 878 | C | LYS | A | 790 | 8.770 | 27.498 | 16.609 | 1.00 | 30.18 | A |
| ATOM | 879 | O | LYS | A | 790 | 9.068 | 27.073 | 15.493 | 1.00 | 28.32 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 880 | N | GLU | A | 791 | 9.591 | 28.251 | 17.330 | 1.00 | 30.15 | A |
| ATOM | 881 | CA | GLU | A | 791 | 10.908 | 28.597 | 16.813 | 1.00 | 33.53 | A |
| ATOM | 882 | CB | GLU | A | 791 | 11.149 | 30.101 | 16.988 | 1.00 | 34.94 | A |
| ATOM | 883 | CG | GLU | A | 791 | 10.733 | 30.663 | 18.334 | 1.00 | 37.89 | A |
| ATOM | 884 | CD | GLU | A | 791 | 10.597 | 32.179 | 18.320 | 1.00 | 38.69 | A |
| ATOM | 885 | OE1 | GLU | A | 791 | 9.722 | 32.700 | 17.596 | 1.00 | 40.52 | A |
| ATOM | 886 | OE2 | GLU | A | 791 | 11.366 | 32.851 | 19.035 | 1.00 | 39.54 | A |
| ATOM | 887 | C | GLU | A | 791 | 12.048 | 27.790 | 17.435 | 1.00 | 33.31 | A |
| ATOM | 888 | O | GLU | A | 791 | 13.198 | 28.230 | 17.440 | 1.00 | 34.67 | A |
| ATOM | 889 | N | SER | A | 792 | 11.726 | 26.595 | 17.926 | 1.00 | 32.17 | A |
| ATOM | 890 | CA | SER | A | 792 | 12.710 | 25.722 | 18.572 | 1.00 | 32.29 | A |
| ATOM | 891 | CB | SER | A | 792 | 12.011 | 24.823 | 19.595 | 1.00 | 31.21 | A |
| ATOM | 892 | OG | SER | A | 792 | 11.197 | 23.862 | 18.942 | 1.00 | 25.26 | A |
| ATOM | 893 | C | SER | A | 792 | 13.514 | 24.827 | 17.624 | 1.00 | 33.43 | A |
| ATOM | 894 | O | SER | A | 792 | 14.676 | 24.512 | 17.902 | 1.00 | 34.87 | A |
| ATOM | 895 | N | SER | A | 793 | 12.871 | 24.417 | 16.531 | 1.00 | 32.81 | A |
| ATOM | 896 | CA | SER | A | 793 | 13.421 | 23.528 | 15.495 | 1.00 | 31.80 | A |
| ATOM | 897 | CB | SER | A | 793 | 14.955 | 23.396 | 15.571 | 1.00 | 34.40 | A |
| ATOM | 898 | OG | SER | A | 793 | 15.367 | 22.397 | 16.494 | 1.00 | 32.53 | A |
| ATOM | 899 | C | SER | A | 793 | 12.774 | 22.151 | 15.648 | 1.00 | 30.98 | A |
| ATOM | 900 | O | SER | A | 793 | 12.882 | 21.299 | 14.764 | 1.00 | 32.51 | A |
| ATOM | 901 | N | PHE | A | 794 | 12.101 | 21.933 | 16.775 | 1.00 | 27.80 | A |
| ATOM | 902 | CA | PHE | A | 794 | 11.408 | 20.669 | 17.012 | 1.00 | 26.68 | A |
| ATOM | 903 | CB | PHE | A | 794 | 12.221 | 19.764 | 17.954 | 1.00 | 24.25 | A |
| ATOM | 904 | CG | PHE | A | 794 | 12.685 | 20.437 | 19.221 | 1.00 | 21.22 | A |
| ATOM | 905 | CD1 | PHE | A | 794 | 11.961 | 20.308 | 20.400 | 1.00 | 23.19 | A |
| ATOM | 906 | CD2 | PHE | A | 794 | 13.870 | 21.166 | 19.241 | 1.00 | 21.45 | A |
| ATOM | 907 | CE1 | PHE | A | 794 | 12.412 | 20.893 | 21.586 | 1.00 | 24.05 | A |
| ATOM | 908 | CE2 | PHE | A | 794 | 14.333 | 21.756 | 20.420 | 1.00 | 20.76 | A |
| ATOM | 909 | CZ | PHE | A | 794 | 13.606 | 21.619 | 21.593 | 1.00 | 23.61 | A |
| ATOM | 910 | C | PHE | A | 794 | 9.996 | 20.928 | 17.552 | 1.00 | 26.57 | A |
| ATOM | 911 | O | PHE | A | 794 | 9.566 | 20.356 | 18.555 | 1.00 | 26.01 | A |
| ATOM | 912 | N | TYR | A | 795 | 9.285 | 21.803 | 16.847 | 1.00 | 25.69 | A |
| ATOM | 913 | CA | TYR | A | 795 | 7.920 | 22.192 | 17.191 | 1.00 | 24.51 | A |
| ATOM | 914 | CB | TYR | A | 795 | 7.382 | 23.150 | 16.120 | 1.00 | 24.31 | A |
| ATOM | 915 | CG | TYR | A | 795 | 5.983 | 23.675 | 16.365 | 1.00 | 27.22 | A |
| ATOM | 916 | CD1 | TYR | A | 795 | 5.605 | 24.166 | 17.619 | 1.00 | 27.70 | A |
| ATOM | 917 | CE1 | TYR | A | 795 | 4.331 | 24.688 | 17.834 | 1.00 | 27.85 | A |
| ATOM | 918 | CD2 | TYR | A | 795 | 5.048 | 23.718 | 15.330 | 1.00 | 27.80 | A |
| ATOM | 919 | CE2 | TYR | A | 795 | 3.771 | 24.239 | 15.534 | 1.00 | 29.91 | A |
| ATOM | 920 | CZ | TYR | A | 795 | 3.419 | 24.723 | 16.788 | 1.00 | 30.25 | A |
| ATOM | 921 | OH | TYR | A | 795 | 2.159 | 25.242 | 16.988 | 1.00 | 30.87 | A |
| ATOM | 922 | C | TYR | A | 795 | 6.991 | 20.993 | 17.336 | 1.00 | 23.82 | A |
| ATOM | 923 | O | TYR | A | 795 | 6.283 | 20.872 | 18.335 | 1.00 | 21.37 | A |
| ATOM | 924 | N | SER | A | 796 | 7.001 | 20.100 | 16.349 | 1.00 | 23.12 | A |
| ATOM | 925 | CA | SER | A | 796 | 6.132 | 18.928 | 16.385 | 1.00 | 23.80 | A |
| ATOM | 926 | CB | SER | A | 796 | 6.296 | 18.106 | 15.104 | 1.00 | 27.03 | A |
| ATOM | 927 | OG | SER | A | 796 | 7.659 | 17.796 | 14.869 | 1.00 | 30.34 | A |
| ATOM | 928 | C | SER | A | 796 | 6.372 | 18.043 | 17.605 | 1.00 | 24.28 | A |
| ATOM | 929 | O | SER | A | 796 | 5.430 | 17.470 | 18.163 | 1.00 | 23.18 | A |
| ATOM | 930 | N | LEU | A | 797 | 7.631 | 17.927 | 18.014 | 1.00 | 22.88 | A |
| ATOM | 931 | CA | LEU | A | 797 | 7.973 | 17.124 | 19.176 | 1.00 | 22.93 | A |
| ATOM | 932 | CB | LEU | A | 797 | 9.492 | 17.019 | 19.327 | 1.00 | 26.10 | A |
| ATOM | 933 | CG | LEU | A | 797 | 9.992 | 15.840 | 20.163 | 1.00 | 27.87 | A |
| ATOM | 934 | CD1 | LEU | A | 797 | 9.676 | 14.545 | 19.430 | 1.00 | 28.16 | A |
| ATOM | 935 | CD2 | LEU | A | 797 | 11.491 | 15.966 | 20.392 | 1.00 | 27.90 | A |
| ATOM | 936 | C | LEU | A | 797 | 7.386 | 17.809 | 20.407 | 1.00 | 20.98 | A |
| ATOM | 937 | O | LEU | A | 797 | 6.837 | 17.151 | 21.287 | 1.00 | 20.95 | A |
| ATOM | 938 | N | CYS | A | 798 | 7.513 | 19.133 | 20.461 | 1.00 | 20.57 | A |
| ATOM | 939 | CA | CYS | A | 798 | 6.973 | 19.903 | 21.579 | 1.00 | 20.61 | A |
| ATOM | 940 | CB | CYS | A | 798 | 7.265 | 21.399 | 21.404 | 1.00 | 20.74 | A |
| ATOM | 941 | SG | CYS | A | 798 | 8.989 | 21.866 | 21.726 | 1.00 | 21.60 | A |
| ATOM | 942 | C | CYS | A | 798 | 5.469 | 19.690 | 21.678 | 1.00 | 20.72 | A |
| ATOM | 943 | O | CYS | A | 798 | 4.926 | 19.504 | 22.773 | 1.00 | 19.17 | A |
| ATOM | 944 | N | LEU | A | 799 | 4.793 | 19.722 | 20.533 | 1.00 | 19.90 | A |
| ATOM | 945 | CA | LEU | A | 799 | 3.349 | 19.526 | 20.518 | 1.00 | 21.06 | A |
| ATOM | 946 | CB | LEU | A | 799 | 2.798 | 19.688 | 19.099 | 1.00 | 21.78 | A |
| ATOM | 947 | CG | LEU | A | 799 | 2.933 | 21.096 | 18.505 | 1.00 | 21.95 | A |
| ATOM | 948 | CD1 | LEU | A | 799 | 2.376 | 21.100 | 17.093 | 1.00 | 24.69 | A |
| ATOM | 949 | CD2 | LEU | A | 799 | 2.194 | 22.114 | 19.377 | 1.00 | 21.59 | A |
| ATOM | 950 | C | LEU | A | 799 | 3.007 | 18.146 | 21.060 | 1.00 | 22.12 | A |
| ATOM | 951 | O | LEU | A | 799 | 2.035 | 17.984 | 21.797 | 1.00 | 23.00 | A |
| ATOM | 952 | N | THR | A | 800 | 3.813 | 17.153 | 20.698 | 1.00 | 21.35 | A |
| ATOM | 953 | CA | THR | A | 800 | 3.593 | 15.789 | 21.170 | 1.00 | 22.13 | A |
| ATOM | 954 | CB | THR | A | 800 | 4.621 | 14.818 | 20.539 | 1.00 | 22.94 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 955 | OG1 | THR | A | 800 | 4.413 | 14.770 | 19.124 | 1.00 | 22.16 | A |
| ATOM | 956 | CG2 | THR | A | 800 | 4.469 | 13.414 | 21.116 | 1.00 | 24.15 | A |
| ATOM | 957 | C | THR | A | 800 | 3.696 | 15.727 | 22.693 | 1.00 | 20.94 | A |
| ATOM | 958 | O | THR | A | 800 | 2.861 | 15.125 | 23.361 | 1.00 | 21.14 | A |
| ATOM | 959 | N | MET | A | 801 | 4.723 | 16.356 | 23.247 | 1.00 | 21.63 | A |
| ATOM | 960 | CA | MET | A | 801 | 4.890 | 16.363 | 24.691 | 1.00 | 20.90 | A |
| ATOM | 961 | CB | MET | A | 801 | 6.251 | 16.960 | 25.059 | 1.00 | 21.60 | A |
| ATOM | 962 | CG | MET | A | 801 | 7.439 | 16.115 | 24.604 | 1.00 | 22.22 | A |
| ATOM | 963 | SD | MET | A | 801 | 9.029 | 16.740 | 25.194 | 1.00 | 24.57 | A |
| ATOM | 964 | CE | MET | A | 801 | 9.415 | 17.955 | 23.949 | 1.00 | 24.02 | A |
| ATOM | 965 | C | MET | A | 801 | 3.770 | 17.165 | 25.363 | 1.00 | 22.02 | A |
| ATOM | 966 | O | MET | A | 801 | 3.265 | 16.786 | 26.421 | 1.00 | 21.68 | A |
| ATOM | 967 | N | TRP | A | 802 | 3.373 | 18.259 | 24.720 | 1.00 | 21.19 | A |
| ATOM | 968 | CA | TRP | A | 802 | 2.337 | 19.155 | 25.232 | 1.00 | 21.40 | A |
| ATOM | 969 | CB | TRP | A | 802 | 2.214 | 20.360 | 24.290 | 1.00 | 20.55 | A |
| ATOM | 970 | CG | TRP | A | 802 | 1.627 | 21.606 | 24.910 | 1.00 | 21.30 | A |
| ATOM | 971 | CD2 | TRP | A | 802 | 1.238 | 22.802 | 24.219 | 1.00 | 21.96 | A |
| ATOM | 972 | CE2 | TRP | A | 802 | 0.797 | 23.727 | 25.193 | 1.00 | 20.55 | A |
| ATOM | 973 | CE3 | TRP | A | 802 | 1.225 | 23.182 | 22.869 | 1.00 | 22.42 | A |
| ATOM | 974 | CD1 | TRP | A | 802 | 1.409 | 21.847 | 26.239 | 1.00 | 21.16 | A |
| ATOM | 975 | NE1 | TRP | A | 802 | 0.910 | 23.121 | 26.416 | 1.00 | 20.99 | A |
| ATOM | 976 | CZ2 | TRP | A | 802 | 0.343 | 25.011 | 24.860 | 1.00 | 21.73 | A |
| ATOM | 977 | CZ3 | TRP | A | 802 | 0.775 | 24.461 | 22.536 | 1.00 | 23.05 | A |
| ATOM | 978 | CH2 | TRP | A | 802 | 0.342 | 25.359 | 23.531 | 1.00 | 23.08 | A |
| ATOM | 979 | C | TRP | A | 802 | 0.974 | 18.479 | 25.419 | 1.00 | 21.76 | A |
| ATOM | 980 | O | TRP | A | 802 | 0.126 | 18.973 | 26.168 | 1.00 | 21.60 | A |
| ATOM | 981 | N | GLN | A | 803 | 0.766 | 17.350 | 24.747 | 1.00 | 21.02 | A |
| ATOM | 982 | CA | GLN | A | 803 | −0.496 | 16.619 | 24.856 | 1.00 | 21.96 | A |
| ATOM | 983 | CB | GLN | A | 803 | −0.488 | 15.404 | 23.921 | 1.00 | 23.91 | A |
| ATOM | 984 | CG | GLN | A | 803 | −0.267 | 15.756 | 22.447 | 1.00 | 27.15 | A |
| ATOM | 985 | CD | GLN | A | 803 | −0.209 | 14.537 | 21.537 | 1.00 | 31.34 | A |
| ATOM | 986 | OE1 | GLN | A | 803 | 0.116 | 14.648 | 20.352 | 1.00 | 35.35 | A |
| ATOM | 987 | NE2 | GLN | A | 803 | −0.526 | 13.372 | 22.084 | 1.00 | 32.57 | A |
| ATOM | 988 | C | GLN | A | 803 | −0.759 | 16.152 | 26.289 | 1.00 | 23.03 | A |
| ATOM | 989 | O | GLN | A | 803 | −1.898 | 16.173 | 26.759 | 1.00 | 21.44 | A |
| ATOM | 990 | N | ILE | A | 804 | 0.299 | 15.736 | 26.980 | 1.00 | 21.25 | A |
| ATOM | 991 | CA | ILE | A | 804 | 0.170 | 15.242 | 28.344 | 1.00 | 22.31 | A |
| ATOM | 992 | CB | ILE | A | 804 | 1.532 | 14.758 | 28.891 | 1.00 | 21.58 | A |
| ATOM | 993 | CG2 | ILE | A | 804 | 1.381 | 14.289 | 30.331 | 1.00 | 22.10 | A |
| ATOM | 994 | CG1 | ILE | A | 804 | 2.051 | 13.609 | 28.020 | 1.00 | 25.42 | A |
| ATOM | 995 | CD1 | ILE | A | 804 | 3.379 | 13.044 | 28.464 | 1.00 | 28.79 | A |
| ATOM | 996 | C | ILE | A | 804 | −0.432 | 16.270 | 29.297 | 1.00 | 21.32 | A |
| ATOM | 997 | O | ILE | A | 804 | −1.415 | 15.984 | 29.981 | 1.00 | 21.18 | A |
| ATOM | 998 | N | PRO | A | 805 | 0.153 | 17.476 | 29.366 | 1.00 | 21.85 | A |
| ATOM | 999 | CD | PRO | A | 805 | 1.379 | 17.971 | 28.716 | 1.00 | 19.76 | A |
| ATOM | 1000 | CA | PRO | A | 805 | −0.409 | 18.484 | 30.270 | 1.00 | 22.32 | A |
| ATOM | 1001 | CB | PRO | A | 805 | 0.439 | 19.718 | 29.981 | 1.00 | 23.10 | A |
| ATOM | 1002 | CG | PRO | A | 805 | 1.758 | 19.134 | 29.593 | 1.00 | 24.27 | A |
| ATOM | 1003 | C | PRO | A | 805 | −1.880 | 18.716 | 29.932 | 1.00 | 22.86 | A |
| ATOM | 1004 | O | PRO | A | 805 | −2.726 | 18.842 | 30.820 | 1.00 | 21.86 | A |
| ATOM | 1005 | N | GLN | A | 806 | −2.178 | 18.767 | 28.637 | 1.00 | 21.67 | A |
| ATOM | 1006 | CA | GLN | A | 806 | −3.549 | 18.991 | 28.199 | 1.00 | 24.13 | A |
| ATOM | 1007 | CB | GLN | A | 806 | −3.601 | 19.119 | 26.669 | 1.00 | 25.09 | A |
| ATOM | 1008 | CG | GLN | A | 806 | −2.740 | 20.270 | 26.116 | 1.00 | 25.65 | A |
| ATOM | 1009 | CD | GLN | A | 806 | −3.241 | 21.661 | 26.516 | 1.00 | 29.07 | A |
| ATOM | 1010 | OE1 | GLN | A | 806 | −3.896 | 21.832 | 27.546 | 1.00 | 26.16 | A |
| ATOM | 1011 | NE2 | GLN | A | 806 | −2.914 | 22.666 | 25.701 | 1.00 | 30.40 | A |
| ATOM | 1012 | C | GLN | A | 806 | −4.481 | 17.882 | 28.696 | 1.00 | 23.92 | A |
| ATOM | 1013 | O | GLN | A | 806 | −5.624 | 18.152 | 29.062 | 1.00 | 23.37 | A |
| ATOM | 1014 | N | GLU | A | 807 | −3.998 | 16.640 | 28.726 | 1.00 | 24.30 | A |
| ATOM | 1015 | CA | GLU | A | 807 | −4.818 | 15.532 | 29.215 | 1.00 | 25.08 | A |
| ATOM | 1016 | CB | GLU | A | 807 | −4.175 | 14.180 | 28.893 | 1.00 | 27.80 | A |
| ATOM | 1017 | CG | GLU | A | 807 | −4.461 | 13.676 | 27.495 | 1.00 | 32.53 | A |
| ATOM | 1018 | CD | GLU | A | 807 | −5.951 | 13.489 | 27.238 | 1.00 | 34.70 | A |
| ATOM | 1019 | OE1 | GLU | A | 807 | −6.570 | 12.623 | 27.893 | 1.00 | 35.52 | A |
| ATOM | 1020 | OE2 | GLU | A | 807 | −6.501 | 14.211 | 26.381 | 1.00 | 36.62 | A |
| ATOM | 1021 | C | GLU | A | 807 | −5.025 | 15.641 | 30.723 | 1.00 | 24.42 | A |
| ATOM | 1022 | O | GLU | A | 807 | −6.056 | 15.222 | 31.251 | 1.00 | 22.60 | A |
| ATOM | 1023 | N | PHE | A | 808 | −4.034 | 16.189 | 31.418 | 1.00 | 23.73 | A |
| ATOM | 1024 | CA | PHE | A | 808 | −4.143 | 16.357 | 32.860 | 1.00 | 23.36 | A |
| ATOM | 1025 | CB | PHE | A | 808 | −2.818 | 16.857 | 33.443 | 1.00 | 24.21 | A |
| ATOM | 1026 | CG | PHE | A | 808 | −1.785 | 15.774 | 33.622 | 1.00 | 25.04 | A |
| ATOM | 1027 | CD1 | PHE | A | 808 | −2.118 | 14.433 | 33.439 | 1.00 | 26.18 | A |
| ATOM | 1028 | CD2 | PHE | A | 808 | −0.490 | 16.091 | 34.010 | 1.00 | 26.53 | A |
| ATOM | 1029 | CE1 | PHE | A | 808 | −1.173 | 13.422 | 33.648 | 1.00 | 27.84 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1030 | CE2 | PHE | A | 808 | 0.462 | 15.088 | 34.222 | 1.00 | 27.25 | A |
| ATOM | 1031 | CZ | PHE | A | 808 | 0.119 | 13.754 | 34.040 | 1.00 | 25.53 | A |
| ATOM | 1032 | C | PHE | A | 808 | −5.264 | 17.349 | 33.150 | 1.00 | 22.79 | A |
| ATOM | 1033 | O | PHE | A | 808 | −6.074 | 17.142 | 34.057 | 1.00 | 22.62 | A |
| ATOM | 1034 | N | VAL | A | 809 | −5.312 | 18.418 | 32.359 | 1.00 | 22.34 | A |
| ATOM | 1035 | CA | VAL | A | 809 | −6.345 | 19.440 | 32.512 | 1.00 | 22.35 | A |
| ATOM | 1036 | CB | VAL | A | 809 | −6.140 | 20.590 | 31.500 | 1.00 | 21.96 | A |
| ATOM | 1037 | CG1 | VAL | A | 809 | −7.325 | 21.541 | 31.545 | 1.00 | 22.83 | A |
| ATOM | 1038 | CG2 | VAL | A | 809 | −4.863 | 21.346 | 31.818 | 1.00 | 20.25 | A |
| ATOM | 1039 | C | VAL | A | 809 | −7.734 | 18.844 | 32.285 | 1.00 | 23.40 | A |
| ATOM | 1040 | O | VAL | A | 809 | −8.658 | 19.059 | 33.073 | 1.00 | 22.44 | A |
| ATOM | 1041 | N | LYS | A | 810 | −7.880 | 18.088 | 31.204 | 1.00 | 24.89 | A |
| ATOM | 1042 | CA | LYS | A | 810 | −9.168 | 17.493 | 30.873 | 1.00 | 26.91 | A |
| ATOM | 1043 | CB | LYS | A | 810 | −9.105 | 16.836 | 29.491 | 1.00 | 29.69 | A |
| ATOM | 1044 | CG | LYS | A | 810 | −8.893 | 17.826 | 28.355 | 1.00 | 33.08 | A |
| ATOM | 1045 | CD | LYS | A | 810 | −8.741 | 17.116 | 27.014 | 1.00 | 38.27 | A |
| ATOM | 1046 | CE | LYS | A | 810 | −8.498 | 18.114 | 25.881 | 1.00 | 40.99 | A |
| ATOM | 1047 | NZ | LYS | A | 810 | −8.286 | 17.433 | 24.568 | 1.00 | 43.19 | A |
| ATOM | 1048 | C | LYS | A | 810 | −9.663 | 16.486 | 31.907 | 1.00 | 27.41 | A |
| ATOM | 1049 | O | LYS | A | 810 | −10.855 | 16.444 | 32.214 | 1.00 | 26.62 | A |
| ATOM | 1050 | N | LEU | A | 811 | −8.753 | 15.677 | 32.440 | 1.00 | 24.95 | A |
| ATOM | 1051 | CA | LEU | A | 811 | −9.123 | 14.683 | 33.438 | 1.00 | 25.56 | A |
| ATOM | 1052 | CB | LEU | A | 811 | −8.217 | 13.458 | 33.318 | 1.00 | 25.67 | A |
| ATOM | 1053 | CG | LEU | A | 811 | −8.421 | 12.595 | 32.078 | 1.00 | 26.38 | A |
| ATOM | 1054 | CD1 | LEU | A | 811 | −7.289 | 11.591 | 31.949 | 1.00 | 26.98 | A |
| ATOM | 1055 | CD2 | LEU | A | 811 | −9.760 | 11.893 | 32.186 | 1.00 | 26.29 | A |
| ATOM | 1056 | C | LEU | A | 811 | −9.044 | 15.220 | 34.863 | 1.00 | 24.44 | A |
| ATOM | 1057 | O | LEU | A | 811 | −9.522 | 14.579 | 35.793 | 1.00 | 24.86 | A |
| ATOM | 1058 | N | GLN | A | 812 | −8.458 | 16.401 | 35.026 | 1.00 | 25.33 | A |
| ATOM | 1059 | CA | GLN | A | 812 | −8.288 | 16.989 | 36.351 | 1.00 | 26.61 | A |
| ATOM | 1060 | CB | GLN | A | 812 | −9.635 | 17.477 | 36.905 | 1.00 | 30.42 | A |
| ATOM | 1061 | CG | GLN | A | 812 | −10.100 | 18.777 | 36.256 | 1.00 | 35.79 | A |
| ATOM | 1062 | CD | GLN | A | 812 | −11.386 | 19.328 | 36.849 | 1.00 | 40.76 | A |
| ATOM | 1063 | OE1 | GLN | A | 812 | −11.736 | 20.489 | 36.621 | 1.00 | 45.20 | A |
| ATOM | 1064 | NE2 | GLN | A | 812 | −12.099 | 18.499 | 37.608 | 1.00 | 42.16 | A |
| ATOM | 1065 | C | GLN | A | 812 | −7.655 | 15.950 | 37.281 | 1.00 | 24.37 | A |
| ATOM | 1066 | O | GLN | A | 812 | −8.185 | 15.625 | 38.348 | 1.00 | 22.99 | A |
| ATOM | 1067 | N | VAL | A | 813 | −6.513 | 15.423 | 36.846 | 1.00 | 22.72 | A |
| ATOM | 1068 | CA | VAL | A | 813 | −5.776 | 14.422 | 37.607 | 1.00 | 20.15 | A |
| ATOM | 1069 | CB | VAL | A | 813 | −4.501 | 13.989 | 36.853 | 1.00 | 21.18 | A |
| ATOM | 1070 | CG1 | VAL | A | 813 | −3.707 | 12.977 | 37.694 | 1.00 | 19.93 | A |
| ATOM | 1071 | CG2 | VAL | A | 813 | −4.882 | 13.388 | 35.506 | 1.00 | 19.31 | A |
| ATOM | 1072 | C | VAL | A | 813 | −5.380 | 14.998 | 38.958 | 1.00 | 20.32 | A |
| ATOM | 1073 | O | VAL | A | 813 | −4.906 | 16.134 | 39.042 | 1.00 | 18.09 | A |
| ATOM | 1074 | N | SER | A | 814 | −5.579 | 14.220 | 40.016 | 1.00 | 18.44 | A |
| ATOM | 1075 | CA | SER | A | 814 | −5.235 | 14.690 | 41.353 | 1.00 | 20.30 | A |
| ATOM | 1076 | CB | SER | A | 814 | −6.143 | 14.057 | 42.408 | 1.00 | 18.76 | A |
| ATOM | 1077 | OG | SER | A | 814 | −5.858 | 12.674 | 42.549 | 1.00 | 17.92 | A |
| ATOM | 1078 | C | SER | A | 814 | −3.794 | 14.348 | 41.687 | 1.00 | 21.13 | A |
| ATOM | 1079 | O | SER | A | 814 | −3.173 | 13.496 | 41.050 | 1.00 | 21.63 | A |
| ATOM | 1080 | N | GLN | A | 815 | −3.276 | 15.024 | 42.700 | 1.00 | 21.79 | A |
| ATOM | 1081 | CA | GLN | A | 815 | −1.916 | 14.807 | 43.164 | 1.00 | 23.69 | A |
| ATOM | 1082 | CB | GLN | A | 815 | −1.648 | 15.736 | 44.349 | 1.00 | 27.86 | A |
| ATOM | 1083 | CG | GLN | A | 815 | −0.226 | 15.755 | 44.851 | 1.00 | 34.98 | A |
| ATOM | 1084 | CD | GLN | A | 815 | −0.029 | 16.804 | 45.927 | 1.00 | 38.93 | A |
| ATOM | 1085 | OE1 | GLN | A | 815 | 1.084 | 17.036 | 46.386 | 1.00 | 42.97 | A |
| ATOM | 1086 | NE2 | GLN | A | 815 | −1.120 | 17.448 | 46.333 | 1.00 | 42.31 | A |
| ATOM | 1087 | C | GLN | A | 815 | −1.748 | 13.348 | 43.585 | 1.00 | 21.52 | A |
| ATOM | 1088 | O | GLN | A | 815 | −0.710 | 12.729 | 43.325 | 1.00 | 21.53 | A |
| ATOM | 1089 | N | GLU | A | 816 | −2.782 | 12.794 | 44.215 | 1.00 | 19.19 | A |
| ATOM | 1090 | CA | GLU | A | 816 | −2.744 | 11.410 | 44.682 | 1.00 | 19.04 | A |
| ATOM | 1091 | CB | GLU | A | 816 | −3.946 | 11.116 | 45.582 | 1.00 | 20.60 | A |
| ATOM | 1092 | CG | GLU | A | 816 | −3.983 | 11.908 | 46.885 | 1.00 | 22.06 | A |
| ATOM | 1093 | CD | GLU | A | 816 | −4.344 | 13.374 | 46.692 | 1.00 | 24.05 | A |
| ATOM | 1094 | OE1 | GLU | A | 816 | −4.903 | 13.729 | 45.632 | 1.00 | 21.48 | A |
| ATOM | 1095 | OE2 | GLU | A | 816 | −4.078 | 14.171 | 47.615 | 1.00 | 26.29 | A |
| ATOM | 1096 | C | GLU | A | 816 | −2.720 | 10.408 | 43.534 | 1.00 | 18.03 | A |
| ATOM | 1097 | O | GLU | A | 816 | −2.003 | 9.409 | 43.586 | 1.00 | 16.07 | A |
| ATOM | 1098 | N | GLU | A | 817 | −3.516 | 10.664 | 42.503 | 1.00 | 17.72 | A |
| ATOM | 1099 | CA | GLU | A | 817 | −3.553 | 9.772 | 41.352 | 1.00 | 18.37 | A |
| ATOM | 1100 | CB | GLU | A | 817 | −4.700 | 10.163 | 40.413 | 1.00 | 19.36 | A |
| ATOM | 1101 | CG | GLU | A | 817 | −6.089 | 10.025 | 41.036 | 1.00 | 18.88 | A |
| ATOM | 1102 | CD | GLU | A | 817 | −7.186 | 10.619 | 40.164 | 1.00 | 20.98 | A |
| ATOM | 1103 | OE1 | GLU | A | 817 | −6.934 | 11.652 | 39.510 | 1.00 | 19.85 | A |
| ATOM | 1104 | OE2 | GLU | A | 817 | −8.305 | 10.067 | 40.143 | 1.00 | 20.28 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1105 | C | GLU | A | 817 | −2.214 | 9.869 | 40.615 | 1.00 | 17.45 | A |
| ATOM | 1106 | O | GLU | A | 817 | −1.654 | 8.859 | 40.203 | 1.00 | 18.12 | A |
| ATOM | 1107 | N | PHE | A | 818 | −1.710 | 11.092 | 40.464 | 1.00 | 17.39 | A |
| ATOM | 1108 | CA | PHE | A | 818 | −0.443 | 11.339 | 39.778 | 1.00 | 17.67 | A |
| ATOM | 1109 | CB | PHE | A | 818 | −0.108 | 12.836 | 39.820 | 1.00 | 18.87 | A |
| ATOM | 1110 | CG | PHE | A | 818 | 1.307 | 13.158 | 39.396 | 1.00 | 20.11 | A |
| ATOM | 1111 | CD1 | PHE | A | 818 | 1.697 | 13.039 | 38.065 | 1.00 | 21.04 | A |
| ATOM | 1112 | CD2 | PHE | A | 818 | 2.255 | 13.551 | 40.337 | 1.00 | 22.59 | A |
| ATOM | 1113 | CE1 | PHE | A | 818 | 3.018 | 13.306 | 37.673 | 1.00 | 21.13 | A |
| ATOM | 1114 | CE2 | PHE | A | 818 | 3.577 | 13.821 | 39.961 | 1.00 | 22.38 | A |
| ATOM | 1115 | CZ | PHE | A | 818 | 3.959 | 13.696 | 38.624 | 1.00 | 21.87 | A |
| ATOM | 1116 | C | PHE | A | 818 | 0.690 | 10.543 | 40.423 | 1.00 | 17.61 | A |
| ATOM | 1117 | O | PHE | A | 818 | 1.426 | 9.828 | 39.745 | 1.00 | 17.85 | A |
| ATOM | 1118 | N | LEU | A | 819 | 0.820 | 10.668 | 41.739 | 1.00 | 17.17 | A |
| ATOM | 1119 | CA | LEU | A | 819 | 1.857 | 9.966 | 42.476 | 1.00 | 16.75 | A |
| ATOM | 1120 | CB | LEU | A | 819 | 1.712 | 10.259 | 43.972 | 1.00 | 17.20 | A |
| ATOM | 1121 | CG | LEU | A | 819 | 2.030 | 11.713 | 44.349 | 1.00 | 17.53 | A |
| ATOM | 1122 | CD1 | LEU | A | 819 | 1.682 | 11.970 | 45.816 | 1.00 | 18.42 | A |
| ATOM | 1123 | CD2 | LEU | A | 819 | 3.509 | 11.989 | 44.089 | 1.00 | 18.88 | A |
| ATOM | 1124 | C | LEU | A | 819 | 1.844 | 8.456 | 42.217 | 1.00 | 18.00 | A |
| ATOM | 1125 | O | LEU | A | 819 | 2.890 | 7.864 | 41.954 | 1.00 | 17.24 | A |
| ATOM | 1126 | N | CYS | A | 820 | 0.665 | 7.840 | 42.273 | 1.00 | 16.25 | A |
| ATOM | 1127 | CA | CYS | A | 820 | 0.549 | 6.400 | 42.034 | 1.00 | 16.35 | A |
| ATOM | 1128 | CB | CYS | A | 820 | −0.851 | 5.911 | 42.419 | 1.00 | 13.68 | A |
| ATOM | 1129 | SG | CYS | A | 820 | −1.192 | 5.999 | 44.186 | 1.00 | 18.53 | A |
| ATOM | 1130 | C | CYS | A | 820 | 0.837 | 6.027 | 40.580 | 1.00 | 17.21 | A |
| ATOM | 1131 | O | CYS | A | 820 | 1.516 | 5.027 | 40.305 | 1.00 | 16.67 | A |
| ATOM | 1132 | N | MET | A | 821 | 0.318 | 6.826 | 39.652 | 1.00 | 15.37 | A |
| ATOM | 1133 | CA | MET | A | 821 | 0.530 | 6.573 | 38.234 | 1.00 | 16.27 | A |
| ATOM | 1134 | CB | MET | A | 821 | −0.265 | 7.573 | 37.392 | 1.00 | 17.92 | A |
| ATOM | 1135 | CG | MET | A | 821 | −1.771 | 7.383 | 37.460 | 1.00 | 17.69 | A |
| ATOM | 1136 | SD | MET | A | 821 | −2.643 | 8.818 | 36.774 | 1.00 | 19.79 | A |
| ATOM | 1137 | CE | MET | A | 821 | −2.555 | 8.439 | 35.021 | 1.00 | 15.33 | A |
| ATOM | 1138 | C | MET | A | 821 | 2.015 | 6.677 | 37.897 | 1.00 | 15.93 | A |
| ATOM | 1139 | O | MET | A | 821 | 2.531 | 5.902 | 37.097 | 1.00 | 14.16 | A |
| ATOM | 1140 | N | LYS | A | 822 | 2.707 | 7.628 | 38.515 | 1.00 | 14.88 | A |
| ATOM | 1141 | CA | LYS | A | 822 | 4.130 | 7.774 | 38.239 | 1.00 | 16.59 | A |
| ATOM | 1142 | CB | LYS | A | 822 | 4.698 | 9.016 | 38.936 | 1.00 | 16.10 | A |
| ATOM | 1143 | CG | LYS | A | 822 | 6.140 | 9.301 | 38.551 | 1.00 | 16.38 | A |
| ATOM | 1144 | CD | LYS | A | 822 | 6.486 | 10.792 | 38.596 | 1.00 | 17.94 | A |
| ATOM | 1145 | CE | LYS | A | 822 | 6.423 | 11.366 | 40.004 | 1.00 | 16.34 | A |
| ATOM | 1146 | NZ | LYS | A | 822 | 7.308 | 10.632 | 40.944 | 1.00 | 18.00 | A |
| ATOM | 1147 | C | LYS | A | 822 | 4.892 | 6.516 | 38.664 | 1.00 | 15.81 | A |
| ATOM | 1148 | O | LYS | A | 822 | 5.834 | 6.104 | 37.992 | 1.00 | 14.75 | A |
| ATOM | 1149 | N | VAL | A | 823 | 4.487 | 5.894 | 39.772 | 1.00 | 16.36 | A |
| ATOM | 1150 | CA | VAL | A | 823 | 5.160 | 4.672 | 40.203 | 1.00 | 14.72 | A |
| ATOM | 1151 | CB | VAL | A | 823 | 4.703 | 4.200 | 41.613 | 1.00 | 15.84 | A |
| ATOM | 1152 | CG1 | VAL | A | 823 | 5.305 | 2.824 | 41.917 | 1.00 | 15.64 | A |
| ATOM | 1153 | CG2 | VAL | A | 823 | 5.167 | 5.197 | 42.684 | 1.00 | 14.56 | A |
| ATOM | 1154 | C | VAL | A | 823 | 4.889 | 3.550 | 39.204 | 1.00 | 14.32 | A |
| ATOM | 1155 | O | VAL | A | 823 | 5.776 | 2.753 | 38.899 | 1.00 | 13.04 | A |
| ATOM | 1156 | N | LEU | A | 824 | 3.668 | 3.484 | 38.684 | 1.00 | 13.35 | A |
| ATOM | 1157 | CA | LEU | A | 824 | 3.340 | 2.437 | 37.725 | 1.00 | 14.01 | A |
| ATOM | 1158 | CB | LEU | A | 824 | 1.834 | 2.433 | 37.434 | 1.00 | 13.91 | A |
| ATOM | 1159 | CG | LEU | A | 824 | 0.993 | 2.089 | 38.671 | 1.00 | 16.39 | A |
| ATOM | 1160 | CD1 | LEU | A | 824 | −0.493 | 2.176 | 38.350 | 1.00 | 15.94 | A |
| ATOM | 1161 | CD2 | LEU | A | 824 | 1.360 | 0.683 | 39.158 | 1.00 | 15.40 | A |
| ATOM | 1162 | C | LEU | A | 824 | 4.152 | 2.572 | 36.437 | 1.00 | 11.71 | A |
| ATOM | 1163 | O | LEU | A | 824 | 4.466 | 1.573 | 35.792 | 1.00 | 13.59 | A |
| ATOM | 1164 | N | LEU | A | 825 | 4.497 | 3.800 | 36.062 | 1.00 | 12.33 | A |
| ATOM | 1165 | CA | LEU | A | 825 | 5.301 | 4.012 | 34.862 | 1.00 | 12.91 | A |
| ATOM | 1166 | CB | LEU | A | 825 | 5.418 | 5.507 | 34.542 | 1.00 | 12.32 | A |
| ATOM | 1167 | CG | LEU | A | 825 | 4.228 | 6.126 | 33.799 | 1.00 | 14.73 | A |
| ATOM | 1168 | CD1 | LEU | A | 825 | 4.491 | 7.612 | 33.545 | 1.00 | 16.34 | A |
| ATOM | 1169 | CD2 | LEU | A | 825 | 4.023 | 5.389 | 32.478 | 1.00 | 12.28 | A |
| ATOM | 1170 | C | LEU | A | 825 | 6.698 | 3.407 | 35.058 | 1.00 | 13.79 | A |
| ATOM | 1171 | O | LEU | A | 825 | 7.252 | 2.791 | 34.147 | 1.00 | 13.59 | A |
| ATOM | 1172 | N | LEU | A | 826 | 7.262 | 3.583 | 36.251 | 1.00 | 12.61 | A |
| ATOM | 1173 | CA | LEU | A | 826 | 8.576 | 3.027 | 36.554 | 1.00 | 14.11 | A |
| ATOM | 1174 | CB | LEU | A | 826 | 8.977 | 3.375 | 37.994 | 1.00 | 14.02 | A |
| ATOM | 1175 | CG | LEU | A | 826 | 10.211 | 2.635 | 38.531 | 1.00 | 17.91 | A |
| ATOM | 1176 | CD1 | LEU | A | 826 | 11.464 | 3.153 | 37.824 | 1.00 | 16.45 | A |
| ATOM | 1177 | CD2 | LEU | A | 826 | 10.333 | 2.838 | 40.038 | 1.00 | 17.97 | A |
| ATOM | 1178 | C | LEU | A | 826 | 8.526 | 1.501 | 36.391 | 1.00 | 14.93 | A |
| ATOM | 1179 | O | LEU | A | 826 | 9.505 | 0.875 | 35.995 | 1.00 | 15.99 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1180 | N | LEU | A | 827 | 7.364 | 0.918 | 36.676 | 1.00 | 15.65 | A |
| ATOM | 1181 | CA | LEU | A | 827 | 7.168 | −0.528 | 36.590 | 1.00 | 15.35 | A |
| ATOM | 1182 | CB | LEU | A | 827 | 6.430 | −1.000 | 37.848 | 1.00 | 15.51 | A |
| ATOM | 1183 | CG | LEU | A | 827 | 6.949 | −0.493 | 39.202 | 1.00 | 16.57 | A |
| ATOM | 1184 | CD1 | LEU | A | 827 | 5.966 | −0.846 | 40.304 | 1.00 | 15.59 | A |
| ATOM | 1185 | CD2 | LEU | A | 827 | 8.320 | −1.110 | 39.486 | 1.00 | 18.43 | A |
| ATOM | 1186 | C | LEU | A | 827 | 6.350 | −0.952 | 35.362 | 1.00 | 17.65 | A |
| ATOM | 1187 | O | LEU | A | 827 | 5.749 | −2.031 | 35.361 | 1.00 | 16.15 | A |
| ATOM | 1188 | N | ASN | A | 828 | 6.346 | −0.131 | 34.314 | 1.00 | 18.51 | A |
| ATOM | 1189 | CA | ASN | A | 828 | 5.520 | −0.424 | 33.141 | 1.00 | 16.99 | A |
| ATOM | 1190 | CB | ASN | A | 828 | 4.881 | 0.877 | 32.649 | 1.00 | 17.83 | A |
| ATOM | 1191 | CG | ASN | A | 828 | 3.418 | 0.703 | 32.307 | 1.00 | 20.51 | A |
| ATOM | 1192 | OD1 | ASN | A | 828 | 2.743 | −0.175 | 32.858 | 1.00 | 17.90 | A |
| ATOM | 1193 | ND2 | ASN | A | 828 | 2.912 | 1.541 | 31.411 | 1.00 | 17.96 | A |
| ATOM | 1194 | C | ASN | A | 828 | 6.126 | −1.180 | 31.958 | 1.00 | 17.76 | A |
| ATOM | 1195 | O | ASN | A | 828 | 5.448 | −1.412 | 30.960 | 1.00 | 17.82 | A |
| ATOM | 1196 | N | THR | A | 829 | 7.391 | −1.566 | 32.066 | 1.00 | 16.44 | A |
| ATOM | 1197 | CA | THR | A | 829 | 8.056 | −2.318 | 31.013 | 1.00 | 16.99 | A |
| ATOM | 1198 | CB | THR | A | 829 | 8.866 | −1.396 | 30.056 | 1.00 | 18.11 | A |
| ATOM | 1199 | OG1 | THR | A | 829 | 8.008 | −0.394 | 29.494 | 1.00 | 17.42 | A |
| ATOM | 1200 | CG2 | THR | A | 829 | 9.474 | −2.219 | 28.920 | 1.00 | 20.30 | A |
| ATOM | 1201 | C | THR | A | 829 | 9.031 | −3.292 | 31.673 | 1.00 | 17.73 | A |
| ATOM | 1202 | O | THR | A | 829 | 9.717 | −2.930 | 32.629 | 1.00 | 17.99 | A |
| ATOM | 1203 | N | ILE | A | 830 | 9.071 | −4.531 | 31.189 | 1.00 | 17.90 | A |
| ATOM | 1204 | CA | ILE | A | 830 | 10.002 | −5.519 | 31.724 | 1.00 | 18.71 | A |
| ATOM | 1205 | CB | ILE | A | 830 | 9.311 | −6.520 | 32.685 | 1.00 | 19.83 | A |
| ATOM | 1206 | CG2 | ILE | A | 830 | 8.568 | −5.753 | 33.781 | 1.00 | 20.83 | A |
| ATOM | 1207 | CG1 | ILE | A | 830 | 8.338 | −7.423 | 31.922 | 1.00 | 18.24 | A |
| ATOM | 1208 | CD1 | ILE | A | 830 | 7.762 | −8.554 | 32.782 | 1.00 | 19.69 | A |
| ATOM | 1209 | C | ILE | A | 830 | 10.661 | −6.278 | 30.572 | 1.00 | 19.02 | A |
| ATOM | 1210 | O | ILE | A | 830 | 10.193 | −6.224 | 29.434 | 1.00 | 18.72 | A |
| ATOM | 1211 | N | PRO | A | 831 | 11.771 | −6.981 | 30.849 | 1.00 | 19.69 | A |
| ATOM | 1212 | CD | PRO | A | 831 | 12.515 | −7.077 | 32.118 | 1.00 | 17.13 | A |
| ATOM | 1213 | CA | PRO | A | 831 | 12.451 | −7.725 | 29.789 | 1.00 | 20.61 | A |
| ATOM | 1214 | CB | PRO | A | 831 | 13.691 | −8.289 | 30.491 | 1.00 | 20.77 | A |
| ATOM | 1215 | CG | PRO | A | 831 | 13.920 | −7.336 | 31.637 | 1.00 | 19.58 | A |
| ATOM | 1216 | C | PRO | A | 831 | 11.555 | −8.830 | 29.256 | 1.00 | 21.97 | A |
| ATOM | 1217 | O | PRO | A | 831 | 10.610 | −9.247 | 29.922 | 1.00 | 21.43 | A |
| ATOM | 1218 | N | LEU | A | 832 | 11.855 | −9.297 | 28.051 | 1.00 | 23.36 | A |
| ATOM | 1219 | CA | LEU | A | 832 | 11.082 | −10.371 | 27.448 | 1.00 | 25.72 | A |
| ATOM | 1220 | CB | LEU | A | 832 | 11.617 | −10.676 | 26.047 | 1.00 | 26.92 | A |
| ATOM | 1221 | CG | LEU | A | 832 | 11.334 | −9.596 | 25.003 | 1.00 | 28.15 | A |
| ATOM | 1222 | CD1 | LEU | A | 832 | 12.033 | −9.942 | 23.699 | 1.00 | 30.17 | A |
| ATOM | 1223 | CD2 | LEU | A | 832 | 9.827 | −9.476 | 24.801 | 1.00 | 28.94 | A |
| ATOM | 1224 | C | LEU | A | 832 | 11.180 | −11.619 | 28.318 | 1.00 | 26.21 | A |
| ATOM | 1225 | O | LEU | A | 832 | 10.217 | −12.373 | 28.447 | 1.00 | 25.46 | A |
| ATOM | 1226 | N | GLU | A | 833 | 12.348 | −11.822 | 28.918 | 1.00 | 25.70 | A |
| ATOM | 1227 | CA | GLU | A | 833 | 12.592 | −12.982 | 29.770 | 1.00 | 27.45 | A |
| ATOM | 1228 | CB | GLU | A | 833 | 14.083 | −13.354 | 29.741 | 1.00 | 29.43 | A |
| ATOM | 1229 | CG | GLU | A | 833 | 15.009 | −12.303 | 30.357 | 1.00 | 32.13 | A |
| ATOM | 1230 | CD | GLU | A | 833 | 15.437 | −11.215 | 29.378 | 1.00 | 33.98 | A |
| ATOM | 1231 | OE1 | GLU | A | 833 | 14.668 | −10.884 | 28.454 | 1.00 | 33.06 | A |
| ATOM | 1232 | OE2 | GLU | A | 833 | 16.550 | −10.675 | 29.545 | 1.00 | 36.26 | A |
| ATOM | 1233 | C | GLU | A | 833 | 12.156 | −12.739 | 31.219 | 1.00 | 27.20 | A |
| ATOM | 1234 | O | GLU | A | 833 | 12.334 | −13.599 | 32.081 | 1.00 | 27.90 | A |
| ATOM | 1235 | N | GLY | A | 834 | 11.583 | −11.569 | 31.480 | 1.00 | 25.12 | A |
| ATOM | 1236 | CA | GLY | A | 834 | 11.153 | −11.246 | 32.827 | 1.00 | 24.64 | A |
| ATOM | 1237 | C | GLY | A | 834 | 12.292 | −10.725 | 33.687 | 1.00 | 23.57 | A |
| ATOM | 1238 | O | GLY | A | 834 | 13.425 | −10.611 | 33.225 | 1.00 | 23.20 | A |
| ATOM | 1239 | N | LEU | A | 835 | 11.992 | −10.409 | 34.941 | 1.00 | 22.62 | A |
| ATOM | 1240 | CA | LEU | A | 835 | 12.994 | −9.896 | 35.868 | 1.00 | 23.78 | A |
| ATOM | 1241 | CB | LEU | A | 835 | 12.384 | −8.781 | 36.718 | 1.00 | 21.76 | A |
| ATOM | 1242 | CG | LEU | A | 835 | 11.886 | −7.540 | 35.965 | 1.00 | 22.76 | A |
| ATOM | 1243 | CD1 | LEU | A | 835 | 11.025 | −6.680 | 36.888 | 1.00 | 21.31 | A |
| ATOM | 1244 | CD2 | LEU | A | 835 | 13.072 | −6.745 | 35.448 | 1.00 | 21.97 | A |
| ATOM | 1245 | C | LEU | A | 835 | 13.517 | −11.011 | 36.772 | 1.00 | 23.97 | A |
| ATOM | 1246 | O | LEU | A | 835 | 12.925 | −12.085 | 36.847 | 1.00 | 23.94 | A |
| ATOM | 1247 | N | ARG | A | 836 | 14.632 | −10.761 | 37.451 | 1.00 | 25.83 | A |
| ATOM | 1248 | CA | ARG | A | 836 | 15.198 | −11.760 | 38.352 | 1.00 | 27.17 | A |
| ATOM | 1249 | CB | ARG | A | 836 | 16.594 | −11.346 | 38.828 | 1.00 | 30.08 | A |
| ATOM | 1250 | CG | ARG | A | 836 | 17.643 | −11.247 | 37.733 | 1.00 | 36.54 | A |
| ATOM | 1251 | CD | ARG | A | 836 | 19.056 | −11.242 | 38.313 | 1.00 | 41.84 | A |
| ATOM | 1252 | NE | ARG | A | 836 | 19.633 | −12.586 | 38.408 | 1.00 | 48.33 | A |
| ATOM | 1253 | CZ | ARG | A | 836 | 19.195 | −13.552 | 39.214 | 1.00 | 50.99 | A |
| ATOM | 1254 | NH1 | ARG | A | 836 | 18.164 | −13.342 | 40.021 | 1.00 | 53.00 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1255 | NH2 | ARG | A | 836 | 19.783 | −14.741 | 39.205 | 1.00 | 52.15 | A |
| ATOM | 1256 | C | ARG | A | 836 | 14.286 | −11.915 | 39.565 | 1.00 | 26.30 | A |
| ATOM | 1257 | O | ARG | A | 836 | 14.091 | −13.021 | 40.068 | 1.00 | 25.88 | A |
| ATOM | 1258 | N | SER | A | 837 | 13.735 | −10.797 | 40.029 | 1.00 | 23.15 | A |
| ATOM | 1259 | CA | SER | A | 837 | 12.840 | −10.797 | 41.181 | 1.00 | 23.00 | A |
| ATOM | 1260 | CB | SER | A | 837 | 13.198 | −9.644 | 42.128 | 1.00 | 23.75 | A |
| ATOM | 1261 | OG | SER | A | 837 | 14.548 | −9.705 | 42.557 | 1.00 | 23.11 | A |
| ATOM | 1262 | C | SER | A | 837 | 11.403 | −10.628 | 40.693 | 1.00 | 22.34 | A |
| ATOM | 1263 | O | SER | A | 837 | 10.647 | −9.822 | 41.233 | 1.00 | 19.84 | A |
| ATOM | 1264 | N | GLN | A | 838 | 11.035 | −11.398 | 39.671 | 1.00 | 23.15 | A |
| ATOM | 1265 | CA | GLN | A | 838 | 9.698 | −11.326 | 39.081 | 1.00 | 24.26 | A |
| ATOM | 1266 | CB | GLN | A | 838 | 9.527 | −12.422 | 38.020 | 1.00 | 25.27 | A |
| ATOM | 1267 | CG | GLN | A | 838 | 8.289 | −12.273 | 37.134 | 1.00 | 22.45 | A |
| ATOM | 1268 | CD | GLN | A | 838 | 8.307 | −10.999 | 36.290 | 1.00 | 25.56 | A |
| ATOM | 1269 | OE1 | GLN | A | 838 | 9.336 | −10.627 | 35.725 | 1.00 | 24.82 | A |
| ATOM | 1270 | NE2 | GLN | A | 838 | 7.157 | −10.338 | 36.187 | 1.00 | 23.08 | A |
| ATOM | 1271 | C | GLN | A | 838 | 8.565 | −11.423 | 40.094 | 1.00 | 24.82 | A |
| ATOM | 1272 | O | GLN | A | 838 | 7.569 | −10.706 | 39.983 | 1.00 | 23.75 | A |
| ATOM | 1273 | N | THR | A | 839 | 8.702 | −12.314 | 41.074 | 1.00 | 26.33 | A |
| ATOM | 1274 | CA | THR | A | 839 | 7.662 | −12.474 | 42.088 | 1.00 | 26.16 | A |
| ATOM | 1275 | CB | THR | A | 839 | 8.004 | −13.597 | 43.088 | 1.00 | 28.64 | A |
| ATOM | 1276 | OG1 | THR | A | 839 | 8.256 | −14.816 | 42.378 | 1.00 | 30.75 | A |
| ATOM | 1277 | CG2 | THR | A | 839 | 6.845 | −13.817 | 44.050 | 1.00 | 26.66 | A |
| ATOM | 1278 | C | THR | A | 839 | 7.475 | −11.179 | 42.873 | 1.00 | 25.53 | A |
| ATOM | 1279 | O | THR | A | 839 | 6.358 | −10.681 | 43.010 | 1.00 | 25.17 | A |
| ATOM | 1280 | N | GLN | A | 840 | 8.576 | −10.637 | 43.385 | 1.00 | 24.47 | A |
| ATOM | 1281 | CA | GLN | A | 840 | 8.526 | −9.404 | 44.157 | 1.00 | 24.83 | A |
| ATOM | 1282 | CB | GLN | A | 840 | 9.912 | −9.072 | 44.721 | 1.00 | 26.45 | A |
| ATOM | 1283 | CG | GLN | A | 840 | 10.482 | −10.137 | 45.663 | 1.00 | 30.94 | A |
| ATOM | 1284 | CD | GLN | A | 840 | 11.324 | −11.185 | 44.951 | 1.00 | 33.60 | A |
| ATOM | 1285 | OE1 | GLN | A | 840 | 10.894 | −11.795 | 43.966 | 1.00 | 32.51 | A |
| ATOM | 1286 | NE2 | GLN | A | 840 | 12.534 | −11.405 | 45.456 | 1.00 | 35.22 | A |
| ATOM | 1287 | C | GLN | A | 840 | 8.010 | −8.242 | 43.307 | 1.00 | 23.05 | A |
| ATOM | 1288 | O | GLN | A | 840 | 7.231 | −7.417 | 43.780 | 1.00 | 23.69 | A |
| ATOM | 1289 | N | PHE | A | 841 | 8.447 | −8.180 | 42.052 | 1.00 | 21.65 | A |
| ATOM | 1290 | CA | PHE | A | 841 | 8.006 | −7.123 | 41.145 | 1.00 | 20.44 | A |
| ATOM | 1291 | CB | PHE | A | 841 | 8.640 | −7.311 | 39.763 | 1.00 | 19.26 | A |
| ATOM | 1292 | CG | PHE | A | 841 | 8.031 | −6.441 | 38.697 | 1.00 | 18.62 | A |
| ATOM | 1293 | CD1 | PHE | A | 841 | 8.448 | −5.125 | 38.528 | 1.00 | 18.04 | A |
| ATOM | 1294 | CD2 | PHE | A | 841 | 7.021 | −6.932 | 37.877 | 1.00 | 19.63 | A |
| ATOM | 1295 | CE1 | PHE | A | 841 | 7.865 | −4.314 | 37.569 | 1.00 | 17.16 | A |
| ATOM | 1296 | CE2 | PHE | A | 841 | 6.428 | −6.123 | 36.913 | 1.00 | 18.19 | A |
| ATOM | 1297 | CZ | PHE | A | 841 | 6.855 | −4.811 | 36.758 | 1.00 | 17.63 | A |
| ATOM | 1298 | C | PHE | A | 841 | 6.489 | −7.195 | 41.007 | 1.00 | 20.37 | A |
| ATOM | 1299 | O | PHE | A | 841 | 5.790 | −6.186 | 41.078 | 1.00 | 15.98 | A |
| ATOM | 1300 | N | GLU | A | 842 | 5.987 | −8.405 | 40.797 | 1.00 | 20.47 | A |
| ATOM | 1301 | CA | GLU | A | 842 | 4.557 | −8.607 | 40.635 | 1.00 | 23.77 | A |
| ATOM | 1302 | CB | GLU | A | 842 | 4.274 | −10.091 | 40.400 | 1.00 | 27.79 | A |
| ATOM | 1303 | CG | GLU | A | 842 | 3.228 | −10.343 | 39.345 | 1.00 | 32.65 | A |
| ATOM | 1304 | CD | GLU | A | 842 | 3.644 | −9.861 | 37.961 | 1.00 | 32.93 | A |
| ATOM | 1305 | OE1 | GLU | A | 842 | 4.434 | −10.554 | 37.291 | 1.00 | 36.77 | A |
| ATOM | 1306 | OE2 | GLU | A | 842 | 3.179 | −8.786 | 37.542 | 1.00 | 33.52 | A |
| ATOM | 1307 | C | GLU | A | 842 | 3.800 | −8.095 | 41.866 | 1.00 | 23.22 | A |
| ATOM | 1308 | O | GLU | A | 842 | 2.794 | −7.399 | 41.740 | 1.00 | 22.93 | A |
| ATOM | 1309 | N | GLU | A | 843 | 4.293 | −8.429 | 43.053 | 1.00 | 23.18 | A |
| ATOM | 1310 | CA | GLU | A | 843 | 3.658 | −7.982 | 44.290 | 1.00 | 24.02 | A |
| ATOM | 1311 | CB | GLU | A | 843 | 4.334 | −8.640 | 45.499 | 1.00 | 27.96 | A |
| ATOM | 1312 | CG | GLU | A | 843 | 3.980 | −10.118 | 45.676 | 1.00 | 33.63 | A |
| ATOM | 1313 | CD | GLU | A | 843 | 4.660 | −10.752 | 46.880 | 1.00 | 37.86 | A |
| ATOM | 1314 | OE1 | GLU | A | 843 | 4.585 | −10.176 | 47.986 | 1.00 | 41.00 | A |
| ATOM | 1315 | OE2 | GLU | A | 843 | 5.265 | −11.833 | 46.725 | 1.00 | 41.92 | A |
| ATOM | 1316 | C | GLU | A | 843 | 3.713 | −6.457 | 44.426 | 1.00 | 21.45 | A |
| ATOM | 1317 | O | GLU | A | 843 | 2.748 | −5.825 | 44.848 | 1.00 | 20.19 | A |
| ATOM | 1318 | N | MET | A | 844 | 4.842 | −5.869 | 44.055 | 1.00 | 19.19 | A |
| ATOM | 1319 | CA | MET | A | 844 | 5.005 | −4.418 | 44.143 | 1.00 | 19.24 | A |
| ATOM | 1320 | CB | MET | A | 844 | 6.454 | −4.032 | 43.832 | 1.00 | 19.91 | A |
| ATOM | 1321 | CG | MET | A | 844 | 6.747 | −2.542 | 43.974 | 1.00 | 19.06 | A |
| ATOM | 1322 | SD | MET | A | 844 | 8.449 | −2.108 | 43.505 | 1.00 | 21.31 | A |
| ATOM | 1323 | CE | MET | A | 844 | 8.364 | −0.338 | 43.669 | 1.00 | 16.72 | A |
| ATOM | 1324 | C | MET | A | 844 | 4.064 | −3.703 | 43.172 | 1.00 | 18.33 | A |
| ATOM | 1325 | O | MET | A | 844 | 3.332 | −2.793 | 43.558 | 1.00 | 17.42 | A |
| ATOM | 1326 | N | ARG | A | 845 | 4.087 | −4.121 | 41.910 | 1.00 | 18.70 | A |
| ATOM | 1327 | CA | ARG | A | 845 | 3.230 | −3.511 | 40.894 | 1.00 | 19.90 | A |
| ATOM | 1328 | CB | ARG | A | 845 | 3.474 | −4.180 | 39.539 | 1.00 | 20.02 | A |
| ATOM | 1329 | CG | ARG | A | 845 | 2.649 | −3.614 | 38.385 | 1.00 | 21.73 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1330 | CD | ARG | A | 845 | 3.201 | −4.107 | 37.053 | 1.00 | 24.38 | A |
| ATOM | 1331 | NE | ARG | A | 845 | 2.496 | −3.542 | 35.903 | 1.00 | 28.68 | A |
| ATOM | 1332 | CZ | ARG | A | 845 | 1.308 | −3.950 | 35.474 | 1.00 | 29.80 | A |
| ATOM | 1333 | NH1 | ARG | A | 845 | 0.677 | −4.939 | 36.096 | 1.00 | 31.71 | A |
| ATOM | 1334 | NH2 | ARG | A | 845 | 0.750 | −3.369 | 34.419 | 1.00 | 32.30 | A |
| ATOM | 1335 | C | ARG | A | 845 | 1.754 | −3.631 | 41.284 | 1.00 | 19.74 | A |
| ATOM | 1336 | O | ARG | A | 845 | 1.004 | −2.657 | 41.227 | 1.00 | 18.83 | A |
| ATOM | 1337 | N | SER | A | 846 | 1.341 | −4.824 | 41.692 | 1.00 | 18.87 | A |
| ATOM | 1338 | CA | SER | A | 846 | −0.044 | −5.025 | 42.083 | 1.00 | 19.72 | A |
| ATOM | 1339 | CB | SER | A | 846 | −0.275 | −6.491 | 42.452 | 1.00 | 21.67 | A |
| ATOM | 1340 | OG | SER | A | 846 | −0.127 | −7.322 | 41.306 | 1.00 | 21.71 | A |
| ATOM | 1341 | C | SER | A | 846 | −0.420 | −4.107 | 43.247 | 1.00 | 20.41 | A |
| ATOM | 1342 | O | SER | A | 846 | −1.524 | −3.563 | 43.291 | 1.00 | 19.34 | A |
| ATOM | 1343 | N | SER | A | 847 | 0.506 | −3.923 | 44.184 | 1.00 | 19.04 | A |
| ATOM | 1344 | CA | SER | A | 847 | 0.247 | −3.063 | 45.329 | 1.00 | 18.35 | A |
| ATOM | 1345 | CB | SER | A | 847 | 1.408 | −3.137 | 46.323 | 1.00 | 20.48 | A |
| ATOM | 1346 | OG | SER | A | 847 | 1.220 | −2.210 | 47.372 | 1.00 | 24.25 | A |
| ATOM | 1347 | C | SER | A | 847 | 0.016 | −1.612 | 44.918 | 1.00 | 17.69 | A |
| ATOM | 1348 | O | SER | A | 847 | −0.853 | −0.938 | 45.465 | 1.00 | 16.70 | A |
| ATOM | 1349 | N | TYR | A | 848 | 0.794 | −1.120 | 43.960 | 1.00 | 16.16 | A |
| ATOM | 1350 | CA | TYR | A | 848 | 0.615 | 0.258 | 43.525 | 1.00 | 16.48 | A |
| ATOM | 1351 | CB | TYR | A | 848 | 1.873 | 0.740 | 42.804 | 1.00 | 16.12 | A |
| ATOM | 1352 | CG | TYR | A | 848 | 2.954 | 1.112 | 43.796 | 1.00 | 15.32 | A |
| ATOM | 1353 | CD1 | TYR | A | 848 | 2.862 | 2.292 | 44.541 | 1.00 | 15.55 | A |
| ATOM | 1354 | CE1 | TYR | A | 848 | 3.817 | 2.616 | 45.507 | 1.00 | 15.99 | A |
| ATOM | 1355 | CD2 | TYR | A | 848 | 4.031 | 0.264 | 44.040 | 1.00 | 16.08 | A |
| ATOM | 1356 | CE2 | TYR | A | 848 | 4.993 | 0.579 | 45.005 | 1.00 | 15.10 | A |
| ATOM | 1357 | CZ | TYR | A | 848 | 4.878 | 1.756 | 45.733 | 1.00 | 17.33 | A |
| ATOM | 1358 | OH | TYR | A | 848 | 5.825 | 2.076 | 46.682 | 1.00 | 16.56 | A |
| ATOM | 1359 | C | TYR | A | 848 | −0.643 | 0.428 | 42.674 | 1.00 | 16.19 | A |
| ATOM | 1360 | O | TYR | A | 848 | −1.233 | 1.509 | 42.636 | 1.00 | 16.16 | A |
| ATOM | 1361 | N | ILE | A | 849 | −1.060 | −0.640 | 42.003 | 1.00 | 16.12 | A |
| ATOM | 1362 | CA | ILE | A | 849 | −2.286 | −0.588 | 41.209 | 1.00 | 17.53 | A |
| ATOM | 1363 | CB | ILE | A | 849 | −2.487 | −1.883 | 40.375 | 1.00 | 16.60 | A |
| ATOM | 1364 | CG2 | ILE | A | 849 | −3.915 | −1.928 | 39.806 | 1.00 | 11.46 | A |
| ATOM | 1365 | CG1 | ILE | A | 849 | −1.443 | −1.943 | 39.255 | 1.00 | 16.24 | A |
| ATOM | 1366 | CD1 | ILE | A | 849 | −1.505 | −3.204 | 38.413 | 1.00 | 17.37 | A |
| ATOM | 1367 | C | ILE | A | 849 | −3.419 | −0.459 | 42.232 | 1.00 | 17.52 | A |
| ATOM | 1368 | O | ILE | A | 849 | −4.350 | 0.331 | 42.062 | 1.00 | 19.29 | A |
| ATOM | 1369 | N | ARG | A | 850 | −3.327 | −1.237 | 43.306 | 1.00 | 18.62 | A |
| ATOM | 1370 | CA | ARG | A | 850 | −4.337 | −1.179 | 44.356 | 1.00 | 19.04 | A |
| ATOM | 1371 | CB | ARG | A | 850 | −4.081 | −2.252 | 45.425 | 1.00 | 17.63 | A |
| ATOM | 1372 | CG | ARG | A | 850 | −4.325 | −3.677 | 44.942 | 1.00 | 20.04 | A |
| ATOM | 1373 | CD | ARG | A | 850 | −4.508 | −4.651 | 46.104 | 1.00 | 19.34 | A |
| ATOM | 1374 | NE | ARG | A | 850 | −3.302 | −4.816 | 46.905 | 1.00 | 21.22 | A |
| ATOM | 1375 | CZ | ARG | A | 850 | −2.261 | −5.569 | 46.558 | 1.00 | 23.77 | A |
| ATOM | 1376 | NH1 | ARG | A | 850 | −2.266 | −6.246 | 45.413 | 1.00 | 20.56 | A |
| ATOM | 1377 | NH2 | ARG | A | 850 | −1.202 | −5.641 | 47.360 | 1.00 | 23.31 | A |
| ATOM | 1378 | C | ARG | A | 850 | −4.333 | 0.206 | 45.002 | 1.00 | 18.72 | A |
| ATOM | 1379 | O | ARG | A | 850 | −5.384 | 0.717 | 45.410 | 1.00 | 17.53 | A |
| ATOM | 1380 | N | GLU | A | 851 | −3.158 | 0.825 | 45.080 | 1.00 | 17.58 | A |
| ATOM | 1381 | CA | GLU | A | 851 | −3.049 | 2.154 | 45.687 | 1.00 | 16.80 | A |
| ATOM | 1382 | CB | GLU | A | 851 | −1.580 | 2.476 | 45.987 | 1.00 | 17.63 | A |
| ATOM | 1383 | CG | GLU | A | 851 | −1.378 | 3.485 | 47.117 | 1.00 | 18.50 | A |
| ATOM | 1384 | CD | GLU | A | 851 | −1.946 | 2.995 | 48.444 | 1.00 | 17.77 | A |
| ATOM | 1385 | OE1 | GLU | A | 851 | −2.123 | 1.767 | 48.597 | 1.00 | 17.44 | A |
| ATOM | 1386 | OE2 | GLU | A | 851 | −2.198 | 3.834 | 49.340 | 1.00 | 18.22 | A |
| ATOM | 1387 | C | GLU | A | 851 | −3.657 | 3.222 | 44.768 | 1.00 | 16.79 | A |
| ATOM | 1388 | O | GLU | A | 851 | −4.258 | 4.200 | 45.235 | 1.00 | 20.29 | A |
| ATOM | 1389 | N | LEU | A | 852 | −3.497 | 3.040 | 43.462 | 1.00 | 15.37 | A |
| ATOM | 1390 | CA | LEU | A | 852 | −4.063 | 3.973 | 42.493 | 1.00 | 16.55 | A |
| ATOM | 1391 | CB | LEU | A | 852 | −3.708 | 3.554 | 41.063 | 1.00 | 15.51 | A |
| ATOM | 1392 | CG | LEU | A | 852 | −4.438 | 4.310 | 39.941 | 1.00 | 16.71 | A |
| ATOM | 1393 | CD1 | LEU | A | 852 | −4.188 | 5.810 | 40.076 | 1.00 | 14.65 | A |
| ATOM | 1394 | CD2 | LEU | A | 852 | −3.972 | 3.807 | 38.582 | 1.00 | 16.68 | A |
| ATOM | 1395 | C | LEU | A | 852 | −5.576 | 3.934 | 42.666 | 1.00 | 17.16 | A |
| ATOM | 1396 | O | LEU | A | 852 | −6.251 | 4.959 | 42.593 | 1.00 | 17.80 | A |
| ATOM | 1397 | N | ILE | A | 853 | −6.102 | 2.734 | 42.890 | 1.00 | 17.86 | A |
| ATOM | 1398 | CA | ILE | A | 853 | −7.535 | 2.563 | 43.078 | 1.00 | 18.24 | A |
| ATOM | 1399 | CB | ILE | A | 853 | −7.898 | 1.061 | 43.173 | 1.00 | 17.18 | A |
| ATOM | 1400 | CG2 | ILE | A | 853 | −9.353 | 0.880 | 43.639 | 1.00 | 18.01 | A |
| ATOM | 1401 | CG1 | ILE | A | 853 | −7.700 | 0.415 | 41.797 | 1.00 | 15.66 | A |
| ATOM | 1402 | CD1 | ILE | A | 853 | −7.798 | −1.103 | 41.795 | 1.00 | 15.60 | A |
| ATOM | 1403 | C | ILE | A | 853 | −8.003 | 3.322 | 44.316 | 1.00 | 18.88 | A |
| ATOM | 1404 | O | ILE | A | 853 | −9.065 | 3.946 | 44.294 | 1.00 | 20.72 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1405 | N | LYS | A | 854 | −7.207 | 3.290 | 45.385 | 1.00 | 19.21 | A |
| ATOM | 1406 | CA | LYS | A | 854 | −7.559 | 4.009 | 46.609 | 1.00 | 19.73 | A |
| ATOM | 1407 | CB | LYS | A | 854 | −6.574 | 3.697 | 47.739 | 1.00 | 19.29 | A |
| ATOM | 1408 | CG | LYS | A | 854 | −6.560 | 2.276 | 48.255 | 1.00 | 23.21 | A |
| ATOM | 1409 | CD | LYS | A | 854 | −5.459 | 2.177 | 49.304 | 1.00 | 25.78 | A |
| ATOM | 1410 | CE | LYS | A | 854 | −5.237 | 0.771 | 49.787 | 1.00 | 27.22 | A |
| ATOM | 1411 | NZ | LYS | A | 854 | −4.022 | 0.746 | 50.645 | 1.00 | 27.63 | A |
| ATOM | 1412 | C | LYS | A | 854 | −7.530 | 5.517 | 46.352 | 1.00 | 18.40 | A |
| ATOM | 1413 | O | LYS | A | 854 | −8.353 | 6.267 | 46.882 | 1.00 | 17.47 | A |
| ATOM | 1414 | N | ALA | A | 855 | −6.559 | 5.956 | 45.554 | 1.00 | 18.32 | A |
| ATOM | 1415 | CA | ALA | A | 855 | −6.414 | 7.371 | 45.216 | 1.00 | 19.46 | A |
| ATOM | 1416 | CB | ALA | A | 855 | −5.177 | 7.574 | 44.332 | 1.00 | 18.11 | A |
| ATOM | 1417 | C | ALA | A | 855 | −7.668 | 7.854 | 44.486 | 1.00 | 20.08 | A |
| ATOM | 1418 | O | ALA | A | 855 | −8.194 | 8.931 | 44.771 | 1.00 | 20.31 | A |
| ATOM | 1419 | N | ILE | A | 856 | −8.138 | 7.054 | 43.535 | 1.00 | 21.87 | A |
| ATOM | 1420 | CA | ILE | A | 856 | −9.341 | 7.393 | 42.779 | 1.00 | 22.21 | A |
| ATOM | 1421 | CB | ILE | A | 856 | −9.663 | 6.312 | 41.720 | 1.00 | 21.32 | A |
| ATOM | 1422 | CG2 | ILE | A | 856 | −11.043 | 6.574 | 41.106 | 1.00 | 22.81 | A |
| ATOM | 1423 | CG1 | ILE | A | 856 | −8.591 | 6.318 | 40.626 | 1.00 | 21.10 | A |
| ATOM | 1424 | CD1 | ILE | A | 856 | −8.721 | 5.169 | 39.625 | 1.00 | 17.78 | A |
| ATOM | 1425 | C | ILE | A | 856 | −10.525 | 7.495 | 43.739 | 1.00 | 23.75 | A |
| ATOM | 1426 | O | ILE | A | 856 | −11.333 | 8.417 | 43.651 | 1.00 | 23.51 | A |
| ATOM | 1427 | N | GLY | A | 857 | −10.617 | 6.539 | 44.657 | 1.00 | 24.69 | A |
| ATOM | 1428 | CA | GLY | A | 857 | −11.712 | 6.531 | 45.611 | 1.00 | 25.96 | A |
| ATOM | 1429 | C | GLY | A | 857 | −11.791 | 7.754 | 46.508 | 1.00 | 27.36 | A |
| ATOM | 1430 | O | GLY | A | 857 | −12.818 | 7.993 | 47.145 | 1.00 | 25.78 | A |
| ATOM | 1431 | N | LEU | A | 858 | −10.713 | 8.533 | 46.566 | 1.00 | 28.12 | A |
| ATOM | 1432 | CA | LEU | A | 858 | −10.687 | 9.733 | 47.400 | 1.00 | 29.63 | A |
| ATOM | 1433 | CB | LEU | A | 858 | −9.275 | 10.330 | 47.437 | 1.00 | 28.28 | A |
| ATOM | 1434 | CG | LEU | A | 858 | −8.196 | 9.521 | 48.153 | 1.00 | 27.33 | A |
| ATOM | 1435 | CD1 | LEU | A | 858 | −6.867 | 10.264 | 48.070 | 1.00 | 27.66 | A |
| ATOM | 1436 | CD2 | LEU | A | 858 | −8.611 | 9.294 | 49.606 | 1.00 | 27.32 | A |
| ATOM | 1437 | C | LEU | A | 858 | −11.663 | 10.807 | 46.921 | 1.00 | 32.53 | A |
| ATOM | 1438 | O | LEU | A | 858 | −12.139 | 11.621 | 47.714 | 1.00 | 31.16 | A |
| ATOM | 1439 | N | ARG | A | 859 | −11.956 | 10.816 | 45.626 | 1.00 | 35.00 | A |
| ATOM | 1440 | CA | ARG | A | 859 | −12.864 | 11.814 | 45.076 | 1.00 | 40.11 | A |
| ATOM | 1441 | CB | ARG | A | 859 | −12.079 | 12.810 | 44.218 | 1.00 | 41.59 | A |
| ATOM | 1442 | CG | ARG | A | 859 | −10.950 | 13.477 | 44.983 | 1.00 | 45.19 | A |
| ATOM | 1443 | CD | ARG | A | 859 | −10.168 | 14.479 | 44.149 | 1.00 | 46.94 | A |
| ATOM | 1444 | NE | ARG | A | 859 | −9.060 | 15.024 | 44.929 | 1.00 | 49.30 | A |
| ATOM | 1445 | CZ | ARG | A | 859 | −8.256 | 16.000 | 44.524 | 1.00 | 50.75 | A |
| ATOM | 1446 | NH1 | ARG | A | 859 | −8.426 | 16.560 | 43.333 | 1.00 | 52.23 | A |
| ATOM | 1447 | NH2 | ARG | A | 859 | −7.278 | 16.418 | 45.317 | 1.00 | 50.68 | A |
| ATOM | 1448 | C | ARG | A | 859 | −13.964 | 11.169 | 44.251 | 1.00 | 43.10 | A |
| ATOM | 1449 | O | ARG | A | 859 | −15.145 | 11.469 | 44.429 | 1.00 | 43.32 | A |
| ATOM | 1450 | N | GLN | A | 860 | −13.568 | 10.282 | 43.346 | 1.00 | 45.83 | A |
| ATOM | 1451 | CA | GLN | A | 860 | −14.521 | 9.592 | 42.493 | 1.00 | 48.83 | A |
| ATOM | 1452 | CB | GLN | A | 860 | −13.782 | 8.786 | 41.424 | 1.00 | 49.90 | A |
| ATOM | 1453 | CG | GLN | A | 860 | −12.820 | 9.633 | 40.604 | 1.00 | 50.95 | A |
| ATOM | 1454 | CD | GLN | A | 860 | −13.514 | 10.785 | 39.901 | 1.00 | 51.85 | A |
| ATOM | 1455 | OE1 | GLN | A | 860 | −12.874 | 11.756 | 39.498 | 1.00 | 52.01 | A |
| ATOM | 1456 | NE2 | GLN | A | 860 | −14.829 | 10.677 | 39.742 | 1.00 | 52.02 | A |
| ATOM | 1457 | C | GLN | A | 860 | −15.386 | 8.682 | 43.346 | 1.00 | 50.16 | A |
| ATOM | 1458 | O | GLN | A | 860 | −15.055 | 7.519 | 43.580 | 1.00 | 51.05 | A |
| ATOM | 1459 | N | LYS | A | 861 | −16.496 | 9.235 | 43.821 | 1.00 | 50.99 | A |
| ATOM | 1460 | CA | LYS | A | 861 | −17.425 | 8.497 | 44.657 | 1.00 | 51.23 | A |
| ATOM | 1461 | CB | LYS | A | 861 | −18.081 | 9.450 | 45.657 | 1.00 | 52.22 | A |
| ATOM | 1462 | CG | LYS | A | 861 | −17.072 | 10.173 | 46.543 | 1.00 | 53.62 | A |
| ATOM | 1463 | CD | LYS | A | 861 | −17.738 | 11.203 | 47.441 | 1.00 | 56.57 | A |
| ATOM | 1464 | CE | LYS | A | 861 | −18.380 | 12.322 | 46.629 | 1.00 | 57.51 | A |
| ATOM | 1465 | NZ | LYS | A | 861 | −19.063 | 13.320 | 47.501 | 1.00 | 57.72 | A |
| ATOM | 1466 | C | LYS | A | 861 | −18.469 | 7.844 | 43.763 | 1.00 | 50.75 | A |
| ATOM | 1467 | O | LYS | A | 861 | −19.079 | 8.499 | 42.917 | 1.00 | 51.25 | A |
| ATOM | 1468 | N | GLY | A | 862 | −18.660 | 6.544 | 43.950 | 1.00 | 48.78 | A |
| ATOM | 1469 | CA | GLY | A | 862 | −19.614 | 5.815 | 43.139 | 1.00 | 46.59 | A |
| ATOM | 1470 | C | GLY | A | 862 | −18.891 | 4.728 | 42.371 | 1.00 | 45.09 | A |
| ATOM | 1471 | O | GLY | A | 862 | −17.832 | 4.966 | 41.789 | 1.00 | 42.61 | A |
| ATOM | 1472 | N | VAL | A | 863 | −19.464 | 3.532 | 42.367 | 1.00 | 43.94 | A |
| ATOM | 1473 | CA | VAL | A | 863 | −18.859 | 2.401 | 41.678 | 1.00 | 44.09 | A |
| ATOM | 1474 | CB | VAL | A | 863 | −19.721 | 1.130 | 41.853 | 1.00 | 44.83 | A |
| ATOM | 1475 | CG1 | VAL | A | 863 | −19.897 | 0.829 | 43.334 | 1.00 | 46.10 | A |
| ATOM | 1476 | CG2 | VAL | A | 863 | −21.074 | 1.319 | 41.193 | 1.00 | 45.96 | A |
| ATOM | 1477 | C | VAL | A | 863 | −18.624 | 2.641 | 40.186 | 1.00 | 42.90 | A |
| ATOM | 1478 | O | VAL | A | 863 | −17.542 | 2.357 | 39.671 | 1.00 | 43.15 | A |
| ATOM | 1479 | N | VAL | A | 864 | −19.628 | 3.168 | 39.493 | 1.00 | 40.87 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1480 | CA | VAL | A | 864 | −19.506 | 3.414 | 38.061 | 1.00 | 39.53 | A |
| ATOM | 1481 | CB | VAL | A | 864 | −20.878 | 3.775 | 37.430 | 1.00 | 39.71 | A |
| ATOM | 1482 | CG1 | VAL | A | 864 | −21.395 | 5.075 | 38.002 | 1.00 | 40.62 | A |
| ATOM | 1483 | CG2 | VAL | A | 864 | −20.745 | 3.874 | 35.921 | 1.00 | 41.26 | A |
| ATOM | 1484 | C | VAL | A | 864 | −18.500 | 4.519 | 37.748 | 1.00 | 37.88 | A |
| ATOM | 1485 | O | VAL | A | 864 | −17.720 | 4.403 | 36.806 | 1.00 | 37.34 | A |
| ATOM | 1486 | N | SER | A | 865 | −18.518 | 5.585 | 38.540 | 1.00 | 35.74 | A |
| ATOM | 1487 | CA | SER | A | 865 | −17.598 | 6.696 | 38.338 | 1.00 | 35.39 | A |
| ATOM | 1488 | CB | SER | A | 865 | −17.972 | 7.865 | 39.251 | 1.00 | 37.79 | A |
| ATOM | 1489 | OG | SER | A | 865 | −17.071 | 8.943 | 39.081 | 1.00 | 41.84 | A |
| ATOM | 1490 | C | SER | A | 865 | −16.153 | 6.283 | 38.614 | 1.00 | 33.45 | A |
| ATOM | 1491 | O | SER | A | 865 | −15.262 | 6.529 | 37.800 | 1.00 | 31.58 | A |
| ATOM | 1492 | N | SER | A | 866 | −15.927 | 5.654 | 39.764 | 1.00 | 30.19 | A |
| ATOM | 1493 | CA | SER | A | 866 | −14.584 | 5.224 | 40.136 | 1.00 | 29.83 | A |
| ATOM | 1494 | CB | SER | A | 866 | −14.567 | 4.714 | 41.584 | 1.00 | 30.55 | A |
| ATOM | 1495 | OG | SER | A | 866 | −15.330 | 3.528 | 41.733 | 1.00 | 35.07 | A |
| ATOM | 1496 | C | SER | A | 866 | −14.073 | 4.142 | 39.186 | 1.00 | 28.90 | A |
| ATOM | 1497 | O | SER | A | 866 | −12.871 | 4.046 | 38.925 | 1.00 | 26.65 | A |
| ATOM | 1498 | N | SER | A | 867 | −14.991 | 3.338 | 38.661 | 1.00 | 28.37 | A |
| ATOM | 1499 | CA | SER | A | 867 | −14.634 | 2.268 | 37.732 | 1.00 | 30.83 | A |
| ATOM | 1500 | CB | SER | A | 867 | −15.815 | 1.313 | 37.549 | 1.00 | 32.58 | A |
| ATOM | 1501 | OG | SER | A | 867 | −15.419 | 0.156 | 36.834 | 1.00 | 39.29 | A |
| ATOM | 1502 | C | SER | A | 867 | −14.214 | 2.845 | 36.376 | 1.00 | 30.15 | A |
| ATOM | 1503 | O | SER | A | 867 | −13.253 | 2.376 | 35.760 | 1.00 | 29.63 | A |
| ATOM | 1504 | N | GLN | A | 868 | −14.940 | 3.857 | 35.912 | 1.00 | 29.59 | A |
| ATOM | 1505 | CA | GLN | A | 868 | −14.616 | 4.501 | 34.643 | 1.00 | 30.50 | A |
| ATOM | 1506 | CB | GLN | A | 868 | −15.735 | 5.459 | 34.225 | 1.00 | 33.42 | A |
| ATOM | 1507 | CG | GLN | A | 868 | −17.027 | 4.768 | 33.798 | 1.00 | 40.79 | A |
| ATOM | 1508 | CD | GLN | A | 868 | −18.021 | 5.727 | 33.160 | 1.00 | 44.38 | A |
| ATOM | 1509 | OE1 | GLN | A | 868 | −17.714 | 6.387 | 32.164 | 1.00 | 48.14 | A |
| ATOM | 1510 | NE2 | GLN | A | 868 | −19.219 | 5.806 | 33.729 | 1.00 | 47.00 | A |
| ATOM | 1511 | C | GLN | A | 868 | −13.306 | 5.279 | 34.780 | 1.00 | 28.76 | A |
| ATOM | 1512 | O | GLN | A | 868 | −12.501 | 5.339 | 33.847 | 1.00 | 28.37 | A |
| ATOM | 1513 | N | ARG | A | 869 | −13.106 | 5.875 | 35.952 | 1.00 | 25.54 | A |
| ATOM | 1514 | CA | ARG | A | 869 | −11.904 | 6.651 | 36.239 | 1.00 | 23.93 | A |
| ATOM | 1515 | CB | ARG | A | 869 | −12.001 | 7.257 | 37.643 | 1.00 | 24.14 | A |
| ATOM | 1516 | CG | ARG | A | 869 | −10.842 | 8.165 | 38.026 | 1.00 | 24.38 | A |
| ATOM | 1517 | CD | ARG | A | 869 | −10.865 | 9.446 | 37.230 | 1.00 | 26.98 | A |
| ATOM | 1518 | NE | ARG | A | 869 | −9.901 | 10.419 | 37.734 | 1.00 | 26.60 | A |
| ATOM | 1519 | CZ | ARG | A | 869 | −9.722 | 11.624 | 37.209 | 1.00 | 27.32 | A |
| ATOM | 1520 | NH1 | ARG | A | 869 | −10.443 | 12.002 | 36.159 | 1.00 | 27.79 | A |
| ATOM | 1521 | NH2 | ARG | A | 869 | −8.831 | 12.453 | 37.734 | 1.00 | 26.20 | A |
| ATOM | 1522 | C | ARG | A | 869 | −10.667 | 5.760 | 36.142 | 1.00 | 21.71 | A |
| ATOM | 1523 | O | ARG | A | 869 | −9.640 | 6.159 | 35.589 | 1.00 | 21.09 | A |
| ATOM | 1524 | N | PHE | A | 870 | −10.767 | 4.553 | 36.689 | 1.00 | 20.52 | A |
| ATOM | 1525 | CA | PHE | A | 870 | −9.657 | 3.607 | 36.649 | 1.00 | 21.95 | A |
| ATOM | 1526 | CB | PHE | A | 870 | −10.030 | 2.313 | 37.380 | 1.00 | 23.09 | A |
| ATOM | 1527 | CG | PHE | A | 870 | −8.945 | 1.273 | 37.361 | 1.00 | 23.44 | A |
| ATOM | 1528 | CD1 | PHE | A | 870 | −7.878 | 1.342 | 38.252 | 1.00 | 24.31 | A |
| ATOM | 1529 | CD2 | PHE | A | 870 | −8.975 | 0.237 | 36.432 | 1.00 | 23.49 | A |
| ATOM | 1530 | CE1 | PHE | A | 870 | −6.858 | 0.391 | 38.215 | 1.00 | 23.31 | A |
| ATOM | 1531 | CE2 | PHE | A | 870 | −7.960 | −0.717 | 36.388 | 1.00 | 23.17 | A |
| ATOM | 1532 | CZ | PHE | A | 870 | −6.902 | −0.639 | 37.281 | 1.00 | 22.88 | A |
| ATOM | 1533 | C | PHE | A | 870 | −9.316 | 3.290 | 35.192 | 1.00 | 22.30 | A |
| ATOM | 1534 | O | PHE | A | 870 | −8.145 | 3.189 | 34.818 | 1.00 | 19.13 | A |
| ATOM | 1535 | N | TYR | A | 871 | −10.346 | 3.131 | 34.367 | 1.00 | 22.40 | A |
| ATOM | 1536 | CA | TYR | A | 871 | −10.132 | 2.835 | 32.957 | 1.00 | 23.09 | A |
| ATOM | 1537 | CB | TYR | A | 871 | −11.466 | 2.628 | 32.234 | 1.00 | 25.44 | A |
| ATOM | 1538 | CG | TYR | A | 871 | −11.291 | 2.436 | 30.743 | 1.00 | 29.50 | A |
| ATOM | 1539 | CD1 | TYR | A | 871 | −10.944 | 1.192 | 30.216 | 1.00 | 31.45 | A |
| ATOM | 1540 | CE1 | TYR | A | 871 | −10.709 | 1.027 | 28.846 | 1.00 | 34.54 | A |
| ATOM | 1541 | CD2 | TYR | A | 871 | −11.404 | 3.516 | 29.865 | 1.00 | 30.74 | A |
| ATOM | 1542 | CE2 | TYR | A | 871 | −11.168 | 3.362 | 28.499 | 1.00 | 33.34 | A |
| ATOM | 1543 | CZ | TYR | A | 871 | −10.821 | 2.117 | 27.998 | 1.00 | 34.38 | A |
| ATOM | 1544 | OH | TYR | A | 871 | −10.579 | 1.966 | 26.650 | 1.00 | 38.83 | A |
| ATOM | 1545 | C | TYR | A | 871 | −9.388 | 3.986 | 32.285 | 1.00 | 21.64 | A |
| ATOM | 1546 | O | TYR | A | 871 | −8.399 | 3.778 | 31.587 | 1.00 | 20.89 | A |
| ATOM | 1547 | N | GLN | A | 872 | −9.881 | 5.200 | 32.501 | 1.00 | 21.08 | A |
| ATOM | 1548 | CA | GLN | A | 872 | −9.295 | 6.394 | 31.899 | 1.00 | 21.63 | A |
| ATOM | 1549 | CB | GLN | A | 872 | −10.088 | 7.627 | 32.309 | 1.00 | 23.97 | A |
| ATOM | 1550 | CG | GLN | A | 872 | −11.548 | 7.594 | 31.907 | 1.00 | 29.50 | A |
| ATOM | 1551 | CD | GLN | A | 872 | −12.270 | 8.844 | 32.344 | 1.00 | 32.02 | A |
| ATOM | 1552 | OE1 | GLN | A | 872 | −12.344 | 9.148 | 33.536 | 1.00 | 35.43 | A |
| ATOM | 1553 | NE2 | GLN | A | 872 | −12.800 | 9.585 | 31.381 | 1.00 | 36.11 | A |
| ATOM | 1554 | C | GLN | A | 872 | −7.833 | 6.626 | 32.263 | 1.00 | 20.95 | A |

TABLE 2-continued

Structure coordinates (Table discloses SEQ ID NO: 6 twice)

| | # | Name | Res. | Chain | Res # | X | Y | Z | occ | B | SegID |
|---|---|---|---|---|---|---|---|---|---|---|---|
| ATOM | 1555 | O | GLN | A | 872 | −6.998 | 6.879 | 31.392 | 1.00 | 17.56 | A |
| ATOM | 1556 | N | LEU | A | 873 | −7.533 | 6.557 | 33.553 | 1.00 | 18.12 | A |
| ATOM | 1557 | CA | LEU | A | 873 | −6.175 | 6.791 | 34.007 | 1.00 | 19.84 | A |
| ATOM | 1558 | CB | LEU | A | 873 | −6.145 | 6.878 | 35.538 | 1.00 | 19.94 | A |
| ATOM | 1559 | CG | LEU | A | 873 | −6.994 | 8.036 | 36.083 | 1.00 | 20.53 | A |
| ATOM | 1560 | CD1 | LEU | A | 873 | −6.851 | 8.145 | 37.598 | 1.00 | 20.93 | A |
| ATOM | 1561 | CD2 | LEU | A | 873 | −6.551 | 9.336 | 35.417 | 1.00 | 23.05 | A |
| ATOM | 1562 | C | LEU | A | 873 | −5.221 | 5.724 | 33.500 | 1.00 | 20.65 | A |
| ATOM | 1563 | O | LEU | A | 873 | −4.110 | 6.033 | 33.062 | 1.00 | 19.40 | A |
| ATOM | 1564 | N | THR | A | 874 | −5.656 | 4.468 | 33.542 | 1.00 | 20.04 | A |
| ATOM | 1565 | CA | THR | A | 874 | −4.811 | 3.382 | 33.077 | 1.00 | 20.77 | A |
| ATOM | 1566 | CB | THR | A | 874 | −5.361 | 2.017 | 33.538 | 1.00 | 20.85 | A |
| ATOM | 1567 | OG1 | THR | A | 874 | −6.725 | 1.878 | 33.126 | 1.00 | 21.70 | A |
| ATOM | 1568 | CG2 | THR | A | 874 | −5.279 | 1.905 | 35.062 | 1.00 | 20.63 | A |
| ATOM | 1569 | C | THR | A | 874 | −4.689 | 3.425 | 31.553 | 1.00 | 22.66 | A |
| ATOM | 1570 | O | THR | A | 874 | −3.623 | 3.132 | 30.992 | 1.00 | 23.26 | A |
| ATOM | 1571 | N | LYS | A | 875 | −5.773 | 3.806 | 30.885 | 1.00 | 22.44 | A |
| ATOM | 1572 | CA | LYS | A | 875 | −5.752 | 3.915 | 29.431 | 1.00 | 23.45 | A |
| ATOM | 1573 | CB | LYS | A | 875 | −7.129 | 4.316 | 28.890 | 1.00 | 24.25 | A |
| ATOM | 1574 | CG | LYS | A | 875 | −7.208 | 4.331 | 27.369 | 1.00 | 27.73 | A |
| ATOM | 1575 | CD | LYS | A | 875 | −6.942 | 2.944 | 26.792 | 1.00 | 30.15 | A |
| ATOM | 1576 | CE | LYS | A | 875 | −6.923 | 2.964 | 25.270 | 1.00 | 31.96 | A |
| ATOM | 1577 | NZ | LYS | A | 875 | −6.757 | 1.594 | 24.705 | 1.00 | 35.36 | A |
| ATOM | 1578 | C | LYS | A | 875 | −4.722 | 4.976 | 29.047 | 1.00 | 22.41 | A |
| ATOM | 1579 | O | LYS | A | 875 | −3.984 | 4.810 | 28.079 | 1.00 | 23.26 | A |
| ATOM | 1580 | N | LEU | A | 876 | −4.679 | 6.066 | 29.813 | 1.00 | 22.49 | A |
| ATOM | 1581 | CA | LEU | A | 876 | −3.728 | 7.149 | 29.565 | 1.00 | 22.37 | A |
| ATOM | 1582 | CB | LEU | A | 876 | −3.914 | 8.264 | 30.606 | 1.00 | 22.36 | A |
| ATOM | 1583 | CG | LEU | A | 876 | −3.128 | 9.579 | 30.483 | 1.00 | 24.28 | A |
| ATOM | 1584 | CD1 | LEU | A | 876 | −3.717 | 10.604 | 31.439 | 1.00 | 24.81 | A |
| ATOM | 1585 | CD2 | LEU | A | 876 | −1.654 | 9.362 | 30.796 | 1.00 | 23.97 | A |
| ATOM | 1586 | C | LEU | A | 876 | −2.305 | 6.589 | 29.640 | 1.00 | 22.30 | A |
| ATOM | 1587 | O | LEU | A | 876 | −1.469 | 6.875 | 28.777 | 1.00 | 19.88 | A |
| ATOM | 1588 | N | LEU | A | 877 | −2.033 | 5.788 | 30.668 | 1.00 | 20.81 | A |
| ATOM | 1589 | CA | LEU | A | 877 | −0.708 | 5.198 | 30.814 | 1.00 | 20.51 | A |
| ATOM | 1590 | CB | LEU | A | 877 | −0.609 | 4.409 | 32.125 | 1.00 | 18.01 | A |
| ATOM | 1591 | CG | LEU | A | 877 | −0.722 | 5.272 | 33.391 | 1.00 | 19.57 | A |
| ATOM | 1592 | CD1 | LEU | A | 877 | −0.644 | 4.381 | 34.623 | 1.00 | 19.95 | A |
| ATOM | 1593 | CD2 | LEU | A | 877 | 0.397 | 6.318 | 33.422 | 1.00 | 19.10 | A |
| ATOM | 1594 | C | LEU | A | 877 | −0.404 | 4.300 | 29.614 | 1.00 | 20.50 | A |
| ATOM | 1595 | O | LEU | A | 877 | 0.714 | 4.322 | 29.085 | 1.00 | 17.23 | A |
| ATOM | 1596 | N | ASP | A | 878 | −1.389 | 3.518 | 29.177 | 1.00 | 20.16 | A |
| ATOM | 1597 | CA | ASP | A | 878 | −1.191 | 2.651 | 28.014 | 1.00 | 21.77 | A |
| ATOM | 1598 | CB | ASP | A | 878 | −2.474 | 1.885 | 27.657 | 1.00 | 22.61 | A |
| ATOM | 1599 | CG | ASP | A | 878 | −2.712 | 0.658 | 28.530 | 1.00 | 24.90 | A |
| ATOM | 1600 | OD1 | ASP | A | 878 | −1.883 | 0.338 | 29.408 | 1.00 | 20.69 | A |
| ATOM | 1601 | OD2 | ASP | A | 878 | −3.756 | −0.002 | 28.323 | 1.00 | 27.24 | A |
| ATOM | 1602 | C | ASP | A | 878 | −0.802 | 3.518 | 26.813 | 1.00 | 21.54 | A |
| ATOM | 1603 | O | ASP | A | 878 | 0.132 | 3.194 | 26.076 | 1.00 | 22.58 | A |
| ATOM | 1604 | N | ASN | A | 879 | −1.524 | 4.620 | 26.625 | 1.00 | 21.91 | A |
| ATOM | 1605 | CA | ASN | A | 879 | −1.275 | 5.529 | 25.509 | 1.00 | 24.62 | A |
| ATOM | 1606 | CB | ASN | A | 879 | −2.361 | 6.612 | 25.432 | 1.00 | 23.63 | A |
| ATOM | 1607 | CG | ASN | A | 879 | −3.730 | 6.054 | 25.063 | 1.00 | 26.89 | A |
| ATOM | 1608 | OD1 | ASN | A | 879 | −3.840 | 4.973 | 24.486 | 1.00 | 26.87 | A |
| ATOM | 1609 | ND2 | ASN | A | 879 | −4.781 | 6.807 | 25.381 | 1.00 | 26.39 | A |
| ATOM | 1610 | C | ASN | A | 879 | 0.098 | 6.203 | 25.549 | 1.00 | 25.62 | A |
| ATOM | 1611 | O | ASN | A | 879 | 0.593 | 6.658 | 24.517 | 1.00 | 26.49 | A |
| ATOM | 1612 | N | LEU | A | 880 | 0.711 | 6.276 | 26.727 | 1.00 | 24.07 | A |
| ATOM | 1613 | CA | LEU | A | 880 | 2.028 | 6.900 | 26.838 | 1.00 | 25.83 | A |
| ATOM | 1614 | CB | LEU | A | 880 | 2.456 | 7.033 | 28.298 | 1.00 | 25.52 | A |
| ATOM | 1615 | CG | LEU | A | 880 | 1.906 | 8.225 | 29.081 | 1.00 | 29.53 | A |
| ATOM | 1616 | CD1 | LEU | A | 880 | 2.583 | 8.268 | 30.450 | 1.00 | 27.82 | A |
| ATOM | 1617 | CD2 | LEU | A | 880 | 2.170 | 9.524 | 28.315 | 1.00 | 28.47 | A |
| ATOM | 1618 | C | LEU | A | 880 | 3.112 | 6.146 | 26.078 | 1.00 | 25.34 | A |
| ATOM | 1619 | O | LEU | A | 880 | 4.035 | 6.760 | 25.549 | 1.00 | 25.19 | A |
| ATOM | 1620 | N | HIS | A | 881 | 3.007 | 4.818 | 26.038 | 1.00 | 26.40 | A |
| ATOM | 1621 | CA | HIS | A | 881 | 3.987 | 3.995 | 25.335 | 1.00 | 26.00 | A |
| ATOM | 1622 | CB | HIS | A | 881 | 3.520 | 2.532 | 25.290 | 1.00 | 27.74 | A |
| ATOM | 1623 | CG | HIS | A | 881 | 3.805 | 1.765 | 26.548 | 1.00 | 29.80 | A |
| ATOM | 1624 | CD2 | HIS | A | 881 | 4.934 | 1.656 | 27.289 | 1.00 | 29.97 | A |
| ATOM | 1625 | ND1 | HIS | A | 881 | 2.866 | 0.962 | 27.162 | 1.00 | 31.29 | A |
| ATOM | 1626 | CE1 | HIS | A | 881 | 3.404 | 0.391 | 28.226 | 1.00 | 30.71 | A |
| ATOM | 1627 | NE2 | HIS | A | 881 | 4.659 | 0.796 | 28.325 | 1.00 | 32.87 | A |
| ATOM | 1628 | C | HIS | A | 881 | 4.235 | 4.508 | 23.916 | 1.00 | 26.38 | A |
| ATOM | 1629 | O | HIS | A | 881 | 5.379 | 4.641 | 23.483 | 1.00 | 25.86 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1630 | N | ASP | A | 882 | 3.159 | 4.816 | 23.203 | 1.00 | 25.87 | A |
| ATOM | 1631 | CA | ASP | A | 882 | 3.267 | 5.303 | 21.835 | 1.00 | 25.66 | A |
| ATOM | 1632 | CB | ASP | A | 882 | 1.891 | 5.273 | 21.179 | 1.00 | 31.45 | A |
| ATOM | 1633 | CG | ASP | A | 882 | 1.262 | 3.900 | 21.238 | 1.00 | 35.82 | A |
| ATOM | 1634 | OD1 | ASP | A | 882 | 1.688 | 3.017 | 20.460 | 1.00 | 37.06 | A |
| ATOM | 1635 | OD2 | ASP | A | 882 | 0.359 | 3.699 | 22.081 | 1.00 | 39.76 | A |
| ATOM | 1636 | C | ASP | A | 882 | 3.853 | 6.706 | 21.757 | 1.00 | 23.14 | A |
| ATOM | 1637 | O | ASP | A | 882 | 4.692 | 6.990 | 20.904 | 1.00 | 23.94 | A |
| ATOM | 1638 | N | LEU | A | 883 | 3.412 | 7.583 | 22.648 | 1.00 | 20.96 | A |
| ATOM | 1639 | CA | LEU | A | 883 | 3.914 | 8.950 | 22.671 | 1.00 | 20.25 | A |
| ATOM | 1640 | CB | LEU | A | 883 | 3.146 | 9.759 | 23.719 | 1.00 | 20.75 | A |
| ATOM | 1641 | CG | LEU | A | 883 | 3.408 | 11.260 | 23.836 | 1.00 | 23.11 | A |
| ATOM | 1642 | CD1 | LEU | A | 883 | 2.206 | 11.911 | 24.517 | 1.00 | 24.84 | A |
| ATOM | 1643 | CD2 | LEU | A | 883 | 4.692 | 11.525 | 24.624 | 1.00 | 24.63 | A |
| ATOM | 1644 | C | LEU | A | 883 | 5.414 | 8.925 | 22.989 | 1.00 | 19.01 | A |
| ATOM | 1645 | O | LEU | A | 883 | 6.209 | 9.615 | 22.354 | 1.00 | 16.78 | A |
| ATOM | 1646 | N | VAL | A | 884 | 5.794 | 8.116 | 23.971 | 1.00 | 18.69 | A |
| ATOM | 1647 | CA | VAL | A | 884 | 7.193 | 7.987 | 24.370 | 1.00 | 16.95 | A |
| ATOM | 1648 | CB | VAL | A | 884 | 7.301 | 7.148 | 25.666 | 1.00 | 17.81 | A |
| ATOM | 1649 | CG1 | VAL | A | 884 | 8.753 | 6.772 | 25.953 | 1.00 | 15.34 | A |
| ATOM | 1650 | CG2 | VAL | A | 884 | 6.724 | 7.954 | 26.831 | 1.00 | 15.89 | A |
| ATOM | 1651 | C | VAL | A | 884 | 8.061 | 7.377 | 23.261 | 1.00 | 17.62 | A |
| ATOM | 1652 | O | VAL | A | 884 | 9.264 | 7.631 | 23.189 | 1.00 | 17.21 | A |
| ATOM | 1653 | N | LYS | A | 885 | 7.458 | 6.585 | 22.384 | 1.00 | 18.89 | A |
| ATOM | 1654 | CA | LYS | A | 885 | 8.227 | 5.995 | 21.296 | 1.00 | 19.66 | A |
| ATOM | 1655 | CB | LYS | A | 885 | 7.388 | 4.976 | 20.532 | 1.00 | 22.16 | A |
| ATOM | 1656 | CG | LYS | A | 885 | 8.142 | 4.308 | 19.388 | 1.00 | 24.56 | A |
| ATOM | 1657 | CD | LYS | A | 885 | 7.292 | 3.222 | 18.738 | 1.00 | 27.97 | A |
| ATOM | 1658 | CE | LYS | A | 885 | 7.977 | 2.647 | 17.506 | 1.00 | 30.89 | A |
| ATOM | 1659 | NZ | LYS | A | 885 | 7.178 | 1.532 | 16.917 | 1.00 | 33.14 | A |
| ATOM | 1660 | C | LYS | A | 885 | 8.741 | 7.078 | 20.341 | 1.00 | 19.41 | A |
| ATOM | 1661 | O | LYS | A | 885 | 9.855 | 6.976 | 19.820 | 1.00 | 17.34 | A |
| ATOM | 1662 | N | GLN | A | 886 | 7.943 | 8.117 | 20.114 | 1.00 | 20.30 | A |
| ATOM | 1663 | CA | GLN | A | 886 | 8.368 | 9.208 | 19.237 | 1.00 | 20.05 | A |
| ATOM | 1664 | CB | GLN | A | 886 | 7.214 | 10.175 | 18.982 | 1.00 | 24.07 | A |
| ATOM | 1665 | CG | GLN | A | 886 | 6.098 | 9.593 | 18.119 | 1.00 | 31.54 | A |
| ATOM | 1666 | CD | GLN | A | 886 | 4.942 | 10.566 | 17.914 | 1.00 | 36.15 | A |
| ATOM | 1667 | OE1 | GLN | A | 886 | 3.995 | 10.271 | 17.188 | 1.00 | 41.20 | A |
| ATOM | 1668 | NE2 | GLN | A | 886 | 5.016 | 11.728 | 18.557 | 1.00 | 38.67 | A |
| ATOM | 1669 | C | GLN | A | 886 | 9.546 | 9.963 | 19.863 | 1.00 | 20.53 | A |
| ATOM | 1670 | O | GLN | A | 886 | 10.483 | 10.365 | 19.168 | 1.00 | 17.99 | A |
| ATOM | 1671 | N | LEU | A | 887 | 9.495 | 10.153 | 21.178 | 1.00 | 18.09 | A |
| ATOM | 1672 | CA | LEU | A | 887 | 10.568 | 10.849 | 21.880 | 1.00 | 17.27 | A |
| ATOM | 1673 | CB | LEU | A | 887 | 10.163 | 11.118 | 23.336 | 1.00 | 17.29 | A |
| ATOM | 1674 | CG | LEU | A | 887 | 8.846 | 11.886 | 23.520 | 1.00 | 19.30 | A |
| ATOM | 1675 | CD1 | LEU | A | 887 | 8.660 | 12.252 | 24.997 | 1.00 | 16.99 | A |
| ATOM | 1676 | CD2 | LEU | A | 887 | 8.850 | 13.137 | 22.661 | 1.00 | 16.70 | A |
| ATOM | 1677 | C | LEU | A | 887 | 11.835 | 9.999 | 21.825 | 1.00 | 16.42 | A |
| ATOM | 1678 | O | LEU | A | 887 | 12.927 | 10.507 | 21.574 | 1.00 | 18.79 | A |
| ATOM | 1679 | N | HIS | A | 888 | 11.678 | 8.700 | 22.048 | 1.00 | 15.31 | A |
| ATOM | 1680 | CA | HIS | A | 888 | 12.799 | 7.771 | 22.006 | 1.00 | 15.69 | A |
| ATOM | 1681 | CB | HIS | A | 888 | 12.316 | 6.343 | 22.279 | 1.00 | 13.45 | A |
| ATOM | 1682 | CG | HIS | A | 888 | 12.170 | 6.018 | 23.733 | 1.00 | 16.95 | A |
| ATOM | 1683 | CD2 | HIS | A | 888 | 12.609 | 6.662 | 24.840 | 1.00 | 16.73 | A |
| ATOM | 1684 | ND1 | HIS | A | 888 | 11.553 | 4.869 | 24.180 | 1.00 | 18.43 | A |
| ATOM | 1685 | CE1 | HIS | A | 888 | 11.622 | 4.816 | 25.498 | 1.00 | 19.06 | A |
| ATOM | 1686 | NE2 | HIS | A | 888 | 12.259 | 5.892 | 25.924 | 1.00 | 19.99 | A |
| ATOM | 1687 | C | HIS | A | 888 | 13.546 | 7.802 | 20.677 | 1.00 | 14.55 | A |
| ATOM | 1688 | O | HIS | A | 888 | 14.776 | 7.862 | 20.654 | 1.00 | 15.76 | A |
| ATOM | 1689 | N | LEU | A | 889 | 12.807 | 7.751 | 19.571 | 1.00 | 14.95 | A |
| ATOM | 1690 | CA | LEU | A | 889 | 13.426 | 7.763 | 18.247 | 1.00 | 15.66 | A |
| ATOM | 1691 | CB | LEU | A | 889 | 12.371 | 7.551 | 17.146 | 1.00 | 15.15 | A |
| ATOM | 1692 | CG | LEU | A | 889 | 12.885 | 7.571 | 15.693 | 1.00 | 16.45 | A |
| ATOM | 1693 | CD1 | LEU | A | 889 | 13.998 | 6.548 | 15.523 | 1.00 | 14.91 | A |
| ATOM | 1694 | CD2 | LEU | A | 889 | 11.751 | 7.283 | 14.712 | 1.00 | 15.91 | A |
| ATOM | 1695 | C | LEU | A | 889 | 14.171 | 9.069 | 18.000 | 1.00 | 16.20 | A |
| ATOM | 1696 | O | LEU | A | 889 | 15.296 | 9.061 | 17.498 | 1.00 | 15.72 | A |
| ATOM | 1697 | N | TYR | A | 890 | 13.544 | 10.189 | 18.353 | 1.00 | 15.89 | A |
| ATOM | 1698 | CA | TYR | A | 890 | 14.167 | 11.497 | 18.165 | 1.00 | 15.42 | A |
| ATOM | 1699 | CB | TYR | A | 890 | 13.181 | 12.612 | 18.545 | 1.00 | 16.23 | A |
| ATOM | 1700 | CG | TYR | A | 890 | 13.720 | 14.017 | 18.336 | 1.00 | 19.79 | A |
| ATOM | 1701 | CD1 | TYR | A | 890 | 14.631 | 14.580 | 19.232 | 1.00 | 17.47 | A |
| ATOM | 1702 | CE1 | TYR | A | 890 | 15.146 | 15.863 | 19.026 | 1.00 | 20.88 | A |
| ATOM | 1703 | CD2 | TYR | A | 890 | 13.336 | 14.775 | 17.225 | 1.00 | 20.09 | A |
| ATOM | 1704 | CE2 | TYR | A | 890 | 13.851 | 16.059 | 17.009 | 1.00 | 20.17 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1705 | CZ | TYR | A | 890 | 14.754 | 16.593 | 17.912 | 1.00 | 21.65 | A |
| ATOM | 1706 | OH | TYR | A | 890 | 15.283 | 17.846 | 17.694 | 1.00 | 22.11 | A |
| ATOM | 1707 | C | TYR | A | 890 | 15.432 | 11.604 | 19.022 | 1.00 | 14.92 | A |
| ATOM | 1708 | O | TYR | A | 890 | 16.451 | 12.143 | 18.584 | 1.00 | 15.02 | A |
| ATOM | 1709 | N | CYS | A | 891 | 15.355 | 11.092 | 20.246 | 1.00 | 13.56 | A |
| ATOM | 1710 | CA | CYS | A | 891 | 16.488 | 11.125 | 21.164 | 1.00 | 13.38 | A |
| ATOM | 1711 | CB | CYS | A | 891 | 16.060 | 10.621 | 22.549 | 1.00 | 15.61 | A |
| ATOM | 1712 | SG | CYS | A | 891 | 17.401 | 10.546 | 23.778 | 1.00 | 17.44 | A |
| ATOM | 1713 | C | CYS | A | 891 | 17.634 | 10.272 | 20.625 | 1.00 | 12.47 | A |
| ATOM | 1714 | O | CYS | A | 891 | 18.789 | 10.704 | 20.604 | 1.00 | 14.79 | A |
| ATOM | 1715 | N | LEU | A | 892 | 17.322 | 9.061 | 20.178 | 1.00 | 13.99 | A |
| ATOM | 1716 | CA | LEU | A | 892 | 18.366 | 8.190 | 19.646 | 1.00 | 13.42 | A |
| ATOM | 1717 | CB | LEU | A | 892 | 17.802 | 6.798 | 19.325 | 1.00 | 14.16 | A |
| ATOM | 1718 | CG | LEU | A | 892 | 18.817 | 5.779 | 18.779 | 1.00 | 16.50 | A |
| ATOM | 1719 | CD1 | LEU | A | 892 | 19.976 | 5.645 | 19.750 | 1.00 | 17.30 | A |
| ATOM | 1720 | CD2 | LEU | A | 892 | 18.146 | 4.430 | 18.564 | 1.00 | 15.85 | A |
| ATOM | 1721 | C | LEU | A | 892 | 19.035 | 8.786 | 18.408 | 1.00 | 13.65 | A |
| ATOM | 1722 | O | LEU | A | 892 | 20.259 | 8.745 | 18.286 | 1.00 | 14.68 | A |
| ATOM | 1723 | N | ASN | A | 893 | 18.244 | 9.331 | 17.486 | 1.00 | 13.74 | A |
| ATOM | 1724 | CA | ASN | A | 893 | 18.817 | 9.921 | 16.284 | 1.00 | 15.86 | A |
| ATOM | 1725 | CB | ASN | A | 893 | 17.726 | 10.436 | 15.337 | 1.00 | 18.00 | A |
| ATOM | 1726 | CG | ASN | A | 893 | 17.040 | 9.322 | 14.578 | 1.00 | 19.28 | A |
| ATOM | 1727 | OD1 | ASN | A | 893 | 17.694 | 8.407 | 14.081 | 1.00 | 20.97 | A |
| ATOM | 1728 | ND2 | ASN | A | 893 | 15.716 | 9.403 | 14.465 | 1.00 | 21.13 | A |
| ATOM | 1729 | C | ASN | A | 893 | 19.733 | 11.071 | 16.663 | 1.00 | 16.82 | A |
| ATOM | 1730 | O | ASN | A | 893 | 20.837 | 11.205 | 16.124 | 1.00 | 14.75 | A |
| ATOM | 1731 | N | THR | A | 894 | 19.273 | 11.898 | 17.600 | 1.00 | 14.78 | A |
| ATOM | 1732 | CA | THR | A | 894 | 20.061 | 13.037 | 18.046 | 1.00 | 16.39 | A |
| ATOM | 1733 | CB | THR | A | 894 | 19.258 | 13.912 | 19.033 | 1.00 | 18.69 | A |
| ATOM | 1734 | OG1 | THR | A | 894 | 18.055 | 14.371 | 18.394 | 1.00 | 18.55 | A |
| ATOM | 1735 | CG2 | THR | A | 894 | 20.091 | 15.113 | 19.484 | 1.00 | 18.34 | A |
| ATOM | 1736 | C | THR | A | 894 | 21.359 | 12.566 | 18.715 | 1.00 | 17.20 | A |
| ATOM | 1737 | O | THR | A | 894 | 22.425 | 13.153 | 18.501 | 1.00 | 15.61 | A |
| ATOM | 1738 | N | PHE | A | 895 | 21.269 | 11.501 | 19.509 | 1.00 | 14.74 | A |
| ATOM | 1739 | CA | PHE | A | 895 | 22.435 | 10.947 | 20.199 | 1.00 | 16.10 | A |
| ATOM | 1740 | CB | PHE | A | 895 | 22.004 | 9.768 | 21.080 | 1.00 | 18.24 | A |
| ATOM | 1741 | CG | PHE | A | 895 | 23.129 | 9.135 | 21.849 | 1.00 | 17.59 | A |
| ATOM | 1742 | CD1 | PHE | A | 895 | 23.674 | 9.767 | 22.964 | 1.00 | 19.36 | A |
| ATOM | 1743 | CD2 | PHE | A | 895 | 23.637 | 7.900 | 21.464 | 1.00 | 18.77 | A |
| ATOM | 1744 | CE1 | PHE | A | 895 | 24.712 | 9.173 | 23.691 | 1.00 | 19.72 | A |
| ATOM | 1745 | CE2 | PHE | A | 895 | 24.676 | 7.295 | 22.181 | 1.00 | 20.89 | A |
| ATOM | 1746 | CZ | PHE | A | 895 | 25.214 | 7.933 | 23.298 | 1.00 | 19.53 | A |
| ATOM | 1747 | C | PHE | A | 895 | 23.470 | 10.472 | 19.170 | 1.00 | 17.01 | A |
| ATOM | 1748 | O | PHE | A | 895 | 24.665 | 10.740 | 19.300 | 1.00 | 16.55 | A |
| ATOM | 1749 | N | ILE | A | 896 | 22.993 | 9.754 | 18.157 | 1.00 | 16.61 | A |
| ATOM | 1750 | CA | ILE | A | 896 | 23.843 | 9.243 | 17.084 | 1.00 | 18.06 | A |
| ATOM | 1751 | CB | ILE | A | 896 | 22.997 | 8.447 | 16.052 | 1.00 | 18.72 | A |
| ATOM | 1752 | CG2 | ILE | A | 896 | 23.783 | 8.231 | 14.758 | 1.00 | 20.23 | A |
| ATOM | 1753 | CG1 | ILE | A | 896 | 22.575 | 7.106 | 16.649 | 1.00 | 18.11 | A |
| ATOM | 1754 | CD1 | ILE | A | 896 | 21.537 | 6.382 | 15.811 | 1.00 | 19.50 | A |
| ATOM | 1755 | C | ILE | A | 896 | 24.542 | 10.394 | 16.360 | 1.00 | 18.68 | A |
| ATOM | 1756 | O | ILE | A | 896 | 25.724 | 10.310 | 16.029 | 1.00 | 19.12 | A |
| ATOM | 1757 | N | GLN | A | 897 | 23.807 | 11.477 | 16.132 | 1.00 | 17.29 | A |
| ATOM | 1758 | CA | GLN | A | 897 | 24.349 | 12.637 | 15.427 | 1.00 | 19.03 | A |
| ATOM | 1759 | CB | GLN | A | 897 | 23.305 | 13.146 | 14.427 | 1.00 | 19.67 | A |
| ATOM | 1760 | CG | GLN | A | 897 | 22.667 | 12.039 | 13.596 | 1.00 | 21.81 | A |
| ATOM | 1761 | CD | GLN | A | 897 | 21.462 | 12.510 | 12.804 | 1.00 | 22.65 | A |
| ATOM | 1762 | OE1 | GLN | A | 897 | 20.568 | 11.720 | 12.483 | 1.00 | 23.76 | A |
| ATOM | 1763 | NE2 | GLN | A | 897 | 21.434 | 13.793 | 12.476 | 1.00 | 21.56 | A |
| ATOM | 1764 | C | GLN | A | 897 | 24.743 | 13.780 | 16.366 | 1.00 | 18.17 | A |
| ATOM | 1765 | O | GLN | A | 897 | 24.892 | 14.922 | 15.925 | 1.00 | 17.24 | A |
| ATOM | 1766 | N | SER | A | 898 | 24.927 | 13.475 | 17.646 | 1.00 | 19.29 | A |
| ATOM | 1767 | CA | SER | A | 898 | 25.256 | 14.498 | 18.641 | 1.00 | 19.48 | A |
| ATOM | 1768 | CB | SER | A | 898 | 25.482 | 13.857 | 20.016 | 1.00 | 19.59 | A |
| ATOM | 1769 | OG | SER | A | 898 | 26.612 | 13.015 | 20.014 | 1.00 | 23.61 | A |
| ATOM | 1770 | C | SER | A | 898 | 26.431 | 15.428 | 18.321 | 1.00 | 20.34 | A |
| ATOM | 1771 | O | SER | A | 898 | 26.339 | 16.629 | 18.563 | 1.00 | 19.85 | A |
| ATOM | 1772 | N | ARG | A | 899 | 27.528 | 14.892 | 17.790 | 1.00 | 20.10 | A |
| ATOM | 1773 | CA | ARG | A | 899 | 28.679 | 15.736 | 17.468 | 1.00 | 23.31 | A |
| ATOM | 1774 | CB | ARG | A | 899 | 29.880 | 14.876 | 17.052 | 1.00 | 27.16 | A |
| ATOM | 1775 | CG | ARG | A | 899 | 30.420 | 13.995 | 18.169 | 1.00 | 33.57 | A |
| ATOM | 1776 | CD | ARG | A | 899 | 31.727 | 13.320 | 17.775 | 1.00 | 39.72 | A |
| ATOM | 1777 | NE | ARG | A | 899 | 32.308 | 12.568 | 18.885 | 1.00 | 45.23 | A |
| ATOM | 1778 | CZ | ARG | A | 899 | 33.516 | 12.013 | 18.862 | 1.00 | 48.88 | A |
| ATOM | 1779 | NH1 | ARG | A | 899 | 33.963 | 11.345 | 19.919 | 1.00 | 50.43 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1780 | NH2 | ARG | A | 899 | 34.282 | 12.126 | 17.784 | 1.00 | 49.70 | A |
| ATOM | 1781 | C | ARG | A | 899 | 28.359 | 16.743 | 16.363 | 1.00 | 24.46 | A |
| ATOM | 1782 | O | ARG | A | 899 | 28.630 | 17.938 | 16.497 | 1.00 | 23.89 | A |
| ATOM | 1783 | N | ALA | A | 900 | 27.781 | 16.254 | 15.271 | 1.00 | 23.66 | A |
| ATOM | 1784 | CA | ALA | A | 900 | 27.424 | 17.113 | 14.150 | 1.00 | 25.41 | A |
| ATOM | 1785 | CB | ALA | A | 900 | 26.821 | 16.276 | 13.022 | 1.00 | 24.80 | A |
| ATOM | 1786 | C | ALA | A | 900 | 26.436 | 18.198 | 14.576 | 1.00 | 25.89 | A |
| ATOM | 1787 | O | ALA | A | 900 | 26.536 | 19.341 | 14.141 | 1.00 | 24.07 | A |
| ATOM | 1788 | N | LEU | A | 901 | 25.496 | 17.836 | 15.446 | 1.00 | 24.94 | A |
| ATOM | 1789 | CA | LEU | A | 901 | 24.471 | 18.765 | 15.908 | 1.00 | 25.72 | A |
| ATOM | 1790 | CB | LEU | A | 901 | 23.180 | 17.993 | 16.198 | 1.00 | 26.87 | A |
| ATOM | 1791 | CG | LEU | A | 901 | 22.684 | 17.065 | 15.088 | 1.00 | 26.25 | A |
| ATOM | 1792 | CD1 | LEU | A | 901 | 21.458 | 16.312 | 15.569 | 1.00 | 26.78 | A |
| ATOM | 1793 | CD2 | LEU | A | 901 | 22.361 | 17.869 | 13.841 | 1.00 | 28.03 | A |
| ATOM | 1794 | C | LEU | A | 901 | 24.852 | 19.587 | 17.139 | 1.00 | 26.55 | A |
| ATOM | 1795 | O | LEU | A | 901 | 24.058 | 20.402 | 17.610 | 1.00 | 25.12 | A |
| ATOM | 1796 | N | SER | A | 902 | 26.058 | 19.374 | 17.660 | 1.00 | 25.57 | A |
| ATOM | 1797 | CA | SER | A | 902 | 26.526 | 20.094 | 18.846 | 1.00 | 25.20 | A |
| ATOM | 1798 | CB | SER | A | 902 | 26.683 | 21.589 | 18.549 | 1.00 | 26.76 | A |
| ATOM | 1799 | OG | SER | A | 902 | 27.664 | 21.806 | 17.552 | 1.00 | 32.11 | A |
| ATOM | 1800 | C | SER | A | 902 | 25.595 | 19.922 | 20.042 | 1.00 | 24.98 | A |
| ATOM | 1801 | O | SER | A | 902 | 25.303 | 20.874 | 20.768 | 1.00 | 22.85 | A |
| ATOM | 1802 | N | VAL | A | 903 | 25.121 | 18.702 | 20.247 | 1.00 | 23.89 | A |
| ATOM | 1803 | CA | VAL | A | 903 | 24.244 | 18.430 | 21.375 | 1.00 | 22.49 | A |
| ATOM | 1804 | CB | VAL | A | 903 | 22.960 | 17.712 | 20.917 | 1.00 | 21.00 | A |
| ATOM | 1805 | CG1 | VAL | A | 903 | 22.100 | 17.373 | 22.115 | 1.00 | 20.35 | A |
| ATOM | 1806 | CG2 | VAL | A | 903 | 22.190 | 18.601 | 19.942 | 1.00 | 21.63 | A |
| ATOM | 1807 | C | VAL | A | 903 | 25.004 | 17.551 | 22.357 | 1.00 | 22.22 | A |
| ATOM | 1808 | O | VAL | A | 903 | 25.462 | 16.468 | 22.004 | 1.00 | 22.99 | A |
| ATOM | 1809 | N | GLU | A | 904 | 25.149 | 18.023 | 23.588 | 1.00 | 22.49 | A |
| ATOM | 1810 | CA | GLU | A | 904 | 25.863 | 17.261 | 24.605 | 1.00 | 22.99 | A |
| ATOM | 1811 | CB | GLU | A | 904 | 26.494 | 18.201 | 25.636 | 1.00 | 26.54 | A |
| ATOM | 1812 | CG | GLU | A | 904 | 27.496 | 19.191 | 25.070 | 1.00 | 32.93 | A |
| ATOM | 1813 | CD | GLU | A | 904 | 27.985 | 20.166 | 26.123 | 1.00 | 35.69 | A |
| ATOM | 1814 | OE1 | GLU | A | 904 | 28.416 | 19.703 | 27.203 | 1.00 | 38.41 | A |
| ATOM | 1815 | OE2 | GLU | A | 904 | 27.939 | 21.390 | 25.872 | 1.00 | 36.80 | A |
| ATOM | 1816 | C | GLU | A | 904 | 24.947 | 16.294 | 25.344 | 1.00 | 22.46 | A |
| ATOM | 1817 | O | GLU | A | 904 | 23.801 | 16.624 | 25.660 | 1.00 | 21.31 | A |
| ATOM | 1818 | N | PHE | A | 905 | 25.467 | 15.102 | 25.621 | 1.00 | 19.52 | A |
| ATOM | 1819 | CA | PHE | A | 905 | 24.736 | 14.088 | 26.370 | 1.00 | 20.13 | A |
| ATOM | 1820 | CB | PHE | A | 905 | 24.483 | 12.833 | 25.521 | 1.00 | 17.67 | A |
| ATOM | 1821 | CG | PHE | A | 905 | 23.378 | 12.993 | 24.517 | 1.00 | 20.01 | A |
| ATOM | 1822 | CD1 | PHE | A | 905 | 23.611 | 13.625 | 23.299 | 1.00 | 18.40 | A |
| ATOM | 1823 | CD2 | PHE | A | 905 | 22.095 | 12.519 | 24.795 | 1.00 | 16.55 | A |
| ATOM | 1824 | CE1 | PHE | A | 905 | 22.589 | 13.785 | 22.373 | 1.00 | 18.70 | A |
| ATOM | 1825 | CE2 | PHE | A | 905 | 21.066 | 12.675 | 23.877 | 1.00 | 18.48 | A |
| ATOM | 1826 | CZ | PHE | A | 905 | 21.311 | 13.309 | 22.660 | 1.00 | 18.42 | A |
| ATOM | 1827 | C | PHE | A | 905 | 25.604 | 13.715 | 27.565 | 1.00 | 19.48 | A |
| ATOM | 1828 | O | PHE | A | 905 | 26.663 | 13.115 | 27.395 | 1.00 | 18.97 | A |
| ATOM | 1829 | N | PRO | A | 906 | 25.179 | 14.083 | 28.786 | 1.00 | 19.52 | A |
| ATOM | 1830 | CD | PRO | A | 906 | 24.084 | 15.010 | 29.128 | 1.00 | 20.38 | A |
| ATOM | 1831 | CA | PRO | A | 906 | 25.963 | 13.756 | 29.981 | 1.00 | 19.87 | A |
| ATOM | 1832 | CB | PRO | A | 906 | 25.157 | 14.397 | 31.108 | 1.00 | 19.03 | A |
| ATOM | 1833 | CG | PRO | A | 906 | 24.561 | 15.594 | 30.442 | 1.00 | 20.40 | A |
| ATOM | 1834 | C | PRO | A | 906 | 26.147 | 12.252 | 30.170 | 1.00 | 20.93 | A |
| ATOM | 1835 | O | PRO | A | 906 | 25.532 | 11.448 | 29.471 | 1.00 | 19.74 | A |
| ATOM | 1836 | N | GLU | A | 907 | 26.982 | 11.892 | 31.138 | 1.00 | 22.35 | A |
| ATOM | 1837 | CA | GLU | A | 907 | 27.317 | 10.504 | 31.435 | 1.00 | 23.45 | A |
| ATOM | 1838 | CB | GLU | A | 907 | 28.243 | 10.457 | 32.656 | 1.00 | 28.12 | A |
| ATOM | 1839 | CG | GLU | A | 907 | 29.018 | 9.154 | 32.788 | 1.00 | 34.86 | A |
| ATOM | 1840 | CD | GLU | A | 907 | 29.942 | 9.140 | 33.993 | 1.00 | 38.06 | A |
| ATOM | 1841 | OE1 | GLU | A | 907 | 30.637 | 10.154 | 34.220 | 1.00 | 41.07 | A |
| ATOM | 1842 | OE2 | GLU | A | 907 | 29.978 | 8.114 | 34.706 | 1.00 | 38.81 | A |
| ATOM | 1843 | C | GLU | A | 907 | 26.166 | 9.517 | 31.646 | 1.00 | 21.79 | A |
| ATOM | 1844 | O | GLU | A | 907 | 26.042 | 8.543 | 30.908 | 1.00 | 21.49 | A |
| ATOM | 1845 | N | MET | A | 908 | 25.344 | 9.742 | 32.665 | 1.00 | 22.08 | A |
| ATOM | 1846 | CA | MET | A | 908 | 24.241 | 8.822 | 32.937 | 1.00 | 23.28 | A |
| ATOM | 1847 | CB | MET | A | 908 | 23.538 | 9.193 | 34.245 | 1.00 | 27.12 | A |
| ATOM | 1848 | CG | MET | A | 908 | 24.346 | 8.860 | 35.489 | 1.00 | 34.62 | A |
| ATOM | 1849 | SD | MET | A | 908 | 23.440 | 9.197 | 37.025 | 1.00 | 43.74 | A |
| ATOM | 1850 | CE | MET | A | 908 | 22.199 | 7.897 | 36.981 | 1.00 | 38.86 | A |
| ATOM | 1851 | C | MET | A | 908 | 23.230 | 8.757 | 31.799 | 1.00 | 20.83 | A |
| ATOM | 1852 | O | MET | A | 908 | 22.700 | 7.686 | 31.504 | 1.00 | 20.86 | A |
| ATOM | 1853 | N | MET | A | 909 | 22.967 | 9.898 | 31.166 | 1.00 | 18.93 | A |
| ATOM | 1854 | CA | MET | A | 909 | 22.036 | 9.958 | 30.041 | 1.00 | 19.79 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1855 | CB | MET | A | 909 | 21.883 | 11.402 | 29.542 | 1.00 | 21.27 | A |
| ATOM | 1856 | CG | MET | A | 909 | 20.947 | 12.269 | 30.359 | 1.00 | 20.34 | A |
| ATOM | 1857 | SD | MET | A | 909 | 19.199 | 11.802 | 30.150 | 1.00 | 26.91 | A |
| ATOM | 1858 | CE | MET | A | 909 | 18.993 | 12.166 | 28.374 | 1.00 | 23.59 | A |
| ATOM | 1859 | C | MET | A | 909 | 22.576 | 9.087 | 28.910 | 1.00 | 19.04 | A |
| ATOM | 1860 | O | MET | A | 909 | 21.854 | 8.282 | 28.330 | 1.00 | 19.89 | A |
| ATOM | 1861 | N | SER | A | 910 | 23.858 | 9.251 | 28.604 | 1.00 | 18.89 | A |
| ATOM | 1862 | CA | SER | A | 910 | 24.484 | 8.469 | 27.546 | 1.00 | 20.47 | A |
| ATOM | 1863 | CB | SER | A | 910 | 25.938 | 8.908 | 27.364 | 1.00 | 20.19 | A |
| ATOM | 1864 | OG | SER | A | 910 | 25.998 | 10.249 | 26.900 | 1.00 | 20.62 | A |
| ATOM | 1865 | C | SER | A | 910 | 24.427 | 6.976 | 27.869 | 1.00 | 21.20 | A |
| ATOM | 1866 | O | SER | A | 910 | 24.210 | 6.153 | 26.982 | 1.00 | 19.29 | A |
| ATOM | 1867 | N | GLU | A | 911 | 24.610 | 6.638 | 29.142 | 1.00 | 22.27 | A |
| ATOM | 1868 | CA | GLU | A | 911 | 24.587 | 5.244 | 29.578 | 1.00 | 24.86 | A |
| ATOM | 1869 | CB | GLU | A | 911 | 24.965 | 5.149 | 31.060 | 1.00 | 29.31 | A |
| ATOM | 1870 | CG | GLU | A | 911 | 24.950 | 3.736 | 31.626 | 1.00 | 35.80 | A |
| ATOM | 1871 | CD | GLU | A | 911 | 25.165 | 3.700 | 33.136 | 1.00 | 40.80 | A |
| ATOM | 1872 | OE1 | GLU | A | 911 | 26.207 | 4.204 | 33.609 | 1.00 | 45.47 | A |
| ATOM | 1873 | OE2 | GLU | A | 911 | 24.290 | 3.166 | 33.854 | 1.00 | 43.61 | A |
| ATOM | 1874 | C | GLU | A | 911 | 23.231 | 4.574 | 29.347 | 1.00 | 23.81 | A |
| ATOM | 1875 | O | GLU | A | 911 | 23.164 | 3.493 | 28.756 | 1.00 | 22.59 | A |
| ATOM | 1876 | N | VAL | A | 912 | 22.151 | 5.202 | 29.807 | 1.00 | 20.88 | A |
| ATOM | 1877 | CA | VAL | A | 912 | 20.827 | 4.613 | 29.623 | 1.00 | 22.23 | A |
| ATOM | 1878 | CB | VAL | A | 912 | 19.718 | 5.404 | 30.374 | 1.00 | 22.28 | A |
| ATOM | 1879 | CG1 | VAL | A | 912 | 20.025 | 5.441 | 31.868 | 1.00 | 23.61 | A |
| ATOM | 1880 | CG2 | VAL | A | 912 | 19.602 | 6.807 | 29.819 | 1.00 | 23.21 | A |
| ATOM | 1881 | C | VAL | A | 912 | 20.454 | 4.535 | 28.149 | 1.00 | 20.96 | A |
| ATOM | 1882 | O | VAL | A | 912 | 19.876 | 3.546 | 27.699 | 1.00 | 21.47 | A |
| ATOM | 1883 | N | ILE | A | 913 | 20.794 | 5.571 | 27.392 | 1.00 | 20.47 | A |
| ATOM | 1884 | CA | ILE | A | 913 | 20.477 | 5.589 | 25.969 | 1.00 | 21.45 | A |
| ATOM | 1885 | CB | ILE | A | 913 | 20.875 | 6.949 | 25.330 | 1.00 | 21.91 | A |
| ATOM | 1886 | CG2 | ILE | A | 913 | 20.829 | 6.862 | 23.810 | 1.00 | 21.47 | A |
| ATOM | 1887 | CG1 | ILE | A | 913 | 19.926 | 8.042 | 25.830 | 1.00 | 19.94 | A |
| ATOM | 1888 | CD1 | ILE | A | 913 | 20.320 | 9.446 | 25.420 | 1.00 | 23.22 | A |
| ATOM | 1889 | C | ILE | A | 913 | 21.188 | 4.448 | 25.249 | 1.00 | 22.68 | A |
| ATOM | 1890 | O | ILE | A | 913 | 20.570 | 3.694 | 24.503 | 1.00 | 23.60 | A |
| ATOM | 1891 | N | ALA | A | 914 | 22.486 | 4.313 | 25.492 | 1.00 | 23.11 | A |
| ATOM | 1892 | CA | ALA | A | 914 | 23.276 | 3.270 | 24.857 | 1.00 | 24.55 | A |
| ATOM | 1893 | CB | ALA | A | 914 | 24.757 | 3.453 | 25.203 | 1.00 | 24.17 | A |
| ATOM | 1894 | C | ALA | A | 914 | 22.823 | 1.878 | 25.268 | 1.00 | 24.85 | A |
| ATOM | 1895 | O | ALA | A | 914 | 22.738 | 0.973 | 24.441 | 1.00 | 24.84 | A |
| ATOM | 1896 | N | ALA | A | 915 | 22.532 | 1.715 | 26.551 | 1.00 | 26.25 | A |
| ATOM | 1897 | CA | ALA | A | 915 | 22.119 | 0.425 | 27.077 | 1.00 | 27.16 | A |
| ATOM | 1898 | CB | ALA | A | 915 | 22.155 | 0.460 | 28.602 | 1.00 | 26.43 | A |
| ATOM | 1899 | C | ALA | A | 915 | 20.759 | −0.093 | 26.616 | 1.00 | 27.28 | A |
| ATOM | 1900 | O | ALA | A | 915 | 20.627 | −1.277 | 26.315 | 1.00 | 28.47 | A |
| ATOM | 1901 | N | GLN | A | 916 | 19.754 | 0.773 | 26.526 | 1.00 | 24.56 | A |
| ATOM | 1902 | CA | GLN | A | 916 | 18.429 | 0.272 | 26.178 | 1.00 | 23.88 | A |
| ATOM | 1903 | CB | GLN | A | 916 | 17.529 | 0.337 | 27.418 | 1.00 | 23.68 | A |
| ATOM | 1904 | CG | GLN | A | 916 | 18.134 | −0.202 | 28.704 | 1.00 | 25.94 | A |
| ATOM | 1905 | CD | GLN | A | 916 | 18.337 | −1.704 | 28.688 | 1.00 | 28.66 | A |
| ATOM | 1906 | OE1 | GLN | A | 916 | 17.808 | −2.408 | 27.828 | 1.00 | 29.30 | A |
| ATOM | 1907 | NE2 | GLN | A | 916 | 19.101 | −2.206 | 29.654 | 1.00 | 29.87 | A |
| ATOM | 1908 | C | GLN | A | 916 | 17.622 | 0.830 | 25.011 | 1.00 | 21.93 | A |
| ATOM | 1909 | O | GLN | A | 916 | 16.766 | 0.119 | 24.496 | 1.00 | 20.48 | A |
| ATOM | 1910 | N | LEU | A | 917 | 17.856 | 2.073 | 24.588 | 1.00 | 21.01 | A |
| ATOM | 1911 | CA | LEU | A | 917 | 17.030 | 2.639 | 23.518 | 1.00 | 21.54 | A |
| ATOM | 1912 | CB | LEU | A | 917 | 17.484 | 4.062 | 23.150 | 1.00 | 24.24 | A |
| ATOM | 1913 | CG | LEU | A | 917 | 16.864 | 5.165 | 24.010 | 1.00 | 27.14 | A |
| ATOM | 1914 | CD1 | LEU | A | 917 | 17.113 | 6.536 | 23.371 | 1.00 | 25.74 | A |
| ATOM | 1915 | CD2 | LEU | A | 917 | 15.367 | 4.913 | 24.147 | 1.00 | 27.44 | A |
| ATOM | 1916 | C | LEU | A | 917 | 16.846 | 1.826 | 22.243 | 1.00 | 21.71 | A |
| ATOM | 1917 | O | LEU | A | 917 | 15.717 | 1.662 | 21.771 | 1.00 | 22.26 | A |
| ATOM | 1918 | N | PRO | A | 918 | 17.939 | 1.315 | 21.656 | 1.00 | 20.55 | A |
| ATOM | 1919 | CD | PRO | A | 918 | 19.368 | 1.494 | 21.970 | 1.00 | 21.89 | A |
| ATOM | 1920 | CA | PRO | A | 918 | 17.764 | 0.530 | 20.429 | 1.00 | 20.41 | A |
| ATOM | 1921 | CB | PRO | A | 918 | 19.190 | 0.106 | 20.082 | 1.00 | 21.03 | A |
| ATOM | 1922 | CG | PRO | A | 918 | 20.017 | 1.247 | 20.622 | 1.00 | 21.48 | A |
| ATOM | 1923 | C | PRO | A | 918 | 16.851 | −0.670 | 20.683 | 1.00 | 19.91 | A |
| ATOM | 1924 | O | PRO | A | 918 | 15.918 | −0.932 | 19.924 | 1.00 | 18.25 | A |
| ATOM | 1925 | N | LYS | A | 919 | 17.132 | −1.386 | 21.766 | 1.00 | 19.57 | A |
| ATOM | 1926 | CA | LYS | A | 919 | 16.356 | −2.561 | 22.154 | 1.00 | 19.46 | A |
| ATOM | 1927 | CB | LYS | A | 919 | 16.944 | −3.152 | 23.436 | 1.00 | 22.54 | A |
| ATOM | 1928 | CG | LYS | A | 919 | 16.263 | −4.419 | 23.930 | 1.00 | 27.11 | A |
| ATOM | 1929 | CD | LYS | A | 919 | 16.667 | −4.723 | 25.374 | 1.00 | 28.80 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 1930 | CE | LYS | A | 919 | 18.180 | −4.789 | 25.536 | 1.00 | 29.86 | A |
| ATOM | 1931 | NZ | LYS | A | 919 | 18.598 | −4.886 | 26.971 | 1.00 | 33.98 | A |
| ATOM | 1932 | C | LYS | A | 919 | 14.882 | −2.213 | 22.375 | 1.00 | 20.15 | A |
| ATOM | 1933 | O | LYS | A | 919 | 13.986 | −2.941 | 21.944 | 1.00 | 19.14 | A |
| ATOM | 1934 | N | ILE | A | 920 | 14.631 | −1.099 | 23.057 | 1.00 | 20.31 | A |
| ATOM | 1935 | CA | ILE | A | 920 | 13.262 | −0.669 | 23.321 | 1.00 | 18.33 | A |
| ATOM | 1936 | CB | ILE | A | 920 | 13.242 | 0.552 | 24.267 | 1.00 | 20.86 | A |
| ATOM | 1937 | CG2 | ILE | A | 920 | 11.820 | 1.098 | 24.402 | 1.00 | 22.14 | A |
| ATOM | 1938 | CG1 | ILE | A | 920 | 13.781 | 0.138 | 25.640 | 1.00 | 18.33 | A |
| ATOM | 1939 | CD1 | ILE | A | 920 | 13.903 | 1.284 | 26.619 | 1.00 | 23.66 | A |
| ATOM | 1940 | C | ILE | A | 920 | 12.540 | −0.328 | 22.025 | 1.00 | 19.54 | A |
| ATOM | 1941 | O | ILE | A | 920 | 11.424 | −0.788 | 21.788 | 1.00 | 19.13 | A |
| ATOM | 1942 | N | LEU | A | 921 | 13.180 | 0.472 | 21.179 | 1.00 | 20.13 | A |
| ATOM | 1943 | CA | LEU | A | 921 | 12.585 | 0.851 | 19.904 | 1.00 | 20.63 | A |
| ATOM | 1944 | CB | LEU | A | 921 | 13.503 | 1.829 | 19.167 | 1.00 | 21.68 | A |
| ATOM | 1945 | CG | LEU | A | 921 | 13.416 | 3.266 | 19.680 | 1.00 | 22.69 | A |
| ATOM | 1946 | CD1 | LEU | A | 921 | 14.462 | 4.139 | 18.995 | 1.00 | 21.07 | A |
| ATOM | 1947 | CD2 | LEU | A | 921 | 12.005 | 3.796 | 19.409 | 1.00 | 20.56 | A |
| ATOM | 1948 | C | LEU | A | 921 | 12.304 | −0.362 | 19.022 | 1.00 | 21.94 | A |
| ATOM | 1949 | O | LEU | A | 921 | 11.324 | −0.386 | 18.280 | 1.00 | 24.08 | A |
| ATOM | 1950 | N | ALA | A | 922 | 13.162 | −1.372 | 19.107 | 1.00 | 20.43 | A |
| ATOM | 1951 | CA | ALA | A | 922 | 12.989 | −2.578 | 18.305 | 1.00 | 21.49 | A |
| ATOM | 1952 | CB | ALA | A | 922 | 14.294 | −3.354 | 18.243 | 1.00 | 20.05 | A |
| ATOM | 1953 | C | ALA | A | 922 | 11.889 | −3.466 | 18.866 | 1.00 | 22.02 | A |
| ATOM | 1954 | O | ALA | A | 922 | 11.546 | −4.489 | 18.274 | 1.00 | 21.77 | A |
| ATOM | 1955 | N | GLY | A | 923 | 11.342 | −3.075 | 20.012 | 1.00 | 21.48 | A |
| ATOM | 1956 | CA | GLY | A | 923 | 10.286 | −3.860 | 20.629 | 1.00 | 21.95 | A |
| ATOM | 1957 | C | GLY | A | 923 | 10.794 | −5.142 | 21.266 | 1.00 | 21.42 | A |
| ATOM | 1958 | O | GLY | A | 923 | 10.031 | −6.092 | 21.456 | 1.00 | 22.31 | A |
| ATOM | 1959 | N | MET | A | 924 | 12.080 | −5.179 | 21.601 | 1.00 | 19.45 | A |
| ATOM | 1960 | CA | MET | A | 924 | 12.658 | −6.364 | 22.215 | 1.00 | 20.79 | A |
| ATOM | 1961 | CB | MET | A | 924 | 14.091 | −6.580 | 21.722 | 1.00 | 22.02 | A |
| ATOM | 1962 | CG | MET | A | 924 | 14.178 | −6.895 | 20.238 | 1.00 | 25.40 | A |
| ATOM | 1963 | SD | MET | A | 924 | 13.141 | −8.295 | 19.764 | 1.00 | 28.65 | A |
| ATOM | 1964 | CE | MET | A | 924 | 14.164 | −9.661 | 20.270 | 1.00 | 27.15 | A |
| ATOM | 1965 | C | MET | A | 924 | 12.631 | −6.293 | 23.737 | 1.00 | 20.36 | A |
| ATOM | 1966 | O | MET | A | 924 | 13.603 | −6.635 | 24.404 | 1.00 | 20.04 | A |
| ATOM | 1967 | N | VAL | A | 925 | 11.499 | −5.829 | 24.259 | 1.00 | 20.45 | A |
| ATOM | 1968 | CA | VAL | A | 925 | 11.235 | −5.718 | 25.689 | 1.00 | 19.83 | A |
| ATOM | 1969 | CB | VAL | A | 925 | 11.571 | −4.319 | 26.262 | 1.00 | 19.54 | A |
| ATOM | 1970 | CG1 | VAL | A | 925 | 13.067 | −4.040 | 26.133 | 1.00 | 18.25 | A |
| ATOM | 1971 | CG2 | VAL | A | 925 | 10.745 | −3.252 | 25.555 | 1.00 | 17.24 | A |
| ATOM | 1972 | C | VAL | A | 925 | 9.730 | −5.924 | 25.773 | 1.00 | 20.81 | A |
| ATOM | 1973 | O | VAL | A | 925 | 9.053 | −5.958 | 24.739 | 1.00 | 17.16 | A |
| ATOM | 1974 | N | LYS | A | 926 | 9.206 | −6.052 | 26.986 | 1.00 | 20.03 | A |
| ATOM | 1975 | CA | LYS | A | 926 | 7.776 | −6.271 | 27.157 | 1.00 | 22.62 | A |
| ATOM | 1976 | CB | LYS | A | 926 | 7.532 | −7.544 | 27.977 | 1.00 | 24.15 | A |
| ATOM | 1977 | CG | LYS | A | 926 | 6.062 | −7.903 | 28.123 | 1.00 | 27.68 | A |
| ATOM | 1978 | CD | LYS | A | 926 | 5.884 | −9.233 | 28.839 | 1.00 | 32.47 | A |
| ATOM | 1979 | CE | LYS | A | 926 | 4.412 | −9.611 | 28.927 | 1.00 | 33.32 | A |
| ATOM | 1980 | NZ | LYS | A | 926 | 4.224 | −10.923 | 29.603 | 1.00 | 35.99 | A |
| ATOM | 1981 | C | LYS | A | 926 | 7.037 | −5.103 | 27.803 | 1.00 | 22.57 | A |
| ATOM | 1982 | O | LYS | A | 926 | 7.076 | −4.921 | 29.026 | 1.00 | 22.63 | A |
| ATOM | 1983 | N | PRO | A | 927 | 6.367 | −4.280 | 26.986 | 1.00 | 23.30 | A |
| ATOM | 1984 | CD | PRO | A | 927 | 6.374 | −4.224 | 25.516 | 1.00 | 23.83 | A |
| ATOM | 1985 | CA | PRO | A | 927 | 5.629 | −3.149 | 27.551 | 1.00 | 23.76 | A |
| ATOM | 1986 | CB | PRO | A | 927 | 5.220 | −2.339 | 26.316 | 1.00 | 24.30 | A |
| ATOM | 1987 | CG | PRO | A | 927 | 6.229 | −2.751 | 25.265 | 1.00 | 25.51 | A |
| ATOM | 1988 | C | PRO | A | 927 | 4.417 | −3.750 | 28.253 | 1.00 | 24.23 | A |
| ATOM | 1989 | O | PRO | A | 927 | 3.801 | −4.686 | 27.740 | 1.00 | 22.94 | A |
| ATOM | 1990 | N | LEU | A | 928 | 4.081 | −3.241 | 29.427 | 1.00 | 22.92 | A |
| ATOM | 1991 | CA | LEU | A | 928 | 2.930 | −3.773 | 30.132 | 1.00 | 24.28 | A |
| ATOM | 1992 | CB | LEU | A | 928 | 3.200 | −3.825 | 31.640 | 1.00 | 22.59 | A |
| ATOM | 1993 | CG | LEU | A | 928 | 4.419 | −4.655 | 32.060 | 1.00 | 24.35 | A |
| ATOM | 1994 | CD1 | LEU | A | 928 | 4.460 | −4.776 | 33.579 | 1.00 | 23.99 | A |
| ATOM | 1995 | CD2 | LEU | A | 928 | 4.350 | −6.038 | 31.426 | 1.00 | 26.06 | A |
| ATOM | 1996 | C | LEU | A | 928 | 1.726 | −2.896 | 29.824 | 1.00 | 25.03 | A |
| ATOM | 1997 | O | LEU | A | 928 | 1.826 | −1.666 | 29.812 | 1.00 | 27.49 | A |
| ATOM | 1998 | N | LEU | A | 929 | 0.596 | −3.533 | 29.549 | 1.00 | 24.29 | A |
| ATOM | 1999 | CA | LEU | A | 929 | −0.627 | −2.809 | 29.234 | 1.00 | 24.19 | A |
| ATOM | 2000 | CB | LEU | A | 929 | −1.107 | −3.163 | 27.825 | 1.00 | 25.39 | A |
| ATOM | 2001 | CG | LEU | A | 929 | −0.272 | −2.680 | 26.640 | 1.00 | 23.43 | A |
| ATOM | 2002 | CD1 | LEU | A | 929 | −0.739 | −3.371 | 25.363 | 1.00 | 23.68 | A |
| ATOM | 2003 | CD2 | LEU | A | 929 | −0.397 | −1.166 | 26.520 | 1.00 | 23.94 | A |
| ATOM | 2004 | C | LEU | A | 929 | −1.722 | −3.150 | 30.226 | 1.00 | 25.66 | A |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2005 | O | LEU | A | 929 | −1.820 | −4.286 | 30.699 | 1.00 | 23.46 | A |
| ATOM | 2006 | N | PHE | A | 930 | −2.541 | −2.152 | 30.535 | 1.00 | 26.75 | A |
| ATOM | 2007 | CA | PHE | A | 930 | −3.657 | −2.315 | 31.451 | 1.00 | 28.37 | A |
| ATOM | 2008 | CB | PHE | A | 930 | −3.949 | −0.987 | 32.151 | 1.00 | 25.94 | A |
| ATOM | 2009 | CG | PHE | A | 930 | −2.857 | −0.545 | 33.093 | 1.00 | 24.34 | A |
| ATOM | 2010 | CD1 | PHE | A | 930 | −2.662 | −1.198 | 34.306 | 1.00 | 24.73 | A |
| ATOM | 2011 | CD2 | PHE | A | 930 | −2.015 | 0.511 | 32.758 | 1.00 | 22.44 | A |
| ATOM | 2012 | CE1 | PHE | A | 930 | −1.641 | −0.802 | 35.175 | 1.00 | 24.82 | A |
| ATOM | 2013 | CE2 | PHE | A | 930 | −0.994 | 0.914 | 33.617 | 1.00 | 23.39 | A |
| ATOM | 2014 | CZ | PHE | A | 930 | −0.805 | 0.256 | 34.828 | 1.00 | 23.89 | A |
| ATOM | 2015 | C | PHE | A | 930 | −4.880 | −2.776 | 30.660 | 1.00 | 30.68 | A |
| ATOM | 2016 | O | PHE | A | 930 | −5.794 | −3.391 | 31.215 | 1.00 | 29.02 | A |
| ATOM | 2017 | N | HIS | A | 931 | −4.881 | −2.476 | 29.362 | 1.00 | 33.18 | A |
| ATOM | 2018 | CA | HIS | A | 931 | −5.976 | −2.856 | 28.475 | 1.00 | 38.68 | A |
| ATOM | 2019 | CB | HIS | A | 931 | −6.909 | −1.666 | 28.238 | 1.00 | 39.02 | A |
| ATOM | 2020 | CG | HIS | A | 931 | −7.356 | −0.994 | 29.497 | 1.00 | 40.32 | A |
| ATOM | 2021 | CD2 | HIS | A | 931 | −7.249 | 0.292 | 29.906 | 1.00 | 40.17 | A |
| ATOM | 2022 | ND1 | HIS | A | 931 | −7.976 | −1.674 | 30.523 | 1.00 | 40.39 | A |
| ATOM | 2023 | CE1 | HIS | A | 931 | −8.229 | −0.836 | 31.513 | 1.00 | 40.76 | A |
| ATOM | 2024 | NE2 | HIS | A | 931 | −7.798 | 0.363 | 31.164 | 1.00 | 41.79 | A |
| ATOM | 2025 | C | HIS | A | 931 | −5.439 | −3.341 | 27.134 | 1.00 | 41.55 | A |
| ATOM | 2026 | O | HIS | A | 931 | −4.304 | −3.045 | 26.762 | 1.00 | 41.94 | A |
| ATOM | 2027 | N | LYS | A | 932 | −6.264 | −4.087 | 26.409 | 1.00 | 45.37 | A |
| ATOM | 2028 | CA | LYS | A | 932 | −5.871 | −4.607 | 25.107 | 1.00 | 49.31 | A |
| ATOM | 2029 | CB | LYS | A | 932 | −6.553 | −5.953 | 24.850 | 1.00 | 51.25 | A |
| ATOM | 2030 | CG | LYS | A | 932 | −8.041 | −5.969 | 25.159 | 1.00 | 53.19 | A |
| ATOM | 2031 | CD | LYS | A | 932 | −8.607 | −7.375 | 25.030 | 1.00 | 55.91 | A |
| ATOM | 2032 | CE | LYS | A | 932 | −10.000 | −7.477 | 25.642 | 1.00 | 57.08 | A |
| ATOM | 2033 | NZ | LYS | A | 932 | −10.971 | −6.540 | 25.010 | 1.00 | 58.49 | A |
| ATOM | 2034 | C | LYS | A | 932 | −6.219 | −3.625 | 23.997 | 1.00 | 50.69 | A |
| ATOM | 2035 | O | LYS | A | 932 | −6.726 | −2.528 | 24.316 | 1.00 | 51.64 | A |
| ATOM | 2036 | OXT | LYS | A | 932 | −5.971 | −3.965 | 22.820 | 1.00 | 53.42 | A |
| ATOM | 2037 | CB | GLN | B | 682 | 18.994 | −21.280 | −25.886 | 1.00 | 64.64 | B |
| ATOM | 2038 | CG | GLN | B | 682 | 20.304 | −21.103 | −26.640 | 1.00 | 67.42 | B |
| ATOM | 2039 | CD | GLN | B | 682 | 20.213 | −21.557 | −28.085 | 1.00 | 69.58 | B |
| ATOM | 2040 | OE1 | GLN | B | 682 | 19.707 | −22.642 | −28.379 | 1.00 | 70.69 | B |
| ATOM | 2041 | NE2 | GLN | B | 682 | 20.711 | −20.728 | −28.997 | 1.00 | 70.72 | B |
| ATOM | 2042 | C | GLN | B | 682 | 17.739 | −20.948 | −23.741 | 1.00 | 60.54 | B |
| ATOM | 2043 | O | GLN | B | 682 | 16.624 | −20.450 | −23.891 | 1.00 | 61.01 | B |
| ATOM | 2044 | N | GLN | B | 682 | 20.194 | −20.628 | −23.821 | 1.00 | 62.94 | B |
| ATOM | 2045 | CA | GLN | B | 682 | 18.922 | −20.478 | −24.585 | 1.00 | 62.30 | B |
| ATOM | 2046 | N | LEU | B | 683 | 17.986 | −21.915 | −22.863 | 1.00 | 57.86 | B |
| ATOM | 2047 | CA | LEU | B | 683 | 16.949 | −22.424 | −21.976 | 1.00 | 54.52 | B |
| ATOM | 2048 | CB | LEU | B | 683 | 17.296 | −23.831 | −21.481 | 1.00 | 56.05 | B |
| ATOM | 2049 | CG | LEU | B | 683 | 17.347 | −24.973 | −22.497 | 1.00 | 56.91 | B |
| ATOM | 2050 | CD1 | LEU | B | 683 | 17.763 | −26.253 | −21.789 | 1.00 | 57.17 | B |
| ATOM | 2051 | CD2 | LEU | B | 683 | 15.988 | −25.149 | −23.158 | 1.00 | 57.28 | B |
| ATOM | 2052 | C | LEU | B | 683 | 16.906 | −21.464 | −20.797 | 1.00 | 51.41 | B |
| ATOM | 2053 | O | LEU | B | 683 | 15.849 | −21.218 | −20.214 | 1.00 | 51.78 | B |
| ATOM | 2054 | N | ILE | B | 684 | 18.074 | −20.923 | −20.458 | 1.00 | 46.89 | B |
| ATOM | 2055 | CA | ILE | B | 684 | 18.197 | −19.974 | −19.360 | 1.00 | 42.41 | B |
| ATOM | 2056 | CB | ILE | B | 684 | 19.665 | −19.802 | −18.918 | 1.00 | 42.31 | B |
| ATOM | 2057 | CG2 | ILE | B | 684 | 19.742 | −18.819 | −17.754 | 1.00 | 41.95 | B |
| ATOM | 2058 | CG1 | ILE | B | 684 | 20.259 | −21.152 | −18.516 | 1.00 | 43.99 | B |
| ATOM | 2059 | CD1 | ILE | B | 684 | 19.612 | −21.778 | −17.297 | 1.00 | 44.53 | B |
| ATOM | 2060 | C | ILE | B | 684 | 17.685 | −18.616 | −19.825 | 1.00 | 38.54 | B |
| ATOM | 2061 | O | ILE | B | 684 | 18.255 | −18.010 | −20.729 | 1.00 | 36.91 | B |
| ATOM | 2062 | N | PRO | B | 685 | 16.598 | −18.123 | −19.213 | 1.00 | 35.60 | B |
| ATOM | 2063 | CD | PRO | B | 685 | 15.838 | −18.725 | −18.103 | 1.00 | 35.69 | B |
| ATOM | 2064 | CA | PRO | B | 685 | 16.032 | −16.824 | −19.587 | 1.00 | 33.16 | B |
| ATOM | 2065 | CB | PRO | B | 685 | 15.030 | −16.555 | −18.469 | 1.00 | 33.62 | B |
| ATOM | 2066 | CG | PRO | B | 685 | 14.553 | −17.922 | −18.121 | 1.00 | 34.50 | B |
| ATOM | 2067 | C | PRO | B | 685 | 17.134 | −15.763 | −19.652 | 1.00 | 30.56 | B |
| ATOM | 2068 | O | PRO | B | 685 | 18.029 | −15.738 | −18.808 | 1.00 | 29.11 | B |
| ATOM | 2069 | N | PRO | B | 686 | 17.081 | −14.880 | −20.658 | 1.00 | 28.12 | B |
| ATOM | 2070 | CD | PRO | B | 686 | 16.116 | −14.858 | −21.772 | 1.00 | 28.97 | B |
| ATOM | 2071 | CA | PRO | B | 686 | 18.083 | −13.823 | −20.822 | 1.00 | 27.69 | B |
| ATOM | 2072 | CB | PRO | B | 686 | 17.532 | −13.010 | −21.990 | 1.00 | 28.13 | B |
| ATOM | 2073 | CG | PRO | B | 686 | 16.862 | −14.063 | −22.820 | 1.00 | 29.95 | B |
| ATOM | 2074 | C | PRO | B | 686 | 18.321 | −12.967 | −19.575 | 1.00 | 25.10 | B |
| ATOM | 2075 | O | PRO | B | 686 | 19.464 | −12.648 | −19.247 | 1.00 | 25.19 | B |
| ATOM | 2076 | N | LEU | B | 687 | 17.252 | −12.601 | −18.878 | 1.00 | 22.87 | B |
| ATOM | 2077 | CA | LEU | B | 687 | 17.396 | −11.771 | −17.685 | 1.00 | 22.31 | B |
| ATOM | 2078 | CB | LEU | B | 687 | 16.025 | −11.372 | −17.141 | 1.00 | 20.28 | B |
| ATOM | 2079 | CG | LEU | B | 687 | 16.037 | −10.547 | −15.848 | 1.00 | 21.32 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2080 | CD1 | LEU | B | 687 | 16.936 | −9.323 | −16.015 | 1.00 | 21.04 | B |
| ATOM | 2081 | CD2 | LEU | B | 687 | 14.616 | −10.132 | −15.501 | 1.00 | 22.03 | B |
| ATOM | 2082 | C | LEU | B | 687 | 18.207 | −12.467 | −16.592 | 1.00 | 21.06 | B |
| ATOM | 2083 | O | LEU | B | 687 | 19.025 | −11.840 | −15.921 | 1.00 | 23.05 | B |
| ATOM | 2084 | N | ILE | B | 688 | 17.974 | −13.760 | −16.409 | 1.00 | 21.09 | B |
| ATOM | 2085 | CA | ILE | B | 688 | 18.702 | −14.512 | −15.399 | 1.00 | 20.07 | B |
| ATOM | 2086 | CB | ILE | B | 688 | 18.120 | −15.927 | −15.252 | 1.00 | 21.05 | B |
| ATOM | 2087 | CG2 | ILE | B | 688 | 19.059 | −16.808 | −14.438 | 1.00 | 21.46 | B |
| ATOM | 2088 | CG1 | ILE | B | 688 | 16.741 | −15.831 | −14.594 | 1.00 | 20.53 | B |
| ATOM | 2089 | CD1 | ILE | B | 688 | 15.968 | −17.135 | −14.567 | 1.00 | 20.95 | B |
| ATOM | 2090 | C | ILE | B | 688 | 20.166 | −14.572 | −15.804 | 1.00 | 21.10 | B |
| ATOM | 2091 | O | ILE | B | 688 | 21.056 | −14.491 | −14.960 | 1.00 | 18.80 | B |
| ATOM | 2092 | N | ASN | B | 689 | 20.411 | −14.696 | −17.104 | 1.00 | 21.37 | B |
| ATOM | 2093 | CA | ASN | B | 689 | 21.776 | −14.743 | −17.613 | 1.00 | 24.08 | B |
| ATOM | 2094 | CB | ASN | B | 689 | 21.770 | −14.963 | −19.132 | 1.00 | 28.04 | B |
| ATOM | 2095 | CG | ASN | B | 689 | 23.165 | −15.126 | −19.700 | 1.00 | 34.12 | B |
| ATOM | 2096 | OD1 | ASN | B | 689 | 23.885 | −16.064 | −19.350 | 1.00 | 37.11 | B |
| ATOM | 2097 | ND2 | ASN | B | 689 | 23.560 | −14.210 | −20.582 | 1.00 | 37.70 | B |
| ATOM | 2098 | C | ASN | B | 689 | 22.451 | −13.415 | −17.288 | 1.00 | 22.87 | B |
| ATOM | 2099 | O | ASN | B | 689 | 23.612 | −13.370 | −16.873 | 1.00 | 23.07 | B |
| ATOM | 2100 | N | LEU | B | 690 | 21.712 | −12.332 | −17.482 | 1.00 | 22.51 | B |
| ATOM | 2101 | CA | LEU | B | 690 | 22.232 | −11.000 | −17.200 | 1.00 | 21.77 | B |
| ATOM | 2102 | CB | LEU | B | 690 | 21.199 | −9.942 | −17.587 | 1.00 | 21.00 | B |
| ATOM | 2103 | CG | LEU | B | 690 | 21.628 | −8.481 | −17.421 | 1.00 | 24.94 | B |
| ATOM | 2104 | CD1 | LEU | B | 690 | 20.798 | −7.601 | −18.349 | 1.00 | 26.36 | B |
| ATOM | 2105 | CD2 | LEU | B | 690 | 21.469 | −8.047 | −15.963 | 1.00 | 23.11 | B |
| ATOM | 2106 | C | LEU | B | 690 | 22.570 | −10.893 | −15.715 | 1.00 | 20.64 | B |
| ATOM | 2107 | O | LEU | B | 690 | 23.637 | −10.395 | −15.347 | 1.00 | 20.56 | B |
| ATOM | 2108 | N | LEU | B | 691 | 21.666 | −11.376 | −14.866 | 1.00 | 20.00 | B |
| ATOM | 2109 | CA | LEU | B | 691 | 21.882 | −11.331 | −13.421 | 1.00 | 18.30 | B |
| ATOM | 2110 | CB | LEU | B | 691 | 20.669 | −11.906 | −12.675 | 1.00 | 14.83 | B |
| ATOM | 2111 | CG | LEU | B | 691 | 19.385 | −11.068 | −12.715 | 1.00 | 16.41 | B |
| ATOM | 2112 | CD1 | LEU | B | 691 | 18.292 | −11.772 | −11.925 | 1.00 | 14.23 | B |
| ATOM | 2113 | CD2 | LEU | B | 691 | 19.648 | −9.672 | −12.136 | 1.00 | 16.13 | B |
| ATOM | 2114 | C | LEU | B | 691 | 23.145 | −12.097 | −13.029 | 1.00 | 18.65 | B |
| ATOM | 2115 | O | LEU | B | 691 | 23.826 | −11.728 | −12.079 | 1.00 | 17.99 | B |
| ATOM | 2116 | N | MET | B | 692 | 23.450 | −13.167 | −13.757 | 1.00 | 19.64 | B |
| ATOM | 2117 | CA | MET | B | 692 | 24.646 | −13.956 | −13.470 | 1.00 | 21.71 | B |
| ATOM | 2118 | CB | MET | B | 692 | 24.676 | −15.237 | −14.319 | 1.00 | 23.95 | B |
| ATOM | 2119 | CG | MET | B | 692 | 23.620 | −16.280 | −13.983 | 1.00 | 28.81 | B |
| ATOM | 2120 | SD | MET | B | 692 | 23.860 | −17.830 | −14.932 | 1.00 | 34.88 | B |
| ATOM | 2121 | CE | MET | B | 692 | 22.791 | −17.547 | −16.333 | 1.00 | 34.64 | B |
| ATOM | 2122 | C | MET | B | 692 | 25.887 | −13.130 | −13.793 | 1.00 | 20.55 | B |
| ATOM | 2123 | O | MET | B | 692 | 26.827 | −13.062 | −13.003 | 1.00 | 19.66 | B |
| ATOM | 2124 | N | SER | B | 693 | 25.872 | −12.490 | −14.959 | 1.00 | 20.66 | B |
| ATOM | 2125 | CA | SER | B | 693 | 27.003 | −11.691 | −15.417 | 1.00 | 22.33 | B |
| ATOM | 2126 | CB | SER | B | 693 | 26.811 | −11.303 | −16.888 | 1.00 | 24.97 | B |
| ATOM | 2127 | OG | SER | B | 693 | 25.751 | −10.374 | −17.040 | 1.00 | 29.96 | B |
| ATOM | 2128 | C | SER | B | 693 | 27.298 | −10.430 | −14.609 | 1.00 | 21.68 | B |
| ATOM | 2129 | O | SER | B | 693 | 28.428 | −9.938 | −14.623 | 1.00 | 21.77 | B |
| ATOM | 2130 | N | ILE | B | 694 | 26.305 | −9.891 | −13.912 | 1.00 | 20.69 | B |
| ATOM | 2131 | CA | ILE | B | 694 | 26.559 | −8.674 | −13.141 | 1.00 | 20.69 | B |
| ATOM | 2132 | CB | ILE | B | 694 | 25.397 | −7.667 | −13.264 | 1.00 | 19.13 | B |
| ATOM | 2133 | CG2 | ILE | B | 694 | 25.199 | −7.291 | −14.732 | 1.00 | 19.95 | B |
| ATOM | 2134 | CG1 | ILE | B | 694 | 24.115 | −8.262 | −12.685 | 1.00 | 18.02 | B |
| ATOM | 2135 | CD1 | ILE | B | 694 | 22.973 | −7.256 | −12.567 | 1.00 | 16.95 | B |
| ATOM | 2136 | C | ILE | B | 694 | 26.833 | −8.939 | −11.667 | 1.00 | 20.67 | B |
| ATOM | 2137 | O | ILE | B | 694 | 27.035 | −8.009 | −10.888 | 1.00 | 20.17 | B |
| ATOM | 2138 | N | GLU | B | 695 | 26.840 | −10.212 | −11.288 | 1.00 | 21.75 | B |
| ATOM | 2139 | CA | GLU | B | 695 | 27.104 | −10.583 | −9.908 | 1.00 | 24.75 | B |
| ATOM | 2140 | CB | GLU | B | 695 | 27.027 | −12.100 | −9.745 | 1.00 | 24.51 | B |
| ATOM | 2141 | CG | GLU | B | 695 | 27.077 | −12.547 | −8.310 | 1.00 | 28.80 | B |
| ATOM | 2142 | CD | GLU | B | 695 | 25.739 | −12.415 | −7.615 | 1.00 | 28.02 | B |
| ATOM | 2143 | OE1 | GLU | B | 695 | 24.997 | −11.445 | −7.898 | 1.00 | 25.16 | B |
| ATOM | 2144 | OE2 | GLU | B | 695 | 25.436 | −13.288 | −6.776 | 1.00 | 29.89 | B |
| ATOM | 2145 | C | GLU | B | 695 | 28.502 | −10.086 | −9.541 | 1.00 | 26.27 | B |
| ATOM | 2146 | O | GLU | B | 695 | 29.416 | −10.100 | −10.368 | 1.00 | 25.29 | B |
| ATOM | 2147 | N | PRO | B | 696 | 28.681 | −9.625 | −8.296 | 1.00 | 29.47 | B |
| ATOM | 2148 | CD | PRO | B | 696 | 27.624 | −9.400 | −7.293 | 1.00 | 31.49 | B |
| ATOM | 2149 | CA | PRO | B | 696 | 29.968 | −9.116 | −7.812 | 1.00 | 30.81 | B |
| ATOM | 2150 | CB | PRO | B | 696 | 29.662 | −8.727 | −6.366 | 1.00 | 30.96 | B |
| ATOM | 2151 | CG | PRO | B | 696 | 28.228 | −8.311 | −6.433 | 1.00 | 32.91 | B |
| ATOM | 2152 | C | PRO | B | 696 | 31.122 | −10.113 | −7.891 | 1.00 | 30.70 | B |
| ATOM | 2153 | O | PRO | B | 696 | 30.926 | −11.327 | −7.848 | 1.00 | 29.38 | B |
| ATOM | 2154 | N | ASP | B | 697 | 32.331 | −9.578 | −8.005 | 1.00 | 31.64 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2155 | CA | ASP | B | 697 | 33.531 | −10.396 | −8.051 | 1.00 | 32.72 | B |
| ATOM | 2156 | CB | ASP | B | 697 | 34.676 | −9.592 | −8.668 | 1.00 | 37.63 | B |
| ATOM | 2157 | CG | ASP | B | 697 | 35.443 | −10.374 | −9.710 | 1.00 | 41.79 | B |
| ATOM | 2158 | OD1 | ASP | B | 697 | 34.805 | −10.892 | −10.655 | 1.00 | 43.16 | B |
| ATOM | 2159 | OD2 | ASP | B | 697 | 36.684 | −10.464 | −9.585 | 1.00 | 44.61 | B |
| ATOM | 2160 | C | ASP | B | 697 | 33.833 | −10.722 | −6.587 | 1.00 | 29.84 | B |
| ATOM | 2161 | O | ASP | B | 697 | 33.262 | −10.101 | −5.693 | 1.00 | 28.09 | B |
| ATOM | 2162 | N | VAL | B | 698 | 34.706 | −11.694 | −6.344 | 1.00 | 28.32 | B |
| ATOM | 2163 | CA | VAL | B | 698 | 35.069 | −12.083 | −4.981 | 1.00 | 27.02 | B |
| ATOM | 2164 | CB | VAL | B | 698 | 36.205 | −13.140 | −4.974 | 1.00 | 28.37 | B |
| ATOM | 2165 | CG1 | VAL | B | 698 | 36.747 | −13.323 | −3.560 | 1.00 | 28.43 | B |
| ATOM | 2166 | CG2 | VAL | B | 698 | 35.682 | −14.470 | −5.502 | 1.00 | 28.67 | B |
| ATOM | 2167 | C | VAL | B | 698 | 35.532 | −10.881 | −4.168 | 1.00 | 25.36 | B |
| ATOM | 2168 | O | VAL | B | 698 | 36.328 | −10.076 | −4.639 | 1.00 | 25.06 | B |
| ATOM | 2169 | N | ILE | B | 699 | 35.030 | −10.767 | −2.944 | 1.00 | 24.97 | B |
| ATOM | 2170 | CA | ILE | B | 699 | 35.397 | −9.658 | −2.071 | 1.00 | 22.14 | B |
| ATOM | 2171 | CB | ILE | B | 699 | 34.156 | −8.823 | −1.679 | 1.00 | 20.66 | B |
| ATOM | 2172 | CG2 | ILE | B | 699 | 34.545 | −7.726 | −0.690 | 1.00 | 20.23 | B |
| ATOM | 2173 | CG1 | ILE | B | 699 | 33.545 | −8.188 | −2.931 | 1.00 | 21.51 | B |
| ATOM | 2174 | CD1 | ILE | B | 699 | 32.271 | −7.432 | −2.666 | 1.00 | 19.96 | B |
| ATOM | 2175 | C | ILE | B | 699 | 36.089 | −10.142 | −0.800 | 1.00 | 21.77 | B |
| ATOM | 2176 | O | ILE | B | 699 | 35.546 | −10.957 | −0.044 | 1.00 | 16.92 | B |
| ATOM | 2177 | N | TYR | B | 700 | 37.296 | −9.636 | −0.579 | 1.00 | 20.63 | B |
| ATOM | 2178 | CA | TYR | B | 700 | 38.069 | −9.988 | 0.602 | 1.00 | 23.86 | B |
| ATOM | 2179 | CB | TYR | B | 700 | 39.566 | −10.003 | 0.285 | 1.00 | 26.68 | B |
| ATOM | 2180 | CG | TYR | B | 700 | 39.969 | −11.095 | −0.676 | 1.00 | 32.41 | B |
| ATOM | 2181 | CD1 | TYR | B | 700 | 39.640 | −11.018 | −2.027 | 1.00 | 34.57 | B |
| ATOM | 2182 | CE1 | TYR | B | 700 | 39.979 | −12.036 | −2.909 | 1.00 | 38.16 | B |
| ATOM | 2183 | CD2 | TYR | B | 700 | 40.651 | −12.224 | −0.228 | 1.00 | 33.94 | B |
| ATOM | 2184 | CE2 | TYR | B | 700 | 40.993 | −13.251 | −1.104 | 1.00 | 37.69 | B |
| ATOM | 2185 | CZ | TYR | B | 700 | 40.652 | −13.149 | −2.442 | 1.00 | 38.33 | B |
| ATOM | 2186 | OH | TYR | B | 700 | 40.974 | −14.165 | −3.315 | 1.00 | 43.13 | B |
| ATOM | 2187 | C | TYR | B | 700 | 37.798 | −8.979 | 1.706 | 1.00 | 23.63 | B |
| ATOM | 2188 | O | TYR | B | 700 | 37.501 | −7.816 | 1.439 | 1.00 | 24.64 | B |
| ATOM | 2189 | N | ALA | B | 701 | 37.892 | −9.427 | 2.949 | 1.00 | 23.12 | B |
| ATOM | 2190 | CA | ALA | B | 701 | 37.664 | −8.541 | 4.080 | 1.00 | 23.90 | B |
| ATOM | 2191 | CB | ALA | B | 701 | 37.177 | −9.345 | 5.276 | 1.00 | 21.97 | B |
| ATOM | 2192 | C | ALA | B | 701 | 38.947 | −7.795 | 4.439 | 1.00 | 25.27 | B |
| ATOM | 2193 | O | ALA | B | 701 | 38.907 | −6.764 | 5.117 | 1.00 | 23.66 | B |
| ATOM | 2194 | N | GLY | B | 702 | 40.078 | −8.316 | 3.971 | 1.00 | 26.40 | B |
| ATOM | 2195 | CA | GLY | B | 702 | 41.361 | −7.706 | 4.282 | 1.00 | 30.27 | B |
| ATOM | 2196 | C | GLY | B | 702 | 41.693 | −7.977 | 5.740 | 1.00 | 33.57 | B |
| ATOM | 2197 | O | GLY | B | 702 | 42.346 | −7.170 | 6.410 | 1.00 | 32.31 | B |
| ATOM | 2198 | N | HIS | B | 703 | 41.238 | −9.130 | 6.229 | 1.00 | 35.31 | B |
| ATOM | 2199 | CA | HIS | B | 703 | 41.441 | −9.529 | 7.616 | 1.00 | 39.69 | B |
| ATOM | 2200 | CB | HIS | B | 703 | 40.355 | −10.529 | 8.021 | 1.00 | 39.47 | B |
| ATOM | 2201 | CG | HIS | B | 703 | 40.516 | −11.070 | 9.406 | 1.00 | 40.61 | B |
| ATOM | 2202 | CD2 | HIS | B | 703 | 39.934 | −10.715 | 10.575 | 1.00 | 41.64 | B |
| ATOM | 2203 | ND1 | HIS | B | 703 | 41.390 | −12.092 | 9.707 | 1.00 | 42.57 | B |
| ATOM | 2204 | CE1 | HIS | B | 703 | 41.338 | −12.345 | 11.003 | 1.00 | 42.52 | B |
| ATOM | 2205 | NE2 | HIS | B | 703 | 40.462 | −11.523 | 11.553 | 1.00 | 42.74 | B |
| ATOM | 2206 | C | HIS | B | 703 | 42.824 | −10.107 | 7.909 | 1.00 | 43.10 | B |
| ATOM | 2207 | O | HIS | B | 703 | 43.437 | −10.747 | 7.058 | 1.00 | 42.57 | B |
| ATOM | 2208 | N | ASP | B | 704 | 43.301 | −9.876 | 9.130 | 1.00 | 48.46 | B |
| ATOM | 2209 | CA | ASP | B | 704 | 44.613 | −10.353 | 9.561 | 1.00 | 53.34 | B |
| ATOM | 2210 | CB | ASP | B | 704 | 45.215 | −9.389 | 10.588 | 1.00 | 55.90 | B |
| ATOM | 2211 | CG | ASP | B | 704 | 45.145 | −7.941 | 10.147 | 1.00 | 59.16 | B |
| ATOM | 2212 | OD1 | ASP | B | 704 | 44.020 | −7.417 | 9.988 | 1.00 | 60.18 | B |
| ATOM | 2213 | OD2 | ASP | B | 704 | 46.219 | −7.326 | 9.963 | 1.00 | 61.84 | B |
| ATOM | 2214 | C | ASP | B | 704 | 44.552 | −11.745 | 10.187 | 1.00 | 55.32 | B |
| ATOM | 2215 | O | ASP | B | 704 | 44.445 | −11.872 | 11.407 | 1.00 | 55.54 | B |
| ATOM | 2216 | N | ASN | B | 705 | 44.619 | −12.785 | 9.362 | 1.00 | 57.68 | B |
| ATOM | 2217 | CA | ASN | B | 705 | 44.593 | −14.148 | 9.881 | 1.00 | 60.68 | B |
| ATOM | 2218 | CB | ASN | B | 705 | 44.482 | −15.162 | 8.738 | 1.00 | 60.99 | B |
| ATOM | 2219 | CG | ASN | B | 705 | 43.096 | −15.201 | 8.126 | 1.00 | 61.69 | B |
| ATOM | 2220 | OD1 | ASN | B | 705 | 42.623 | −14.215 | 7.561 | 1.00 | 61.90 | B |
| ATOM | 2221 | ND2 | ASN | B | 705 | 42.434 | −16.345 | 8.241 | 1.00 | 62.70 | B |
| ATOM | 2222 | C | ASN | B | 705 | 45.878 | −14.391 | 10.665 | 1.00 | 62.22 | B |
| ATOM | 2223 | O | ASN | B | 705 | 45.965 | −15.311 | 11.478 | 1.00 | 62.97 | B |
| ATOM | 2224 | N | THR | B | 706 | 46.870 | −13.544 | 10.410 | 1.00 | 63.73 | B |
| ATOM | 2225 | CA | THR | B | 706 | 48.166 | −13.629 | 11.069 | 1.00 | 64.99 | B |
| ATOM | 2226 | CB | THR | B | 706 | 49.068 | −12.445 | 10.655 | 1.00 | 64.95 | B |
| ATOM | 2227 | OG1 | THR | B | 706 | 50.196 | −12.373 | 11.534 | 1.00 | 65.67 | B |
| ATOM | 2228 | CG2 | THR | B | 706 | 48.293 | −11.132 | 10.710 | 1.00 | 65.66 | B |
| ATOM | 2229 | C | THR | B | 706 | 48.064 | −13.652 | 12.591 | 1.00 | 65.48 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2230 | O | THR | B | 706 | 48.428 | −14.636 | 13.233 | 1.00 | 65.69 | B |
| ATOM | 2231 | N | LYS | B | 707 | 47.559 | −12.561 | 13.158 | 1.00 | 66.27 | B |
| ATOM | 2232 | CA | LYS | B | 707 | 47.419 | −12.424 | 14.604 | 1.00 | 66.72 | B |
| ATOM | 2233 | CB | LYS | B | 707 | 47.443 | −10.944 | 14.983 | 1.00 | 67.27 | B |
| ATOM | 2234 | CG | LYS | B | 707 | 48.563 | −10.151 | 14.333 | 1.00 | 68.66 | B |
| ATOM | 2235 | CD | LYS | B | 707 | 48.407 | −8.666 | 14.617 | 1.00 | 69.39 | B |
| ATOM | 2236 | CE | LYS | B | 707 | 49.468 | −7.847 | 13.901 | 1.00 | 69.82 | B |
| ATOM | 2237 | NZ | LYS | B | 707 | 49.310 | −6.392 | 14.181 | 1.00 | 70.19 | B |
| ATOM | 2238 | C | LYS | B | 707 | 46.127 | −13.043 | 15.125 | 1.00 | 66.65 | B |
| ATOM | 2239 | O | LYS | B | 707 | 45.153 | −13.186 | 14.385 | 1.00 | 66.82 | B |
| ATOM | 2240 | N | PRO | B | 708 | 46.106 | −13.422 | 16.414 | 1.00 | 66.47 | B |
| ATOM | 2241 | CD | PRO | B | 708 | 47.218 | −13.402 | 17.381 | 1.00 | 66.43 | B |
| ATOM | 2242 | CA | PRO | B | 708 | 44.908 | −14.019 | 17.011 | 1.00 | 65.90 | B |
| ATOM | 2243 | CB | PRO | B | 708 | 45.291 | −14.151 | 18.482 | 1.00 | 66.34 | B |
| ATOM | 2244 | CG | PRO | B | 708 | 46.763 | −14.410 | 18.413 | 1.00 | 66.16 | B |
| ATOM | 2245 | C | PRO | B | 708 | 43.727 | −13.075 | 16.799 | 1.00 | 64.68 | B |
| ATOM | 2246 | O | PRO | B | 708 | 43.917 | −11.868 | 16.654 | 1.00 | 64.70 | B |
| ATOM | 2247 | N | ASP | B | 709 | 42.514 | −13.615 | 16.781 | 1.00 | 63.45 | B |
| ATOM | 2248 | CA | ASP | B | 709 | 41.341 | −12.781 | 16.563 | 1.00 | 62.09 | B |
| ATOM | 2249 | CB | ASP | B | 709 | 40.410 | −13.430 | 15.527 | 1.00 | 64.40 | B |
| ATOM | 2250 | CG | ASP | B | 709 | 39.736 | −14.691 | 16.047 | 1.00 | 65.90 | B |
| ATOM | 2251 | OD1 | ASP | B | 709 | 40.448 | −15.647 | 16.421 | 1.00 | 67.51 | B |
| ATOM | 2252 | OD2 | ASP | B | 709 | 38.487 | −14.726 | 16.079 | 1.00 | 66.80 | B |
| ATOM | 2253 | C | ASP | B | 709 | 40.565 | −12.493 | 17.841 | 1.00 | 59.94 | B |
| ATOM | 2254 | O | ASP | B | 709 | 40.223 | −13.405 | 18.595 | 1.00 | 60.20 | B |
| ATOM | 2255 | N | THR | B | 710 | 40.300 | −11.212 | 18.081 | 1.00 | 56.60 | B |
| ATOM | 2256 | CA | THR | B | 710 | 39.538 | −10.786 | 19.247 | 1.00 | 52.69 | B |
| ATOM | 2257 | CB | THR | B | 710 | 40.152 | −9.532 | 19.901 | 1.00 | 53.13 | B |
| ATOM | 2258 | OG1 | THR | B | 710 | 40.264 | −8.488 | 18.925 | 1.00 | 52.57 | B |
| ATOM | 2259 | CG2 | THR | B | 710 | 41.527 | −9.843 | 20.466 | 1.00 | 52.58 | B |
| ATOM | 2260 | C | THR | B | 710 | 38.125 | −10.460 | 18.781 | 1.00 | 50.35 | B |
| ATOM | 2261 | O | THR | B | 710 | 37.880 | −10.302 | 17.586 | 1.00 | 48.41 | B |
| ATOM | 2262 | N | SER | B | 711 | 37.196 | −10.361 | 19.721 | 1.00 | 48.24 | B |
| ATOM | 2263 | CA | SER | B | 711 | 35.816 | −10.060 | 19.376 | 1.00 | 46.44 | B |
| ATOM | 2264 | CB | SER | B | 711 | 34.943 | −10.057 | 20.634 | 1.00 | 47.23 | B |
| ATOM | 2265 | OG | SER | B | 711 | 33.572 | −9.910 | 20.303 | 1.00 | 49.85 | B |
| ATOM | 2266 | C | SER | B | 711 | 35.709 | −8.711 | 18.668 | 1.00 | 43.95 | B |
| ATOM | 2267 | O | SER | B | 711 | 34.900 | −8.544 | 17.757 | 1.00 | 43.72 | B |
| ATOM | 2268 | N | SER | B | 712 | 36.531 | −7.753 | 19.081 | 1.00 | 41.06 | B |
| ATOM | 2269 | CA | SER | B | 712 | 36.502 | −6.429 | 18.475 | 1.00 | 38.56 | B |
| ATOM | 2270 | CB | SER | B | 712 | 37.143 | −5.402 | 19.417 | 1.00 | 39.63 | B |
| ATOM | 2271 | OG | SER | B | 712 | 38.524 | −5.659 | 19.593 | 1.00 | 42.74 | B |
| ATOM | 2272 | C | SER | B | 712 | 37.207 | −6.400 | 17.117 | 1.00 | 35.92 | B |
| ATOM | 2273 | O | SER | B | 712 | 36.779 | −5.695 | 16.201 | 1.00 | 33.99 | B |
| ATOM | 2274 | N | SER | B | 713 | 38.285 | −7.167 | 16.983 | 1.00 | 32.54 | B |
| ATOM | 2275 | CA | SER | B | 713 | 39.025 | −7.200 | 15.728 | 1.00 | 30.34 | B |
| ATOM | 2276 | CB | SER | B | 713 | 40.357 | −7.934 | 15.904 | 1.00 | 31.13 | B |
| ATOM | 2277 | OG | SER | B | 713 | 40.161 | −9.335 | 15.964 | 1.00 | 31.92 | B |
| ATOM | 2278 | C | SER | B | 713 | 38.186 | −7.912 | 14.673 | 1.00 | 28.11 | B |
| ATOM | 2279 | O | SER | B | 713 | 38.265 | −7.607 | 13.487 | 1.00 | 24.98 | B |
| ATOM | 2280 | N | LEU | B | 714 | 37.380 | −8.864 | 15.125 | 1.00 | 26.38 | B |
| ATOM | 2281 | CA | LEU | B | 714 | 36.517 | −9.626 | 14.240 | 1.00 | 26.52 | B |
| ATOM | 2282 | CB | LEU | B | 714 | 35.972 | −10.848 | 14.986 | 1.00 | 29.55 | B |
| ATOM | 2283 | CG | LEU | B | 714 | 35.155 | −11.892 | 14.226 | 1.00 | 31.86 | B |
| ATOM | 2284 | CD1 | LEU | B | 714 | 35.842 | −12.254 | 12.917 | 1.00 | 34.03 | B |
| ATOM | 2285 | CD2 | LEU | B | 714 | 34.997 | −13.129 | 15.106 | 1.00 | 32.83 | B |
| ATOM | 2286 | C | LEU | B | 714 | 35.373 | −8.746 | 13.745 | 1.00 | 25.49 | B |
| ATOM | 2287 | O | LEU | B | 714 | 35.045 | −8.749 | 12.557 | 1.00 | 22.75 | B |
| ATOM | 2288 | N | LEU | B | 715 | 34.770 | −7.982 | 14.652 | 1.00 | 23.34 | B |
| ATOM | 2289 | CA | LEU | B | 715 | 33.679 | −7.101 | 14.266 | 1.00 | 22.41 | B |
| ATOM | 2290 | CB | LEU | B | 715 | 33.040 | −6.480 | 15.509 | 1.00 | 23.20 | B |
| ATOM | 2291 | CG | LEU | B | 715 | 32.283 | −7.511 | 16.358 | 1.00 | 25.47 | B |
| ATOM | 2292 | CD1 | LEU | B | 715 | 31.802 | −6.887 | 17.658 | 1.00 | 25.60 | B |
| ATOM | 2293 | CD2 | LEU | B | 715 | 31.110 | −8.056 | 15.551 | 1.00 | 24.95 | B |
| ATOM | 2294 | C | LEU | B | 715 | 34.203 | −6.021 | 13.318 | 1.00 | 21.60 | B |
| ATOM | 2295 | O | LEU | B | 715 | 33.537 | −5.655 | 12.346 | 1.00 | 20.68 | B |
| ATOM | 2296 | N | THR | B | 716 | 35.406 | −5.527 | 13.595 | 1.00 | 19.50 | B |
| ATOM | 2297 | CA | THR | B | 716 | 36.021 | −4.513 | 12.750 | 1.00 | 18.98 | B |
| ATOM | 2298 | CB | THR | B | 716 | 37.385 | −4.066 | 13.337 | 1.00 | 18.83 | B |
| ATOM | 2299 | OG1 | THR | B | 716 | 37.155 | −3.304 | 14.531 | 1.00 | 20.73 | B |
| ATOM | 2300 | CG2 | THR | B | 716 | 38.156 | −3.220 | 12.345 | 1.00 | 18.41 | B |
| ATOM | 2301 | C | THR | B | 716 | 36.210 | −5.059 | 11.330 | 1.00 | 20.03 | B |
| ATOM | 2302 | O | THR | B | 716 | 35.944 | −4.365 | 10.350 | 1.00 | 18.15 | B |
| ATOM | 2303 | N | SER | B | 717 | 36.657 | −6.306 | 11.217 | 1.00 | 20.54 | B |
| ATOM | 2304 | CA | SER | B | 717 | 36.857 | −6.901 | 9.898 | 1.00 | 21.70 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2305 | CB | SER | B | 717 | 37.588 | −8.241 | 10.010 | 1.00 | 23.38 | B |
| ATOM | 2306 | OG | SER | B | 717 | 38.960 | −8.031 | 10.299 | 1.00 | 28.56 | B |
| ATOM | 2307 | C | SER | B | 717 | 35.533 | −7.090 | 9.168 | 1.00 | 20.61 | B |
| ATOM | 2308 | O | SER | B | 717 | 35.466 | −6.914 | 7.952 | 1.00 | 20.71 | B |
| ATOM | 2309 | N | LEU | B | 718 | 34.484 | −7.449 | 9.905 | 1.00 | 18.62 | B |
| ATOM | 2310 | CA | LEU | B | 718 | 33.164 | −7.638 | 9.306 | 1.00 | 18.51 | B |
| ATOM | 2311 | CB | LEU | B | 718 | 32.193 | −8.240 | 10.321 | 1.00 | 18.50 | B |
| ATOM | 2312 | CG | LEU | B | 718 | 32.302 | −9.746 | 10.585 | 1.00 | 19.89 | B |
| ATOM | 2313 | CD1 | LEU | B | 718 | 31.510 | −10.098 | 11.833 | 1.00 | 20.48 | B |
| ATOM | 2314 | CD2 | LEU | B | 718 | 31.781 | −10.517 | 9.369 | 1.00 | 18.28 | B |
| ATOM | 2315 | C | LEU | B | 718 | 32.625 | −6.294 | 8.826 | 1.00 | 18.13 | B |
| ATOM | 2316 | O | LEU | B | 718 | 31.889 | −6.220 | 7.837 | 1.00 | 16.53 | B |
| ATOM | 2317 | N | ASN | B | 719 | 32.985 | −5.229 | 9.534 | 1.00 | 18.23 | B |
| ATOM | 2318 | CA | ASN | B | 719 | 32.528 | −3.902 | 9.144 | 1.00 | 17.99 | B |
| ATOM | 2319 | CB | ASN | B | 719 | 32.704 | −2.907 | 10.292 | 1.00 | 19.22 | B |
| ATOM | 2320 | CG | ASN | B | 719 | 31.682 | −3.107 | 11.390 | 1.00 | 20.19 | B |
| ATOM | 2321 | OD1 | ASN | B | 719 | 30.611 | −3.667 | 11.156 | 1.00 | 20.66 | B |
| ATOM | 2322 | ND2 | ASN | B | 719 | 31.997 | −2.632 | 12.593 | 1.00 | 19.69 | B |
| ATOM | 2323 | C | ASN | B | 719 | 33.294 | −3.432 | 7.915 | 1.00 | 19.00 | B |
| ATOM | 2324 | O | ASN | B | 719 | 32.745 | −2.727 | 7.067 | 1.00 | 16.93 | B |
| ATOM | 2325 | N | GLN | B | 720 | 34.562 | −3.834 | 7.820 | 1.00 | 17.58 | B |
| ATOM | 2326 | CA | GLN | B | 720 | 35.391 | −3.463 | 6.679 | 1.00 | 18.94 | B |
| ATOM | 2327 | CB | GLN | B | 720 | 36.851 | −3.859 | 6.925 | 1.00 | 19.50 | B |
| ATOM | 2328 | CG | GLN | B | 720 | 37.736 | −3.733 | 5.695 | 1.00 | 22.84 | B |
| ATOM | 2329 | CD | GLN | B | 720 | 37.784 | −2.318 | 5.149 | 1.00 | 23.37 | B |
| ATOM | 2330 | OE1 | GLN | B | 720 | 37.894 | −2.117 | 3.941 | 1.00 | 21.74 | B |
| ATOM | 2331 | NE2 | GLN | B | 720 | 37.711 | −1.332 | 6.038 | 1.00 | 22.07 | B |
| ATOM | 2332 | C | GLN | B | 720 | 34.846 | −4.200 | 5.463 | 1.00 | 19.76 | B |
| ATOM | 2333 | O | GLN | B | 720 | 34.714 | −3.636 | 4.372 | 1.00 | 15.95 | B |
| ATOM | 2334 | N | LEU | B | 721 | 34.526 | −5.474 | 5.665 | 1.00 | 18.87 | B |
| ATOM | 2335 | CA | LEU | B | 721 | 33.973 | −6.293 | 4.599 | 1.00 | 18.03 | B |
| ATOM | 2336 | CB | LEU | B | 721 | 33.763 | −7.726 | 5.102 | 1.00 | 18.09 | B |
| ATOM | 2337 | CG | LEU | B | 721 | 33.182 | −8.735 | 4.113 | 1.00 | 19.65 | B |
| ATOM | 2338 | CD1 | LEU | B | 721 | 34.094 | −8.844 | 2.893 | 1.00 | 16.27 | B |
| ATOM | 2339 | CD2 | LEU | B | 721 | 33.033 | −10.090 | 4.810 | 1.00 | 18.08 | B |
| ATOM | 2340 | C | LEU | B | 721 | 32.643 | −5.660 | 4.204 | 1.00 | 17.35 | B |
| ATOM | 2341 | O | LEU | B | 721 | 32.301 | −5.592 | 3.027 | 1.00 | 17.63 | B |
| ATOM | 2342 | N | GLY | B | 722 | 31.901 | −5.188 | 5.202 | 1.00 | 16.11 | B |
| ATOM | 2343 | CA | GLY | B | 722 | 30.622 | −4.547 | 4.942 | 1.00 | 17.12 | B |
| ATOM | 2344 | C | GLY | B | 722 | 30.780 | −3.281 | 4.109 | 1.00 | 19.60 | B |
| ATOM | 2345 | O | GLY | B | 722 | 29.948 | −2.985 | 3.239 | 1.00 | 17.68 | B |
| ATOM | 2346 | N | GLU | B | 723 | 31.847 | −2.526 | 4.366 | 1.00 | 17.38 | B |
| ATOM | 2347 | CA | GLU | B | 723 | 32.095 | −1.296 | 3.612 | 1.00 | 17.59 | B |
| ATOM | 2348 | CB | GLU | B | 723 | 33.322 | −0.563 | 4.162 | 1.00 | 16.95 | B |
| ATOM | 2349 | CG | GLU | B | 723 | 33.590 | 0.782 | 3.490 | 1.00 | 16.70 | B |
| ATOM | 2350 | CD | GLU | B | 723 | 32.710 | 1.898 | 4.032 | 1.00 | 18.40 | B |
| ATOM | 2351 | OE1 | GLU | B | 723 | 31.667 | 1.582 | 4.637 | 1.00 | 18.46 | B |
| ATOM | 2352 | OE2 | GLU | B | 723 | 33.057 | 3.092 | 3.847 | 1.00 | 15.57 | B |
| ATOM | 2353 | C | GLU | B | 723 | 32.340 | −1.629 | 2.143 | 1.00 | 17.94 | B |
| ATOM | 2354 | O | GLU | B | 723 | 31.844 | −0.946 | 1.241 | 1.00 | 18.69 | B |
| ATOM | 2355 | N | ARG | B | 724 | 33.122 | −2.679 | 1.910 | 1.00 | 18.32 | B |
| ATOM | 2356 | CA | ARG | B | 724 | 33.451 | −3.099 | 0.555 | 1.00 | 18.63 | B |
| ATOM | 2357 | CB | ARG | B | 724 | 34.591 | −4.125 | 0.586 | 1.00 | 18.71 | B |
| ATOM | 2358 | CG | ARG | B | 724 | 35.845 | −3.613 | 1.289 | 1.00 | 19.29 | B |
| ATOM | 2359 | CD | ARG | B | 724 | 36.992 | −4.604 | 1.193 | 1.00 | 20.38 | B |
| ATOM | 2360 | NE | ARG | B | 724 | 38.173 | −4.123 | 1.903 | 1.00 | 22.22 | B |
| ATOM | 2361 | CZ | ARG | B | 724 | 39.355 | −4.728 | 1.892 | 1.00 | 23.91 | B |
| ATOM | 2362 | NH1 | ARG | B | 724 | 39.526 | −5.849 | 1.205 | 1.00 | 22.36 | B |
| ATOM | 2363 | NH2 | ARG | B | 724 | 40.372 | −4.205 | 2.568 | 1.00 | 26.01 | B |
| ATOM | 2364 | C | ARG | B | 724 | 32.230 | −3.683 | −0.148 | 1.00 | 18.31 | B |
| ATOM | 2365 | O | ARG | B | 724 | 32.021 | −3.465 | −1.339 | 1.00 | 16.69 | B |
| ATOM | 2366 | N | GLN | B | 725 | 31.414 | −4.422 | 0.590 | 1.00 | 17.60 | B |
| ATOM | 2367 | CA | GLN | B | 725 | 30.227 | −5.000 | −0.011 | 1.00 | 18.87 | B |
| ATOM | 2368 | CB | GLN | B | 725 | 29.637 | −6.073 | 0.908 | 1.00 | 17.78 | B |
| ATOM | 2369 | CG | GLN | B | 725 | 30.538 | −7.305 | 1.030 | 1.00 | 23.54 | B |
| ATOM | 2370 | CD | GLN | B | 725 | 29.853 | −8.468 | 1.714 | 1.00 | 25.93 | B |
| ATOM | 2371 | OE1 | GLN | B | 725 | 30.443 | −9.532 | 1.901 | 1.00 | 29.72 | B |
| ATOM | 2372 | NE2 | GLN | B | 725 | 28.599 | −8.274 | 2.088 | 1.00 | 28.88 | B |
| ATOM | 2373 | C | GLN | B | 725 | 29.195 | −3.920 | −0.332 | 1.00 | 18.08 | B |
| ATOM | 2374 | O | GLN | B | 725 | 28.440 | −4.036 | −1.298 | 1.00 | 18.14 | B |
| ATOM | 2375 | N | LEU | B | 726 | 29.172 | −2.855 | 0.459 | 1.00 | 18.05 | B |
| ATOM | 2376 | CA | LEU | B | 726 | 28.227 | −1.777 | 0.203 | 1.00 | 18.04 | B |
| ATOM | 2377 | CB | LEU | B | 726 | 28.323 | −0.727 | 1.314 | 1.00 | 20.54 | B |
| ATOM | 2378 | CG | LEU | B | 726 | 27.263 | 0.376 | 1.383 | 1.00 | 20.94 | B |
| ATOM | 2379 | CD1 | LEU | B | 726 | 25.859 | −0.216 | 1.325 | 1.00 | 19.79 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2380 | CD2 | LEU | B | 726 | 27.472 | 1.171 | 2.681 | 1.00 | 21.03 | B |
| ATOM | 2381 | C | LEU | B | 726 | 28.551 | −1.172 | −1.167 | 1.00 | 18.14 | B |
| ATOM | 2382 | O | LEU | B | 726 | 27.658 | −0.933 | −1.986 | 1.00 | 17.87 | B |
| ATOM | 2383 | N | LEU | B | 727 | 29.836 | −0.950 | −1.426 | 1.00 | 16.39 | B |
| ATOM | 2384 | CA | LEU | B | 727 | 30.259 | −0.401 | −2.706 | 1.00 | 18.19 | B |
| ATOM | 2385 | CB | LEU | B | 727 | 31.775 | −0.179 | −2.715 | 1.00 | 19.81 | B |
| ATOM | 2386 | CG | LEU | B | 727 | 32.387 | 0.233 | −4.060 | 1.00 | 22.06 | B |
| ATOM | 2387 | CD1 | LEU | B | 727 | 31.828 | 1.578 | −4.498 | 1.00 | 24.00 | B |
| ATOM | 2388 | CD2 | LEU | B | 727 | 33.905 | 0.309 | −3.932 | 1.00 | 24.38 | B |
| ATOM | 2389 | C | LEU | B | 727 | 29.868 | −1.334 | −3.860 | 1.00 | 18.39 | B |
| ATOM | 2390 | O | LEU | B | 727 | 29.457 | −0.872 | −4.929 | 1.00 | 18.62 | B |
| ATOM | 2391 | N | SER | B | 728 | 29.986 | −2.644 | −3.646 | 1.00 | 17.14 | B |
| ATOM | 2392 | CA | SER | B | 728 | 29.643 | −3.598 | −4.696 | 1.00 | 19.54 | B |
| ATOM | 2393 | CB | SER | B | 728 | 30.125 | −5.013 | −4.343 | 1.00 | 20.37 | B |
| ATOM | 2394 | OG | SER | B | 728 | 29.369 | −5.558 | −3.280 | 1.00 | 27.70 | B |
| ATOM | 2395 | C | SER | B | 728 | 28.138 | −3.610 | −4.943 | 1.00 | 17.78 | B |
| ATOM | 2396 | O | SER | B | 728 | 27.698 | −3.747 | −6.079 | 1.00 | 18.32 | B |
| ATOM | 2397 | N | VAL | B | 729 | 27.352 | −3.476 | −3.880 | 1.00 | 17.66 | B |
| ATOM | 2398 | CA | VAL | B | 729 | 25.895 | −3.446 | −4.020 | 1.00 | 18.18 | B |
| ATOM | 2399 | CB | VAL | B | 729 | 25.201 | −3.329 | −2.642 | 1.00 | 19.59 | B |
| ATOM | 2400 | CG1 | VAL | B | 729 | 23.712 | −3.029 | −2.816 | 1.00 | 19.79 | B |
| ATOM | 2401 | CG2 | VAL | B | 729 | 25.381 | −4.630 | −1.869 | 1.00 | 22.69 | B |
| ATOM | 2402 | C | VAL | B | 729 | 25.467 | −2.261 | −4.888 | 1.00 | 18.00 | B |
| ATOM | 2403 | O | VAL | B | 729 | 24.630 | −2.402 | −5.781 | 1.00 | 18.81 | B |
| ATOM | 2404 | N | VAL | B | 730 | 26.040 | −1.092 | −4.624 | 1.00 | 16.70 | B |
| ATOM | 2405 | CA | VAL | B | 730 | 25.694 | 0.092 | −5.401 | 1.00 | 18.31 | B |
| ATOM | 2406 | CB | VAL | B | 730 | 26.364 | 1.364 | −4.822 | 1.00 | 17.54 | B |
| ATOM | 2407 | CG1 | VAL | B | 730 | 25.962 | 2.587 | −5.646 | 1.00 | 20.82 | B |
| ATOM | 2408 | CG2 | VAL | B | 730 | 25.940 | 1.561 | −3.363 | 1.00 | 20.52 | B |
| ATOM | 2409 | C | VAL | B | 730 | 26.102 | −0.086 | −6.865 | 1.00 | 17.87 | B |
| ATOM | 2410 | O | VAL | B | 730 | 25.331 | 0.230 | −7.770 | 1.00 | 21.04 | B |
| ATOM | 2411 | N | LYS | B | 731 | 27.303 | −0.598 | −7.108 | 1.00 | 17.34 | B |
| ATOM | 2412 | CA | LYS | B | 731 | 27.739 | −0.803 | −8.485 | 1.00 | 18.71 | B |
| ATOM | 2413 | CB | LYS | B | 731 | 29.190 | −1.289 | −8.527 | 1.00 | 22.00 | B |
| ATOM | 2414 | CG | LYS | B | 731 | 30.213 | −0.192 | −8.223 | 1.00 | 23.19 | B |
| ATOM | 2415 | CD | LYS | B | 731 | 31.632 | −0.719 | −8.378 | 1.00 | 28.30 | B |
| ATOM | 2416 | CE | LYS | B | 731 | 32.657 | 0.390 | −8.185 | 1.00 | 30.48 | B |
| ATOM | 2417 | NZ | LYS | B | 731 | 34.053 | −0.126 | −8.247 | 1.00 | 34.47 | B |
| ATOM | 2418 | C | LYS | B | 731 | 26.825 | −1.808 | −9.183 | 1.00 | 19.77 | B |
| ATOM | 2419 | O | LYS | B | 731 | 26.421 | −1.605 | −10.331 | 1.00 | 17.95 | B |
| ATOM | 2420 | N | TRP | B | 732 | 26.509 | −2.887 | −8.473 | 1.00 | 17.50 | B |
| ATOM | 2421 | CA | TRP | B | 732 | 25.630 | −3.937 | −8.975 | 1.00 | 17.41 | B |
| ATOM | 2422 | CB | TRP | B | 732 | 25.438 | −4.996 | −7.883 | 1.00 | 16.91 | B |
| ATOM | 2423 | CG | TRP | B | 732 | 24.321 | −5.985 | −8.112 | 1.00 | 15.88 | B |
| ATOM | 2424 | CD2 | TRP | B | 732 | 23.100 | −6.073 | −7.371 | 1.00 | 15.43 | B |
| ATOM | 2425 | CE2 | TRP | B | 732 | 22.388 | −7.191 | −7.863 | 1.00 | 16.91 | B |
| ATOM | 2426 | CE3 | TRP | B | 732 | 22.539 | −5.317 | −6.331 | 1.00 | 14.91 | B |
| ATOM | 2427 | CD1 | TRP | B | 732 | 24.299 | −7.019 | −9.011 | 1.00 | 16.77 | B |
| ATOM | 2428 | NE1 | TRP | B | 732 | 23.140 | −7.751 | −8.863 | 1.00 | 16.21 | B |
| ATOM | 2429 | CZ2 | TRP | B | 732 | 21.140 | −7.571 | −7.350 | 1.00 | 16.15 | B |
| ATOM | 2430 | CZ3 | TRP | B | 732 | 21.299 | −5.694 | −5.818 | 1.00 | 14.22 | B |
| ATOM | 2431 | CH2 | TRP | B | 732 | 20.614 | −6.813 | −6.330 | 1.00 | 16.68 | B |
| ATOM | 2432 | C | TRP | B | 732 | 24.279 | −3.350 | −9.378 | 1.00 | 16.02 | B |
| ATOM | 2433 | O | TRP | B | 732 | 23.783 | −3.617 | −10.472 | 1.00 | 16.45 | B |
| ATOM | 2434 | N | SER | B | 733 | 23.699 | −2.541 | −8.495 | 1.00 | 16.26 | B |
| ATOM | 2435 | CA | SER | B | 733 | 22.390 | −1.939 | −8.749 | 1.00 | 17.13 | B |
| ATOM | 2436 | CB | SER | B | 733 | 21.945 | −1.105 | −7.543 | 1.00 | 15.29 | B |
| ATOM | 2437 | OG | SER | B | 733 | 22.713 | 0.081 | −7.434 | 1.00 | 16.35 | B |
| ATOM | 2438 | C | SER | B | 733 | 22.365 | −1.068 | −10.009 | 1.00 | 18.91 | B |
| ATOM | 2439 | O | SER | B | 733 | 21.318 | −0.901 | −10.633 | 1.00 | 18.17 | B |
| ATOM | 2440 | N | LYS | B | 734 | 23.519 | −0.524 | −10.383 | 1.00 | 18.91 | B |
| ATOM | 2441 | CA | LYS | B | 734 | 23.612 | 0.329 | −11.564 | 1.00 | 21.91 | B |
| ATOM | 2442 | CB | LYS | B | 734 | 24.952 | 1.073 | −11.576 | 1.00 | 26.10 | B |
| ATOM | 2443 | CG | LYS | B | 734 | 25.042 | 2.153 | −10.518 | 1.00 | 30.52 | B |
| ATOM | 2444 | CD | LYS | B | 734 | 26.320 | 2.954 | −10.644 | 1.00 | 35.02 | B |
| ATOM | 2445 | CE | LYS | B | 734 | 26.159 | 4.306 | −9.974 | 1.00 | 37.63 | B |
| ATOM | 2446 | NZ | LYS | B | 734 | 25.095 | 5.122 | −10.632 | 1.00 | 39.56 | B |
| ATOM | 2447 | C | LYS | B | 734 | 23.444 | −0.447 | −12.863 | 1.00 | 21.73 | B |
| ATOM | 2448 | O | LYS | B | 734 | 23.125 | 0.133 | −13.905 | 1.00 | 19.82 | B |
| ATOM | 2449 | N | SER | B | 735 | 23.659 | −1.758 | −12.798 | 1.00 | 19.96 | B |
| ATOM | 2450 | CA | SER | B | 735 | 23.517 | −2.616 | −13.969 | 1.00 | 19.76 | B |
| ATOM | 2451 | CB | SER | B | 735 | 24.748 | −3.519 | −14.126 | 1.00 | 19.35 | B |
| ATOM | 2452 | OG | SER | B | 735 | 25.918 | −2.756 | −14.356 | 1.00 | 23.17 | B |
| ATOM | 2453 | C | SER | B | 735 | 22.267 | −3.488 | −13.878 | 1.00 | 18.19 | B |
| ATOM | 2454 | O | SER | B | 735 | 21.932 | −4.189 | −14.833 | 1.00 | 17.56 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2455 | N | LEU | B | 736 | 21.589 | −3.446 | −12.731 | 1.00 | 17.46 | B |
| ATOM | 2456 | CA | LEU | B | 736 | 20.375 | −4.239 | −12.503 | 1.00 | 16.58 | B |
| ATOM | 2457 | CB | LEU | B | 736 | 19.991 | −4.193 | −11.017 | 1.00 | 16.96 | B |
| ATOM | 2458 | CG | LEU | B | 736 | 18.736 | −4.939 | −10.547 | 1.00 | 19.34 | B |
| ATOM | 2459 | CD1 | LEU | B | 736 | 18.886 | −6.439 | −10.793 | 1.00 | 18.13 | B |
| ATOM | 2460 | CD2 | LEU | B | 736 | 18.525 | −4.679 | −9.058 | 1.00 | 18.75 | B |
| ATOM | 2461 | C | LEU | B | 736 | 19.230 | −3.680 | −13.344 | 1.00 | 17.27 | B |
| ATOM | 2462 | O | LEU | B | 736 | 18.776 | −2.562 | −13.111 | 1.00 | 16.74 | B |
| ATOM | 2463 | N | PRO | B | 737 | 18.738 | −4.458 | −14.322 | 1.00 | 18.08 | B |
| ATOM | 2464 | CD | PRO | B | 737 | 19.117 | −5.847 | −14.643 | 1.00 | 17.66 | B |
| ATOM | 2465 | CA | PRO | B | 737 | 17.643 | −4.005 | −15.188 | 1.00 | 18.21 | B |
| ATOM | 2466 | CB | PRO | B | 737 | 17.247 | −5.275 | −15.943 | 1.00 | 18.86 | B |
| ATOM | 2467 | CG | PRO | B | 737 | 18.556 | −6.022 | −16.035 | 1.00 | 17.53 | B |
| ATOM | 2468 | C | PRO | B | 737 | 16.470 | −3.390 | −14.438 | 1.00 | 18.80 | B |
| ATOM | 2469 | O | PRO | B | 737 | 15.890 | −4.013 | −13.544 | 1.00 | 19.03 | B |
| ATOM | 2470 | N | GLY | B | 738 | 16.145 | −2.152 | −14.800 | 1.00 | 18.43 | B |
| ATOM | 2471 | CA | GLY | B | 738 | 15.031 | −1.455 | −14.187 | 1.00 | 17.85 | B |
| ATOM | 2472 | C | GLY | B | 738 | 15.338 | −0.574 | −12.991 | 1.00 | 16.86 | B |
| ATOM | 2473 | O | GLY | B | 738 | 14.678 | 0.444 | −12.791 | 1.00 | 15.62 | B |
| ATOM | 2474 | N | PHE | B | 739 | 16.350 | −0.932 | −12.205 | 1.00 | 15.96 | B |
| ATOM | 2475 | CA | PHE | B | 739 | 16.662 | −0.163 | −11.010 | 1.00 | 14.50 | B |
| ATOM | 2476 | CB | PHE | B | 739 | 17.791 | −0.829 | −10.216 | 1.00 | 14.29 | B |
| ATOM | 2477 | CG | PHE | B | 739 | 17.917 | −0.307 | −8.818 | 1.00 | 14.77 | B |
| ATOM | 2478 | CD1 | PHE | B | 739 | 17.021 | −0.712 | −7.832 | 1.00 | 17.58 | B |
| ATOM | 2479 | CD2 | PHE | B | 739 | 18.916 | 0.601 | −8.483 | 1.00 | 16.38 | B |
| ATOM | 2480 | CE1 | PHE | B | 739 | 17.116 | −0.217 | −6.528 | 1.00 | 19.63 | B |
| ATOM | 2481 | CE2 | PHE | B | 739 | 19.022 | 1.102 | −7.187 | 1.00 | 18.02 | B |
| ATOM | 2482 | CZ | PHE | B | 739 | 18.120 | 0.689 | −6.205 | 1.00 | 15.95 | B |
| ATOM | 2483 | C | PHE | B | 739 | 17.031 | 1.296 | −11.247 | 1.00 | 15.95 | B |
| ATOM | 2484 | O | PHE | B | 739 | 16.554 | 2.180 | −10.532 | 1.00 | 15.43 | B |
| ATOM | 2485 | N | ARG | B | 740 | 17.893 | 1.542 | −12.233 | 1.00 | 14.92 | B |
| ATOM | 2486 | CA | ARG | B | 740 | 18.336 | 2.898 | −12.546 | 1.00 | 18.27 | B |
| ATOM | 2487 | CB | ARG | B | 740 | 19.414 | 2.868 | −13.631 | 1.00 | 20.12 | B |
| ATOM | 2488 | CG | ARG | B | 740 | 18.933 | 2.276 | −14.956 | 1.00 | 20.07 | B |
| ATOM | 2489 | CD | ARG | B | 740 | 19.951 | 2.489 | −16.074 | 1.00 | 20.49 | B |
| ATOM | 2490 | NE | ARG | B | 740 | 19.432 | 2.001 | −17.347 | 1.00 | 21.32 | B |
| ATOM | 2491 | CZ | ARG | B | 740 | 20.021 | 2.190 | −18.524 | 1.00 | 22.16 | B |
| ATOM | 2492 | NH1 | ARG | B | 740 | 21.164 | 2.862 | −18.601 | 1.00 | 20.37 | B |
| ATOM | 2493 | NH2 | ARG | B | 740 | 19.460 | 1.704 | −19.625 | 1.00 | 20.63 | B |
| ATOM | 2494 | C | ARG | B | 740 | 17.185 | 3.783 | −13.013 | 1.00 | 18.64 | B |
| ATOM | 2495 | O | ARG | B | 740 | 17.324 | 5.001 | −13.090 | 1.00 | 18.88 | B |
| ATOM | 2496 | N | ASN | B | 741 | 16.048 | 3.167 | −13.315 | 1.00 | 18.88 | B |
| ATOM | 2497 | CA | ASN | B | 741 | 14.883 | 3.904 | −13.786 | 1.00 | 19.14 | B |
| ATOM | 2498 | CB | ASN | B | 741 | 14.088 | 3.015 | −14.742 | 1.00 | 22.68 | B |
| ATOM | 2499 | CG | ASN | B | 741 | 14.904 | 2.633 | −15.964 | 1.00 | 23.46 | B |
| ATOM | 2500 | OD1 | ASN | B | 741 | 14.743 | 1.551 | −16.533 | 1.00 | 25.91 | B |
| ATOM | 2501 | ND2 | ASN | B | 741 | 15.798 | 3.530 | −16.371 | 1.00 | 22.56 | B |
| ATOM | 2502 | C | ASN | B | 741 | 14.001 | 4.448 | −12.666 | 1.00 | 18.84 | B |
| ATOM | 2503 | O | ASN | B | 741 | 13.090 | 5.241 | −12.906 | 1.00 | 18.36 | B |
| ATOM | 2504 | N | LEU | B | 742 | 14.282 | 4.034 | −11.436 | 1.00 | 16.78 | B |
| ATOM | 2505 | CA | LEU | B | 742 | 13.529 | 4.532 | −10.293 | 1.00 | 17.18 | B |
| ATOM | 2506 | CB | LEU | B | 742 | 13.660 | 3.583 | −9.090 | 1.00 | 17.93 | B |
| ATOM | 2507 | CG | LEU | B | 742 | 13.275 | 2.111 | −9.273 | 1.00 | 19.23 | B |
| ATOM | 2508 | CD1 | LEU | B | 742 | 13.651 | 1.333 | −8.019 | 1.00 | 20.55 | B |
| ATOM | 2509 | CD2 | LEU | B | 742 | 11.782 | 1.993 | −9.554 | 1.00 | 21.11 | B |
| ATOM | 2510 | C | LEU | B | 742 | 14.125 | 5.886 | −9.919 | 1.00 | 17.11 | B |
| ATOM | 2511 | O | LEU | B | 742 | 15.287 | 6.171 | −10.219 | 1.00 | 16.40 | B |
| ATOM | 2512 | N | HIS | B | 743 | 13.323 | 6.720 | −9.273 | 1.00 | 17.11 | B |
| ATOM | 2513 | CA | HIS | B | 743 | 13.779 | 8.030 | −8.826 | 1.00 | 20.34 | B |
| ATOM | 2514 | CB | HIS | B | 743 | 12.670 | 8.667 | −7.981 | 1.00 | 22.04 | B |
| ATOM | 2515 | CG | HIS | B | 743 | 12.930 | 10.087 | −7.590 | 1.00 | 26.50 | B |
| ATOM | 2516 | CD2 | HIS | B | 743 | 12.372 | 11.244 | −8.018 | 1.00 | 28.30 | B |
| ATOM | 2517 | ND1 | HIS | B | 743 | 13.842 | 10.439 | −6.617 | 1.00 | 27.58 | B |
| ATOM | 2518 | CE1 | HIS | B | 743 | 13.832 | 11.751 | −6.461 | 1.00 | 28.99 | B |
| ATOM | 2519 | NE2 | HIS | B | 743 | 12.948 | 12.263 | −7.299 | 1.00 | 27.82 | B |
| ATOM | 2520 | C | HIS | B | 743 | 15.046 | 7.777 | −7.990 | 1.00 | 20.44 | B |
| ATOM | 2521 | O | HIS | B | 743 | 15.121 | 6.782 | −7.264 | 1.00 | 18.79 | B |
| ATOM | 2522 | N | ILE | B | 744 | 16.041 | 8.652 | −8.109 | 1.00 | 20.57 | B |
| ATOM | 2523 | CA | ILE | B | 744 | 17.289 | 8.483 | −7.365 | 1.00 | 19.99 | B |
| ATOM | 2524 | CB | ILE | B | 744 | 18.279 | 9.638 | −7.666 | 1.00 | 21.19 | B |
| ATOM | 2525 | CG2 | ILE | B | 744 | 19.513 | 9.538 | −6.760 | 1.00 | 19.18 | B |
| ATOM | 2526 | CG1 | ILE | B | 744 | 18.701 | 9.569 | −9.138 | 1.00 | 20.37 | B |
| ATOM | 2527 | CD1 | ILE | B | 744 | 19.690 | 10.646 | −9.566 | 1.00 | 25.65 | B |
| ATOM | 2528 | C | ILE | B | 744 | 17.086 | 8.352 | −5.857 | 1.00 | 20.50 | B |
| ATOM | 2529 | O | ILE | B | 744 | 17.802 | 7.595 | −5.196 | 1.00 | 20.10 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2530 | N | ASP | B | 745 | 16.114 | 9.073 | −5.304 | 1.00 | 19.58 | B |
| ATOM | 2531 | CA | ASP | B | 745 | 15.857 | 8.974 | −3.868 | 1.00 | 21.19 | B |
| ATOM | 2532 | CB | ASP | B | 745 | 14.768 | 9.952 | −3.416 | 1.00 | 24.33 | B |
| ATOM | 2533 | CG | ASP | B | 745 | 15.233 | 11.387 | −3.413 | 1.00 | 27.99 | B |
| ATOM | 2534 | OD1 | ASP | B | 745 | 16.458 | 11.622 | −3.380 | 1.00 | 30.68 | B |
| ATOM | 2535 | OD2 | ASP | B | 745 | 14.364 | 12.280 | −3.426 | 1.00 | 30.97 | B |
| ATOM | 2536 | C | ASP | B | 745 | 15.400 | 7.566 | −3.517 | 1.00 | 19.87 | B |
| ATOM | 2537 | O | ASP | B | 745 | 15.752 | 7.044 | −2.462 | 1.00 | 20.15 | B |
| ATOM | 2538 | N | ASP | B | 746 | 14.591 | 6.971 | −4.389 | 1.00 | 19.04 | B |
| ATOM | 2539 | CA | ASP | B | 746 | 14.097 | 5.618 | −4.152 | 1.00 | 18.78 | B |
| ATOM | 2540 | CB | ASP | B | 746 | 13.055 | 5.201 | −5.197 | 1.00 | 18.11 | B |
| ATOM | 2541 | CG | ASP | B | 746 | 11.817 | 6.078 | −5.191 | 1.00 | 21.37 | B |
| ATOM | 2542 | OD1 | ASP | B | 746 | 11.580 | 6.816 | −4.207 | 1.00 | 19.54 | B |
| ATOM | 2543 | OD2 | ASP | B | 746 | 11.065 | 6.004 | −6.188 | 1.00 | 22.68 | B |
| ATOM | 2544 | C | ASP | B | 746 | 15.261 | 4.631 | −4.213 | 1.00 | 17.19 | B |
| ATOM | 2545 | O | ASP | B | 746 | 15.319 | 3.689 | −3.423 | 1.00 | 18.41 | B |
| ATOM | 2546 | N | GLN | B | 747 | 16.176 | 4.836 | −5.157 | 1.00 | 16.73 | B |
| ATOM | 2547 | CA | GLN | B | 747 | 17.320 | 3.936 | −5.282 | 1.00 | 16.32 | B |
| ATOM | 2548 | CB | GLN | B | 747 | 18.227 | 4.357 | −6.439 | 1.00 | 16.06 | B |
| ATOM | 2549 | CG | GLN | B | 747 | 17.570 | 4.282 | −7.815 | 1.00 | 14.64 | B |
| ATOM | 2550 | CD | GLN | B | 747 | 18.478 | 4.787 | −8.916 | 1.00 | 16.67 | B |
| ATOM | 2551 | OE1 | GLN | B | 747 | 18.021 | 5.411 | −9.874 | 1.00 | 18.54 | B |
| ATOM | 2552 | NE2 | GLN | B | 747 | 19.775 | 4.518 | −8.789 | 1.00 | 12.03 | B |
| ATOM | 2553 | C | GLN | B | 747 | 18.116 | 3.929 | −3.984 | 1.00 | 15.90 | B |
| ATOM | 2554 | O | GLN | B | 747 | 18.426 | 2.870 | −3.445 | 1.00 | 15.22 | B |
| ATOM | 2555 | N | ILE | B | 748 | 18.441 | 5.119 | −3.486 | 1.00 | 15.67 | B |
| ATOM | 2556 | CA | ILE | B | 748 | 19.199 | 5.247 | −2.250 | 1.00 | 14.76 | B |
| ATOM | 2557 | CB | ILE | B | 748 | 19.447 | 6.726 | −1.901 | 1.00 | 17.21 | B |
| ATOM | 2558 | CG2 | ILE | B | 748 | 20.131 | 6.831 | −0.544 | 1.00 | 18.09 | B |
| ATOM | 2559 | CG1 | ILE | B | 748 | 20.314 | 7.376 | −2.981 | 1.00 | 16.97 | B |
| ATOM | 2560 | CD1 | ILE | B | 748 | 20.562 | 8.874 | −2.767 | 1.00 | 19.77 | B |
| ATOM | 2561 | C | ILE | B | 748 | 18.459 | 4.588 | −1.094 | 1.00 | 15.63 | B |
| ATOM | 2562 | O | ILE | B | 748 | 19.046 | 3.826 | −0.320 | 1.00 | 15.86 | B |
| ATOM | 2563 | N | THR | B | 749 | 17.166 | 4.884 | −0.984 | 1.00 | 14.70 | B |
| ATOM | 2564 | CA | THR | B | 749 | 16.336 | 4.323 | 0.072 | 1.00 | 14.94 | B |
| ATOM | 2565 | CB | THR | B | 749 | 14.891 | 4.858 | −0.037 | 1.00 | 16.72 | B |
| ATOM | 2566 | OG1 | THR | B | 749 | 14.894 | 6.268 | 0.218 | 1.00 | 18.70 | B |
| ATOM | 2567 | CG2 | THR | B | 749 | 13.974 | 4.173 | 0.969 | 1.00 | 17.71 | B |
| ATOM | 2568 | C | THR | B | 749 | 16.320 | 2.793 | 0.055 | 1.00 | 14.91 | B |
| ATOM | 2569 | O | THR | B | 749 | 16.499 | 2.151 | 1.096 | 1.00 | 15.12 | B |
| ATOM | 2570 | N | LEU | B | 750 | 16.117 | 2.204 | −1.122 | 1.00 | 13.93 | B |
| ATOM | 2571 | CA | LEU | B | 750 | 16.073 | 0.745 | −1.232 | 1.00 | 14.49 | B |
| ATOM | 2572 | CB | LEU | B | 750 | 15.667 | 0.327 | −2.654 | 1.00 | 14.19 | B |
| ATOM | 2573 | CG | LEU | B | 750 | 14.214 | 0.702 | −2.987 | 1.00 | 16.47 | B |
| ATOM | 2574 | CD1 | LEU | B | 750 | 13.922 | 0.449 | −4.476 | 1.00 | 16.09 | B |
| ATOM | 2575 | CD2 | LEU | B | 750 | 13.272 | −0.115 | −2.101 | 1.00 | 14.27 | B |
| ATOM | 2576 | C | LEU | B | 750 | 17.407 | 0.108 | −0.853 | 1.00 | 14.83 | B |
| ATOM | 2577 | O | LEU | B | 750 | 17.437 | −0.924 | −0.177 | 1.00 | 15.56 | B |
| ATOM | 2578 | N | ILE | B | 751 | 18.508 | 0.719 | −1.277 | 1.00 | 14.16 | B |
| ATOM | 2579 | CA | ILE | B | 751 | 19.824 | 0.179 | −0.942 | 1.00 | 16.07 | B |
| ATOM | 2580 | CB | ILE | B | 751 | 20.952 | 0.904 | −1.719 | 1.00 | 15.86 | B |
| ATOM | 2581 | CG2 | ILE | B | 751 | 22.326 | 0.534 | −1.138 | 1.00 | 15.95 | B |
| ATOM | 2582 | CG1 | ILE | B | 751 | 20.874 | 0.525 | −3.202 | 1.00 | 15.28 | B |
| ATOM | 2583 | CD1 | ILE | B | 751 | 21.803 | 1.311 | −4.093 | 1.00 | 20.05 | B |
| ATOM | 2584 | C | ILE | B | 751 | 20.077 | 0.298 | 0.561 | 1.00 | 16.75 | B |
| ATOM | 2585 | O | ILE | B | 751 | 20.543 | −0.650 | 1.196 | 1.00 | 16.19 | B |
| ATOM | 2586 | N | GLN | B | 752 | 19.763 | 1.454 | 1.136 | 1.00 | 17.86 | B |
| ATOM | 2587 | CA | GLN | B | 752 | 19.976 | 1.646 | 2.567 | 1.00 | 18.49 | B |
| ATOM | 2588 | CB | GLN | B | 752 | 19.788 | 3.120 | 2.950 | 1.00 | 17.93 | B |
| ATOM | 2589 | CG | GLN | B | 752 | 20.754 | 4.049 | 2.212 | 1.00 | 19.72 | B |
| ATOM | 2590 | CD | GLN | B | 752 | 20.823 | 5.449 | 2.800 | 1.00 | 21.05 | B |
| ATOM | 2591 | OE1 | GLN | B | 752 | 19.825 | 5.986 | 3.282 | 1.00 | 22.57 | B |
| ATOM | 2592 | NE2 | GLN | B | 752 | 22.006 | 6.056 | 2.742 | 1.00 | 20.90 | B |
| ATOM | 2593 | C | GLN | B | 752 | 19.067 | 0.748 | 3.407 | 1.00 | 19.34 | B |
| ATOM | 2594 | O | GLN | B | 752 | 19.457 | 0.315 | 4.488 | 1.00 | 19.27 | B |
| ATOM | 2595 | N | TYR | B | 753 | 17.865 | 0.461 | 2.909 | 1.00 | 17.95 | B |
| ATOM | 2596 | CA | TYR | B | 753 | 16.919 | −0.407 | 3.616 | 1.00 | 16.98 | B |
| ATOM | 2597 | CB | TYR | B | 753 | 15.519 | −0.316 | 2.994 | 1.00 | 19.29 | B |
| ATOM | 2598 | CG | TYR | B | 753 | 14.634 | 0.837 | 3.424 | 1.00 | 18.86 | B |
| ATOM | 2599 | CD1 | TYR | B | 753 | 15.116 | 1.891 | 4.204 | 1.00 | 19.58 | B |
| ATOM | 2600 | CE1 | TYR | B | 753 | 14.275 | 2.973 | 4.552 | 1.00 | 20.49 | B |
| ATOM | 2601 | CD2 | TYR | B | 753 | 13.304 | 0.884 | 3.007 | 1.00 | 20.96 | B |
| ATOM | 2602 | CE2 | TYR | B | 753 | 12.472 | 1.943 | 3.342 | 1.00 | 20.37 | B |
| ATOM | 2603 | CZ | TYR | B | 753 | 12.956 | 2.980 | 4.106 | 1.00 | 19.88 | B |
| ATOM | 2604 | OH | TYR | B | 753 | 12.108 | 4.021 | 4.401 | 1.00 | 21.79 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2605 | C | TYR | B | 753 | 17.318 | −1.888 | 3.574 | 1.00 | 18.67 | B |
| ATOM | 2606 | O | TYR | B | 753 | 17.142 | −2.612 | 4.555 | 1.00 | 17.27 | B |
| ATOM | 2607 | N | SER | B | 754 | 17.845 | −2.327 | 2.431 | 1.00 | 17.61 | B |
| ATOM | 2608 | CA | SER | B | 754 | 18.198 | −3.736 | 2.215 | 1.00 | 17.75 | B |
| ATOM | 2609 | CB | SER | B | 754 | 17.769 | −4.150 | 0.807 | 1.00 | 16.13 | B |
| ATOM | 2610 | OG | SER | B | 754 | 18.566 | −3.484 | −0.156 | 1.00 | 17.94 | B |
| ATOM | 2611 | C | SER | B | 754 | 19.659 | −4.129 | 2.392 | 1.00 | 17.86 | B |
| ATOM | 2612 | O | SER | B | 754 | 20.004 | −5.303 | 2.253 | 1.00 | 17.64 | B |
| ATOM | 2613 | N | TRP | B | 755 | 20.513 | −3.157 | 2.678 | 1.00 | 17.38 | B |
| ATOM | 2614 | CA | TRP | B | 755 | 21.941 | −3.410 | 2.853 | 1.00 | 19.81 | B |
| ATOM | 2615 | CB | TRP | B | 755 | 22.569 | −2.169 | 3.497 | 1.00 | 24.07 | B |
| ATOM | 2616 | CG | TRP | B | 755 | 23.816 | −2.413 | 4.246 | 1.00 | 30.04 | B |
| ATOM | 2617 | CD2 | TRP | B | 755 | 23.997 | −2.283 | 5.656 | 1.00 | 31.44 | B |
| ATOM | 2618 | CE2 | TRP | B | 755 | 25.333 | −2.639 | 5.942 | 1.00 | 33.80 | B |
| ATOM | 2619 | CE3 | TRP | B | 755 | 23.159 | −1.900 | 6.709 | 1.00 | 30.73 | B |
| ATOM | 2620 | CD1 | TRP | B | 755 | 25.013 | −2.826 | 3.739 | 1.00 | 33.58 | B |
| ATOM | 2621 | NE1 | TRP | B | 755 | 25.934 | −2.966 | 4.754 | 1.00 | 35.50 | B |
| ATOM | 2622 | CZ2 | TRP | B | 755 | 25.850 | −2.625 | 7.239 | 1.00 | 34.63 | B |
| ATOM | 2623 | CZ3 | TRP | B | 755 | 23.673 | −1.886 | 7.998 | 1.00 | 31.07 | B |
| ATOM | 2624 | CH2 | TRP | B | 755 | 25.007 | −2.247 | 8.251 | 1.00 | 32.77 | B |
| ATOM | 2625 | C | TRP | B | 755 | 22.263 | −4.683 | 3.662 | 1.00 | 18.91 | B |
| ATOM | 2626 | O | TRP | B | 755 | 22.919 | −5.599 | 3.160 | 1.00 | 18.50 | B |
| ATOM | 2627 | N | MET | B | 756 | 21.794 | −4.745 | 4.903 | 1.00 | 16.98 | B |
| ATOM | 2628 | CA | MET | B | 756 | 22.054 | −5.902 | 5.765 | 1.00 | 16.75 | B |
| ATOM | 2629 | CB | MET | B | 756 | 21.488 | −5.652 | 7.169 | 1.00 | 15.08 | B |
| ATOM | 2630 | CG | MET | B | 756 | 21.834 | −6.735 | 8.207 | 1.00 | 18.13 | B |
| ATOM | 2631 | SD | MET | B | 756 | 23.609 | −6.843 | 8.597 | 1.00 | 21.78 | B |
| ATOM | 2632 | CE | MET | B | 756 | 23.790 | −5.506 | 9.806 | 1.00 | 22.86 | B |
| ATOM | 2633 | C | MET | B | 756 | 21.477 | −7.205 | 5.205 | 1.00 | 16.39 | B |
| ATOM | 2634 | O | MET | B | 756 | 22.135 | −8.243 | 5.236 | 1.00 | 16.19 | B |
| ATOM | 2635 | N | SER | B | 757 | 20.251 | −7.155 | 4.694 | 1.00 | 15.29 | B |
| ATOM | 2636 | CA | SER | B | 757 | 19.619 | −8.349 | 4.150 | 1.00 | 17.08 | B |
| ATOM | 2637 | CB | SER | B | 757 | 18.174 | −8.055 | 3.728 | 1.00 | 20.88 | B |
| ATOM | 2638 | OG | SER | B | 757 | 18.141 | −7.124 | 2.662 | 1.00 | 28.77 | B |
| ATOM | 2639 | C | SER | B | 757 | 20.401 | −8.895 | 2.960 | 1.00 | 17.10 | B |
| ATOM | 2640 | O | SER | B | 757 | 20.589 | −10.101 | 2.846 | 1.00 | 17.47 | B |
| ATOM | 2641 | N | LEU | B | 758 | 20.861 | −8.013 | 2.078 | 1.00 | 17.47 | B |
| ATOM | 2642 | CA | LEU | B | 758 | 21.620 | −8.452 | 0.911 | 1.00 | 17.62 | B |
| ATOM | 2643 | CB | LEU | B | 758 | 21.922 | −7.270 | −0.018 | 1.00 | 17.52 | B |
| ATOM | 2644 | CG | LEU | B | 758 | 20.713 | −6.633 | −0.715 | 1.00 | 21.15 | B |
| ATOM | 2645 | CD1 | LEU | B | 758 | 21.172 | −5.516 | −1.651 | 1.00 | 21.27 | B |
| ATOM | 2646 | CD2 | LEU | B | 758 | 19.964 | −7.696 | −1.500 | 1.00 | 21.66 | B |
| ATOM | 2647 | C | LEU | B | 758 | 22.922 | −9.103 | 1.356 | 1.00 | 16.78 | B |
| ATOM | 2648 | O | LEU | B | 758 | 23.342 | −10.114 | 0.795 | 1.00 | 16.30 | B |
| ATOM | 2649 | N | MET | B | 759 | 23.556 | −8.529 | 2.373 | 1.00 | 14.76 | B |
| ATOM | 2650 | CA | MET | B | 759 | 24.808 | −9.077 | 2.863 | 1.00 | 17.48 | B |
| ATOM | 2651 | CB | MET | B | 759 | 25.458 | −8.126 | 3.863 | 1.00 | 19.24 | B |
| ATOM | 2652 | CG | MET | B | 759 | 26.046 | −6.892 | 3.211 | 1.00 | 25.62 | B |
| ATOM | 2653 | SD | MET | B | 759 | 27.036 | −5.967 | 4.372 | 1.00 | 30.32 | B |
| ATOM | 2654 | CE | MET | B | 759 | 27.629 | −4.686 | 3.275 | 1.00 | 31.96 | B |
| ATOM | 2655 | C | MET | B | 759 | 24.659 | −10.452 | 3.494 | 1.00 | 16.79 | B |
| ATOM | 2656 | O | MET | B | 759 | 25.465 | −11.344 | 3.229 | 1.00 | 17.13 | B |
| ATOM | 2657 | N | VAL | B | 760 | 23.639 | −10.626 | 4.329 | 1.00 | 16.12 | B |
| ATOM | 2658 | CA | VAL | B | 760 | 23.429 | −11.912 | 4.980 | 1.00 | 16.70 | B |
| ATOM | 2659 | CB | VAL | B | 760 | 22.425 | −11.788 | 6.163 | 1.00 | 18.09 | B |
| ATOM | 2660 | CG1 | VAL | B | 760 | 21.012 | −11.598 | 5.652 | 1.00 | 18.30 | B |
| ATOM | 2661 | CG2 | VAL | B | 760 | 22.524 | −13.005 | 7.059 | 1.00 | 18.55 | B |
| ATOM | 2662 | C | VAL | B | 760 | 22.945 | −12.966 | 3.972 | 1.00 | 17.46 | B |
| ATOM | 2663 | O | VAL | B | 760 | 23.260 | −14.146 | 4.098 | 1.00 | 16.23 | B |
| ATOM | 2664 | N | PHE | B | 761 | 22.195 | −12.533 | 2.963 | 1.00 | 15.44 | B |
| ATOM | 2665 | CA | PHE | B | 761 | 21.700 | −13.451 | 1.938 | 1.00 | 15.94 | B |
| ATOM | 2666 | CB | PHE | B | 761 | 20.686 | −12.732 | 1.040 | 1.00 | 13.58 | B |
| ATOM | 2667 | CG | PHE | B | 761 | 19.770 | −13.657 | 0.281 | 1.00 | 15.45 | B |
| ATOM | 2668 | CD1 | PHE | B | 761 | 18.904 | −14.516 | 0.957 | 1.00 | 15.98 | B |
| ATOM | 2669 | CD2 | PHE | B | 761 | 19.745 | −13.643 | −1.110 | 1.00 | 14.81 | B |
| ATOM | 2670 | CE1 | PHE | B | 761 | 18.028 | −15.343 | 0.261 | 1.00 | 16.60 | B |
| ATOM | 2671 | CE2 | PHE | B | 761 | 18.867 | −14.470 | −1.815 | 1.00 | 15.63 | B |
| ATOM | 2672 | CZ | PHE | B | 761 | 18.009 | −15.319 | −1.125 | 1.00 | 14.90 | B |
| ATOM | 2673 | C | PHE | B | 761 | 22.907 | −13.922 | 1.116 | 1.00 | 15.74 | B |
| ATOM | 2674 | O | PHE | B | 761 | 23.038 | −15.110 | 0.812 | 1.00 | 15.94 | B |
| ATOM | 2675 | N | GLY | B | 762 | 23.788 | −12.986 | 0.767 | 1.00 | 14.42 | B |
| ATOM | 2676 | CA | GLY | B | 762 | 24.979 | −13.330 | 0.003 | 1.00 | 15.82 | B |
| ATOM | 2677 | C | GLY | B | 762 | 25.858 | −14.267 | 0.822 | 1.00 | 15.85 | B |
| ATOM | 2678 | O | GLY | B | 762 | 26.462 | −15.198 | 0.293 | 1.00 | 15.53 | B |
| ATOM | 2679 | N | LEU | B | 763 | 25.934 | −14.005 | 2.123 | 1.00 | 13.94 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2680 | CA | LEU | B | 763 | 26.709 | −14.838 | 3.033 | 1.00 | 14.37 | B |
| ATOM | 2681 | CB | LEU | B | 763 | 26.599 | −14.290 | 4.460 | 1.00 | 14.34 | B |
| ATOM | 2682 | CG | LEU | B | 763 | 26.948 | −15.255 | 5.596 | 1.00 | 13.19 | B |
| ATOM | 2683 | CD1 | LEU | B | 763 | 28.420 | −15.626 | 5.511 | 1.00 | 13.63 | B |
| ATOM | 2684 | CD2 | LEU | B | 763 | 26.631 | −14.599 | 6.948 | 1.00 | 14.36 | B |
| ATOM | 2685 | C | LEU | B | 763 | 26.163 | −16.270 | 2.985 | 1.00 | 13.49 | B |
| ATOM | 2686 | O | LEU | B | 763 | 26.921 | −17.244 | 2.939 | 1.00 | 13.17 | B |
| ATOM | 2687 | N | GLY | B | 764 | 24.841 | −16.392 | 2.992 | 1.00 | 13.47 | B |
| ATOM | 2688 | CA | GLY | B | 764 | 24.230 | −17.708 | 2.943 | 1.00 | 15.22 | B |
| ATOM | 2689 | C | GLY | B | 764 | 24.621 | −18.453 | 1.677 | 1.00 | 16.83 | B |
| ATOM | 2690 | O | GLY | B | 764 | 24.932 | −19.647 | 1.718 | 1.00 | 14.60 | B |
| ATOM | 2691 | N | TRP | B | 765 | 24.615 | −17.747 | 0.550 | 1.00 | 15.62 | B |
| ATOM | 2692 | CA | TRP | B | 765 | 24.974 | −18.360 | −0.729 | 1.00 | 16.29 | B |
| ATOM | 2693 | CB | TRP | B | 765 | 24.776 | −17.364 | −1.877 | 1.00 | 17.83 | B |
| ATOM | 2694 | CG | TRP | B | 765 | 25.067 | −17.960 | −3.226 | 1.00 | 19.06 | B |
| ATOM | 2695 | CD2 | TRP | B | 765 | 24.298 | −18.961 | −3.901 | 1.00 | 21.11 | B |
| ATOM | 2696 | CE2 | TRP | B | 765 | 24.981 | −19.278 | −5.097 | 1.00 | 22.22 | B |
| ATOM | 2697 | CE3 | TRP | B | 765 | 23.099 | −19.625 | −3.610 | 1.00 | 20.70 | B |
| ATOM | 2698 | CD1 | TRP | B | 765 | 26.149 | −17.711 | −4.017 | 1.00 | 21.91 | B |
| ATOM | 2699 | NE1 | TRP | B | 765 | 26.107 | −18.500 | −5.146 | 1.00 | 21.48 | B |
| ATOM | 2700 | CZ2 | TRP | B | 765 | 24.504 | −20.231 | −6.003 | 1.00 | 20.86 | B |
| ATOM | 2701 | CZ3 | TRP | B | 765 | 22.625 | −20.574 | −4.515 | 1.00 | 21.28 | B |
| ATOM | 2702 | CH2 | TRP | B | 765 | 23.331 | −20.866 | −5.695 | 1.00 | 20.63 | B |
| ATOM | 2703 | C | TRP | B | 765 | 26.413 | −18.863 | −0.727 | 1.00 | 14.88 | B |
| ATOM | 2704 | O | TRP | B | 765 | 26.676 | −20.009 | −1.079 | 1.00 | 14.96 | B |
| ATOM | 2705 | N | ARG | B | 766 | 27.350 | −18.010 | −0.329 | 1.00 | 15.86 | B |
| ATOM | 2706 | CA | ARG | B | 766 | 28.755 | −18.414 | −0.293 | 1.00 | 15.20 | B |
| ATOM | 2707 | CB | ARG | B | 766 | 29.645 | −17.219 | 0.059 | 1.00 | 15.13 | B |
| ATOM | 2708 | CG | ARG | B | 766 | 29.681 | −16.130 | −1.027 | 1.00 | 14.72 | B |
| ATOM | 2709 | CD | ARG | B | 766 | 30.770 | −15.102 | −0.715 | 1.00 | 17.05 | B |
| ATOM | 2710 | NE | ARG | B | 766 | 30.520 | −14.418 | 0.553 | 1.00 | 15.75 | B |
| ATOM | 2711 | CZ | ARG | B | 766 | 29.649 | −13.424 | 0.706 | 1.00 | 17.31 | B |
| ATOM | 2712 | NH1 | ARG | B | 766 | 28.939 | −12.992 | −0.327 | 1.00 | 14.99 | B |
| ATOM | 2713 | NH2 | ARG | B | 766 | 29.499 | −12.847 | 1.889 | 1.00 | 15.66 | B |
| ATOM | 2714 | C | ARG | B | 766 | 29.031 | −19.569 | 0.678 | 1.00 | 14.85 | B |
| ATOM | 2715 | O | ARG | B | 766 | 29.819 | −20.463 | 0.371 | 1.00 | 15.12 | B |
| ATOM | 2716 | N | SER | B | 767 | 28.396 | −19.556 | 1.846 | 1.00 | 14.72 | B |
| ATOM | 2717 | CA | SER | B | 767 | 28.605 | −20.623 | 2.826 | 1.00 | 15.93 | B |
| ATOM | 2718 | CB | SER | B | 767 | 27.876 | −20.284 | 4.128 | 1.00 | 16.70 | B |
| ATOM | 2719 | OG | SER | B | 767 | 28.307 | −19.035 | 4.638 | 1.00 | 17.22 | B |
| ATOM | 2720 | C | SER | B | 767 | 28.071 | −21.941 | 2.253 | 1.00 | 16.52 | B |
| ATOM | 2721 | O | SER | B | 767 | 28.680 | −23.007 | 2.397 | 1.00 | 17.28 | B |
| ATOM | 2722 | N | TYR | B | 768 | 26.918 | −21.842 | 1.604 | 1.00 | 16.21 | B |
| ATOM | 2723 | CA | TYR | B | 768 | 26.255 | −22.969 | 0.966 | 1.00 | 15.35 | B |
| ATOM | 2724 | CB | TYR | B | 768 | 24.914 | −22.476 | 0.405 | 1.00 | 16.96 | B |
| ATOM | 2725 | CG | TYR | B | 768 | 24.224 | −23.359 | −0.615 | 1.00 | 17.34 | B |
| ATOM | 2726 | CD1 | TYR | B | 768 | 23.962 | −24.707 | −0.358 | 1.00 | 16.25 | B |
| ATOM | 2727 | CE1 | TYR | B | 768 | 23.226 | −25.481 | −1.263 | 1.00 | 16.76 | B |
| ATOM | 2728 | CD2 | TYR | B | 768 | 23.742 | −22.811 | −1.805 | 1.00 | 17.37 | B |
| ATOM | 2729 | CE2 | TYR | B | 768 | 23.009 | −23.569 | −2.705 | 1.00 | 17.14 | B |
| ATOM | 2730 | CZ | TYR | B | 768 | 22.749 | −24.896 | −2.432 | 1.00 | 16.64 | B |
| ATOM | 2731 | OH | TYR | B | 768 | 21.970 | −25.608 | −3.309 | 1.00 | 17.70 | B |
| ATOM | 2732 | C | TYR | B | 768 | 27.148 | −23.536 | −0.140 | 1.00 | 17.02 | B |
| ATOM | 2733 | O | TYR | B | 768 | 27.427 | −24.737 | −0.174 | 1.00 | 16.79 | B |
| ATOM | 2734 | N | LYS | B | 769 | 27.627 | −22.665 | −1.021 | 1.00 | 14.67 | B |
| ATOM | 2735 | CA | LYS | B | 769 | 28.474 | −23.086 | −2.132 | 1.00 | 16.86 | B |
| ATOM | 2736 | CB | LYS | B | 769 | 28.599 | −21.944 | −3.151 | 1.00 | 16.98 | B |
| ATOM | 2737 | CG | LYS | B | 769 | 27.302 | −21.576 | −3.852 | 1.00 | 18.50 | B |
| ATOM | 2738 | CD | LYS | B | 769 | 26.917 | −22.586 | −4.943 | 1.00 | 19.38 | B |
| ATOM | 2739 | CE | LYS | B | 769 | 27.840 | −22.500 | −6.161 | 1.00 | 17.86 | B |
| ATOM | 2740 | NZ | LYS | B | 769 | 27.399 | −23.425 | −7.249 | 1.00 | 15.11 | B |
| ATOM | 2741 | C | LYS | B | 769 | 29.885 | −23.579 | −1.782 | 1.00 | 18.73 | B |
| ATOM | 2742 | O | LYS | B | 769 | 30.337 | −24.590 | −2.318 | 1.00 | 18.48 | B |
| ATOM | 2743 | N | HIS | B | 770 | 30.577 | −22.874 | −0.889 | 1.00 | 17.78 | B |
| ATOM | 2744 | CA | HIS | B | 770 | 31.961 | −23.219 | −0.546 | 1.00 | 18.94 | B |
| ATOM | 2745 | CB | HIS | B | 770 | 32.750 | −21.937 | −0.241 | 1.00 | 20.02 | B |
| ATOM | 2746 | CG | HIS | B | 770 | 32.825 | −20.982 | −1.391 | 1.00 | 21.63 | B |
| ATOM | 2747 | CD2 | HIS | B | 770 | 32.090 | −19.883 | −1.685 | 1.00 | 21.95 | B |
| ATOM | 2748 | ND1 | HIS | B | 770 | 33.712 | −21.142 | −2.434 | 1.00 | 22.29 | B |
| ATOM | 2749 | CE1 | HIS | B | 770 | 33.517 | −20.183 | −3.324 | 1.00 | 23.77 | B |
| ATOM | 2750 | NE2 | HIS | B | 770 | 32.539 | −19.407 | −2.894 | 1.00 | 23.71 | B |
| ATOM | 2751 | C | HIS | B | 770 | 32.214 | −24.202 | 0.592 | 1.00 | 19.97 | B |
| ATOM | 2752 | O | HIS | B | 770 | 33.203 | −24.935 | 0.564 | 1.00 | 19.99 | B |
| ATOM | 2753 | N | VAL | B | 771 | 31.341 | −24.212 | 1.592 | 1.00 | 19.79 | B |
| ATOM | 2754 | CA | VAL | B | 771 | 31.532 | −25.080 | 2.746 | 1.00 | 20.09 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2755 | CB | VAL | B | 771 | 31.993 | −24.242 | 3.968 | 1.00 | 21.67 | B |
| ATOM | 2756 | CG1 | VAL | B | 771 | 33.355 | −23.626 | 3.691 | 1.00 | 21.97 | B |
| ATOM | 2757 | CG2 | VAL | B | 771 | 30.988 | −23.132 | 4.246 | 1.00 | 22.98 | B |
| ATOM | 2758 | C | VAL | B | 771 | 30.274 | −25.864 | 3.110 | 1.00 | 19.76 | B |
| ATOM | 2759 | O | VAL | B | 771 | 30.047 | −26.194 | 4.280 | 1.00 | 20.09 | B |
| ATOM | 2760 | N | SER | B | 772 | 29.465 | −26.162 | 2.099 | 1.00 | 17.17 | B |
| ATOM | 2761 | CA | SER | B | 772 | 28.225 | −26.903 | 2.294 | 1.00 | 18.29 | B |
| ATOM | 2762 | CB | SER | B | 772 | 28.539 | −28.381 | 2.525 | 1.00 | 18.92 | B |
| ATOM | 2763 | OG | SER | B | 772 | 29.220 | −28.907 | 1.397 | 1.00 | 20.36 | B |
| ATOM | 2764 | C | SER | B | 772 | 27.370 | −26.361 | 3.433 | 1.00 | 17.67 | B |
| ATOM | 2765 | O | SER | B | 772 | 26.645 | −27.116 | 4.092 | 1.00 | 17.83 | B |
| ATOM | 2766 | N | GLY | B | 773 | 27.448 | −25.049 | 3.651 | 1.00 | 16.98 | B |
| ATOM | 2767 | CA | GLY | B | 773 | 26.665 | −24.407 | 4.700 | 1.00 | 18.02 | B |
| ATOM | 2768 | C | GLY | B | 773 | 27.068 | −24.727 | 6.134 | 1.00 | 19.19 | B |
| ATOM | 2769 | O | GLY | B | 773 | 26.385 | −24.322 | 7.080 | 1.00 | 19.19 | B |
| ATOM | 2770 | N | GLN | B | 774 | 28.181 | −25.436 | 6.307 | 1.00 | 18.16 | B |
| ATOM | 2771 | CA | GLN | B | 774 | 28.637 | −25.820 | 7.640 | 1.00 | 18.57 | B |
| ATOM | 2772 | CB | GLN | B | 774 | 29.293 | −27.200 | 7.579 | 1.00 | 18.50 | B |
| ATOM | 2773 | CG | GLN | B | 774 | 28.375 | −28.248 | 6.987 | 1.00 | 22.02 | B |
| ATOM | 2774 | CD | GLN | B | 774 | 27.010 | −28.250 | 7.647 | 1.00 | 26.61 | B |
| ATOM | 2775 | OE1 | GLN | B | 774 | 26.879 | −28.545 | 8.841 | 1.00 | 27.59 | B |
| ATOM | 2776 | NE2 | GLN | B | 774 | 25.980 | −27.907 | 6.875 | 1.00 | 28.16 | B |
| ATOM | 2777 | C | GLN | B | 774 | 29.566 | −24.817 | 8.328 | 1.00 | 19.18 | B |
| ATOM | 2778 | O | GLN | B | 774 | 29.995 | −25.033 | 9.460 | 1.00 | 18.70 | B |
| ATOM | 2779 | N | MET | B | 775 | 29.879 | −23.730 | 7.634 | 1.00 | 17.50 | B |
| ATOM | 2780 | CA | MET | B | 775 | 30.705 | −22.653 | 8.176 | 1.00 | 18.41 | B |
| ATOM | 2781 | CB | MET | B | 775 | 32.182 | −22.814 | 7.790 | 1.00 | 19.65 | B |
| ATOM | 2782 | CG | MET | B | 775 | 32.922 | −23.895 | 8.558 | 1.00 | 23.25 | B |
| ATOM | 2783 | SD | MET | B | 775 | 34.702 | −23.859 | 8.249 | 1.00 | 27.85 | B |
| ATOM | 2784 | CE | MET | B | 775 | 35.070 | −25.630 | 8.200 | 1.00 | 29.77 | B |
| ATOM | 2785 | C | MET | B | 775 | 30.159 | −21.370 | 7.569 | 1.00 | 16.57 | B |
| ATOM | 2786 | O | MET | B | 775 | 29.460 | −21.414 | 6.559 | 1.00 | 15.67 | B |
| ATOM | 2787 | N | LEU | B | 776 | 30.452 | −20.233 | 8.189 | 1.00 | 16.83 | B |
| ATOM | 2788 | CA | LEU | B | 776 | 29.976 | −18.963 | 7.657 | 1.00 | 15.86 | B |
| ATOM | 2789 | CB | LEU | B | 776 | 29.558 | −18.022 | 8.797 | 1.00 | 15.81 | B |
| ATOM | 2790 | CG | LEU | B | 776 | 28.302 | −18.480 | 9.556 | 1.00 | 15.03 | B |
| ATOM | 2791 | CD1 | LEU | B | 776 | 27.886 | −17.440 | 10.586 | 1.00 | 16.94 | B |
| ATOM | 2792 | CD2 | LEU | B | 776 | 27.167 | −18.709 | 8.565 | 1.00 | 17.07 | B |
| ATOM | 2793 | C | LEU | B | 776 | 31.089 | −18.355 | 6.817 | 1.00 | 16.39 | B |
| ATOM | 2794 | O | LEU | B | 776 | 32.086 | −17.856 | 7.342 | 1.00 | 16.45 | B |
| ATOM | 2795 | N | TYR | B | 777 | 30.907 | −18.421 | 5.502 | 1.00 | 15.59 | B |
| ATOM | 2796 | CA | TYR | B | 777 | 31.885 | −17.923 | 4.544 | 1.00 | 14.70 | B |
| ATOM | 2797 | CB | TYR | B | 777 | 31.792 | −18.764 | 3.264 | 1.00 | 16.31 | B |
| ATOM | 2798 | CG | TYR | B | 777 | 32.970 | −18.650 | 2.316 | 1.00 | 18.23 | B |
| ATOM | 2799 | CD1 | TYR | B | 777 | 33.118 | −17.544 | 1.476 | 1.00 | 19.16 | B |
| ATOM | 2800 | CE1 | TYR | B | 777 | 34.175 | −17.469 | 0.559 | 1.00 | 19.47 | B |
| ATOM | 2801 | CD2 | TYR | B | 777 | 33.910 | −19.676 | 2.222 | 1.00 | 19.79 | B |
| ATOM | 2802 | CE2 | TYR | B | 777 | 34.969 | −19.610 | 1.307 | 1.00 | 18.50 | B |
| ATOM | 2803 | CZ | TYR | B | 777 | 35.091 | −18.509 | 0.480 | 1.00 | 18.83 | B |
| ATOM | 2804 | OH | TYR | B | 777 | 36.109 | −18.463 | −0.446 | 1.00 | 19.32 | B |
| ATOM | 2805 | C | TYR | B | 777 | 31.662 | −16.441 | 4.236 | 1.00 | 16.02 | B |
| ATOM | 2806 | O | TYR | B | 777 | 31.095 | −16.089 | 3.200 | 1.00 | 13.24 | B |
| ATOM | 2807 | N | PHE | B | 778 | 32.098 | −15.578 | 5.149 | 1.00 | 15.22 | B |
| ATOM | 2808 | CA | PHE | B | 778 | 31.950 | −14.141 | 4.953 | 1.00 | 16.74 | B |
| ATOM | 2809 | CB | PHE | B | 778 | 32.370 | −13.377 | 6.217 | 1.00 | 14.02 | B |
| ATOM | 2810 | CG | PHE | B | 778 | 31.427 | −13.571 | 7.382 | 1.00 | 16.42 | B |
| ATOM | 2811 | CD1 | PHE | B | 778 | 31.654 | −14.568 | 8.328 | 1.00 | 17.13 | B |
| ATOM | 2812 | CD2 | PHE | B | 778 | 30.282 | −12.784 | 7.504 | 1.00 | 16.49 | B |
| ATOM | 2813 | CE1 | PHE | B | 778 | 30.752 | −14.779 | 9.382 | 1.00 | 17.43 | B |
| ATOM | 2814 | CE2 | PHE | B | 778 | 29.374 | −12.986 | 8.553 | 1.00 | 17.31 | B |
| ATOM | 2815 | CZ | PHE | B | 778 | 29.612 | −13.987 | 9.493 | 1.00 | 16.02 | B |
| ATOM | 2816 | C | PHE | B | 778 | 32.798 | −13.719 | 3.758 | 1.00 | 16.59 | B |
| ATOM | 2817 | O | PHE | B | 778 | 32.343 | −12.974 | 2.887 | 1.00 | 18.01 | B |
| ATOM | 2818 | N | ALA | B | 779 | 34.028 | −14.216 | 3.714 | 1.00 | 17.78 | B |
| ATOM | 2819 | CA | ALA | B | 779 | 34.940 | −13.918 | 2.620 | 1.00 | 19.19 | B |
| ATOM | 2820 | CB | ALA | B | 779 | 35.589 | −12.556 | 2.833 | 1.00 | 18.30 | B |
| ATOM | 2821 | C | ALA | B | 779 | 36.010 | −15.004 | 2.550 | 1.00 | 20.69 | B |
| ATOM | 2822 | O | ALA | B | 779 | 36.133 | −15.832 | 3.456 | 1.00 | 19.06 | B |
| ATOM | 2823 | N | PRO | B | 780 | 36.790 | −15.028 | 1.462 | 1.00 | 22.12 | B |
| ATOM | 2824 | CD | PRO | B | 780 | 36.645 | −14.287 | 0.196 | 1.00 | 22.83 | B |
| ATOM | 2825 | CA | PRO | B | 780 | 37.834 | −16.050 | 1.353 | 1.00 | 22.26 | B |
| ATOM | 2826 | CB | PRO | B | 780 | 38.468 | −15.747 | −0.004 | 1.00 | 23.89 | B |
| ATOM | 2827 | CG | PRO | B | 780 | 37.306 | −15.222 | −0.795 | 1.00 | 25.92 | B |
| ATOM | 2828 | C | PRO | B | 780 | 38.838 | −15.949 | 2.502 | 1.00 | 22.45 | B |
| ATOM | 2829 | O | PRO | B | 780 | 39.424 | −16.950 | 2.916 | 1.00 | 22.14 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2830 | N | ASP | B | 781 | 39.014 | −14.740 | 3.029 | 1.00 | 21.57 | B |
| ATOM | 2831 | CA | ASP | B | 781 | 39.954 | −14.512 | 4.126 | 1.00 | 21.92 | B |
| ATOM | 2832 | CB | ASP | B | 781 | 40.814 | −13.282 | 3.820 | 1.00 | 23.49 | B |
| ATOM | 2833 | CG | ASP | B | 781 | 39.991 | −12.017 | 3.661 | 1.00 | 24.54 | B |
| ATOM | 2834 | OD1 | ASP | B | 781 | 38.772 | −12.117 | 3.393 | 1.00 | 22.71 | B |
| ATOM | 2835 | OD2 | ASP | B | 781 | 40.571 | −10.920 | 3.795 | 1.00 | 24.49 | B |
| ATOM | 2836 | C | ASP | B | 781 | 39.267 | −14.340 | 5.476 | 1.00 | 21.74 | B |
| ATOM | 2837 | O | ASP | B | 781 | 39.888 | −13.917 | 6.451 | 1.00 | 22.77 | B |
| ATOM | 2838 | N | LEU | B | 782 | 37.979 | −14.664 | 5.526 | 1.00 | 20.36 | B |
| ATOM | 2839 | CA | LEU | B | 782 | 37.210 | −14.557 | 6.756 | 1.00 | 19.59 | B |
| ATOM | 2840 | CB | LEU | B | 782 | 36.619 | −13.151 | 6.893 | 1.00 | 20.63 | B |
| ATOM | 2841 | CG | LEU | B | 782 | 35.970 | −12.802 | 8.232 | 1.00 | 22.29 | B |
| ATOM | 2842 | CD1 | LEU | B | 782 | 36.949 | −13.088 | 9.370 | 1.00 | 25.24 | B |
| ATOM | 2843 | CD2 | LEU | B | 782 | 35.567 | −11.325 | 8.237 | 1.00 | 21.90 | B |
| ATOM | 2844 | C | LEU | B | 782 | 36.095 | −15.603 | 6.761 | 1.00 | 19.08 | B |
| ATOM | 2845 | O | LEU | B | 782 | 34.954 | −15.320 | 6.389 | 1.00 | 15.84 | B |
| ATOM | 2846 | N | ILE | B | 783 | 36.452 | −16.815 | 7.179 | 1.00 | 18.17 | B |
| ATOM | 2847 | CA | ILE | B | 783 | 35.525 | −17.941 | 7.257 | 1.00 | 17.98 | B |
| ATOM | 2848 | CB | ILE | B | 783 | 36.062 | −19.142 | 6.446 | 1.00 | 17.80 | B |
| ATOM | 2849 | CG2 | ILE | B | 783 | 35.093 | −20.311 | 6.551 | 1.00 | 20.50 | B |
| ATOM | 2850 | CG1 | ILE | B | 783 | 36.282 | −18.723 | 4.988 | 1.00 | 18.65 | B |
| ATOM | 2851 | CD1 | ILE | B | 783 | 37.092 | −19.720 | 4.155 | 1.00 | 20.07 | B |
| ATOM | 2852 | C | ILE | B | 783 | 35.407 | −18.340 | 8.725 | 1.00 | 19.08 | B |
| ATOM | 2853 | O | ILE | B | 783 | 36.402 | −18.697 | 9.358 | 1.00 | 19.55 | B |
| ATOM | 2854 | N | LEU | B | 784 | 34.200 | −18.289 | 9.269 | 1.00 | 19.91 | B |
| ATOM | 2855 | CA | LEU | B | 784 | 34.021 | −18.618 | 10.676 | 1.00 | 22.66 | B |
| ATOM | 2856 | CB | LEU | B | 784 | 33.276 | −17.490 | 11.401 | 1.00 | 21.59 | B |
| ATOM | 2857 | CG | LEU | B | 784 | 33.858 | −16.076 | 11.358 | 1.00 | 24.80 | B |
| ATOM | 2858 | CD1 | LEU | B | 784 | 32.937 | −15.138 | 12.135 | 1.00 | 23.29 | B |
| ATOM | 2859 | CD2 | LEU | B | 784 | 35.257 | −16.062 | 11.941 | 1.00 | 24.21 | B |
| ATOM | 2860 | C | LEU | B | 784 | 33.291 | −19.917 | 10.953 | 1.00 | 24.35 | B |
| ATOM | 2861 | O | LEU | B | 784 | 32.305 | −20.251 | 10.300 | 1.00 | 22.70 | B |
| ATOM | 2862 | N | ASN | B | 785 | 33.799 | −20.645 | 11.939 | 1.00 | 26.14 | B |
| ATOM | 2863 | CA | ASN | B | 785 | 33.186 | −21.885 | 12.376 | 1.00 | 28.52 | B |
| ATOM | 2864 | CB | ASN | B | 785 | 34.158 | −23.058 | 12.240 | 1.00 | 30.54 | B |
| ATOM | 2865 | CG | ASN | B | 785 | 35.509 | −22.761 | 12.841 | 1.00 | 31.69 | B |
| ATOM | 2866 | OD1 | ASN | B | 785 | 35.606 | −22.104 | 13.875 | 1.00 | 33.80 | B |
| ATOM | 2867 | ND2 | ASN | B | 785 | 36.564 | −23.253 | 12.204 | 1.00 | 34.71 | B |
| ATOM | 2868 | C | ASN | B | 785 | 32.835 | −21.648 | 13.843 | 1.00 | 29.93 | B |
| ATOM | 2869 | O | ASN | B | 785 | 33.155 | −20.597 | 14.409 | 1.00 | 28.08 | B |
| ATOM | 2870 | N | GLU | B | 785 | 32.190 | −22.625 | 14.458 | 1.00 | 31.08 | B |
| ATOM | 2871 | CA | GLU | B | 786 | 31.771 | −22.516 | 15.845 | 1.00 | 33.20 | B |
| ATOM | 2872 | CB | GLU | B | 786 | 31.169 | −23.849 | 16.286 | 1.00 | 37.40 | B |
| ATOM | 2873 | CG | GLU | B | 786 | 30.217 | −23.750 | 17.455 | 1.00 | 42.11 | B |
| ATOM | 2874 | CD | GLU | B | 786 | 29.476 | −25.050 | 17.696 | 1.00 | 46.15 | B |
| ATOM | 2875 | OE1 | GLU | B | 786 | 28.841 | −25.555 | 16.743 | 1.00 | 46.80 | B |
| ATOM | 2876 | OE2 | GLU | B | 786 | 29.529 | −25.563 | 18.836 | 1.00 | 48.79 | B |
| ATOM | 2877 | C | GLU | B | 786 | 32.862 | −22.088 | 16.830 | 1.00 | 32.26 | B |
| ATOM | 2878 | O | GLU | B | 786 | 32.624 | −21.246 | 17.696 | 1.00 | 31.14 | B |
| ATOM | 2879 | N | GLN | B | 787 | 34.058 | −22.651 | 16.692 | 1.00 | 32.38 | B |
| ATOM | 2880 | CA | GLN | B | 787 | 35.151 | −22.332 | 17.604 | 1.00 | 34.18 | B |
| ATOM | 2881 | CB | GLN | B | 787 | 36.353 | −23.235 | 17.327 | 1.00 | 37.31 | B |
| ATOM | 2882 | CG | GLN | B | 787 | 37.302 | −22.693 | 16.275 | 1.00 | 41.80 | B |
| ATOM | 2883 | CD | GLN | B | 787 | 38.555 | −23.530 | 16.137 | 1.00 | 45.28 | B |
| ATOM | 2884 | OE1 | GLN | B | 787 | 39.524 | −23.116 | 15.497 | 1.00 | 47.58 | B |
| ATOM | 2885 | NE2 | GLN | B | 787 | 38.542 | −24.722 | 16.733 | 1.00 | 48.17 | B |
| ATOM | 2886 | C | GLN | B | 787 | 35.609 | −20.876 | 17.558 | 1.00 | 34.13 | B |
| ATOM | 2887 | O | GLN | B | 787 | 36.198 | −20.377 | 18.518 | 1.00 | 33.23 | B |
| ATOM | 2888 | N | ARG | B | 788 | 35.355 | −20.200 | 16.441 | 1.00 | 32.22 | B |
| ATOM | 2889 | CA | ARG | B | 788 | 35.767 | −18.810 | 16.294 | 1.00 | 31.78 | B |
| ATOM | 2890 | CB | ARG | B | 788 | 36.169 | −18.528 | 14.842 | 1.00 | 31.05 | B |
| ATOM | 2891 | CG | ARG | B | 788 | 37.322 | −19.393 | 14.343 | 1.00 | 32.23 | B |
| ATOM | 2892 | CD | ARG | B | 788 | 37.772 | −18.988 | 12.938 | 1.00 | 32.79 | B |
| ATOM | 2893 | NE | ARG | B | 788 | 38.365 | −17.652 | 12.923 | 1.00 | 33.62 | B |
| ATOM | 2894 | CZ | ARG | B | 788 | 38.815 | −17.036 | 11.831 | 1.00 | 35.26 | B |
| ATOM | 2895 | NH1 | ARG | B | 788 | 38.742 | −17.630 | 10.643 | 1.00 | 32.75 | B |
| ATOM | 2896 | NH2 | ARG | B | 788 | 39.349 | −15.824 | 11.929 | 1.00 | 33.61 | B |
| ATOM | 2897 | C | ARG | B | 788 | 34.670 | −17.847 | 16.733 | 1.00 | 31.36 | B |
| ATOM | 2898 | O | ARG | B | 788 | 34.773 | −16.637 | 16.532 | 1.00 | 32.48 | B |
| ATOM | 2899 | N | MET | B | 789 | 33.621 | −18.398 | 17.334 | 1.00 | 30.68 | B |
| ATOM | 2900 | CA | MET | B | 789 | 32.490 | −17.613 | 17.824 | 1.00 | 31.24 | B |
| ATOM | 2901 | CB | MET | B | 789 | 31.200 | −18.116 | 17.178 | 1.00 | 29.02 | B |
| ATOM | 2902 | CG | MET | B | 789 | 31.266 | −18.136 | 15.660 | 1.00 | 29.15 | B |
| ATOM | 2903 | SD | MET | B | 789 | 29.905 | −19.023 | 14.891 | 1.00 | 27.19 | B |
| ATOM | 2904 | CE | MET | B | 789 | 30.378 | −18.882 | 13.161 | 1.00 | 27.27 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2905 | C | MET | B | 789 | 32.430 | −17.787 | 19.339 | 1.00 | 31.40 | B |
| ATOM | 2906 | O | MET | B | 789 | 31.528 | −18.433 | 19.870 | 1.00 | 31.70 | B |
| ATOM | 2907 | N | LYS | B | 790 | 33.404 | −17.197 | 20.023 | 1.00 | 33.04 | B |
| ATOM | 2908 | CA | LYS | B | 790 | 33.520 | −17.297 | 21.474 | 1.00 | 34.21 | B |
| ATOM | 2909 | CB | LYS | B | 790 | 34.887 | −16.759 | 21.894 | 1.00 | 33.75 | B |
| ATOM | 2910 | CG | LYS | B | 790 | 36.030 | −17.429 | 21.141 | 1.00 | 34.59 | B |
| ATOM | 2911 | CD | LYS | B | 790 | 37.368 | −16.763 | 21.407 | 1.00 | 35.73 | B |
| ATOM | 2912 | CE | LYS | B | 790 | 38.469 | −17.425 | 20.588 | 1.00 | 37.42 | B |
| ATOM | 2913 | NZ | LYS | B | 790 | 39.785 | −16.747 | 20.754 | 1.00 | 39.03 | B |
| ATOM | 2914 | C | LYS | B | 790 | 32.407 | −16.605 | 22.262 | 1.00 | 36.08 | B |
| ATOM | 2915 | O | LYS | B | 790 | 31.732 | −17.241 | 23.070 | 1.00 | 35.56 | B |
| ATOM | 2916 | N | GLU | B | 791 | 32.222 | −15.308 | 22.033 | 1.00 | 37.31 | B |
| ATOM | 2917 | CA | GLU | B | 791 | 31.186 | −14.545 | 22.728 | 1.00 | 39.12 | B |
| ATOM | 2918 | CB | GLU | B | 791 | 31.231 | −13.080 | 22.288 | 1.00 | 41.76 | B |
| ATOM | 2919 | CG | GLU | B | 791 | 31.625 | −12.115 | 23.390 | 1.00 | 47.66 | B |
| ATOM | 2920 | CD | GLU | B | 791 | 30.594 | −12.053 | 24.508 | 1.00 | 50.47 | B |
| ATOM | 2921 | OE1 | GLU | B | 791 | 29.437 | −11.657 | 24.237 | 1.00 | 51.08 | B |
| ATOM | 2922 | OE2 | GLU | B | 791 | 30.942 | −12.401 | 25.659 | 1.00 | 52.17 | B |
| ATOM | 2923 | C | GLU | B | 791 | 29.804 | −15.128 | 22.445 | 1.00 | 38.82 | B |
| ATOM | 2924 | O | GLU | B | 791 | 29.383 | −15.221 | 21.292 | 1.00 | 39.17 | B |
| ATOM | 2925 | N | SER | B | 792 | 29.099 | −15.513 | 23.504 | 1.00 | 37.75 | B |
| ATOM | 2926 | CA | SER | B | 792 | 27.770 | −16.102 | 23.373 | 1.00 | 37.53 | B |
| ATOM | 2927 | CB | SER | B | 792 | 27.191 | −16.390 | 24.760 | 1.00 | 39.01 | B |
| ATOM | 2928 | OG | SER | B | 792 | 27.172 | −15.215 | 25.549 | 1.00 | 41.88 | B |
| ATOM | 2929 | C | SER | B | 792 | 26.803 | −15.220 | 22.587 | 1.00 | 36.19 | B |
| ATOM | 2930 | O | SER | B | 792 | 25.936 | −15.720 | 21.869 | 1.00 | 35.18 | B |
| ATOM | 2931 | N | SER | B | 793 | 26.955 | −13.908 | 22.736 | 1.00 | 35.25 | B |
| ATOM | 2932 | CA | SER | B | 793 | 26.102 | −12.948 | 22.046 | 1.00 | 34.13 | B |
| ATOM | 2933 | CB | SER | B | 793 | 26.415 | −11.535 | 22.542 | 1.00 | 35.74 | B |
| ATOM | 2934 | OG | SER | B | 793 | 25.504 | −10.594 | 22.006 | 1.00 | 40.72 | B |
| ATOM | 2935 | C | SER | B | 793 | 26.339 | −13.033 | 20.539 | 1.00 | 32.40 | B |
| ATOM | 2936 | O | SER | B | 793 | 25.397 | −13.100 | 19.749 | 1.00 | 30.32 | B |
| ATOM | 2937 | N | PHE | B | 794 | 27.611 | −13.029 | 20.158 | 1.00 | 31.57 | B |
| ATOM | 2938 | CA | PHE | B | 794 | 28.010 | −13.111 | 18.759 | 1.00 | 31.79 | B |
| ATOM | 2939 | CB | PHE | B | 794 | 29.517 | −12.856 | 18.636 | 1.00 | 33.58 | B |
| ATOM | 2940 | CG | PHE | B | 794 | 30.024 | −12.869 | 17.222 | 1.00 | 36.88 | B |
| ATOM | 2941 | CD1 | PHE | B | 794 | 29.579 | −11.926 | 16.300 | 1.00 | 37.56 | B |
| ATOM | 2942 | CD2 | PHE | B | 794 | 30.950 | −13.825 | 16.812 | 1.00 | 38.13 | B |
| ATOM | 2943 | CE1 | PHE | B | 794 | 30.048 | −11.932 | 14.986 | 1.00 | 38.39 | B |
| ATOM | 2944 | CE2 | PHE | B | 794 | 31.426 | −13.841 | 15.500 | 1.00 | 39.25 | B |
| ATOM | 2945 | CZ | PHE | B | 794 | 30.973 | −12.890 | 14.585 | 1.00 | 39.67 | B |
| ATOM | 2946 | C | PHE | B | 794 | 27.664 | −14.487 | 18.194 | 1.00 | 30.57 | B |
| ATOM | 2947 | O | PHE | B | 794 | 27.281 | −14.615 | 17.030 | 1.00 | 29.77 | B |
| ATOM | 2948 | N | TYR | B | 795 | 27.794 | −15.516 | 19.026 | 1.00 | 29.44 | B |
| ATOM | 2949 | CA | TYR | B | 795 | 27.490 | −16.876 | 18.606 | 1.00 | 27.92 | B |
| ATOM | 2950 | CB | TYR | B | 795 | 27.872 | −17.872 | 19.709 | 1.00 | 31.37 | B |
| ATOM | 2951 | CG | TYR | B | 795 | 27.579 | −19.317 | 19.357 | 1.00 | 33.31 | B |
| ATOM | 2952 | CD1 | TYR | B | 795 | 28.001 | −19.860 | 18.141 | 1.00 | 34.81 | B |
| ATOM | 2953 | CE1 | TYR | B | 795 | 27.732 | −21.185 | 17.807 | 1.00 | 35.57 | B |
| ATOM | 2954 | CD2 | TYR | B | 795 | 26.878 | −20.142 | 20.237 | 1.00 | 35.46 | B |
| ATOM | 2955 | CE2 | TYR | B | 795 | 26.603 | −21.473 | 19.913 | 1.00 | 36.78 | B |
| ATOM | 2956 | CZ | TYR | B | 795 | 27.032 | −21.984 | 18.697 | 1.00 | 36.92 | B |
| ATOM | 2957 | OH | TYR | B | 795 | 26.752 | −23.288 | 18.365 | 1.00 | 39.48 | B |
| ATOM | 2958 | C | TYR | B | 795 | 26.008 | −17.008 | 18.267 | 1.00 | 26.49 | B |
| ATOM | 2959 | O | TYR | B | 795 | 25.644 | −17.624 | 17.268 | 1.00 | 23.95 | B |
| ATOM | 2960 | N | SER | B | 796 | 25.150 | −16.423 | 19.095 | 1.00 | 25.20 | B |
| ATOM | 2961 | CA | SER | B | 796 | 23.716 | −16.492 | 18.847 | 1.00 | 26.93 | B |
| ATOM | 2962 | CB | SER | B | 796 | 22.941 | −15.864 | 20.006 | 1.00 | 28.16 | B |
| ATOM | 2963 | OG | SER | B | 796 | 23.161 | −16.592 | 21.200 | 1.00 | 30.73 | B |
| ATOM | 2964 | C | SER | B | 796 | 23.374 | −15.770 | 17.548 | 1.00 | 25.62 | B |
| ATOM | 2965 | O | SER | B | 796 | 22.499 | −16.195 | 16.795 | 1.00 | 25.30 | B |
| ATOM | 2966 | N | LEU | B | 797 | 24.074 | −14.673 | 17.296 | 1.00 | 24.05 | B |
| ATOM | 2967 | CA | LEU | B | 797 | 23.851 | −13.893 | 16.088 | 1.00 | 25.18 | B |
| ATOM | 2968 | CB | LEU | B | 797 | 24.720 | −12.638 | 16.112 | 1.00 | 24.29 | B |
| ATOM | 2969 | CG | LEU | B | 797 | 24.429 | −11.600 | 15.027 | 1.00 | 27.01 | B |
| ATOM | 2970 | CD1 | LEU | B | 797 | 23.024 | −11.043 | 15.197 | 1.00 | 27.55 | B |
| ATOM | 2971 | CD2 | LEU | B | 797 | 25.447 | −10.491 | 15.128 | 1.00 | 28.99 | B |
| ATOM | 2972 | C | LEU | B | 797 | 24.196 | −14.744 | 14.870 | 1.00 | 22.79 | B |
| ATOM | 2973 | O | LEU | B | 797 | 23.429 | −14.809 | 13.907 | 1.00 | 23.34 | B |
| ATOM | 2974 | N | CYS | B | 798 | 25.354 | −15.397 | 14.920 | 1.00 | 22.06 | B |
| ATOM | 2975 | CA | CYS | B | 798 | 25.792 | −16.253 | 13.826 | 1.00 | 21.40 | B |
| ATOM | 2976 | CB | CYS | B | 798 | 27.205 | −16.777 | 14.102 | 1.00 | 22.48 | B |
| ATOM | 2977 | SG | CYS | B | 798 | 28.482 | −15.490 | 14.048 | 1.00 | 23.41 | B |
| ATOM | 2978 | C | CYS | B | 798 | 24.817 | −17.414 | 13.613 | 1.00 | 21.32 | B |
| ATOM | 2979 | O | CYS | B | 798 | 24.535 | −17.793 | 12.473 | 1.00 | 20.28 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 2980 | N | LEU | B | 799 | 24.306 | −17.981 | 14.702 | 1.00 | 19.81 | B |
| ATOM | 2981 | CA | LEU | B | 799 | 23.341 | −19.069 | 14.588 | 1.00 | 19.74 | B |
| ATOM | 2982 | CB | LEU | B | 799 | 22.899 | −19.559 | 15.970 | 1.00 | 23.55 | B |
| ATOM | 2983 | CG | LEU | B | 799 | 23.890 | −20.438 | 16.740 | 1.00 | 24.38 | B |
| ATOM | 2984 | CD1 | LEU | B | 799 | 23.279 | −20.850 | 18.077 | 1.00 | 26.86 | B |
| ATOM | 2985 | CD2 | LEU | B | 799 | 24.226 | −21.674 | 15.911 | 1.00 | 26.58 | B |
| ATOM | 2986 | C | LEU | B | 799 | 22.135 | −18.550 | 13.818 | 1.00 | 20.29 | B |
| ATOM | 2987 | O | LEU | B | 799 | 21.563 | −19.255 | 12.990 | 1.00 | 20.26 | B |
| ATOM | 2988 | N | THR | B | 800 | 21.756 | −17.304 | 14.086 | 1.00 | 20.04 | B |
| ATOM | 2989 | CA | THR | B | 800 | 20.629 | −16.703 | 13.387 | 1.00 | 20.32 | B |
| ATOM | 2990 | CB | THR | B | 800 | 20.289 | −15.308 | 13.967 | 1.00 | 21.13 | B |
| ATOM | 2991 | OG1 | THR | B | 800 | 19.814 | −15.453 | 15.312 | 1.00 | 19.83 | B |
| ATOM | 2992 | CG2 | THR | B | 800 | 19.218 | −14.620 | 13.131 | 1.00 | 21.16 | B |
| ATOM | 2993 | C | THR | B | 800 | 20.937 | −16.574 | 11.893 | 1.00 | 19.37 | B |
| ATOM | 2994 | O | THR | B | 800 | 20.098 | −16.882 | 11.049 | 1.00 | 20.15 | B |
| ATOM | 2995 | N | MET | B | 801 | 22.140 | −16.119 | 11.564 | 1.00 | 18.98 | B |
| ATOM | 2996 | CA | MET | B | 801 | 22.518 | −15.969 | 10.160 | 1.00 | 20.07 | B |
| ATOM | 2997 | CB | MET | B | 801 | 23.854 | −15.229 | 10.042 | 1.00 | 20.74 | B |
| ATOM | 2998 | CG | MET | B | 801 | 23.833 | −13.802 | 10.575 | 1.00 | 20.42 | B |
| ATOM | 2999 | SD | MET | B | 801 | 25.357 | −12.924 | 10.203 | 1.00 | 24.80 | B |
| ATOM | 3000 | CE | MET | B | 801 | 26.385 | −13.408 | 11.562 | 1.00 | 25.72 | B |
| ATOM | 3001 | C | MET | B | 801 | 22.636 | −17.336 | 9.489 | 1.00 | 19.47 | B |
| ATOM | 3002 | O | MET | B | 801 | 22.326 | −17.491 | 8.310 | 1.00 | 17.79 | B |
| ATOM | 3003 | N | TRP | B | 802 | 23.075 | −18.321 | 10.264 | 1.00 | 20.79 | B |
| ATOM | 3004 | CA | TRP | B | 802 | 23.266 | −19.690 | 9.792 | 1.00 | 21.60 | B |
| ATOM | 3005 | CB | TRP | B | 802 | 23.788 | −20.550 | 10.942 | 1.00 | 22.91 | B |
| ATOM | 3006 | CG | TRP | B | 802 | 24.985 | −21.360 | 10.590 | 1.00 | 24.57 | B |
| ATOM | 3007 | CD2 | TRP | B | 802 | 26.211 | −21.434 | 11.323 | 1.00 | 25.80 | B |
| ATOM | 3008 | CE2 | TRP | B | 802 | 27.069 | −22.304 | 10.613 | 1.00 | 25.69 | B |
| ATOM | 3009 | CE3 | TRP | B | 802 | 26.670 | −20.847 | 12.511 | 1.00 | 26.80 | B |
| ATOM | 3010 | CD1 | TRP | B | 802 | 25.140 | −22.168 | 9.497 | 1.00 | 25.78 | B |
| ATOM | 3011 | NE1 | TRP | B | 802 | 26.390 | −22.738 | 9.506 | 1.00 | 25.97 | B |
| ATOM | 3012 | CZ2 | TRP | B | 802 | 28.365 | −22.603 | 11.053 | 1.00 | 27.76 | B |
| ATOM | 3013 | CZ3 | TRP | B | 802 | 27.962 | −21.145 | 12.949 | 1.00 | 26.64 | B |
| ATOM | 3014 | CH2 | TRP | B | 802 | 28.792 | −22.015 | 12.219 | 1.00 | 27.43 | B |
| ATOM | 3015 | C | TRP | B | 802 | 22.005 | −20.345 | 9.227 | 1.00 | 21.64 | B |
| ATOM | 3016 | O | TRP | B | 802 | 22.085 | −21.309 | 8.463 | 1.00 | 20.67 | B |
| ATOM | 3017 | N | GLN | B | 803 | 20.842 | −19.835 | 9.617 | 1.00 | 21.08 | B |
| ATOM | 3018 | CA | GLN | B | 803 | 19.575 | −20.396 | 9.161 | 1.00 | 20.48 | B |
| ATOM | 3019 | CB | GLN | B | 803 | 18.416 | −19.663 | 9.824 | 1.00 | 21.39 | B |
| ATOM | 3020 | CG | GLN | B | 803 | 18.558 | −19.535 | 11.323 | 1.00 | 23.58 | B |
| ATOM | 3021 | CD | GLN | B | 803 | 17.428 | −18.743 | 11.932 | 1.00 | 27.19 | B |
| ATOM | 3022 | OE1 | GLN | B | 803 | 16.344 | −19.274 | 12.181 | 1.00 | 29.06 | B |
| ATOM | 3023 | NE2 | GLN | B | 803 | 17.666 | −17.460 | 12.159 | 1.00 | 28.68 | B |
| ATOM | 3024 | C | GLN | B | 803 | 19.412 | −20.321 | 7.651 | 1.00 | 21.76 | B |
| ATOM | 3025 | O | GLN | B | 803 | 18.786 | −21.191 | 7.039 | 1.00 | 21.16 | B |
| ATOM | 3026 | N | ILE | B | 804 | 19.964 | −19.274 | 7.048 | 1.00 | 20.31 | B |
| ATOM | 3027 | CA | ILE | B | 804 | 19.849 | −19.107 | 5.611 | 1.00 | 19.18 | B |
| ATOM | 3028 | CB | ILE | B | 804 | 20.336 | −17.704 | 5.184 | 1.00 | 18.04 | B |
| ATOM | 3029 | CG2 | ILE | B | 804 | 20.227 | −17.550 | 3.674 | 1.00 | 17.29 | B |
| ATOM | 3030 | CG1 | ILE | B | 804 | 19.478 | −16.633 | 5.875 | 1.00 | 19.81 | B |
| ATOM | 3031 | CD1 | ILE | B | 804 | 19.859 | −15.195 | 5.524 | 1.00 | 20.17 | B |
| ATOM | 3032 | C | ILE | B | 804 | 20.602 | −20.206 | 4.849 | 1.00 | 20.03 | B |
| ATOM | 3033 | O | ILE | B | 804 | 20.019 | −20.884 | 4.005 | 1.00 | 21.05 | B |
| ATOM | 3034 | N | PRO | B | 805 | 21.901 | −20.400 | 5.137 | 1.00 | 20.99 | B |
| ATOM | 3035 | CD | PRO | B | 805 | 22.753 | −19.671 | 6.094 | 1.00 | 20.74 | B |
| ATOM | 3036 | CA | PRO | B | 805 | 22.667 | −21.446 | 4.440 | 1.00 | 21.50 | B |
| ATOM | 3037 | CB | PRO | B | 805 | 24.037 | −21.390 | 5.117 | 1.00 | 22.20 | B |
| ATOM | 3038 | CG | PRO | B | 805 | 24.136 | −19.979 | 5.600 | 1.00 | 22.08 | B |
| ATOM | 3039 | C | PRO | B | 805 | 21.998 | −22.807 | 4.649 | 1.00 | 22.88 | B |
| ATOM | 3040 | O | PRO | B | 805 | 21.897 | −23.624 | 3.730 | 1.00 | 22.43 | B |
| ATOM | 3041 | N | GLN | B | 806 | 21.547 | −23.041 | 5.877 | 1.00 | 22.24 | B |
| ATOM | 3042 | CA | GLN | B | 806 | 20.886 | −24.291 | 6.227 | 1.00 | 22.01 | B |
| ATOM | 3043 | CB | GLN | B | 806 | 20.511 | −24.280 | 7.712 | 1.00 | 23.12 | B |
| ATOM | 3044 | CG | GLN | B | 806 | 21.732 | −24.418 | 8.616 | 1.00 | 27.21 | B |
| ATOM | 3045 | CD | GLN | B | 806 | 21.452 | −24.120 | 10.079 | 1.00 | 31.98 | B |
| ATOM | 3046 | OE1 | GLN | B | 806 | 22.295 | −24.379 | 10.939 | 1.00 | 37.38 | B |
| ATOM | 3047 | NE2 | GLN | B | 806 | 20.276 | −23.569 | 10.370 | 1.00 | 32.65 | B |
| ATOM | 3048 | C | GLN | B | 806 | 19.656 | −24.528 | 5.356 | 1.00 | 23.33 | B |
| ATOM | 3049 | O | GLN | B | 806 | 19.443 | −25.639 | 4.872 | 1.00 | 23.30 | B |
| ATOM | 3050 | N | GLU | B | 807 | 18.855 | −23.487 | 5.144 | 1.00 | 21.25 | B |
| ATOM | 3051 | CA | GLU | B | 807 | 17.662 | −23.611 | 4.306 | 1.00 | 21.78 | B |
| ATOM | 3052 | CB | GLU | B | 807 | 16.770 | −22.375 | 4.441 | 1.00 | 25.31 | B |
| ATOM | 3053 | CG | GLU | B | 807 | 15.931 | −22.353 | 5.698 | 1.00 | 29.26 | B |
| ATOM | 3054 | CD | GLU | B | 807 | 14.962 | −23.520 | 5.762 | 1.00 | 32.50 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 3055 | OE1 | GLU | B | 807 | 14.077 | −23.606 | 4.887 | 1.00 | 33.09 | B |
| ATOM | 3056 | OE2 | GLU | B | 807 | 15.092 | −24.353 | 6.684 | 1.00 | 32.53 | B |
| ATOM | 3057 | C | GLU | B | 807 | 18.043 | −23.805 | 2.843 | 1.00 | 20.58 | B |
| ATOM | 3058 | O | GLU | B | 807 | 17.354 | −24.519 | 2.108 | 1.00 | 19.42 | B |
| ATOM | 3059 | N | PHE | B | 808 | 19.129 | −23.159 | 2.418 | 1.00 | 19.70 | B |
| ATOM | 3060 | CA | PHE | B | 808 | 19.602 | −23.292 | 1.042 | 1.00 | 18.77 | B |
| ATOM | 3061 | CB | PHE | B | 808 | 20.832 | −22.408 | 0.785 | 1.00 | 16.63 | B |
| ATOM | 3062 | CG | PHE | B | 808 | 20.510 | −20.951 | 0.577 | 1.00 | 18.24 | B |
| ATOM | 3063 | CD1 | PHE | B | 808 | 19.195 | −20.495 | 0.604 | 1.00 | 15.60 | B |
| ATOM | 3064 | CD2 | PHE | B | 808 | 21.529 | −20.030 | 0.369 | 1.00 | 17.34 | B |
| ATOM | 3065 | CE1 | PHE | B | 808 | 18.905 | −19.133 | 0.431 | 1.00 | 17.14 | B |
| ATOM | 3066 | CE2 | PHE | B | 808 | 21.248 | −18.672 | 0.196 | 1.00 | 18.78 | B |
| ATOM | 3067 | CZ | PHE | B | 808 | 19.929 | −18.227 | 0.228 | 1.00 | 17.21 | B |
| ATOM | 3068 | C | PHE | B | 808 | 19.964 | −24.751 | 0.802 | 1.00 | 17.37 | B |
| ATOM | 3069 | O | PHE | B | 808 | 19.610 | −25.322 | −0.225 | 1.00 | 17.11 | B |
| ATOM | 3070 | N | VAL | B | 809 | 20.673 | −25.346 | 1.756 | 1.00 | 18.79 | B |
| ATOM | 3071 | CA | VAL | B | 809 | 21.054 | −26.756 | 1.655 | 1.00 | 19.69 | B |
| ATOM | 3072 | CB | VAL | B | 809 | 21.955 | −27.190 | 2.846 | 1.00 | 21.10 | B |
| ATOM | 3073 | CG1 | VAL | B | 809 | 22.113 | −28.704 | 2.855 | 1.00 | 23.52 | B |
| ATOM | 3074 | CG2 | VAL | B | 809 | 23.330 | −26.536 | 2.742 | 1.00 | 19.39 | B |
| ATOM | 3075 | C | VAL | B | 809 | 19.800 | −27.640 | 1.646 | 1.00 | 21.36 | B |
| ATOM | 3076 | O | VAL | B | 809 | 19.685 | −28.560 | 0.830 | 1.00 | 21.94 | B |
| ATOM | 3077 | N | LYS | B | 810 | 18.864 | −27.364 | 2.551 | 1.00 | 21.13 | B |
| ATOM | 3078 | CA | LYS | B | 810 | 17.634 | −28.152 | 2.630 | 1.00 | 23.80 | B |
| ATOM | 3079 | CB | LYS | B | 810 | 16.748 | −27.674 | 3.786 | 1.00 | 27.42 | B |
| ATOM | 3080 | CG | LYS | B | 810 | 17.228 | −28.037 | 5.182 | 1.00 | 31.68 | B |
| ATOM | 3081 | CD | LYS | B | 810 | 16.184 | −27.605 | 6.205 | 1.00 | 35.53 | B |
| ATOM | 3082 | CE | LYS | B | 810 | 16.667 | −27.793 | 7.632 | 1.00 | 39.05 | B |
| ATOM | 3083 | NZ | LYS | B | 810 | 15.639 | −27.331 | 8.608 | 1.00 | 38.71 | B |
| ATOM | 3084 | C | LYS | B | 810 | 16.801 | −28.115 | 1.355 | 1.00 | 23.30 | B |
| ATOM | 3085 | O | LYS | B | 810 | 16.407 | −29.157 | 0.829 | 1.00 | 20.94 | B |
| ATOM | 3086 | N | LEU | B | 811 | 16.514 | −26.910 | 0.871 | 1.00 | 22.91 | B |
| ATOM | 3087 | CA | LEU | B | 811 | 15.700 | −26.747 | −0.331 | 1.00 | 21.97 | B |
| ATOM | 3088 | CB | LEU | B | 811 | 15.015 | −25.374 | −0.315 | 1.00 | 21.71 | B |
| ATOM | 3089 | CG | LEU | B | 811 | 14.081 | −25.064 | 0.861 | 1.00 | 22.02 | B |
| ATOM | 3090 | CD1 | LEU | B | 811 | 13.701 | −23.588 | 0.851 | 1.00 | 22.31 | B |
| ATOM | 3091 | CD2 | LEU | B | 811 | 12.837 | −25.939 | 0.779 | 1.00 | 25.00 | B |
| ATOM | 3092 | C | LEU | B | 811 | 16.507 | −26.900 | −1.619 | 1.00 | 22.54 | B |
| ATOM | 3093 | O | LEU | B | 811 | 15.938 | −26.954 | −2.714 | 1.00 | 21.82 | B |
| ATOM | 3094 | N | GLN | B | 812 | 17.828 | −26.980 | −1.483 | 1.00 | 21.57 | B |
| ATOM | 3095 | CA | GLN | B | 812 | 18.720 | −27.097 | −2.633 | 1.00 | 21.27 | B |
| ATOM | 3096 | CB | GLN | B | 812 | 18.561 | −28.472 | −3.308 | 1.00 | 20.69 | B |
| ATOM | 3097 | CG | GLN | B | 812 | 19.021 | −29.621 | −2.404 | 1.00 | 22.08 | B |
| ATOM | 3098 | CD | GLN | B | 812 | 19.074 | −30.985 | −3.097 | 1.00 | 26.58 | B |
| ATOM | 3099 | OE1 | GLN | B | 812 | 19.622 | −31.944 | −2.550 | 1.00 | 26.47 | B |
| ATOM | 3100 | NE2 | GLN | B | 812 | 18.501 | −31.076 | −4.290 | 1.00 | 25.48 | B |
| ATOM | 3101 | C | GLN | B | 812 | 18.466 | −25.963 | −3.627 | 1.00 | 20.82 | B |
| ATOM | 3102 | O | GLN | B | 812 | 18.251 | −26.189 | −4.815 | 1.00 | 21.92 | B |
| ATOM | 3103 | N | VAL | B | 813 | 18.495 | −24.736 | −3.114 | 1.00 | 19.44 | B |
| ATOM | 3104 | CA | VAL | B | 813 | 18.287 | −23.537 | −3.923 | 1.00 | 19.33 | B |
| ATOM | 3105 | CB | VAL | B | 813 | 18.438 | −22.268 | −3.045 | 1.00 | 18.90 | B |
| ATOM | 3106 | CG1 | VAL | B | 813 | 18.280 | −21.007 | −3.890 | 1.00 | 20.26 | B |
| ATOM | 3107 | CG2 | VAL | B | 813 | 17.412 | −22.297 | −1.921 | 1.00 | 18.94 | B |
| ATOM | 3108 | C | VAL | B | 813 | 19.287 | −23.466 | −5.086 | 1.00 | 18.64 | B |
| ATOM | 3109 | O | VAL | B | 813 | 20.486 | −23.680 | −4.903 | 1.00 | 18.83 | B |
| ATOM | 3110 | N | SER | B | 814 | 18.793 | −23.157 | −6.281 | 1.00 | 18.80 | B |
| ATOM | 3111 | CA | SER | B | 814 | 19.652 | −23.061 | −7.459 | 1.00 | 18.35 | B |
| ATOM | 3112 | CB | SER | B | 814 | 18.863 | −23.440 | −8.715 | 1.00 | 18.95 | B |
| ATOM | 3113 | OG | SER | B | 814 | 17.833 | −22.498 | −8.946 | 1.00 | 17.40 | B |
| ATOM | 3114 | C | SER | B | 814 | 20.186 | −21.638 | −7.616 | 1.00 | 19.62 | B |
| ATOM | 3115 | O | SER | B | 814 | 19.624 | −20.695 | −7.060 | 1.00 | 19.00 | B |
| ATOM | 3116 | N | GLN | B | 815 | 21.266 | −21.477 | −8.375 | 1.00 | 21.03 | B |
| ATOM | 3117 | CA | GLN | B | 815 | 21.815 | −20.142 | −8.589 | 1.00 | 22.06 | B |
| ATOM | 3118 | CB | GLN | B | 815 | 23.037 | −20.177 | −9.513 | 1.00 | 24.38 | B |
| ATOM | 3119 | CG | GLN | B | 815 | 23.720 | −18.810 | −9.642 | 1.00 | 29.34 | B |
| ATOM | 3120 | CD | GLN | B | 815 | 24.757 | −18.746 | −10.754 | 1.00 | 30.23 | B |
| ATOM | 3121 | OE1 | GLN | B | 815 | 25.384 | −17.709 | −10.968 | 1.00 | 35.37 | B |
| ATOM | 3122 | NE2 | GLN | B | 815 | 24.937 | −19.850 | −11.468 | 1.00 | 32.87 | B |
| ATOM | 3123 | C | GLN | B | 815 | 20.758 | −19.250 | −9.228 | 1.00 | 21.09 | B |
| ATOM | 3124 | O | GLN | B | 815 | 20.639 | −18.073 | −8.889 | 1.00 | 20.44 | B |
| ATOM | 3125 | N | GLU | B | 816 | 19.988 | −19.813 | −10.153 | 1.00 | 19.51 | B |
| ATOM | 3126 | CA | GLU | B | 816 | 18.955 | −19.038 | −10.837 | 1.00 | 21.06 | B |
| ATOM | 3127 | CB | GLU | B | 816 | 18.333 | −19.862 | −11.970 | 1.00 | 21.97 | B |
| ATOM | 3128 | CG | GLU | B | 816 | 19.327 | −20.221 | −13.073 | 1.00 | 23.03 | B |
| ATOM | 3129 | CD | GLU | B | 816 | 20.038 | −21.547 | −12.836 | 1.00 | 26.52 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 3130 | OE1 | GLU | B | 816 | 20.073 | −22.025 | −11.681 | 1.00 | 23.85 | B |
| ATOM | 3131 | OE2 | GLU | B | 816 | 20.575 | −22.109 | −13.813 | 1.00 | 28.20 | B |
| ATOM | 3132 | C | GLU | B | 816 | 17.877 | −18.529 | −9.880 | 1.00 | 19.82 | B |
| ATOM | 3133 | O | GLU | B | 816 | 17.435 | −17.383 | −9.993 | 1.00 | 19.18 | B |
| ATOM | 3134 | N | GLU | B | 817 | 17.463 | −19.367 | −8.932 | 1.00 | 17.39 | B |
| ATOM | 3135 | CA | GLU | B | 817 | 16.457 | −18.956 | −7.956 | 1.00 | 18.18 | B |
| ATOM | 3136 | CB | GLU | B | 817 | 15.983 | −20.159 | −7.126 | 1.00 | 18.59 | B |
| ATOM | 3137 | CG | GLU | B | 817 | 15.397 | −21.297 | −7.966 | 1.00 | 22.22 | B |
| ATOM | 3138 | CD | GLU | B | 817 | 15.064 | −22.531 | −7.145 | 1.00 | 23.48 | B |
| ATOM | 3139 | OE1 | GLU | B | 817 | 15.892 | −22.936 | −6.296 | 1.00 | 22.86 | B |
| ATOM | 3140 | OE2 | GLU | B | 817 | 13.976 | −23.106 | −7.363 | 1.00 | 25.72 | B |
| ATOM | 3141 | C | GLU | B | 817 | 17.063 | −17.906 | −7.030 | 1.00 | 17.11 | B |
| ATOM | 3142 | O | GLU | B | 817 | 16.422 | −16.912 | −6.700 | 1.00 | 16.65 | B |
| ATOM | 3143 | N | PHE | B | 818 | 18.305 | −18.142 | −6.618 | 1.00 | 16.93 | B |
| ATOM | 3144 | CA | PHE | B | 818 | 19.018 | −17.239 | −5.723 | 1.00 | 16.13 | B |
| ATOM | 3145 | CB | PHE | B | 818 | 20.435 | −17.769 | −5.456 | 1.00 | 16.83 | B |
| ATOM | 3146 | CG | PHE | B | 818 | 21.349 | −16.761 | −4.791 | 1.00 | 16.89 | B |
| ATOM | 3147 | CD1 | PHE | B | 818 | 21.199 | −16.445 | −3.442 | 1.00 | 15.26 | B |
| ATOM | 3148 | CD2 | PHE | B | 818 | 22.345 | −16.115 | −5.526 | 1.00 | 17.05 | B |
| ATOM | 3149 | CE1 | PHE | B | 818 | 22.027 | −15.499 | −2.830 | 1.00 | 16.92 | B |
| ATOM | 3150 | CE2 | PHE | B | 818 | 23.182 | −15.164 | −4.927 | 1.00 | 17.15 | B |
| ATOM | 3151 | CZ | PHE | B | 818 | 23.022 | −14.855 | −3.576 | 1.00 | 16.27 | B |
| ATOM | 3152 | C | PHE | B | 818 | 19.122 | −15.818 | −6.278 | 1.00 | 16.33 | B |
| ATOM | 3153 | O | PHE | B | 818 | 18.840 | −14.849 | −5.569 | 1.00 | 15.00 | B |
| ATOM | 3154 | N | LEU | B | 819 | 19.538 | −15.706 | −7.538 | 1.00 | 14.54 | B |
| ATOM | 3155 | CA | LEU | B | 819 | 19.716 | −14.404 | −8.177 | 1.00 | 16.83 | B |
| ATOM | 3156 | CB | LEU | B | 819 | 20.311 | −14.581 | −9.582 | 1.00 | 16.07 | B |
| ATOM | 3157 | CG | LEU | B | 819 | 21.722 | −15.189 | −9.612 | 1.00 | 18.18 | B |
| ATOM | 3158 | CD1 | LEU | B | 819 | 22.082 | −15.583 | −11.026 | 1.00 | 18.54 | B |
| ATOM | 3159 | CD2 | LEU | B | 819 | 22.737 | −14.192 | −9.056 | 1.00 | 16.82 | B |
| ATOM | 3160 | C | LEU | B | 819 | 18.424 | −13.597 | −8.245 | 1.00 | 16.62 | B |
| ATOM | 3161 | O | LEU | B | 819 | 18.436 | −12.385 | −8.027 | 1.00 | 18.04 | B |
| ATOM | 3162 | N | CYS | B | 820 | 17.314 | −14.266 | −8.541 | 1.00 | 16.17 | B |
| ATOM | 3163 | CA | CYS | B | 820 | 16.021 | −13.596 | −8.616 | 1.00 | 16.66 | B |
| ATOM | 3164 | CB | CYS | B | 820 | 14.983 | −14.509 | −9.271 | 1.00 | 16.58 | B |
| ATOM | 3165 | SG | CYS | B | 820 | 15.294 | −14.853 | −11.023 | 1.00 | 18.85 | B |
| ATOM | 3166 | C | CYS | B | 820 | 15.551 | −13.197 | −7.223 | 1.00 | 16.30 | B |
| ATOM | 3167 | O | CYS | B | 820 | 15.032 | −12.094 | −7.023 | 1.00 | 14.96 | B |
| ATOM | 3168 | N | MET | B | 821 | 15.737 | −14.099 | −6.263 | 1.00 | 16.45 | B |
| ATOM | 3169 | CA | MET | B | 821 | 15.342 | −13.843 | −4.880 | 1.00 | 15.29 | B |
| ATOM | 3170 | CB | MET | B | 821 | 15.607 | −15.074 | −4.011 | 1.00 | 16.65 | B |
| ATOM | 3171 | CG | MET | B | 821 | 14.675 | −16.244 | −4.269 | 1.00 | 17.53 | B |
| ATOM | 3172 | SD | MET | B | 821 | 15.242 | −17.726 | −3.411 | 1.00 | 19.94 | B |
| ATOM | 3173 | CE | MET | B | 821 | 14.783 | −17.351 | −1.762 | 1.00 | 15.63 | B |
| ATOM | 3174 | C | MET | B | 821 | 16.110 | −12.661 | −4.299 | 1.00 | 15.82 | B |
| ATOM | 3175 | O | MET | B | 821 | 15.564 | −11.868 | −3.535 | 1.00 | 14.99 | B |
| ATOM | 3176 | N | LYS | B | 822 | 17.381 | −12.549 | −4.663 | 1.00 | 16.67 | B |
| ATOM | 3177 | CA | LYS | B | 822 | 18.212 | −11.473 | −4.148 | 1.00 | 16.99 | B |
| ATOM | 3178 | CB | LYS | B | 822 | 19.679 | −11.705 | −4.526 | 1.00 | 18.26 | B |
| ATOM | 3179 | CG | LYS | B | 822 | 20.635 | −10.691 | −3.906 | 1.00 | 19.96 | B |
| ATOM | 3180 | CD | LYS | B | 822 | 22.044 | −11.256 | −3.763 | 1.00 | 20.99 | B |
| ATOM | 3181 | CE | LYS | B | 822 | 22.696 | −11.541 | −5.110 | 1.00 | 23.13 | B |
| ATOM | 3182 | NZ | LYS | B | 822 | 22.880 | −10.302 | −5.919 | 1.00 | 23.24 | B |
| ATOM | 3183 | C | LYS | B | 822 | 17.728 | −10.117 | −4.644 | 1.00 | 17.98 | B |
| ATOM | 3184 | O | LYS | B | 822 | 17.814 | −9.128 | −3.922 | 1.00 | 17.23 | B |
| ATOM | 3185 | N | VAL | B | 823 | 17.220 | −10.066 | −5.872 | 1.00 | 17.29 | B |
| ATOM | 3186 | CA | VAL | B | 823 | 16.698 | −8.814 | −6.404 | 1.00 | 15.85 | B |
| ATOM | 3187 | CB | VAL | B | 823 | 16.379 | −8.919 | −7.905 | 1.00 | 17.02 | B |
| ATOM | 3188 | CG1 | VAL | B | 823 | 15.756 | −7.603 | −8.397 | 1.00 | 15.78 | B |
| ATOM | 3189 | CG2 | VAL | B | 823 | 17.650 | −9.228 | −8.685 | 1.00 | 15.65 | B |
| ATOM | 3190 | C | VAL | B | 823 | 15.412 | −8.467 | −5.653 | 1.00 | 15.49 | B |
| ATOM | 3191 | O | VAL | B | 823 | 15.155 | −7.306 | −5.340 | 1.00 | 14.04 | B |
| ATOM | 3192 | N | LEU | B | 824 | 14.603 | −9.478 | −5.356 | 1.00 | 14.47 | B |
| ATOM | 3193 | CA | LEU | B | 824 | 13.361 | −9.240 | −4.631 | 1.00 | 15.65 | B |
| ATOM | 3194 | CB | LEU | B | 824 | 12.525 | −10.523 | −4.584 | 1.00 | 15.79 | B |
| ATOM | 3195 | CG | LEU | B | 824 | 11.928 | −10.911 | −5.942 | 1.00 | 18.34 | B |
| ATOM | 3196 | CD1 | LEU | B | 824 | 11.245 | −12.262 | −5.835 | 1.00 | 17.24 | B |
| ATOM | 3197 | CD2 | LEU | B | 824 | 10.933 | −9.842 | −6.393 | 1.00 | 16.65 | B |
| ATOM | 3198 | C | LEU | B | 824 | 13.667 | −8.730 | −3.223 | 1.00 | 16.46 | B |
| ATOM | 3199 | O | LEU | B | 824 | 12.907 | −7.931 | −2.662 | 1.00 | 17.28 | B |
| ATOM | 3200 | N | LEU | B | 825 | 14.781 | −9.184 | −2.656 | 1.00 | 16.24 | B |
| ATOM | 3201 | CA | LEU | B | 825 | 15.190 | −8.721 | −1.324 | 1.00 | 17.69 | B |
| ATOM | 3202 | CB | LEU | B | 825 | 16.463 | −9.419 | −0.861 | 1.00 | 17.38 | B |
| ATOM | 3203 | CG | LEU | B | 825 | 16.366 | −10.560 | 0.141 | 1.00 | 23.00 | B |
| ATOM | 3204 | CD1 | LEU | B | 825 | 17.767 | −10.795 | 0.695 | 1.00 | 19.06 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 3205 | CD2 | LEU | B | 825 | 15.396 | −10.217 | 1.276 | 1.00 | 21.23 | B |
| ATOM | 3206 | C | LEU | B | 825 | 15.472 | −7.227 | −1.360 | 1.00 | 15.92 | B |
| ATOM | 3207 | O | LEU | B | 825 | 15.111 | −6.492 | −0.441 | 1.00 | 15.49 | B |
| ATOM | 3208 | N | LEU | B | 826 | 16.151 | −6.793 | −2.416 | 1.00 | 15.55 | B |
| ATOM | 3209 | CA | LEU | B | 826 | 16.477 | −5.380 | −2.587 | 1.00 | 15.43 | B |
| ATOM | 3210 | CB | LEU | B | 826 | 17.235 | −5.179 | −3.906 | 1.00 | 13.00 | B |
| ATOM | 3211 | CG | LEU | B | 826 | 17.367 | −3.755 | −4.447 | 1.00 | 17.08 | B |
| ATOM | 3212 | CD1 | LEU | B | 826 | 18.309 | −2.932 | −3.565 | 1.00 | 15.15 | B |
| ATOM | 3213 | CD2 | LEU | B | 826 | 17.880 | −3.813 | −5.893 | 1.00 | 15.84 | B |
| ATOM | 3214 | C | LEU | B | 826 | 15.192 | −4.552 | −2.605 | 1.00 | 15.22 | B |
| ATOM | 3215 | O | LEU | B | 826 | 15.159 | −3.417 | −2.123 | 1.00 | 15.10 | B |
| ATOM | 3216 | N | LEU | B | 827 | 14.134 | −5.146 | −3.148 | 1.00 | 14.61 | B |
| ATOM | 3217 | CA | LEU | B | 827 | 12.835 | −4.487 | −3.287 | 1.00 | 17.58 | B |
| ATOM | 3218 | CB | LEU | B | 827 | 12.261 | −4.795 | −4.678 | 1.00 | 16.81 | B |
| ATOM | 3219 | CG | LEU | B | 827 | 13.201 | −4.610 | −5.872 | 1.00 | 19.46 | B |
| ATOM | 3220 | CD1 | LEU | B | 827 | 12.564 | −5.176 | −7.146 | 1.00 | 18.89 | B |
| ATOM | 3221 | CD2 | LEU | B | 827 | 13.519 | −3.131 | −6.032 | 1.00 | 15.57 | B |
| ATOM | 3222 | C | LEU | B | 827 | 11.827 | −4.961 | −2.253 | 1.00 | 16.56 | B |
| ATOM | 3223 | O | LEU | B | 827 | 10.625 | −4.866 | −2.487 | 1.00 | 18.58 | B |
| ATOM | 3224 | N | ASN | B | 828 | 12.299 | −5.438 | −1.106 | 1.00 | 15.56 | B |
| ATOM | 3225 | CA | ASN | B | 828 | 11.380 | −5.998 | −0.125 | 1.00 | 17.84 | B |
| ATOM | 3226 | CB | ASN | B | 828 | 11.992 | −7.291 | 0.421 | 1.00 | 19.91 | B |
| ATOM | 3227 | CG | ASN | B | 828 | 10.986 | −8.423 | 0.503 | 1.00 | 24.26 | B |
| ATOM | 3228 | OD1 | ASN | B | 828 | 10.082 | −8.524 | −0.328 | 1.00 | 24.73 | B |
| ATOM | 3229 | ND2 | ASN | B | 828 | 11.153 | −9.294 | 1.495 | 1.00 | 24.40 | B |
| ATOM | 3230 | C | ASN | B | 828 | 10.894 | −5.105 | 1.022 | 1.00 | 17.27 | B |
| ATOM | 3231 | O | ASN | B | 828 | 10.137 | −5.558 | 1.879 | 1.00 | 16.66 | B |
| ATOM | 3232 | N | THR | B | 829 | 11.323 | −3.848 | 1.037 | 1.00 | 14.98 | B |
| ATOM | 3233 | CA | THR | B | 829 | 10.896 | −2.903 | 2.063 | 1.00 | 18.37 | B |
| ATOM | 3234 | CB | THR | B | 829 | 11.914 | −2.802 | 3.232 | 1.00 | 18.06 | B |
| ATOM | 3235 | OG1 | THR | B | 829 | 12.146 | −4.102 | 3.789 | 1.00 | 17.88 | B |
| ATOM | 3236 | CG2 | THR | B | 829 | 11.372 | −1.889 | 4.321 | 1.00 | 20.06 | B |
| ATOM | 3237 | C | THR | B | 829 | 10.775 | −1.523 | 1.426 | 1.00 | 18.82 | B |
| ATOM | 3238 | O | THR | B | 829 | 11.607 | −1.151 | 0.595 | 1.00 | 17.50 | B |
| ATOM | 3239 | N | ILE | B | 830 | 9.736 | −0.775 | 1.792 | 1.00 | 17.45 | B |
| ATOM | 3240 | CA | ILE | B | 830 | 9.548 | 0.572 | 1.258 | 1.00 | 19.79 | B |
| ATOM | 3241 | CB | ILE | B | 830 | 8.523 | 0.594 | 0.089 | 1.00 | 20.43 | B |
| ATOM | 3242 | CG2 | ILE | B | 830 | 8.982 | −0.346 | −1.019 | 1.00 | 19.43 | B |
| ATOM | 3243 | CG1 | ILE | B | 830 | 7.133 | 0.200 | 0.592 | 1.00 | 21.42 | B |
| ATOM | 3244 | CD1 | ILE | B | 830 | 6.083 | 0.164 | −0.493 | 1.00 | 22.07 | B |
| ATOM | 3245 | C | ILE | B | 830 | 9.084 | 1.522 | 2.366 | 1.00 | 19.09 | B |
| ATOM | 3246 | O | ILE | B | 830 | 8.680 | 1.080 | 3.440 | 1.00 | 21.03 | B |
| ATOM | 3247 | N | PRO | B | 831 | 9.159 | 2.840 | 2.126 | 1.00 | 19.68 | B |
| ATOM | 3248 | CD | PRO | B | 831 | 9.738 | 3.505 | 0.949 | 1.00 | 18.90 | B |
| ATOM | 3249 | CA | PRO | B | 831 | 8.738 | 3.828 | 3.129 | 1.00 | 21.03 | B |
| ATOM | 3250 | CB | PRO | B | 831 | 9.057 | 5.164 | 2.460 | 1.00 | 20.87 | B |
| ATOM | 3251 | CG | PRO | B | 831 | 10.192 | 4.821 | 1.528 | 1.00 | 22.56 | B |
| ATOM | 3252 | C | PRO | B | 831 | 7.252 | 3.696 | 3.428 | 1.00 | 22.30 | B |
| ATOM | 3253 | O | PRO | B | 831 | 6.498 | 3.183 | 2.608 | 1.00 | 22.00 | B |
| ATOM | 3254 | N | LEU | B | 832 | 6.827 | 4.161 | 4.597 | 1.00 | 23.69 | B |
| ATOM | 3255 | CA | LEU | B | 832 | 5.413 | 4.088 | 4.957 | 1.00 | 26.10 | B |
| ATOM | 3256 | CB | LEU | B | 832 | 5.190 | 4.686 | 6.351 | 1.00 | 26.82 | B |
| ATOM | 3257 | CG | LEU | B | 832 | 5.745 | 3.874 | 7.529 | 1.00 | 26.56 | B |
| ATOM | 3258 | CD1 | LEU | B | 832 | 5.599 | 4.667 | 8.820 | 1.00 | 28.10 | B |
| ATOM | 3259 | CD2 | LEU | B | 832 | 5.002 | 2.551 | 7.628 | 1.00 | 27.65 | B |
| ATOM | 3260 | C | LEU | B | 832 | 4.550 | 4.823 | 3.929 | 1.00 | 26.82 | B |
| ATOM | 3261 | O | LEU | B | 832 | 3.442 | 4.392 | 3.614 | 1.00 | 26.75 | B |
| ATOM | 3262 | N | GLU | B | 833 | 5.070 | 5.928 | 3.403 | 1.00 | 27.88 | B |
| ATOM | 3263 | CA | GLU | B | 833 | 4.347 | 6.719 | 2.414 | 1.00 | 29.18 | B |
| ATOM | 3264 | CB | GLU | B | 833 | 4.808 | 8.180 | 2.461 | 1.00 | 31.58 | B |
| ATOM | 3265 | CG | GLU | B | 833 | 6.300 | 8.368 | 2.212 | 1.00 | 33.80 | B |
| ATOM | 3266 | CD | GLU | B | 833 | 7.141 | 8.184 | 3.467 | 1.00 | 34.56 | B |
| ATOM | 3267 | OE1 | GLU | B | 833 | 6.840 | 7.282 | 4.272 | 1.00 | 34.98 | B |
| ATOM | 3268 | OE2 | GLU | B | 833 | 8.119 | 8.938 | 3.643 | 1.00 | 36.68 | B |
| ATOM | 3269 | C | GLU | B | 833 | 4.559 | 6.163 | 1.007 | 1.00 | 29.05 | B |
| ATOM | 3270 | O | GLU | B | 833 | 4.009 | 6.682 | 0.032 | 1.00 | 30.18 | B |
| ATOM | 3271 | N | GLY | B | 834 | 5.354 | 5.104 | 0.901 | 1.00 | 25.32 | B |
| ATOM | 3272 | CA | GLY | B | 834 | 5.616 | 4.520 | −0.398 | 1.00 | 23.75 | B |
| ATOM | 3273 | C | GLY | B | 834 | 6.766 | 5.233 | −1.087 | 1.00 | 24.18 | B |
| ATOM | 3274 | O | GLY | B | 834 | 7.334 | 6.179 | −0.547 | 1.00 | 22.28 | B |
| ATOM | 3275 | N | LEU | B | 835 | 7.106 | 4.779 | −2.288 | 1.00 | 23.91 | B |
| ATOM | 3276 | CA | LEU | B | 835 | 8.196 | 5.368 | −3.049 | 1.00 | 24.07 | B |
| ATOM | 3277 | CB | LEU | B | 835 | 8.885 | 4.283 | −3.871 | 1.00 | 23.41 | B |
| ATOM | 3278 | CG | LEU | B | 835 | 9.564 | 3.167 | −3.074 | 1.00 | 22.91 | B |
| ATOM | 3279 | CD1 | LEU | B | 835 | 9.954 | 2.031 | −4.003 | 1.00 | 21.52 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 3280 | CD2 | LEU | B | 835 | 10.778 | 3.732 | −2.361 | 1.00 | 22.16 | B |
| ATOM | 3281 | C | LEU | B | 835 | 7.697 | 6.465 | −3.982 | 1.00 | 25.22 | B |
| ATOM | 3282 | O | LEU | B | 835 | 6.494 | 6.599 | −4.214 | 1.00 | 23.05 | B |
| ATOM | 3283 | N | ARG | B | 836 | 8.625 | 7.250 | −4.518 | 1.00 | 25.18 | B |
| ATOM | 3284 | CA | ARG | B | 836 | 8.251 | 8.305 | −5.450 | 1.00 | 27.41 | B |
| ATOM | 3285 | CB | ARG | B | 836 | 9.410 | 9.289 | −5.629 | 1.00 | 29.23 | B |
| ATOM | 3286 | CG | ARG | B | 836 | 9.790 | 9.972 | −4.326 | 1.00 | 33.63 | B |
| ATOM | 3287 | CD | ARG | B | 836 | 10.699 | 11.168 | −4.531 | 1.00 | 39.98 | B |
| ATOM | 3288 | NE | ARG | B | 836 | 11.086 | 11.742 | −3.244 | 1.00 | 46.27 | B |
| ATOM | 3289 | CZ | ARG | B | 836 | 11.726 | 12.897 | −3.091 | 1.00 | 48.81 | B |
| ATOM | 3290 | NH1 | ARG | B | 836 | 12.032 | 13.327 | −1.873 | 1.00 | 50.05 | B |
| ATOM | 3291 | NH2 | ARG | B | 836 | 12.059 | 13.623 | −4.152 | 1.00 | 50.02 | B |
| ATOM | 3292 | C | ARG | B | 836 | 7.874 | 7.644 | −6.774 | 1.00 | 25.29 | B |
| ATOM | 3293 | O | ARG | B | 836 | 6.886 | 8.015 | −7.405 | 1.00 | 25.23 | B |
| ATOM | 3294 | N | SER | B | 837 | 8.652 | 6.641 | −7.174 | 1.00 | 23.28 | B |
| ATOM | 3295 | CA | SER | B | 837 | 8.387 | 5.906 | −8.408 | 1.00 | 21.91 | B |
| ATOM | 3296 | CB | SER | B | 837 | 9.696 | 5.609 | −9.138 | 1.00 | 22.60 | B |
| ATOM | 3297 | OG | SER | B | 837 | 10.416 | 6.806 | −9.380 | 1.00 | 24.64 | B |
| ATOM | 3298 | C | SER | B | 837 | 7.693 | 4.597 | −8.046 | 1.00 | 21.70 | B |
| ATOM | 3299 | O | SER | B | 837 | 8.145 | 3.518 | −8.427 | 1.00 | 19.42 | B |
| ATOM | 3300 | N | GLN | B | 838 | 6.593 | 4.707 | −7.307 | 1.00 | 21.26 | B |
| ATOM | 3301 | CA | GLN | B | 838 | 5.831 | 3.544 | −6.862 | 1.00 | 22.08 | B |
| ATOM | 3302 | CB | GLN | B | 838 | 4.618 | 4.004 | −6.040 | 1.00 | 22.63 | B |
| ATOM | 3303 | CG | GLN | B | 838 | 3.915 | 2.893 | −5.259 | 1.00 | 26.54 | B |
| ATOM | 3304 | CD | GLN | B | 838 | 4.822 | 2.234 | −4.226 | 1.00 | 26.15 | B |
| ATOM | 3305 | OE1 | GLN | B | 838 | 5.562 | 2.909 | −3.513 | 1.00 | 27.61 | B |
| ATOM | 3306 | NE2 | GLN | B | 838 | 4.755 | 0.911 | −4.135 | 1.00 | 27.61 | B |
| ATOM | 3307 | C | GLN | B | 838 | 5.368 | 2.647 | −8.012 | 1.00 | 21.61 | B |
| ATOM | 3308 | O | GLN | B | 838 | 5.515 | 1.427 | −7.949 | 1.00 | 20.05 | B |
| ATOM | 3309 | N | THR | B | 839 | 4.812 | 3.249 | −9.062 | 1.00 | 22.33 | B |
| ATOM | 3310 | CA | THR | B | 839 | 4.336 | 2.479 | −10.207 | 1.00 | 22.29 | B |
| ATOM | 3311 | CB | THR | B | 839 | 3.694 | 3.386 | −11.276 | 1.00 | 24.97 | B |
| ATOM | 3312 | OG1 | THR | B | 839 | 2.579 | 4.077 | −10.702 | 1.00 | 27.76 | B |
| ATOM | 3313 | CG2 | THR | B | 839 | 3.206 | 2.555 | −12.460 | 1.00 | 24.83 | B |
| ATOM | 3314 | C | THR | B | 839 | 5.463 | 1.690 | −10.855 | 1.00 | 20.46 | B |
| ATOM | 3315 | O | THR | B | 839 | 5.321 | 0.498 | −11.118 | 1.00 | 21.42 | B |
| ATOM | 3316 | N | GLN | B | 840 | 6.582 | 2.354 | −11.111 | 1.00 | 19.38 | B |
| ATOM | 3317 | CA | GLN | B | 840 | 7.725 | 1.690 | −11.722 | 1.00 | 21.53 | B |
| ATOM | 3318 | CB | GLN | B | 840 | 8.831 | 2.702 | −12.013 | 1.00 | 25.28 | B |
| ATOM | 3319 | CG | GLN | B | 840 | 10.059 | 2.081 | −12.661 | 1.00 | 33.27 | B |
| ATOM | 3320 | CD | GLN | B | 840 | 9.737 | 1.408 | −13.983 | 1.00 | 37.68 | B |
| ATOM | 3321 | OE1 | GLN | B | 840 | 9.410 | 2.073 | −14.968 | 1.00 | 41.19 | B |
| ATOM | 3322 | NE2 | GLN | B | 840 | 9.818 | 0.078 | −14.009 | 1.00 | 41.64 | B |
| ATOM | 3323 | C | GLN | B | 840 | 8.259 | 0.599 | −10.793 | 1.00 | 20.93 | B |
| ATOM | 3324 | O | GLN | B | 840 | 8.638 | −0.477 | −11.242 | 1.00 | 22.03 | B |
| ATOM | 3325 | N | PHE | B | 841 | 8.287 | 0.891 | −9.498 | 1.00 | 18.17 | B |
| ATOM | 3326 | CA | PHE | B | 841 | 8.764 | −0.065 | −8.499 | 1.00 | 17.96 | B |
| ATOM | 3327 | CB | PHE | B | 841 | 8.654 | 0.540 | −7.097 | 1.00 | 16.53 | B |
| ATOM | 3328 | CG | PHE | B | 841 | 8.826 | −0.464 | −5.982 | 1.00 | 17.42 | B |
| ATOM | 3329 | CD1 | PHE | B | 841 | 10.092 | −0.912 | −5.612 | 1.00 | 19.52 | B |
| ATOM | 3330 | CD2 | PHE | B | 841 | 7.718 | −0.953 | −5.296 | 1.00 | 16.29 | B |
| ATOM | 3331 | CE1 | PHE | B | 841 | 10.250 | −1.832 | −4.570 | 1.00 | 15.82 | B |
| ATOM | 3332 | CE2 | PHE | B | 841 | 7.867 | −1.877 | −4.253 | 1.00 | 18.30 | B |
| ATOM | 3333 | CZ | PHE | B | 841 | 9.139 | −2.313 | −3.893 | 1.00 | 16.42 | B |
| ATOM | 3334 | C | PHE | B | 841 | 7.938 | −1.341 | −8.554 | 1.00 | 18.36 | B |
| ATOM | 3335 | O | PHE | B | 841 | 8.474 | −2.447 | −8.625 | 1.00 | 16.92 | B |
| ATOM | 3336 | N | GLU | B | 842 | 6.624 | −1.181 | −8.524 | 1.00 | 18.46 | B |
| ATOM | 3337 | CA | GLU | B | 842 | 5.742 | −2.333 | −8.552 | 1.00 | 20.40 | B |
| ATOM | 3338 | CB | GLU | B | 842 | 4.300 | −1.874 | −8.320 | 1.00 | 22.60 | B |
| ATOM | 3339 | CG | GLU | B | 842 | 3.992 | −1.716 | −6.831 | 1.00 | 28.47 | B |
| ATOM | 3340 | CD | GLU | B | 842 | 2.778 | −0.855 | −6.553 | 1.00 | 33.41 | B |
| ATOM | 3341 | OE1 | GLU | B | 842 | 1.849 | −0.848 | −7.387 | 1.00 | 35.95 | B |
| ATOM | 3342 | OE2 | GLU | B | 842 | 2.748 | −0.194 | −5.490 | 1.00 | 34.10 | B |
| ATOM | 3343 | C | GLU | B | 842 | 5.885 | −3.159 | −9.824 | 1.00 | 19.29 | B |
| ATOM | 3344 | O | GLU | B | 842 | 5.856 | −4.388 | −9.769 | 1.00 | 18.69 | B |
| ATOM | 3345 | N | GLU | B | 843 | 6.053 | −2.492 | −10.962 | 1.00 | 19.28 | B |
| ATOM | 3346 | CA | GLU | B | 843 | 6.234 | −3.194 | −12.229 | 1.00 | 20.40 | B |
| ATOM | 3347 | CB | GLU | B | 843 | 6.279 | −2.195 | −13.391 | 1.00 | 23.21 | B |
| ATOM | 3348 | CG | GLU | B | 843 | 4.908 | −1.670 | −13.817 | 1.00 | 26.48 | B |
| ATOM | 3349 | CD | GLU | B | 843 | 4.993 | −0.619 | −14.912 | 1.00 | 28.27 | B |
| ATOM | 3350 | OE1 | GLU | B | 843 | 5.906 | −0.710 | −15.761 | 1.00 | 31.59 | B |
| ATOM | 3351 | OE2 | GLU | B | 843 | 4.140 | 0.289 | −14.933 | 1.00 | 30.69 | B |
| ATOM | 3352 | C | GLU | B | 843 | 7.542 | −3.984 | −12.180 | 1.00 | 21.13 | B |
| ATOM | 3353 | O | GLU | B | 843 | 7.600 | −5.147 | −12.580 | 1.00 | 20.25 | B |
| ATOM | 3354 | N | MET | B | 844 | 8.594 | −3.339 | −11.684 | 1.00 | 20.24 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 3355 | CA | MET | B | 844 | 9.892 | −3.984 | −11.574 | 1.00 | 21.25 | B |
| ATOM | 3356 | CB | MET | B | 844 | 10.920 | −3.004 | −11.001 | 1.00 | 21.39 | B |
| ATOM | 3357 | CG | MET | B | 844 | 12.315 | −3.597 | −10.878 | 1.00 | 21.13 | B |
| ATOM | 3358 | SD | MET | B | 844 | 13.560 | −2.448 | −10.248 | 1.00 | 19.73 | B |
| ATOM | 3359 | CE | MET | B | 844 | 14.982 | −3.557 | −10.182 | 1.00 | 17.38 | B |
| ATOM | 3360 | C | MET | B | 844 | 9.787 | −5.222 | −10.679 | 1.00 | 21.40 | B |
| ATOM | 3361 | O | MET | B | 844 | 10.238 | −6.309 | −11.045 | 1.00 | 21.49 | B |
| ATOM | 3362 | N | ARG | B | 845 | 9.183 | −5.056 | −9.509 | 1.00 | 21.07 | B |
| ATOM | 3363 | CA | ARG | B | 845 | 9.026 | −6.170 | −8.584 | 1.00 | 22.63 | B |
| ATOM | 3364 | CB | ARG | B | 845 | 8.320 | −5.683 | −7.317 | 1.00 | 23.95 | B |
| ATOM | 3365 | CG | ARG | B | 845 | 8.324 | −6.666 | −6.164 | 1.00 | 27.11 | B |
| ATOM | 3366 | CD | ARG | B | 845 | 7.705 | −6.032 | −4.922 | 1.00 | 25.54 | B |
| ATOM | 3367 | NE | ARG | B | 845 | 7.297 | −7.039 | −3.953 | 1.00 | 27.61 | B |
| ATOM | 3368 | CZ | ARG | B | 845 | 8.134 | −7.751 | −3.208 | 1.00 | 30.27 | B |
| ATOM | 3369 | NH1 | ARG | B | 845 | 7.654 | −8.651 | −2.359 | 1.00 | 32.12 | B |
| ATOM | 3370 | NH2 | ARG | B | 845 | 9.447 | −7.552 | −3.295 | 1.00 | 28.99 | B |
| ATOM | 3371 | C | ARG | B | 845 | 8.250 | −7.329 | −9.236 | 1.00 | 23.19 | B |
| ATOM | 3372 | O | ARG | B | 845 | 8.662 | −8.485 | −9.139 | 1.00 | 22.55 | B |
| ATOM | 3373 | N | SER | B | 846 | 7.144 | −7.021 | −9.912 | 1.00 | 21.82 | B |
| ATOM | 3374 | CA | SER | B | 846 | 6.349 | −8.057 | −10.572 | 1.00 | 23.07 | B |
| ATOM | 3375 | CB | SER | B | 846 | 5.115 | −7.449 | −11.252 | 1.00 | 24.12 | B |
| ATOM | 3376 | OG | SER | B | 846 | 4.220 | −6.922 | −10.293 | 1.00 | 26.05 | B |
| ATOM | 3377 | C | SER | B | 846 | 7.184 | −8.791 | −11.614 | 1.00 | 22.04 | B |
| ATOM | 3378 | O | SER | B | 846 | 7.058 | −10.003 | −11.777 | 1.00 | 24.09 | B |
| ATOM | 3379 | N | SER | B | 847 | 8.028 | −8.048 | −12.324 | 1.00 | 21.69 | B |
| ATOM | 3380 | CA | SER | B | 847 | 8.888 | −8.629 | −13.345 | 1.00 | 22.04 | B |
| ATOM | 3381 | CB | SER | B | 847 | 9.734 | −7.545 | −14.020 | 1.00 | 24.55 | B |
| ATOM | 3382 | OG | SER | B | 847 | 8.929 | −6.652 | −14.771 | 1.00 | 31.05 | B |
| ATOM | 3383 | C | SER | B | 847 | 9.816 | −9.682 | −12.748 | 1.00 | 20.47 | B |
| ATOM | 3384 | O | SER | B | 847 | 9.948 | −10.781 | −13.281 | 1.00 | 21.10 | B |
| ATOM | 3385 | N | TYR | B | 848 | 10.468 | −9.343 | −11.644 | 1.00 | 19.70 | B |
| ATOM | 3386 | CA | TYR | B | 848 | 11.379 | −10.279 | −11.010 | 1.00 | 18.31 | B |
| ATOM | 3387 | CB | TYR | B | 848 | 12.288 | −9.526 | −10.043 | 1.00 | 19.17 | B |
| ATOM | 3388 | CG | TYR | B | 848 | 13.362 | −8.765 | −10.800 | 1.00 | 19.76 | B |
| ATOM | 3389 | CD1 | TYR | B | 848 | 14.496 | −9.425 | −11.279 | 1.00 | 18.70 | B |
| ATOM | 3390 | CE1 | TYR | B | 848 | 15.462 | −8.756 | −12.026 | 1.00 | 16.37 | B |
| ATOM | 3391 | CD2 | TYR | B | 848 | 13.218 | −7.407 | −11.088 | 1.00 | 18.08 | B |
| ATOM | 3392 | CE2 | TYR | B | 848 | 14.182 | −6.726 | −11.839 | 1.00 | 17.62 | B |
| ATOM | 3393 | CZ | TYR | B | 848 | 15.301 | −7.409 | −12.302 | 1.00 | 19.15 | B |
| ATOM | 3394 | OH | TYR | B | 848 | 16.272 | −6.751 | −13.028 | 1.00 | 17.87 | B |
| ATOM | 3395 | C | TYR | B | 848 | 10.641 | −11.431 | −10.338 | 1.00 | 18.15 | B |
| ATOM | 3396 | O | TYR | B | 848 | 11.180 | −12.529 | −10.214 | 1.00 | 18.25 | B |
| ATOM | 3397 | N | ILE | B | 849 | 9.411 | −11.191 | −9.903 | 1.00 | 18.38 | B |
| ATOM | 3398 | CA | ILE | B | 849 | 8.631 | −12.274 | −9.316 | 1.00 | 20.21 | B |
| ATOM | 3399 | CB | ILE | B | 849 | 7.286 | −11.758 | −8.723 | 1.00 | 21.49 | B |
| ATOM | 3400 | CG2 | ILE | B | 849 | 6.368 | −12.929 | −8.395 | 1.00 | 21.35 | B |
| ATOM | 3401 | CG1 | ILE | B | 849 | 7.557 | −10.955 | −7.446 | 1.00 | 22.56 | B |
| ATOM | 3402 | CD1 | ILE | B | 849 | 6.316 | −10.343 | −6.811 | 1.00 | 21.72 | B |
| ATOM | 3403 | C | ILE | B | 849 | 8.375 | −13.255 | −10.474 | 1.00 | 21.64 | B |
| ATOM | 3404 | O | ILE | B | 849 | 8.468 | −14.471 | −10.309 | 1.00 | 22.27 | B |
| ATOM | 3405 | N | ARG | B | 850 | 8.080 | −12.724 | −11.659 | 1.00 | 22.31 | B |
| ATOM | 3406 | CA | ARG | B | 850 | 7.849 | −13.588 | −12.813 | 1.00 | 24.41 | B |
| ATOM | 3407 | CB | ARG | B | 850 | 7.375 | −12.781 | −14.030 | 1.00 | 26.21 | B |
| ATOM | 3408 | CG | ARG | B | 850 | 5.921 | −12.320 | −13.957 | 1.00 | 28.80 | B |
| ATOM | 3409 | CD | ARG | B | 850 | 5.417 | −11.832 | −15.319 | 1.00 | 29.74 | B |
| ATOM | 3410 | NE | ARG | B | 850 | 5.971 | −10.537 | −15.710 | 1.00 | 30.41 | B |
| ATOM | 3411 | CZ | ARG | B | 850 | 5.629 | −9.378 | −15.152 | 1.00 | 31.78 | B |
| ATOM | 3412 | NH1 | ARG | B | 850 | 4.733 | −9.348 | −14.175 | 1.00 | 33.98 | B |
| ATOM | 3413 | NH2 | ARG | B | 850 | 6.178 | −8.247 | −15.571 | 1.00 | 29.88 | B |
| ATOM | 3414 | C | ARG | B | 850 | 9.128 | −14.329 | −13.181 | 1.00 | 25.13 | B |
| ATOM | 3415 | O | ARG | B | 850 | 9.090 | −15.501 | −13.568 | 1.00 | 26.48 | B |
| ATOM | 3416 | N | GLU | B | 851 | 10.263 | −13.649 | −13.058 | 1.00 | 22.96 | B |
| ATOM | 3417 | CA | GLU | B | 851 | 11.541 | −14.258 | −13.402 | 1.00 | 22.01 | B |
| ATOM | 3418 | CB | GLU | B | 851 | 12.647 | −13.196 | −13.394 | 1.00 | 22.35 | B |
| ATOM | 3419 | CG | GLU | B | 851 | 13.838 | −13.513 | −14.289 | 1.00 | 21.41 | B |
| ATOM | 3420 | CD | GLU | B | 851 | 13.454 | −13.712 | −15.756 | 1.00 | 25.43 | B |
| ATOM | 3421 | OE1 | GLU | B | 851 | 12.520 | −13.035 | −16.241 | 1.00 | 25.41 | B |
| ATOM | 3422 | OE2 | GLU | B | 851 | 14.103 | −14.540 | −16.435 | 1.00 | 26.71 | B |
| ATOM | 3423 | C | GLU | B | 851 | 11.856 | −15.386 | −12.423 | 1.00 | 22.31 | B |
| ATOM | 3424 | O | GLU | B | 851 | 12.408 | −16.416 | −12.814 | 1.00 | 22.61 | B |
| ATOM | 3425 | N | LEU | B | 852 | 11.497 | −15.196 | −11.155 | 1.00 | 22.07 | B |
| ATOM | 3426 | CA | LEU | B | 852 | 11.718 | −16.226 | −10.140 | 1.00 | 21.52 | B |
| ATOM | 3427 | CB | LEU | B | 852 | 11.274 | −15.724 | −8.759 | 1.00 | 19.90 | B |
| ATOM | 3428 | CG | LEU | B | 852 | 11.214 | −16.726 | −7.598 | 1.00 | 18.71 | B |
| ATOM | 3429 | CD1 | LEU | B | 852 | 12.577 | −17.352 | −7.373 | 1.00 | 20.12 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 3430 | CD2 | LEU | B | 852 | 10.747 | −16.017 | −6.331 | 1.00 | 19.80 | B |
| ATOM | 3431 | C | LEU | B | 852 | 10.910 | −17.468 | −10.520 | 1.00 | 22.67 | B |
| ATOM | 3432 | O | LEU | B | 852 | 11.369 | −18.602 | −10.354 | 1.00 | 20.55 | B |
| ATOM | 3433 | N | ILE | B | 853 | 9.699 | −17.248 | −11.023 | 1.00 | 22.76 | B |
| ATOM | 3434 | CA | ILE | B | 853 | 8.852 | −18.360 | −11.429 | 1.00 | 23.15 | B |
| ATOM | 3435 | CB | ILE | B | 853 | 7.472 | −17.855 | −11.899 | 1.00 | 23.96 | B |
| ATOM | 3436 | CG2 | ILE | B | 853 | 6.652 | −19.005 | −12.471 | 1.00 | 22.33 | B |
| ATOM | 3437 | CG1 | ILE | B | 853 | 6.741 | −17.212 | −10.714 | 1.00 | 22.16 | B |
| ATOM | 3438 | CD1 | ILE | B | 853 | 5.362 | −16.673 | −11.052 | 1.00 | 24.56 | B |
| ATOM | 3439 | C | ILE | B | 853 | 9.559 | −19.127 | −12.542 | 1.00 | 22.87 | B |
| ATOM | 3440 | O | ILE | B | 853 | 9.636 | −20.357 | −12.505 | 1.00 | 22.24 | B |
| ATOM | 3441 | N | LYS | B | 854 | 10.097 | −18.401 | −13.519 | 1.00 | 23.12 | B |
| ATOM | 3442 | CA | LYS | B | 854 | 10.828 | −19.033 | −14.612 | 1.00 | 23.82 | B |
| ATOM | 3443 | CB | LYS | B | 854 | 11.408 | −17.987 | −15.567 | 1.00 | 24.73 | B |
| ATOM | 3444 | CG | LYS | B | 854 | 10.411 | −17.073 | −16.253 | 1.00 | 27.55 | B |
| ATOM | 3445 | CD | LYS | B | 854 | 11.172 | −16.123 | −17.173 | 1.00 | 29.14 | B |
| ATOM | 3446 | CE | LYS | B | 854 | 10.282 | −15.067 | −17.796 | 1.00 | 30.68 | B |
| ATOM | 3447 | NZ | LYS | B | 854 | 11.116 | −14.097 | −18.571 | 1.00 | 30.20 | B |
| ATOM | 3448 | C | LYS | B | 854 | 11.990 | −19.839 | −14.025 | 1.00 | 24.39 | B |
| ATOM | 3449 | O | LYS | B | 854 | 12.232 | −20.987 | −14.417 | 1.00 | 23.69 | B |
| ATOM | 3450 | N | ALA | B | 855 | 12.712 | −19.223 | −13.089 | 1.00 | 22.20 | B |
| ATOM | 3451 | CA | ALA | B | 855 | 13.851 | −19.872 | −12.446 | 1.00 | 21.90 | B |
| ATOM | 3452 | CB | ALA | B | 855 | 14.454 | −18.949 | −11.371 | 1.00 | 20.12 | B |
| ATOM | 3453 | C | ALA | B | 855 | 13.430 | −21.197 | −11.825 | 1.00 | 22.62 | B |
| ATOM | 3454 | O | ALA | B | 855 | 14.129 | −22.199 | −11.954 | 1.00 | 22.66 | B |
| ATOM | 3455 | N | ILE | B | 856 | 12.284 | −21.196 | −11.152 | 1.00 | 24.17 | B |
| ATOM | 3456 | CA | ILE | B | 856 | 11.765 | −22.401 | −10.511 | 1.00 | 26.32 | B |
| ATOM | 3457 | CB | ILE | B | 856 | 10.527 | −22.063 | −9.646 | 1.00 | 25.90 | B |
| ATOM | 3458 | CG2 | ILE | B | 856 | 9.780 | −23.332 | −9.263 | 1.00 | 26.41 | B |
| ATOM | 3459 | CG1 | ILE | B | 856 | 10.962 | −21.282 | −8.402 | 1.00 | 25.34 | B |
| ATOM | 3460 | CD1 | ILE | B | 856 | 9.812 | −20.728 | −7.575 | 1.00 | 23.16 | B |
| ATOM | 3461 | C | ILE | B | 856 | 11.385 | −23.455 | −11.558 | 1.00 | 28.99 | B |
| ATOM | 3462 | O | ILE | B | 856 | 11.572 | −24.655 | −11.342 | 1.00 | 29.74 | B |
| ATOM | 3463 | N | GLY | B | 857 | 10.864 | −22.989 | −12.692 | 1.00 | 29.48 | B |
| ATOM | 3464 | CA | GLY | B | 857 | 10.446 | −23.883 | −13.761 | 1.00 | 30.13 | B |
| ATOM | 3465 | C | GLY | B | 857 | 11.580 | −24.580 | −14.482 | 1.00 | 31.17 | B |
| ATOM | 3466 | O | GLY | B | 857 | 11.366 | −25.568 | −15.188 | 1.00 | 30.36 | B |
| ATOM | 3467 | N | LEU | B | 858 | 12.792 | −24.071 | −14.312 | 1.00 | 30.74 | B |
| ATOM | 3468 | CA | LEU | B | 858 | 13.944 | −24.676 | −14.954 | 1.00 | 33.55 | B |
| ATOM | 3469 | CB | LEU | B | 858 | 15.199 | −23.831 | −14.713 | 1.00 | 30.85 | B |
| ATOM | 3470 | CG | LEU | B | 858 | 15.263 | −22.461 | −15.392 | 1.00 | 29.83 | B |
| ATOM | 3471 | CD1 | LEU | B | 858 | 16.541 | −21.749 | −14.968 | 1.00 | 29.15 | B |
| ATOM | 3472 | CD2 | LEU | B | 858 | 15.222 | −22.628 | −16.914 | 1.00 | 29.41 | B |
| ATOM | 3473 | C | LEU | B | 858 | 14.163 | −26.090 | −14.424 | 1.00 | 36.01 | B |
| ATOM | 3474 | O | LEU | B | 858 | 14.733 | −26.933 | −15.114 | 1.00 | 34.89 | B |
| ATOM | 3475 | N | ARG | B | 859 | 13.697 | −26.344 | −13.204 | 1.00 | 38.73 | B |
| ATOM | 3476 | CA | ARG | B | 859 | 13.862 | −27.652 | −12.585 | 1.00 | 43.94 | B |
| ATOM | 3477 | CB | ARG | B | 859 | 14.929 | −27.562 | −11.490 | 1.00 | 45.40 | B |
| ATOM | 3478 | CG | ARG | B | 859 | 16.243 | −27.004 | −12.026 | 1.00 | 47.91 | B |
| ATOM | 3479 | CD | ARG | B | 859 | 17.346 | −26.903 | −10.988 | 1.00 | 50.31 | B |
| ATOM | 3480 | NE | ARG | B | 859 | 18.531 | −26.277 | −11.574 | 1.00 | 53.12 | B |
| ATOM | 3481 | CZ | ARG | B | 859 | 19.713 | −26.166 | −10.973 | 1.00 | 54.97 | B |
| ATOM | 3482 | NH1 | ARG | B | 859 | 19.895 | −26.641 | −9.746 | 1.00 | 55.64 | B |
| ATOM | 3483 | NH2 | ARG | B | 859 | 20.718 | −25.573 | −11.605 | 1.00 | 54.67 | B |
| ATOM | 3484 | C | ARG | B | 859 | 12.555 | −28.221 | −12.032 | 1.00 | 46.55 | B |
| ATOM | 3485 | O | ARG | B | 859 | 12.298 | −29.420 | −12.159 | 1.00 | 47.71 | B |
| ATOM | 3486 | N | GLN | B | 860 | 11.730 | −27.369 | −11.427 | 1.00 | 49.36 | B |
| ATOM | 3487 | CA | GLN | B | 860 | 10.444 | −27.812 | −10.884 | 1.00 | 51.49 | B |
| ATOM | 3488 | CB | GLN | B | 860 | 9.925 | −26.819 | −9.842 | 1.00 | 53.00 | B |
| ATOM | 3489 | CG | GLN | B | 860 | 10.879 | −26.585 | −8.679 | 1.00 | 56.02 | B |
| ATOM | 3490 | CD | GLN | B | 860 | 11.123 | −27.832 | −7.849 | 1.00 | 57.66 | B |
| ATOM | 3491 | OE1 | GLN | B | 860 | 11.981 | −27.843 | −6.963 | 1.00 | 59.53 | B |
| ATOM | 3492 | NE2 | GLN | B | 860 | 10.367 | −28.888 | −8.125 | 1.00 | 58.86 | B |
| ATOM | 3493 | C | GLN | B | 860 | 9.453 | −27.913 | −12.036 | 1.00 | 52.06 | B |
| ATOM | 3494 | O | GLN | B | 860 | 8.769 | −26.945 | −12.370 | 1.00 | 52.54 | B |
| ATOM | 3495 | N | LYS | B | 861 | 9.384 | −29.097 | −12.633 | 1.00 | 52.72 | B |
| ATOM | 3496 | CA | LYS | B | 861 | 8.514 | −29.353 | −13.775 | 1.00 | 53.52 | B |
| ATOM | 3497 | CB | LYS | B | 861 | 8.954 | −30.648 | −14.463 | 1.00 | 54.01 | B |
| ATOM | 3498 | CG | LYS | B | 861 | 10.407 | −30.634 | −14.922 | 1.00 | 54.24 | B |
| ATOM | 3499 | CD | LYS | B | 861 | 10.654 | −29.511 | −15.920 | 1.00 | 55.39 | B |
| ATOM | 3500 | CE | LYS | B | 861 | 12.105 | −29.470 | −16.371 | 1.00 | 55.75 | B |
| ATOM | 3501 | NZ | LYS | B | 861 | 12.329 | −28.410 | −17.394 | 1.00 | 54.73 | B |
| ATOM | 3502 | C | LYS | B | 861 | 7.017 | −29.415 | −13.470 | 1.00 | 53.18 | B |
| ATOM | 3503 | O | LYS | B | 861 | 6.199 | −28.967 | −14.272 | 1.00 | 54.01 | B |
| ATOM | 3504 | N | GLY | B | 862 | 6.657 | −29.969 | −12.318 | 1.00 | 53.04 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 3505 | CA | GLY | B | 862 | 5.250 | −30.072 | −11.968 | 1.00 | 52.10 | B |
| ATOM | 3506 | C | GLY | B | 862 | 4.610 | −28.753 | −11.577 | 1.00 | 51.07 | B |
| ATOM | 3507 | O | GLY | B | 862 | 5.248 | −27.909 | −10.952 | 1.00 | 50.08 | B |
| ATOM | 3508 | N | VAL | B | 863 | 3.345 | −28.574 | −11.946 | 1.00 | 50.57 | B |
| ATOM | 3509 | CA | VAL | B | 863 | 2.620 | −27.352 | −11.615 | 1.00 | 50.24 | B |
| ATOM | 3510 | CB | VAL | B | 863 | 1.237 | −27.312 | −12.305 | 1.00 | 50.56 | B |
| ATOM | 3511 | CG1 | VAL | B | 863 | 1.411 | −27.323 | −13.814 | 1.00 | 50.62 | B |
| ATOM | 3512 | CG2 | VAL | B | 863 | 0.392 | −28.498 | −11.859 | 1.00 | 51.12 | B |
| ATOM | 3513 | C | VAL | B | 863 | 2.419 | −27.254 | −10.104 | 1.00 | 49.58 | B |
| ATOM | 3514 | O | VAL | B | 863 | 2.575 | −26.184 | −9.512 | 1.00 | 48.75 | B |
| ATOM | 3515 | N | VAL | B | 864 | 2.073 | −28.379 | −9.486 | 1.00 | 48.74 | B |
| ATOM | 3516 | CA | VAL | B | 864 | 1.858 | −28.430 | −8.044 | 1.00 | 47.66 | B |
| ATOM | 3517 | CB | VAL | B | 864 | 1.255 | −29.784 | −7.619 | 1.00 | 47.83 | B |
| ATOM | 3518 | CG1 | VAL | B | 864 | 1.003 | −29.793 | −6.120 | 1.00 | 49.12 | B |
| ATOM | 3519 | CG2 | VAL | B | 864 | −0.036 | −30.036 | −8.376 | 1.00 | 48.15 | B |
| ATOM | 3520 | C | VAL | B | 864 | 3.201 | −28.248 | −7.346 | 1.00 | 46.26 | B |
| ATOM | 3521 | O | VAL | B | 864 | 3.312 | −27.514 | −6.363 | 1.00 | 45.73 | B |
| ATOM | 3522 | N | SER | B | 865 | 4.216 | −28.928 | −7.869 | 1.00 | 44.35 | B |
| ATOM | 3523 | CA | SER | B | 865 | 5.566 | −28.850 | −7.331 | 1.00 | 42.44 | B |
| ATOM | 3524 | CB | SER | B | 865 | 6.481 | −29.811 | −8.097 | 1.00 | 43.32 | B |
| ATOM | 3525 | OG | SER | B | 865 | 7.814 | −29.753 | −7.619 | 1.00 | 46.42 | B |
| ATOM | 3526 | C | SER | B | 865 | 6.089 | −27.414 | −7.455 | 1.00 | 40.83 | B |
| ATOM | 3527 | O | SER | B | 865 | 6.677 | −26.873 | −6.519 | 1.00 | 38.94 | B |
| ATOM | 3528 | N | SER | B | 866 | 5.866 | −26.807 | −8.617 | 1.00 | 39.03 | B |
| ATOM | 3529 | CA | SER | B | 866 | 6.302 | −25.440 | −8.875 | 1.00 | 38.13 | B |
| ATOM | 3530 | CB | SER | B | 866 | 5.976 | −25.041 | −10.315 | 1.00 | 39.12 | B |
| ATOM | 3531 | OG | SER | B | 866 | 6.795 | −25.745 | −11.230 | 1.00 | 42.05 | B |
| ATOM | 3532 | C | SER | B | 866 | 5.655 | −24.447 | −7.922 | 1.00 | 37.24 | B |
| ATOM | 3533 | O | SER | B | 866 | 6.320 | −23.545 | −7.408 | 1.00 | 36.71 | B |
| ATOM | 3534 | N | SER | B | 867 | 4.357 | −24.610 | −7.690 | 1.00 | 35.62 | B |
| ATOM | 3535 | CA | SER | B | 867 | 3.635 | −23.716 | −6.794 | 1.00 | 35.02 | B |
| ATOM | 3536 | CB | SER | B | 867 | 2.132 | −23.979 | −6.875 | 1.00 | 35.17 | B |
| ATOM | 3537 | OG | SER | B | 867 | 1.654 | −23.704 | −8.180 | 1.00 | 38.33 | B |
| ATOM | 3538 | C | SER | B | 867 | 4.116 | −23.882 | −5.361 | 1.00 | 34.04 | B |
| ATOM | 3539 | O | SER | B | 867 | 4.285 | −22.900 | −4.640 | 1.00 | 33.31 | B |
| ATOM | 3540 | N | GLN | B | 868 | 4.335 | −25.124 | −4.945 | 1.00 | 31.60 | B |
| ATOM | 3541 | CA | GLN | B | 868 | 4.810 | −25.373 | −3.592 | 1.00 | 32.33 | B |
| ATOM | 3542 | CB | GLN | B | 868 | 4.856 | −26.871 | −3.308 | 1.00 | 34.57 | B |
| ATOM | 3543 | CG | GLN | B | 868 | 3.502 | −27.494 | −3.071 | 1.00 | 39.81 | B |
| ATOM | 3544 | CD | GLN | B | 868 | 3.579 | −28.998 | −2.949 | 1.00 | 42.53 | B |
| ATOM | 3545 | OE1 | GLN | B | 868 | 4.411 | −29.530 | −2.213 | 1.00 | 45.19 | B |
| ATOM | 3546 | NE2 | GLN | B | 868 | 2.709 | −29.696 | −3.670 | 1.00 | 43.84 | B |
| ATOM | 3547 | C | GLN | B | 868 | 6.202 | −24.779 | −3.417 | 1.00 | 29.48 | B |
| ATOM | 3548 | O | GLN | B | 868 | 6.537 | −24.260 | −2.355 | 1.00 | 28.85 | B |
| ATOM | 3549 | N | ARG | B | 869 | 7.003 | −24.868 | −4.470 | 1.00 | 27.65 | B |
| ATOM | 3550 | CA | ARG | B | 869 | 8.364 | −24.345 | −4.463 | 1.00 | 28.67 | B |
| ATOM | 3551 | CB | ARG | B | 869 | 9.067 | −24.720 | −5.766 | 1.00 | 27.99 | B |
| ATOM | 3552 | CG | ARG | B | 869 | 10.514 | −24.264 | −5.852 | 1.00 | 29.69 | B |
| ATOM | 3553 | CD | ARG | B | 869 | 11.378 | −25.038 | −4.883 | 1.00 | 28.24 | B |
| ATOM | 3554 | NE | ARG | B | 869 | 12.798 | −24.771 | −5.076 | 1.00 | 30.16 | B |
| ATOM | 3555 | CZ | ARG | B | 869 | 13.765 | −25.430 | −4.446 | 1.00 | 28.86 | B |
| ATOM | 3556 | NH1 | ARG | B | 869 | 13.452 | −26.393 | −3.588 | 1.00 | 26.30 | B |
| ATOM | 3557 | NH2 | ARG | B | 869 | 15.040 | −25.130 | −4.672 | 1.00 | 24.34 | B |
| ATOM | 3558 | C | ARG | B | 869 | 8.327 | −22.825 | −4.322 | 1.00 | 27.76 | B |
| ATOM | 3559 | O | ARG | B | 869 | 9.083 | −22.240 | −3.548 | 1.00 | 29.39 | B |
| ATOM | 3560 | N | PHE | B | 870 | 7.437 | −22.195 | −5.080 | 1.00 | 26.99 | B |
| ATOM | 3561 | CA | PHE | B | 870 | 7.286 | −20.749 | −5.045 | 1.00 | 26.48 | B |
| ATOM | 3562 | CB | PHE | B | 870 | 6.215 | −20.309 | −6.041 | 1.00 | 26.94 | B |
| ATOM | 3563 | CG | PHE | B | 870 | 6.003 | −18.824 | −6.085 | 1.00 | 26.83 | B |
| ATOM | 3564 | CD1 | PHE | B | 870 | 6.902 | −17.999 | −6.755 | 1.00 | 28.19 | B |
| ATOM | 3565 | CD2 | PHE | B | 870 | 4.905 | −18.246 | −5.450 | 1.00 | 27.94 | B |
| ATOM | 3566 | CE1 | PHE | B | 870 | 6.711 | −16.616 | −6.796 | 1.00 | 27.85 | B |
| ATOM | 3567 | CE2 | PHE | B | 870 | 4.704 | −16.862 | −5.483 | 1.00 | 28.37 | B |
| ATOM | 3568 | CZ | PHE | B | 870 | 5.612 | −16.048 | −6.161 | 1.00 | 27.70 | B |
| ATOM | 3569 | C | PHE | B | 870 | 6.889 | −20.328 | −3.636 | 1.00 | 26.34 | B |
| ATOM | 3570 | O | PHE | B | 870 | 7.401 | −19.344 | −3.101 | 1.00 | 25.56 | B |
| ATOM | 3571 | N | TYR | B | 871 | 5.974 | −21.078 | −3.032 | 1.00 | 26.21 | B |
| ATOM | 3572 | CA | TYR | B | 871 | 5.542 | −20.763 | −1.682 | 1.00 | 27.42 | B |
| ATOM | 3573 | CB | TYR | B | 871 | 4.494 | −21.767 | −1.193 | 1.00 | 30.77 | B |
| ATOM | 3574 | CG | TYR | B | 871 | 4.073 | −21.517 | 0.234 | 1.00 | 33.19 | B |
| ATOM | 3575 | CD1 | TYR | B | 871 | 3.055 | −20.613 | 0.532 | 1.00 | 35.86 | B |
| ATOM | 3576 | CE1 | TYR | B | 871 | 2.717 | −20.318 | 1.853 | 1.00 | 36.85 | B |
| ATOM | 3577 | CD2 | TYR | B | 871 | 4.743 | −22.126 | 1.293 | 1.00 | 34.60 | B |
| ATOM | 3578 | CE2 | TYR | B | 871 | 4.416 | −21.837 | 2.615 | 1.00 | 36.18 | B |
| ATOM | 3579 | CZ | TYR | B | 871 | 3.405 | −20.933 | 2.888 | 1.00 | 37.44 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 3580 | OH | TYR | B | 871 | 3.092 | −20.633 | 4.196 | 1.00 | 39.18 | B |
| ATOM | 3581 | C | TYR | B | 871 | 6.747 | −20.818 | −0.751 | 1.00 | 26.36 | B |
| ATOM | 3582 | O | TYR | B | 871 | 6.972 | −19.913 | 0.049 | 1.00 | 25.94 | B |
| ATOM | 3583 | N | GLN | B | 872 | 7.518 | −21.895 | −0.865 | 1.00 | 25.60 | B |
| ATOM | 3584 | CA | GLN | B | 872 | 8.691 | −22.091 | −0.026 | 1.00 | 25.57 | B |
| ATOM | 3585 | CB | GLN | B | 872 | 9.364 | −23.421 | −0.359 | 1.00 | 27.35 | B |
| ATOM | 3586 | CG | GLN | B | 872 | 8.531 | −24.643 | −0.039 | 1.00 | 30.68 | B |
| ATOM | 3587 | CD | GLN | B | 872 | 9.221 | −25.925 | −0.453 | 1.00 | 31.86 | B |
| ATOM | 3588 | OE1 | GLN | B | 872 | 9.552 | −26.112 | −1.624 | 1.00 | 34.33 | B |
| ATOM | 3589 | NE2 | GLN | B | 872 | 9.444 | −26.815 | 0.505 | 1.00 | 34.20 | B |
| ATOM | 3590 | C | GLN | B | 872 | 9.713 | −20.978 | −0.164 | 1.00 | 23.41 | B |
| ATOM | 3591 | O | GLN | B | 872 | 10.177 | −20.430 | 0.830 | 1.00 | 21.76 | B |
| ATOM | 3592 | N | LEU | B | 873 | 10.066 | −20.644 | −1.398 | 1.00 | 22.08 | B |
| ATOM | 3593 | CA | LEU | B | 873 | 11.061 | −19.605 | −1.608 | 1.00 | 21.86 | B |
| ATOM | 3594 | CB | LEU | B | 873 | 11.508 | −19.595 | −3.074 | 1.00 | 18.40 | B |
| ATOM | 3595 | CG | LEU | B | 873 | 12.160 | −20.916 | −3.522 | 1.00 | 20.29 | B |
| ATOM | 3596 | CD1 | LEU | B | 873 | 12.594 | −20.822 | −4.972 | 1.00 | 17.60 | B |
| ATOM | 3597 | CD2 | LEU | B | 873 | 13.369 | −21.236 | −2.632 | 1.00 | 19.06 | B |
| ATOM | 3598 | C | LEU | B | 873 | 10.576 | −18.228 | −1.162 | 1.00 | 21.93 | B |
| ATOM | 3599 | O | LEU | B | 873 | 11.348 | −17.461 | −0.584 | 1.00 | 22.49 | B |
| ATOM | 3600 | N | THR | B | 874 | 9.304 | −17.917 | −1.404 | 1.00 | 22.76 | B |
| ATOM | 3601 | CA | THR | B | 874 | 8.767 | −16.621 | −0.999 | 1.00 | 23.91 | B |
| ATOM | 3602 | CB | THR | B | 874 | 7.423 | −16.299 | −1.702 | 1.00 | 24.32 | B |
| ATOM | 3603 | OG1 | THR | B | 874 | 6.458 | −17.318 | −1.412 | 1.00 | 25.03 | B |
| ATOM | 3604 | CG2 | THR | B | 874 | 7.626 | −16.203 | −3.209 | 1.00 | 26.12 | B |
| ATOM | 3605 | C | THR | B | 874 | 8.576 | −16.560 | 0.516 | 1.00 | 25.18 | B |
| ATOM | 3606 | O | THR | B | 874 | 8.635 | −15.483 | 1.113 | 1.00 | 26.18 | B |
| ATOM | 3607 | N | LYS | B | 875 | 8.359 | −17.713 | 1.142 | 1.00 | 24.45 | B |
| ATOM | 3608 | CA | LYS | B | 875 | 8.194 | −17.753 | 2.592 | 1.00 | 23.83 | B |
| ATOM | 3609 | CB | LYS | B | 875 | 7.659 | −19.116 | 3.046 | 1.00 | 25.61 | B |
| ATOM | 3610 | CG | LYS | B | 875 | 7.292 | −19.162 | 4.522 | 1.00 | 28.99 | B |
| ATOM | 3611 | CD | LYS | B | 875 | 6.156 | −18.190 | 4.830 | 1.00 | 33.42 | B |
| ATOM | 3612 | CE | LYS | B | 875 | 5.855 | −18.135 | 6.321 | 1.00 | 35.92 | B |
| ATOM | 3613 | NZ | LYS | B | 875 | 4.702 | −17.238 | 6.602 | 1.00 | 37.34 | B |
| ATOM | 3614 | C | LYS | B | 875 | 9.558 | −17.506 | 3.230 | 1.00 | 23.31 | B |
| ATOM | 3615 | O | LYS | B | 875 | 9.664 | −16.887 | 4.287 | 1.00 | 21.67 | B |
| ATOM | 3616 | N | LEU | B | 876 | 10.604 | −17.999 | 2.580 | 1.00 | 21.64 | B |
| ATOM | 3617 | CA | LEU | B | 876 | 11.957 | −17.808 | 3.088 | 1.00 | 22.58 | B |
| ATOM | 3618 | CB | LEU | B | 876 | 12.966 | −18.543 | 2.198 | 1.00 | 21.81 | B |
| ATOM | 3619 | CG | LEU | B | 876 | 14.434 | −18.534 | 2.645 | 1.00 | 22.37 | B |
| ATOM | 3620 | CD1 | LEU | B | 876 | 15.194 | −19.641 | 1.927 | 1.00 | 23.69 | B |
| ATOM | 3621 | CD2 | LEU | B | 876 | 15.059 | −17.179 | 2.358 | 1.00 | 22.29 | B |
| ATOM | 3622 | C | LEU | B | 876 | 12.248 | −16.308 | 3.100 | 1.00 | 21.74 | B |
| ATOM | 3623 | O | LEU | B | 876 | 12.800 | −15.782 | 4.061 | 1.00 | 21.27 | B |
| ATOM | 3624 | N | LEU | B | 877 | 11.863 | −15.625 | 2.028 | 1.00 | 21.67 | B |
| ATOM | 3625 | CA | LEU | B | 877 | 12.072 | −14.183 | 1.935 | 1.00 | 21.91 | B |
| ATOM | 3626 | CB | LEU | B | 877 | 11.643 | −13.669 | 0.556 | 1.00 | 20.68 | B |
| ATOM | 3627 | CG | LEU | B | 877 | 12.504 | −14.111 | −0.631 | 1.00 | 22.24 | B |
| ATOM | 3628 | CD1 | LEU | B | 877 | 11.906 | −13.568 | −1.916 | 1.00 | 22.05 | B |
| ATOM | 3629 | CD2 | LEU | B | 877 | 13.941 | −13.609 | −0.466 | 1.00 | 20.37 | B |
| ATOM | 3630 | C | LEU | B | 877 | 11.287 | −13.476 | 3.040 | 1.00 | 20.65 | B |
| ATOM | 3631 | O | LEU | B | 877 | 11.817 | −12.593 | 3.709 | 1.00 | 19.22 | B |
| ATOM | 3632 | N | ASP | B | 878 | 10.028 | −13.869 | 3.233 | 1.00 | 19.37 | B |
| ATOM | 3633 | CA | ASP | B | 878 | 9.202 | −13.283 | 4.289 | 1.00 | 20.36 | B |
| ATOM | 3634 | CB | ASP | B | 878 | 7.866 | −14.022 | 4.415 | 1.00 | 21.34 | B |
| ATOM | 3635 | CG | ASP | B | 878 | 6.822 | −13.532 | 3.438 | 1.00 | 23.18 | B |
| ATOM | 3636 | OD1 | ASP | B | 878 | 7.165 | −12.760 | 2.516 | 1.00 | 24.47 | B |
| ATOM | 3637 | OD2 | ASP | B | 878 | 5.649 | −13.933 | 3.597 | 1.00 | 24.18 | B |
| ATOM | 3638 | C | ASP | B | 878 | 9.918 | −13.391 | 5.631 | 1.00 | 20.20 | B |
| ATOM | 3639 | O | ASP | B | 878 | 10.034 | −12.413 | 6.371 | 1.00 | 18.45 | B |
| ATOM | 3640 | N | ASN | B | 879 | 10.397 | −14.593 | 5.940 | 1.00 | 19.35 | B |
| ATOM | 3641 | CA | ASN | B | 879 | 11.080 | −14.836 | 7.203 | 1.00 | 21.08 | B |
| ATOM | 3642 | CB | ASN | B | 879 | 11.361 | −16.332 | 7.380 | 1.00 | 23.62 | B |
| ATOM | 3643 | CG | ASN | B | 879 | 10.099 | −17.166 | 7.343 | 1.00 | 27.77 | B |
| ATOM | 3644 | OD1 | ASN | B | 879 | 9.044 | −16.740 | 7.819 | 1.00 | 29.01 | B |
| ATOM | 3645 | ND2 | ASN | B | 879 | 10.200 | −18.368 | 6.787 | 1.00 | 29.13 | B |
| ATOM | 3646 | C | ASN | B | 879 | 12.379 | −14.062 | 7.377 | 1.00 | 21.21 | B |
| ATOM | 3647 | O | ASN | B | 879 | 12.904 | −13.972 | 8.487 | 1.00 | 21.00 | B |
| ATOM | 3648 | N | LEU | B | 880 | 12.910 | −13.501 | 6.297 | 1.00 | 20.95 | B |
| ATOM | 3649 | CA | LEU | B | 880 | 14.152 | −12.752 | 6.424 | 1.00 | 21.38 | B |
| ATOM | 3650 | CB | LEU | B | 880 | 14.770 | −12.486 | 5.052 | 1.00 | 20.58 | B |
| ATOM | 3651 | CG | LEU | B | 880 | 15.371 | −13.739 | 4.406 | 1.00 | 24.77 | B |
| ATOM | 3652 | CD1 | LEU | B | 880 | 16.034 | −13.370 | 3.100 | 1.00 | 24.40 | B |
| ATOM | 3653 | CD2 | LEU | B | 880 | 16.386 | −14.364 | 5.346 | 1.00 | 24.56 | B |
| ATOM | 3654 | C | LEU | B | 880 | 13.981 | −11.445 | 7.188 | 1.00 | 19.74 | B |

TABLE 2-continued

Structure coordinates (Table discloses SEQ ID NO: 6 twice)

| | # | Name | Res. | Chain | Res # | X | Y | Z | occ | B | SegID |
|---|---|---|---|---|---|---|---|---|---|---|---|
| ATOM | 3655 | O | LEU | B | 880 | 14.925 | −10.972 | 7.809 | 1.00 | 20.66 | B |
| ATOM | 3656 | N | HIS | B | 881 | 12.786 | −10.861 | 7.154 | 1.00 | 19.70 | B |
| ATOM | 3657 | CA | HIS | B | 881 | 12.562 | −9.613 | 7.876 | 1.00 | 19.35 | B |
| ATOM | 3658 | CB | HIS | B | 881 | 11.121 | −9.123 | 7.680 | 1.00 | 20.71 | B |
| ATOM | 3659 | CG | HIS | B | 881 | 10.856 | −8.537 | 6.323 | 1.00 | 20.01 | B |
| ATOM | 3660 | CD2 | HIS | B | 881 | 11.379 | −7.452 | 5.704 | 1.00 | 17.82 | B |
| ATOM | 3661 | ND1 | HIS | B | 881 | 9.942 | −9.076 | 5.443 | 1.00 | 21.77 | B |
| ATOM | 3662 | CE1 | HIS | B | 881 | 9.909 | −8.345 | 4.341 | 1.00 | 18.83 | B |
| ATOM | 3663 | NE2 | HIS | B | 881 | 10.772 | −7.353 | 4.475 | 1.00 | 21.49 | B |
| ATOM | 3664 | C | HIS | B | 881 | 12.855 | −9.806 | 9.368 | 1.00 | 20.98 | B |
| ATOM | 3665 | O | HIS | B | 881 | 13.581 | −9.018 | 9.974 | 1.00 | 18.74 | B |
| ATOM | 3666 | N | ASP | B | 882 | 12.299 | −10.858 | 9.958 | 1.00 | 22.20 | B |
| ATOM | 3667 | CA | ASP | B | 882 | 12.525 | −11.130 | 11.377 | 1.00 | 22.92 | B |
| ATOM | 3668 | CB | ASP | B | 882 | 11.698 | −12.329 | 11.842 | 1.00 | 27.90 | B |
| ATOM | 3669 | CG | ASP | B | 882 | 10.216 | −12.047 | 11.853 | 1.00 | 33.60 | B |
| ATOM | 3670 | OD1 | ASP | B | 882 | 9.816 | −10.997 | 12.399 | 1.00 | 34.59 | B |
| ATOM | 3671 | OD2 | ASP | B | 882 | 9.449 | −12.884 | 11.327 | 1.00 | 39.23 | B |
| ATOM | 3672 | C | ASP | B | 882 | 13.987 | −11.418 | 11.666 | 1.00 | 22.16 | B |
| ATOM | 3673 | O | ASP | B | 882 | 14.532 | −10.963 | 12.670 | 1.00 | 21.45 | B |
| ATOM | 3674 | N | LEU | B | 883 | 14.617 | −12.189 | 10.785 | 1.00 | 20.81 | B |
| ATOM | 3675 | CA | LEU | B | 883 | 16.018 | −12.554 | 10.953 | 1.00 | 18.58 | B |
| ATOM | 3676 | CB | LEU | B | 883 | 16.425 | −13.551 | 9.853 | 1.00 | 19.75 | B |
| ATOM | 3677 | CG | LEU | B | 883 | 17.801 | −14.225 | 9.926 | 1.00 | 22.35 | B |
| ATOM | 3678 | CD1 | LEU | B | 883 | 17.821 | −15.438 | 8.994 | 1.00 | 22.84 | B |
| ATOM | 3679 | CD2 | LEU | B | 883 | 18.896 | −13.235 | 9.550 | 1.00 | 22.64 | B |
| ATOM | 3680 | C | LEU | B | 883 | 16.918 | −11.322 | 10.912 | 1.00 | 18.56 | B |
| ATOM | 3681 | O | LEU | B | 883 | 17.753 | −11.114 | 11.795 | 1.00 | 17.89 | B |
| ATOM | 3682 | N | VAL | B | 884 | 16.733 | −10.506 | 9.882 | 1.00 | 17.78 | B |
| ATOM | 3683 | CA | VAL | B | 884 | 17.523 | −9.295 | 9.702 | 1.00 | 18.13 | B |
| ATOM | 3684 | CB | VAL | B | 884 | 17.191 | −8.640 | 8.354 | 1.00 | 19.53 | B |
| ATOM | 3685 | CG1 | VAL | B | 884 | 17.891 | −7.298 | 8.230 | 1.00 | 21.68 | B |
| ATOM | 3686 | CG2 | VAL | B | 884 | 17.618 | −9.576 | 7.227 | 1.00 | 18.29 | B |
| ATOM | 3687 | C | VAL | B | 884 | 17.329 | −8.287 | 10.826 | 1.00 | 18.10 | B |
| ATOM | 3688 | O | VAL | B | 884 | 18.237 | −7.520 | 11.145 | 1.00 | 18.80 | B |
| ATOM | 3689 | N | LYS | B | 885 | 16.151 | −8.290 | 11.436 | 1.00 | 18.09 | B |
| ATOM | 3690 | CA | LYS | B | 885 | 15.889 | −7.370 | 12.530 | 1.00 | 19.60 | B |
| ATOM | 3691 | CB | LYS | B | 885 | 14.469 | −7.565 | 13.054 | 1.00 | 23.11 | B |
| ATOM | 3692 | CG | LYS | B | 885 | 14.118 | −6.649 | 14.219 | 1.00 | 25.74 | B |
| ATOM | 3693 | CD | LYS | B | 885 | 12.706 | −6.924 | 14.689 | 1.00 | 31.18 | B |
| ATOM | 3694 | CE | LYS | B | 885 | 12.381 | −6.163 | 15.961 | 1.00 | 31.73 | B |
| ATOM | 3695 | NZ | LYS | B | 885 | 11.051 | −6.599 | 16.474 | 1.00 | 38.15 | B |
| ATOM | 3696 | C | LYS | B | 885 | 16.898 | −7.582 | 13.667 | 1.00 | 19.50 | B |
| ATOM | 3697 | O | LYS | B | 885 | 17.378 | −6.618 | 14.265 | 1.00 | 17.26 | B |
| ATOM | 3698 | N | GLN | B | 886 | 17.225 | −8.842 | 13.955 | 1.00 | 19.54 | B |
| ATOM | 3699 | CA | GLN | B | 886 | 18.184 | −9.149 | 15.015 | 1.00 | 19.86 | B |
| ATOM | 3700 | CB | GLN | B | 886 | 18.248 | −10.660 | 15.273 | 1.00 | 25.01 | B |
| ATOM | 3701 | CG | GLN | B | 886 | 16.941 | −11.267 | 15.755 | 1.00 | 31.58 | B |
| ATOM | 3702 | CD | GLN | B | 886 | 16.480 | −10.710 | 17.098 | 1.00 | 36.35 | B |
| ATOM | 3703 | OE1 | GLN | B | 886 | 15.365 | −10.988 | 17.540 | 1.00 | 40.85 | B |
| ATOM | 3704 | NE2 | GLN | B | 886 | 17.337 | −9.930 | 17.754 | 1.00 | 38.26 | B |
| ATOM | 3705 | C | GLN | B | 886 | 19.572 | −8.639 | 14.634 | 1.00 | 18.79 | B |
| ATOM | 3706 | O | GLN | B | 886 | 20.328 | −8.171 | 15.491 | 1.00 | 16.94 | B |
| ATOM | 3707 | N | LEU | B | 887 | 19.910 | −8.736 | 13.352 | 1.00 | 17.04 | B |
| ATOM | 3708 | CA | LEU | B | 887 | 21.205 | −8.259 | 12.881 | 1.00 | 16.54 | B |
| ATOM | 3709 | CB | LEU | B | 887 | 21.445 | −8.685 | 11.427 | 1.00 | 18.52 | B |
| ATOM | 3710 | CG | LEU | B | 887 | 21.471 | −10.184 | 11.104 | 1.00 | 23.04 | B |
| ATOM | 3711 | CD1 | LEU | B | 887 | 21.992 | −10.382 | 9.682 | 1.00 | 22.45 | B |
| ATOM | 3712 | CD2 | LEU | B | 887 | 22.358 | −10.920 | 12.080 | 1.00 | 24.74 | B |
| ATOM | 3713 | C | LEU | B | 887 | 21.245 | −6.733 | 12.988 | 1.00 | 15.32 | B |
| ATOM | 3714 | O | LEU | B | 887 | 22.251 | −6.156 | 13.396 | 1.00 | 16.15 | B |
| ATOM | 3715 | N | HIS | B | 888 | 20.142 | −6.085 | 12.620 | 1.00 | 14.69 | B |
| ATOM | 3716 | CA | HIS | B | 888 | 20.047 | −4.631 | 12.678 | 1.00 | 14.50 | B |
| ATOM | 3717 | CB | HIS | B | 888 | 18.684 | −4.164 | 12.144 | 1.00 | 15.66 | B |
| ATOM | 3718 | CG | HIS | B | 888 | 18.605 | −4.093 | 10.649 | 1.00 | 14.62 | B |
| ATOM | 3719 | CD2 | HIS | B | 888 | 19.574 | −4.009 | 9.706 | 1.00 | 15.13 | B |
| ATOM | 3720 | ND1 | HIS | B | 888 | 17.406 | −4.038 | 9.971 | 1.00 | 15.95 | B |
| ATOM | 3721 | CE1 | HIS | B | 888 | 17.638 | −3.919 | 8.675 | 1.00 | 13.80 | B |
| ATOM | 3722 | NE2 | HIS | B | 888 | 18.945 | −3.900 | 8.487 | 1.00 | 17.55 | B |
| ATOM | 3723 | C | HIS | B | 888 | 20.226 | −4.141 | 14.112 | 1.00 | 15.95 | B |
| ATOM | 3724 | O | HIS | B | 888 | 20.995 | −3.215 | 14.368 | 1.00 | 18.20 | B |
| ATOM | 3725 | N | LEU | B | 889 | 19.518 | −4.762 | 15.049 | 1.00 | 16.97 | B |
| ATOM | 3726 | CA | LEU | B | 889 | 19.617 | −4.360 | 16.449 | 1.00 | 17.38 | B |
| ATOM | 3727 | CB | LEU | B | 889 | 18.647 | −5.176 | 17.306 | 1.00 | 16.53 | B |
| ATOM | 3728 | CG | LEU | B | 889 | 18.667 | −4.889 | 18.814 | 1.00 | 18.28 | B |
| ATOM | 3729 | CD1 | LEU | B | 889 | 18.420 | −3.402 | 19.077 | 1.00 | 18.15 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 3730 | CD2 | LEU | B | 889 | 17.604 | −5.737 | 19.494 | 1.00 | 19.21 | B |
| ATOM | 3731 | C | LEU | B | 889 | 21.042 | −4.528 | 16.971 | 1.00 | 17.72 | B |
| ATOM | 3732 | O | LEU | B | 889 | 21.590 | −3.622 | 17.597 | 1.00 | 17.23 | B |
| ATOM | 3733 | N | TYR | B | 890 | 21.642 | −5.687 | 16.708 | 1.00 | 18.99 | B |
| ATOM | 3734 | CA | TYR | B | 890 | 23.007 | −5.947 | 17.160 | 1.00 | 20.22 | B |
| ATOM | 3735 | CB | TYR | B | 890 | 23.442 | −7.360 | 16.747 | 1.00 | 21.39 | B |
| ATOM | 3736 | CG | TYR | B | 890 | 24.807 | −7.772 | 17.266 | 1.00 | 24.48 | B |
| ATOM | 3737 | CD1 | TYR | B | 890 | 25.974 | −7.278 | 16.688 | 1.00 | 23.63 | B |
| ATOM | 3738 | CE1 | TYR | B | 890 | 27.230 | −7.639 | 17.172 | 1.00 | 26.80 | B |
| ATOM | 3739 | CD2 | TYR | B | 890 | 24.926 | −8.646 | 18.348 | 1.00 | 25.44 | B |
| ATOM | 3740 | CE2 | TYR | B | 890 | 26.180 | −9.016 | 18.842 | 1.00 | 28.35 | B |
| ATOM | 3741 | CZ | TYR | B | 890 | 27.326 | −8.508 | 18.247 | 1.00 | 27.86 | B |
| ATOM | 3742 | OH | TYR | B | 890 | 28.568 | −8.865 | 18.726 | 1.00 | 30.29 | B |
| ATOM | 3743 | C | TYR | B | 890 | 23.951 | −4.905 | 16.563 | 1.00 | 18.18 | B |
| ATOM | 3744 | O | TYR | B | 890 | 24.798 | −4.346 | 17.260 | 1.00 | 18.16 | B |
| ATOM | 3745 | N | CYS | B | 891 | 23.796 | −4.640 | 15.270 | 1.00 | 17.50 | B |
| ATOM | 3746 | CA | CYS | B | 891 | 24.646 | −3.667 | 14.596 | 1.00 | 16.55 | B |
| ATOM | 3747 | CB | CYS | B | 891 | 24.309 | −3.612 | 13.101 | 1.00 | 16.50 | B |
| ATOM | 3748 | SG | CYS | B | 891 | 25.362 | −2.476 | 12.150 | 1.00 | 18.64 | B |
| ATOM | 3749 | C | CYS | B | 891 | 24.517 | −2.268 | 15.211 | 1.00 | 16.80 | B |
| ATOM | 3750 | O | CYS | B | 891 | 25.522 | −1.628 | 15.511 | 1.00 | 17.68 | B |
| ATOM | 3751 | N | LEU | B | 892 | 23.291 | −1.794 | 15.402 | 1.00 | 15.23 | B |
| ATOM | 3752 | CA | LEU | B | 892 | 23.097 | −0.466 | 15.978 | 1.00 | 16.77 | B |
| ATOM | 3753 | CB | LEU | B | 892 | 21.610 | −0.100 | 16.003 | 1.00 | 16.01 | B |
| ATOM | 3754 | CG | LEU | B | 892 | 21.265 | 1.332 | 16.428 | 1.00 | 15.16 | B |
| ATOM | 3755 | CD1 | LEU | B | 892 | 22.059 | 2.342 | 15.586 | 1.00 | 15.59 | B |
| ATOM | 3756 | CD2 | LEU | B | 892 | 19.769 | 1.557 | 16.262 | 1.00 | 15.56 | B |
| ATOM | 3757 | C | LEU | B | 892 | 23.693 | −0.343 | 17.384 | 1.00 | 17.79 | B |
| ATOM | 3758 | O | LEU | B | 892 | 24.342 | 0.659 | 17.696 | 1.00 | 19.65 | B |
| ATOM | 3759 | N | ASN | B | 893 | 23.482 | −1.351 | 18.228 | 1.00 | 17.78 | B |
| ATOM | 3760 | CA | ASN | B | 893 | 24.030 | −1.323 | 19.585 | 1.00 | 19.02 | B |
| ATOM | 3761 | CB | ASN | B | 893 | 23.685 | −2.604 | 20.357 | 1.00 | 19.78 | B |
| ATOM | 3762 | CG | ASN | B | 893 | 22.266 | −2.613 | 20.870 | 1.00 | 22.60 | B |
| ATOM | 3763 | OD1 | ASN | B | 893 | 21.705 | −1.563 | 21.187 | 1.00 | 25.14 | B |
| ATOM | 3764 | ND2 | ASN | B | 893 | 21.679 | −3.804 | 20.976 | 1.00 | 23.61 | B |
| ATOM | 3765 | C | ASN | B | 893 | 25.543 | −1.189 | 19.532 | 1.00 | 20.12 | B |
| ATOM | 3766 | O | ASN | B | 893 | 26.137 | −0.380 | 20.242 | 1.00 | 22.59 | B |
| ATOM | 3767 | N | THR | B | 894 | 26.167 | −2.000 | 18.690 | 1.00 | 19.05 | B |
| ATOM | 3768 | CA | THR | B | 894 | 27.612 | −1.974 | 18.547 | 1.00 | 19.44 | B |
| ATOM | 3769 | CB | THR | B | 894 | 28.076 | −3.079 | 17.586 | 1.00 | 19.42 | B |
| ATOM | 3770 | OG1 | THR | B | 894 | 27.549 | −4.338 | 18.030 | 1.00 | 17.10 | B |
| ATOM | 3771 | CG2 | THR | B | 894 | 29.595 | −3.149 | 17.545 | 1.00 | 18.92 | B |
| ATOM | 3772 | C | THR | B | 894 | 28.076 | −0.616 | 18.023 | 1.00 | 21.22 | B |
| ATOM | 3773 | O | THR | B | 894 | 29.073 | −0.071 | 18.491 | 1.00 | 20.90 | B |
| ATOM | 3774 | N | PHE | B | 895 | 27.348 | −0.079 | 17.047 | 1.00 | 20.38 | B |
| ATOM | 3775 | CA | PHE | B | 895 | 27.677 | 1.215 | 16.460 | 1.00 | 22.73 | B |
| ATOM | 3776 | CB | PHE | B | 895 | 26.662 | 1.558 | 15.363 | 1.00 | 22.12 | B |
| ATOM | 3777 | CG | PHE | B | 895 | 26.933 | 2.856 | 14.664 | 1.00 | 21.75 | B |
| ATOM | 3778 | CD1 | PHE | B | 895 | 28.068 | 3.014 | 13.874 | 1.00 | 23.50 | B |
| ATOM | 3779 | CD2 | PHE | B | 895 | 26.043 | 3.917 | 14.779 | 1.00 | 23.49 | B |
| ATOM | 3780 | CE1 | PHE | B | 895 | 28.312 | 4.210 | 13.206 | 1.00 | 23.87 | B |
| ATOM | 3781 | CE2 | PHE | B | 895 | 26.276 | 5.121 | 14.113 | 1.00 | 24.35 | B |
| ATOM | 3782 | CZ | PHE | B | 895 | 27.414 | 5.268 | 13.326 | 1.00 | 23.84 | B |
| ATOM | 3783 | C | PHE | B | 895 | 27.643 | 2.279 | 17.557 | 1.00 | 23.93 | B |
| ATOM | 3784 | O | PHE | B | 895 | 28.533 | 3.121 | 17.653 | 1.00 | 23.95 | B |
| ATOM | 3785 | N | ILE | B | 896 | 26.606 | 2.223 | 18.384 | 1.00 | 26.93 | B |
| ATOM | 3786 | CA | ILE | B | 896 | 26.435 | 3.160 | 19.488 | 1.00 | 31.13 | B |
| ATOM | 3787 | CB | ILE | B | 896 | 25.090 | 2.900 | 20.213 | 1.00 | 31.72 | B |
| ATOM | 3788 | CG2 | ILE | B | 896 | 25.012 | 3.701 | 21.497 | 1.00 | 34.14 | B |
| ATOM | 3789 | CG1 | ILE | B | 896 | 23.927 | 3.230 | 19.277 | 1.00 | 33.07 | B |
| ATOM | 3790 | CD1 | ILE | B | 896 | 24.014 | 4.596 | 18.654 | 1.00 | 30.60 | B |
| ATOM | 3791 | C | ILE | B | 896 | 27.577 | 3.066 | 20.508 | 1.00 | 33.19 | B |
| ATOM | 3792 | O | ILE | B | 896 | 27.986 | 4.073 | 21.085 | 1.00 | 35.25 | B |
| ATOM | 3793 | N | GLN | B | 897 | 28.089 | 1.859 | 20.727 | 1.00 | 34.17 | B |
| ATOM | 3794 | CA | GLN | B | 897 | 29.169 | 1.654 | 21.692 | 1.00 | 35.56 | B |
| ATOM | 3795 | CB | GLN | B | 897 | 28.817 | 0.494 | 22.624 | 1.00 | 35.80 | B |
| ATOM | 3796 | CG | GLN | B | 897 | 27.338 | 0.369 | 22.930 | 1.00 | 36.67 | B |
| ATOM | 3797 | CD | GLN | B | 897 | 27.000 | −0.946 | 23.601 | 1.00 | 38.80 | B |
| ATOM | 3798 | OE1 | GLN | B | 897 | 25.836 | −1.350 | 23.657 | 1.00 | 39.12 | B |
| ATOM | 3799 | NE2 | GLN | B | 897 | 28.019 | −1.624 | 24.121 | 1.00 | 40.79 | B |
| ATOM | 3800 | C | GLN | B | 897 | 30.484 | 1.337 | 20.990 | 1.00 | 36.74 | B |
| ATOM | 3801 | O | GLN | B | 897 | 31.406 | 0.795 | 21.605 | 1.00 | 36.87 | B |
| ATOM | 3802 | N | SER | B | 898 | 30.569 | 1.681 | 19.706 | 1.00 | 37.12 | B |
| ATOM | 3803 | CA | SER | B | 898 | 31.756 | 1.407 | 18.902 | 1.00 | 37.09 | B |
| ATOM | 3804 | CB | SER | B | 898 | 31.655 | 2.110 | 17.544 | 1.00 | 36.71 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 3805 | OG | SER | B | 898 | 31.802 | 3.513 | 17.674 | 1.00 | 35.33 | B |
| ATOM | 3806 | C | SER | B | 898 | 33.061 | 1.812 | 19.575 | 1.00 | 38.11 | B |
| ATOM | 3807 | O | SER | B | 898 | 34.007 | 1.028 | 19.636 | 1.00 | 36.29 | B |
| ATOM | 3808 | N | ARG | B | 899 | 33.116 | 3.039 | 20.074 | 1.00 | 39.88 | B |
| ATOM | 3809 | CA | ARG | B | 899 | 34.325 | 3.521 | 20.724 | 1.00 | 42.35 | B |
| ATOM | 3810 | CB | ARG | B | 899 | 34.180 | 5.000 | 21.069 | 1.00 | 45.76 | B |
| ATOM | 3811 | CG | ARG | B | 899 | 35.338 | 5.530 | 21.873 | 1.00 | 50.91 | B |
| ATOM | 3812 | CD | ARG | B | 899 | 35.349 | 7.042 | 21.919 | 1.00 | 55.56 | B |
| ATOM | 3813 | NE | ARG | B | 899 | 36.392 | 7.501 | 22.825 | 1.00 | 59.98 | B |
| ATOM | 3814 | CZ | ARG | B | 899 | 36.755 | 8.767 | 22.979 | 1.00 | 61.92 | B |
| ATOM | 3815 | NH1 | ARG | B | 899 | 37.716 | 9.067 | 23.839 | 1.00 | 63.21 | B |
| ATOM | 3816 | NH2 | ARG | B | 899 | 36.166 | 9.727 | 22.274 | 1.00 | 62.81 | B |
| ATOM | 3817 | C | ARG | B | 899 | 34.689 | 2.731 | 21.978 | 1.00 | 41.68 | B |
| ATOM | 3818 | O | ARG | B | 899 | 35.858 | 2.418 | 22.202 | 1.00 | 41.52 | B |
| ATOM | 3819 | N | ALA | B | 900 | 33.686 | 2.407 | 22.787 | 1.00 | 40.82 | B |
| ATOM | 3820 | CA | ALA | B | 900 | 33.909 | 1.657 | 24.018 | 1.00 | 40.31 | B |
| ATOM | 3821 | CB | ALA | B | 900 | 32.679 | 1.750 | 24.910 | 1.00 | 39.86 | B |
| ATOM | 3822 | C | ALA | B | 900 | 34.246 | 0.191 | 23.752 | 1.00 | 40.02 | B |
| ATOM | 3823 | O | ALA | B | 900 | 34.876 | −0.469 | 24.581 | 1.00 | 39.73 | B |
| ATOM | 3824 | N | LEU | B | 901 | 33.823 | −0.317 | 22.599 | 1.00 | 38.18 | B |
| ATOM | 3825 | CA | LEU | B | 901 | 34.081 | −1.706 | 22.241 | 1.00 | 37.31 | B |
| ATOM | 3826 | CB | LEU | B | 901 | 32.867 | −2.299 | 21.518 | 1.00 | 37.48 | B |
| ATOM | 3827 | CG | LEU | B | 901 | 31.545 | −2.292 | 22.285 | 1.00 | 38.53 | B |
| ATOM | 3828 | CD1 | LEU | B | 901 | 30.441 | −2.875 | 21.416 | 1.00 | 38.07 | B |
| ATOM | 3829 | CD2 | LEU | B | 901 | 31.698 | −3.095 | 23.572 | 1.00 | 38.86 | B |
| ATOM | 3830 | C | LEU | B | 901 | 35.310 | −1.826 | 21.348 | 1.00 | 35.77 | B |
| ATOM | 3831 | O | LEU | B | 901 | 35.714 | −2.929 | 20.981 | 1.00 | 35.59 | B |
| ATOM | 3832 | N | SER | B | 902 | 35.901 | −0.685 | 21.009 | 1.00 | 34.11 | B |
| ATOM | 3833 | CA | SER | B | 902 | 37.073 | −0.645 | 20.144 | 1.00 | 33.24 | B |
| ATOM | 3834 | CB | SER | B | 902 | 38.234 | −1.415 | 20.779 | 1.00 | 35.64 | B |
| ATOM | 3835 | OG | SER | B | 902 | 38.654 | −0.802 | 21.982 | 1.00 | 39.63 | B |
| ATOM | 3836 | C | SER | B | 902 | 36.762 | −1.230 | 18.765 | 1.00 | 31.15 | B |
| ATOM | 3837 | O | SER | B | 902 | 37.620 | −1.853 | 18.137 | 1.00 | 29.62 | B |
| ATOM | 3838 | N | VAL | B | 903 | 35.532 | −1.026 | 18.301 | 1.00 | 28.43 | B |
| ATOM | 3839 | CA | VAL | B | 903 | 35.112 | −1.525 | 16.992 | 1.00 | 26.89 | B |
| ATOM | 3840 | CB | VAL | B | 903 | 33.725 | −2.198 | 17.059 | 1.00 | 26.31 | B |
| ATOM | 3841 | CG1 | VAL | B | 903 | 33.320 | −2.700 | 15.668 | 1.00 | 25.67 | B |
| ATOM | 3842 | CG2 | VAL | B | 903 | 33.756 | −3.350 | 18.058 | 1.00 | 28.50 | B |
| ATOM | 3843 | C | VAL | B | 903 | 35.037 | −0.377 | 15.994 | 1.00 | 26.42 | B |
| ATOM | 3844 | O | VAL | B | 903 | 34.369 | 0.625 | 16.243 | 1.00 | 26.76 | B |
| ATOM | 3845 | N | GLU | B | 904 | 35.720 | −0.524 | 14.865 | 1.00 | 24.57 | B |
| ATOM | 3846 | CA | GLU | B | 904 | 35.712 | 0.513 | 13.848 | 1.00 | 25.03 | B |
| ATOM | 3847 | CB | GLU | B | 904 | 37.073 | 0.595 | 13.160 | 1.00 | 28.92 | B |
| ATOM | 3848 | CG | GLU | B | 904 | 38.204 | 0.987 | 14.094 | 1.00 | 38.82 | B |
| ATOM | 3849 | CD | GLU | B | 904 | 39.490 | 1.288 | 13.355 | 1.00 | 43.68 | B |
| ATOM | 3850 | OE1 | GLU | B | 904 | 39.987 | 0.395 | 12.633 | 1.00 | 47.38 | B |
| ATOM | 3851 | OE2 | GLU | B | 904 | 40.004 | 2.419 | 13.497 | 1.00 | 48.28 | B |
| ATOM | 3852 | C | GLU | B | 904 | 34.633 | 0.300 | 12.797 | 1.00 | 23.04 | B |
| ATOM | 3853 | O | GLU | B | 904 | 34.418 | −0.821 | 12.326 | 1.00 | 19.12 | B |
| ATOM | 3854 | N | PHE | B | 905 | 33.957 | 1.394 | 12.448 | 1.00 | 20.12 | B |
| ATOM | 3855 | CA | PHE | B | 905 | 32.912 | 1.395 | 11.431 | 1.00 | 20.96 | B |
| ATOM | 3856 | CB | PHE | B | 905 | 31.575 | 1.886 | 12.006 | 1.00 | 20.87 | B |
| ATOM | 3857 | CG | PHE | B | 905 | 30.861 | 0.877 | 12.856 | 1.00 | 21.25 | B |
| ATOM | 3858 | CD1 | PHE | B | 905 | 31.284 | 0.613 | 14.156 | 1.00 | 18.95 | B |
| ATOM | 3859 | CD2 | PHE | B | 905 | 29.761 | 0.187 | 12.354 | 1.00 | 19.31 | B |
| ATOM | 3860 | CE1 | PHE | B | 905 | 30.621 | −0.327 | 14.946 | 1.00 | 19.88 | B |
| ATOM | 3861 | CE2 | PHE | B | 905 | 29.094 | −0.751 | 13.132 | 1.00 | 22.00 | B |
| ATOM | 3862 | CZ | PHE | B | 905 | 29.526 | −1.010 | 14.438 | 1.00 | 20.34 | B |
| ATOM | 3863 | C | PHE | B | 905 | 33.340 | 2.356 | 10.325 | 1.00 | 19.65 | B |
| ATOM | 3864 | O | PHE | B | 905 | 33.518 | 3.550 | 10.574 | 1.00 | 20.10 | B |
| ATOM | 3865 | N | PRO | B | 906 | 33.525 | 1.851 | 9.096 | 1.00 | 19.13 | B |
| ATOM | 3866 | CD | PRO | B | 906 | 33.677 | 0.436 | 8.715 | 1.00 | 19.13 | B |
| ATOM | 3867 | CA | PRO | B | 906 | 33.933 | 2.733 | 7.994 | 1.00 | 18.54 | B |
| ATOM | 3868 | CB | PRO | B | 906 | 34.170 | 1.762 | 6.842 | 1.00 | 18.01 | B |
| ATOM | 3869 | CG | PRO | B | 906 | 34.661 | 0.526 | 7.560 | 1.00 | 21.07 | B |
| ATOM | 3870 | C | PRO | B | 906 | 32.853 | 3.767 | 7.687 | 1.00 | 17.77 | B |
| ATOM | 3871 | O | PRO | B | 906 | 31.698 | 3.614 | 8.102 | 1.00 | 17.22 | B |
| ATOM | 3872 | N | GLU | B | 907 | 33.230 | 4.800 | 6.938 | 1.00 | 17.56 | B |
| ATOM | 3873 | CA | GLU | B | 907 | 32.330 | 5.909 | 6.609 | 1.00 | 17.42 | B |
| ATOM | 3874 | CB | GLU | B | 907 | 33.106 | 6.988 | 5.856 | 1.00 | 15.83 | B |
| ATOM | 3875 | CG | GLU | B | 907 | 34.261 | 7.598 | 6.643 | 1.00 | 16.09 | B |
| ATOM | 3876 | CD | GLU | B | 907 | 33.823 | 8.322 | 7.906 | 1.00 | 18.31 | B |
| ATOM | 3877 | OE1 | GLU | B | 907 | 32.677 | 8.821 | 7.962 | 1.00 | 17.52 | B |
| ATOM | 3878 | OE2 | GLU | B | 907 | 34.643 | 8.414 | 8.842 | 1.00 | 19.06 | B |
| ATOM | 3879 | C | GLU | B | 907 | 31.026 | 5.634 | 5.864 | 1.00 | 17.19 | B |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 3880 | O | GLU | B | 907 | 29.981 | 6.177 | 6.227 | 1.00 | 16.76 | B |
| ATOM | 3881 | N | MET | B | 908 | 31.066 | 4.819 | 4.819 | 1.00 | 15.73 | B |
| ATOM | 3882 | CA | MET | B | 908 | 29.840 | 4.561 | 4.076 | 1.00 | 17.55 | B |
| ATOM | 3883 | CB | MET | B | 908 | 30.165 | 3.859 | 2.755 | 1.00 | 17.66 | B |
| ATOM | 3884 | CG | MET | B | 908 | 31.054 | 4.709 | 1.842 | 1.00 | 18.47 | B |
| ATOM | 3885 | SD | MET | B | 908 | 31.344 | 4.017 | 0.197 | 1.00 | 19.83 | B |
| ATOM | 3886 | CE | MET | B | 908 | 32.363 | 2.584 | 0.608 | 1.00 | 20.34 | B |
| ATOM | 3887 | C | MET | B | 908 | 28.854 | 3.756 | 4.912 | 1.00 | 19.27 | B |
| ATOM | 3888 | O | MET | B | 908 | 27.654 | 4.057 | 4.944 | 1.00 | 18.84 | B |
| ATOM | 3889 | N | MET | B | 909 | 29.374 | 2.741 | 5.597 | 1.00 | 20.63 | B |
| ATOM | 3890 | CA | MET | B | 909 | 28.586 | 1.884 | 6.477 | 1.00 | 21.59 | B |
| ATOM | 3891 | CB | MET | B | 909 | 29.498 | 0.849 | 7.140 | 1.00 | 26.31 | B |
| ATOM | 3892 | CG | MET | B | 909 | 29.928 | −0.280 | 6.249 | 1.00 | 31.81 | B |
| ATOM | 3893 | SD | MET | B | 909 | 28.744 | −1.626 | 6.369 | 1.00 | 41.30 | B |
| ATOM | 3894 | CE | MET | B | 909 | 29.012 | −2.122 | 8.117 | 1.00 | 35.86 | B |
| ATOM | 3895 | C | MET | B | 909 | 27.952 | 2.732 | 7.573 | 1.00 | 19.52 | B |
| ATOM | 3896 | O | MET | B | 909 | 26.767 | 2.603 | 7.873 | 1.00 | 16.91 | B |
| ATOM | 3897 | N | SER | B | 910 | 28.765 | 3.594 | 8.178 | 1.00 | 19.62 | B |
| ATOM | 3898 | CA | SER | B | 910 | 28.300 | 4.456 | 9.254 | 1.00 | 18.66 | B |
| ATOM | 3899 | CB | SER | B | 910 | 29.438 | 5.358 | 9.740 | 1.00 | 19.13 | B |
| ATOM | 3900 | OG | SER | B | 910 | 30.424 | 4.602 | 10.423 | 1.00 | 21.89 | B |
| ATOM | 3901 | C | SER | B | 910 | 27.108 | 5.308 | 8.840 | 1.00 | 18.32 | B |
| ATOM | 3902 | O | SER | B | 910 | 26.168 | 5.483 | 9.610 | 1.00 | 17.55 | B |
| ATOM | 3903 | N | GLU | B | 911 | 27.146 | 5.829 | 7.618 | 1.00 | 18.37 | B |
| ATOM | 3904 | CA | GLU | B | 911 | 26.068 | 6.669 | 7.112 | 1.00 | 17.93 | B |
| ATOM | 3905 | CB | GLU | B | 911 | 26.467 | 7.267 | 5.759 | 1.00 | 18.99 | B |
| ATOM | 3906 | CG | GLU | B | 911 | 25.386 | 8.098 | 5.091 | 1.00 | 23.81 | B |
| ATOM | 3907 | CD | GLU | B | 911 | 24.898 | 9.231 | 5.965 | 1.00 | 26.02 | B |
| ATOM | 3908 | OE1 | GLU | B | 911 | 25.737 | 9.851 | 6.656 | 1.00 | 29.85 | B |
| ATOM | 3909 | OE2 | GLU | B | 911 | 23.681 | 9.506 | 5.954 | 1.00 | 28.42 | B |
| ATOM | 3910 | C | GLU | B | 911 | 24.769 | 5.877 | 6.971 | 1.00 | 18.59 | B |
| ATOM | 3911 | O | GLU | B | 911 | 23.695 | 6.353 | 7.343 | 1.00 | 17.69 | B |
| ATOM | 3912 | N | VAL | B | 912 | 24.867 | 4.668 | 6.433 | 1.00 | 17.22 | B |
| ATOM | 3913 | CA | VAL | B | 912 | 23.682 | 3.837 | 6.255 | 1.00 | 18.22 | B |
| ATOM | 3914 | CB | VAL | B | 912 | 24.032 | 2.532 | 5.502 | 1.00 | 18.83 | B |
| ATOM | 3915 | CG1 | VAL | B | 912 | 22.898 | 1.531 | 5.628 | 1.00 | 21.35 | B |
| ATOM | 3916 | CG2 | VAL | B | 912 | 24.283 | 2.850 | 4.027 | 1.00 | 18.17 | B |
| ATOM | 3917 | C | VAL | B | 912 | 23.053 | 3.503 | 7.599 | 1.00 | 17.16 | B |
| ATOM | 3918 | O | VAL | B | 912 | 21.831 | 3.551 | 7.760 | 1.00 | 16.31 | B |
| ATOM | 3919 | N | ILE | B | 913 | 23.899 | 3.165 | 8.565 | 1.00 | 15.65 | B |
| ATOM | 3920 | CA | ILE | B | 913 | 23.435 | 2.821 | 9.899 | 1.00 | 17.18 | B |
| ATOM | 3921 | CB | ILE | B | 913 | 24.614 | 2.320 | 10.770 | 1.00 | 17.40 | B |
| ATOM | 3922 | CG2 | ILE | B | 913 | 24.183 | 2.186 | 12.225 | 1.00 | 16.84 | B |
| ATOM | 3923 | CG1 | ILE | B | 913 | 25.116 | 0.972 | 10.232 | 1.00 | 16.47 | B |
| ATOM | 3924 | CD1 | ILE | B | 913 | 26.470 | 0.544 | 10.786 | 1.00 | 20.34 | B |
| ATOM | 3925 | C | ILE | B | 913 | 22.769 | 4.030 | 10.555 | 1.00 | 19.14 | B |
| ATOM | 3926 | O | ILE | B | 913 | 21.637 | 3.946 | 11.028 | 1.00 | 20.38 | B |
| ATOM | 3927 | N | ALA | B | 914 | 23.455 | 5.166 | 10.555 | 1.00 | 20.59 | B |
| ATOM | 3928 | CA | ALA | B | 914 | 22.905 | 6.366 | 11.175 | 1.00 | 21.55 | B |
| ATOM | 3929 | CB | ALA | B | 914 | 23.956 | 7.472 | 11.191 | 1.00 | 20.73 | B |
| ATOM | 3930 | C | ALA | B | 914 | 21.635 | 6.868 | 10.495 | 1.00 | 23.12 | B |
| ATOM | 3931 | O | ALA | B | 914 | 20.707 | 7.327 | 11.157 | 1.00 | 24.41 | B |
| ATOM | 3932 | N | ALA | B | 915 | 21.582 | 6.766 | 9.174 | 1.00 | 24.15 | B |
| ATOM | 3933 | CA | ALA | B | 915 | 20.427 | 7.263 | 8.438 | 1.00 | 23.02 | B |
| ATOM | 3934 | CB | ALA | B | 915 | 20.813 | 7.496 | 6.979 | 1.00 | 23.13 | B |
| ATOM | 3935 | C | ALA | B | 915 | 19.148 | 6.432 | 8.498 | 1.00 | 22.96 | B |
| ATOM | 3936 | O | ALA | B | 915 | 18.052 | 6.992 | 8.515 | 1.00 | 23.53 | B |
| ATOM | 3937 | N | GLN | B | 916 | 19.268 | 5.111 | 8.548 | 1.00 | 20.89 | B |
| ATOM | 3938 | CA | GLN | B | 916 | 18.074 | 4.282 | 8.535 | 1.00 | 22.00 | B |
| ATOM | 3939 | CB | GLN | B | 916 | 18.010 | 3.481 | 7.223 | 1.00 | 24.20 | B |
| ATOM | 3940 | CG | GLN | B | 916 | 18.095 | 4.282 | 5.923 | 1.00 | 27.17 | B |
| ATOM | 3941 | CD | GLN | B | 916 | 17.030 | 5.345 | 5.801 | 1.00 | 29.02 | B |
| ATOM | 3942 | OE1 | GLN | B | 916 | 15.925 | 5.205 | 6.324 | 1.00 | 28.23 | B |
| ATOM | 3943 | NE2 | GLN | B | 916 | 17.353 | 6.417 | 5.087 | 1.00 | 33.25 | B |
| ATOM | 3944 | C | GLN | B | 916 | 17.812 | 3.292 | 9.667 | 1.00 | 21.39 | B |
| ATOM | 3945 | O | GLN | B | 916 | 16.651 | 3.008 | 9.959 | 1.00 | 22.64 | B |
| ATOM | 3946 | N | LEU | B | 917 | 18.849 | 2.742 | 10.295 | 1.00 | 19.37 | B |
| ATOM | 3947 | CA | LEU | B | 917 | 18.588 | 1.727 | 11.317 | 1.00 | 18.64 | B |
| ATOM | 3948 | CB | LEU | B | 917 | 19.895 | 1.152 | 11.885 | 1.00 | 18.07 | B |
| ATOM | 3949 | CG | LEU | B | 917 | 20.687 | 0.240 | 10.936 | 1.00 | 20.90 | B |
| ATOM | 3950 | CD1 | LEU | B | 917 | 21.614 | −0.666 | 11.741 | 1.00 | 17.81 | B |
| ATOM | 3951 | CD2 | LEU | B | 917 | 19.739 | −0.612 | 10.115 | 1.00 | 20.60 | B |
| ATOM | 3952 | C | LEU | B | 917 | 17.635 | 2.090 | 12.450 | 1.00 | 17.99 | B |
| ATOM | 3953 | O | LEU | B | 917 | 16.745 | 1.303 | 12.777 | 1.00 | 19.33 | B |
| ATOM | 3954 | N | PRO | B | 918 | 17.793 | 3.270 | 13.068 | 1.00 | 17.70 | B |

TABLE 2-continued

Structure coordinates (Table dicloses SEQ ID NO: 6 twice)

|  | # | Name | Res. | Chain | Res # | X | Y | Z | occ | B | SegID |
|---|---|---|---|---|---|---|---|---|---|---|---|
| ATOM | 3955 | CD | PRO | B | 918 | 18.853 | 4.290 | 12.994 | 1.00 | 18.75 | B |
| ATOM | 3956 | CA | PRO | B | 918 | 16.848 | 3.575 | 14.148 | 1.00 | 18.53 | B |
| ATOM | 3957 | CB | PRO | B | 918 | 17.285 | 4.966 | 14.596 | 1.00 | 19.15 | B |
| ATOM | 3958 | CG | PRO | B | 918 | 18.779 | 4.916 | 14.375 | 1.00 | 17.58 | B |
| ATOM | 3959 | C | PRO | B | 918 | 15.400 | 3.538 | 13.636 | 1.00 | 18.88 | B |
| ATOM | 3960 | O | PRO | B | 918 | 14.521 | 2.939 | 14.257 | 1.00 | 15.75 | B |
| ATOM | 3961 | N | LYS | B | 919 | 15.176 | 4.173 | 12.490 | 1.00 | 18.61 | B |
| ATOM | 3962 | CA | LYS | B | 919 | 13.860 | 4.234 | 11.852 | 1.00 | 20.51 | B |
| ATOM | 3963 | CB | LYS | B | 919 | 13.960 | 5.063 | 10.569 | 1.00 | 24.87 | B |
| ATOM | 3964 | CG | LYS | B | 919 | 12.673 | 5.155 | 9.765 | 1.00 | 29.78 | B |
| ATOM | 3965 | CD | LYS | B | 919 | 12.926 | 5.776 | 8.402 | 1.00 | 34.28 | B |
| ATOM | 3966 | CE | LYS | B | 919 | 13.531 | 7.168 | 8.525 | 1.00 | 37.85 | B |
| ATOM | 3967 | NZ | LYS | B | 919 | 13.932 | 7.713 | 7.194 | 1.00 | 42.01 | B |
| ATOM | 3968 | C | LYS | B | 919 | 13.317 | 2.842 | 11.515 | 1.00 | 19.41 | B |
| ATOM | 3969 | O | LYS | B | 919 | 12.146 | 2.540 | 11.766 | 1.00 | 19.67 | B |
| ATOM | 3970 | N | ILE | B | 920 | 14.164 | 2.002 | 10.925 | 1.00 | 17.71 | B |
| ATOM | 3971 | CA | ILE | B | 920 | 13.764 | 0.644 | 10.573 | 1.00 | 17.37 | B |
| ATOM | 3972 | CB | ILE | B | 920 | 14.887 | −0.077 | 9.796 | 1.00 | 17.05 | B |
| ATOM | 3973 | CG2 | ILE | B | 920 | 14.474 | −1.515 | 9.497 | 1.00 | 17.48 | B |
| ATOM | 3974 | CG1 | ILE | B | 920 | 15.171 | 0.670 | 8.486 | 1.00 | 16.02 | B |
| ATOM | 3975 | CD1 | ILE | B | 920 | 16.351 | 0.143 | 7.705 | 1.00 | 15.95 | B |
| ATOM | 3976 | C | ILE | B | 920 | 13.411 | −0.172 | 11.825 | 1.00 | 17.73 | B |
| ATOM | 3977 | O | ILE | B | 920 | 12.357 | −0.801 | 11.891 | 1.00 | 19.73 | B |
| ATOM | 3978 | N | LEU | B | 921 | 14.290 | −0.153 | 12.821 | 1.00 | 18.28 | B |
| ATOM | 3979 | CA | LEU | B | 921 | 14.048 | −0.894 | 14.058 | 1.00 | 17.30 | B |
| ATOM | 3980 | CB | LEU | B | 921 | 15.256 | −0.761 | 14.991 | 1.00 | 17.29 | B |
| ATOM | 3981 | CG | LEU | B | 921 | 16.506 | −1.550 | 14.568 | 1.00 | 19.30 | B |
| ATOM | 3982 | CD1 | LEU | B | 921 | 17.685 | −1.192 | 15.458 | 1.00 | 20.25 | B |
| ATOM | 3983 | CD2 | LEU | B | 921 | 16.212 | −3.049 | 14.650 | 1.00 | 18.96 | B |
| ATOM | 3984 | C | LEU | B | 921 | 12.779 | −0.405 | 14.759 | 1.00 | 18.82 | B |
| ATOM | 3985 | O | LEU | B | 921 | 12.060 | −1.189 | 15.386 | 1.00 | 18.43 | B |
| ATOM | 3986 | N | ALA | B | 922 | 12.506 | 0.891 | 14.650 | 1.00 | 18.13 | B |
| ATOM | 3987 | CA | ALA | B | 922 | 11.316 | 1.475 | 15.260 | 1.00 | 20.31 | B |
| ATOM | 3988 | CB | ALA | B | 922 | 11.459 | 2.994 | 15.329 | 1.00 | 18.87 | B |
| ATOM | 3989 | C | ALA | B | 922 | 10.062 | 1.102 | 14.468 | 1.00 | 21.56 | B |
| ATOM | 3990 | O | ALA | B | 922 | 8.958 | 1.530 | 14.799 | 1.00 | 21.69 | B |
| ATOM | 3991 | N | GLY | B | 923 | 10.240 | 0.312 | 13.415 | 1.00 | 21.30 | B |
| ATOM | 3992 | CA | GLY | B | 923 | 9.111 | −0.104 | 12.600 | 1.00 | 22.52 | B |
| ATOM | 3993 | C | GLY | B | 923 | 8.491 | 1.015 | 11.784 | 1.00 | 23.20 | B |
| ATOM | 3994 | O | GLY | B | 923 | 7.301 | 0.977 | 11.474 | 1.00 | 24.52 | B |
| ATOM | 3995 | N | MET | B | 924 | 9.289 | 2.010 | 11.421 | 1.00 | 23.73 | B |
| ATOM | 3996 | CA | MET | B | 924 | 8.778 | 3.134 | 10.651 | 1.00 | 24.27 | B |
| ATOM | 3997 | CB | MET | B | 924 | 9.433 | 4.424 | 11.137 | 1.00 | 26.89 | B |
| ATOM | 3998 | CG | MET | B | 924 | 9.330 | 4.611 | 12.645 | 1.00 | 29.64 | B |
| ATOM | 3999 | SD | MET | B | 924 | 7.622 | 4.544 | 13.234 | 1.00 | 36.14 | B |
| ATOM | 4000 | CE | MET | B | 924 | 7.016 | 6.119 | 12.590 | 1.00 | 32.22 | B |
| ATOM | 4001 | C | MET | B | 924 | 8.968 | 2.973 | 9.141 | 1.00 | 22.97 | B |
| ATOM | 4002 | O | MET | B | 924 | 9.237 | 3.939 | 8.434 | 1.00 | 24.86 | B |
| ATOM | 4003 | N | VAL | B | 925 | 8.834 | 1.737 | 8.669 | 1.00 | 22.70 | B |
| ATOM | 4004 | CA | VAL | B | 925 | 8.945 | 1.394 | 7.254 | 1.00 | 20.11 | B |
| ATOM | 4005 | CB | VAL | B | 925 | 10.357 | 0.879 | 6.873 | 1.00 | 21.32 | B |
| ATOM | 4006 | CG1 | VAL | B | 925 | 11.396 | 1.961 | 7.137 | 1.00 | 18.72 | B |
| ATOM | 4007 | CG2 | VAL | B | 925 | 10.681 | −0.404 | 7.648 | 1.00 | 19.44 | B |
| ATOM | 4008 | C | VAL | B | 925 | 7.951 | 0.269 | 7.008 | 1.00 | 20.72 | B |
| ATOM | 4009 | O | VAL | B | 925 | 7.427 | −0.317 | 7.958 | 1.00 | 17.16 | B |
| ATOM | 4010 | N | LYS | B | 926 | 7.698 | −0.039 | 5.740 | 1.00 | 20.24 | B |
| ATOM | 4011 | CA | LYS | B | 926 | 6.756 | −1.096 | 5.405 | 1.00 | 22.19 | B |
| ATOM | 4012 | CB | LYS | B | 926 | 5.693 | −0.583 | 4.431 | 1.00 | 23.49 | B |
| ATOM | 4013 | CG | LYS | B | 926 | 4.697 | −1.663 | 4.034 | 1.00 | 27.62 | B |
| ATOM | 4014 | CD | LYS | B | 926 | 3.735 | −1.209 | 2.948 | 1.00 | 29.56 | B |
| ATOM | 4015 | CE | LYS | B | 926 | 2.774 | −2.338 | 2.595 | 1.00 | 32.37 | B |
| ATOM | 4016 | NZ | LYS | B | 926 | 1.833 | −1.961 | 1.507 | 1.00 | 35.72 | B |
| ATOM | 4017 | C | LYS | B | 926 | 7.419 | −2.320 | 4.789 | 1.00 | 22.27 | B |
| ATOM | 4018 | O | LYS | B | 926 | 7.812 | −2.300 | 3.620 | 1.00 | 20.78 | B |
| ATOM | 4019 | N | PRO | B | 927 | 7.555 | −3.405 | 5.568 | 1.00 | 23.59 | B |
| ATOM | 4020 | CD | PRO | B | 927 | 7.287 | −3.541 | 7.009 | 1.00 | 23.58 | B |
| ATOM | 4021 | CA | PRO | B | 927 | 8.177 | −4.619 | 5.035 | 1.00 | 23.23 | B |
| ATOM | 4022 | CB | PRO | B | 927 | 8.399 | −5.481 | 6.280 | 1.00 | 24.23 | B |
| ATOM | 4023 | CG | PRO | B | 927 | 8.372 | −4.483 | 7.429 | 1.00 | 26.39 | B |
| ATOM | 4024 | C | PRO | B | 927 | 7.156 | −5.251 | 4.095 | 1.00 | 23.54 | B |
| ATOM | 4025 | O | PRO | B | 927 | 5.968 | −5.295 | 4.417 | 1.00 | 23.62 | B |
| ATOM | 4026 | N | LEU | B | 928 | 7.598 | −5.723 | 2.935 | 1.00 | 21.25 | B |
| ATOM | 4027 | CA | LEU | B | 928 | 6.672 | −6.343 | 2.000 | 1.00 | 21.62 | B |
| ATOM | 4028 | CB | LEU | B | 928 | 7.083 | −6.038 | 0.553 | 1.00 | 20.54 | B |
| ATOM | 4029 | CG | LEU | B | 928 | 7.097 | −4.547 | 0.191 | 1.00 | 19.73 | B |

TABLE 2-continued

Structure coordinates (Table discloses SEQ ID NO: 6 twice)

| | # | Name | Res. | Chain | Res # | X | Y | Z | occ | B | SegID |
|---|---|---|---|---|---|---|---|---|---|---|---|
| ATOM | 4030 | CD1 | LEU | B | 928 | 7.385 | −4.376 | −1.299 | 1.00 | 19.70 | B |
| ATOM | 4031 | CD2 | LEU | B | 928 | 5.751 | −3.916 | 0.530 | 1.00 | 19.69 | B |
| ATOM | 4032 | C | LEU | B | 928 | 6.635 | −7.845 | 2.250 | 1.00 | 22.19 | B |
| ATOM | 4033 | O | LEU | B | 928 | 7.670 | −8.481 | 2.447 | 1.00 | 20.86 | B |
| ATOM | 4034 | N | LEU | B | 929 | 5.431 | −8.404 | 2.255 | 1.00 | 22.00 | B |
| ATOM | 4035 | CA | LEU | B | 929 | 5.252 | −9.828 | 2.499 | 1.00 | 21.93 | B |
| ATOM | 4036 | CB | LEU | B | 929 | 4.480 | −10.042 | 3.804 | 1.00 | 20.94 | B |
| ATOM | 4037 | CG | LEU | B | 929 | 5.072 | −9.503 | 5.105 | 1.00 | 20.69 | B |
| ATOM | 4038 | CD1 | LEU | B | 929 | 4.053 | −9.654 | 6.233 | 1.00 | 21.83 | B |
| ATOM | 4039 | CD2 | LEU | B | 929 | 6.350 | −10.255 | 5.429 | 1.00 | 18.32 | B |
| ATOM | 4040 | C | LEU | B | 929 | 4.498 | −10.517 | 1.370 | 1.00 | 23.95 | B |
| ATOM | 4041 | O | LEU | B | 929 | 3.556 | −9.961 | 0.799 | 1.00 | 22.92 | B |
| ATOM | 4042 | N | PHE | B | 930 | 4.923 | −11.736 | 1.058 | 1.00 | 25.00 | B |
| ATOM | 4043 | CA | PHE | B | 930 | 4.280 | −12.533 | 0.025 | 1.00 | 27.93 | B |
| ATOM | 4044 | CB | PHE | B | 930 | 5.275 | −13.520 | −0.571 | 1.00 | 26.70 | B |
| ATOM | 4045 | CG | PHE | B | 930 | 6.283 | −12.887 | −1.474 | 1.00 | 27.33 | B |
| ATOM | 4046 | CD1 | PHE | B | 930 | 5.979 | −12.641 | −2.807 | 1.00 | 26.64 | B |
| ATOM | 4047 | CD2 | PHE | B | 930 | 7.531 | −12.521 | −0.989 | 1.00 | 26.19 | B |
| ATOM | 4048 | CE1 | PHE | B | 930 | 6.910 | −12.042 | −3.650 | 1.00 | 28.73 | B |
| ATOM | 4049 | CE2 | PHE | B | 930 | 8.470 | −11.920 | −1.822 | 1.00 | 27.94 | B |
| ATOM | 4050 | CZ | PHE | B | 930 | 8.158 | −11.680 | −3.154 | 1.00 | 28.06 | B |
| ATOM | 4051 | C | PHE | B | 930 | 3.120 | −13.302 | 0.645 | 1.00 | 29.58 | B |
| ATOM | 4052 | O | PHE | B | 930 | 2.159 | −13.651 | −0.039 | 1.00 | 30.87 | B |
| ATOM | 4053 | N | HIS | B | 931 | 3.220 | −13.560 | 1.944 | 1.00 | 31.13 | B |
| ATOM | 4054 | CA | HIS | B | 931 | 2.190 | −14.303 | 2.660 | 1.00 | 34.65 | B |
| ATOM | 4055 | CB | HIS | B | 931 | 2.738 | −15.668 | 3.070 | 1.00 | 33.95 | B |
| ATOM | 4056 | CG | HIS | B | 931 | 3.394 | −16.408 | 1.948 | 1.00 | 35.58 | B |
| ATOM | 4057 | CD2 | HIS | B | 931 | 4.685 | −16.765 | 1.751 | 1.00 | 35.09 | B |
| ATOM | 4058 | ND1 | HIS | B | 931 | 2.704 | −16.827 | 0.831 | 1.00 | 35.08 | B |
| ATOM | 4059 | CE1 | HIS | B | 931 | 3.543 | −17.408 | −0.008 | 1.00 | 36.03 | B |
| ATOM | 4060 | NE2 | HIS | B | 931 | 4.751 | −17.384 | 0.526 | 1.00 | 35.91 | B |
| ATOM | 4061 | C | HIS | B | 931 | 1.703 | −13.556 | 3.892 | 1.00 | 37.35 | B |
| ATOM | 4062 | O | HIS | B | 931 | 2.457 | −12.824 | 4.532 | 1.00 | 36.89 | B |
| ATOM | 4063 | N | LYS | B | 932 | 0.433 | −13.753 | 4.221 | 1.00 | 41.41 | B |
| ATOM | 4064 | CA | LYS | B | 932 | −0.177 | −13.105 | 5.376 | 1.00 | 45.14 | B |
| ATOM | 4065 | CB | LYS | B | 932 | −1.702 | −13.161 | 5.241 | 1.00 | 46.49 | B |
| ATOM | 4066 | CG | LYS | B | 932 | −2.196 | −14.436 | 4.585 | 1.00 | 47.98 | B |
| ATOM | 4067 | CD | LYS | B | 932 | −3.679 | −14.370 | 4.259 | 1.00 | 50.28 | B |
| ATOM | 4068 | CE | LYS | B | 932 | −4.073 | −15.492 | 3.306 | 1.00 | 50.95 | B |
| ATOM | 4069 | NZ | LYS | B | 932 | −3.678 | −16.832 | 3.824 | 1.00 | 51.90 | B |
| ATOM | 4070 | C | LYS | B | 932 | 0.261 | −13.748 | 6.690 | 1.00 | 45.88 | B |
| ATOM | 4071 | O | LYS | B | 932 | 0.973 | −14.774 | 6.641 | 1.00 | 46.33 | B |
| ATOM | 4072 | OXT | LYS | B | 932 | −0.114 | −13.213 | 7.755 | 1.00 | 47.76 | B |
| ATOM | 4073 | S | SO4 | Z | 1 | 17.414 | −1.312 | −17.993 | 1.00 | 31.48 | Z |
| ATOM | 4074 | O1 | SO4 | Z | 1 | 18.530 | −2.281 | −17.932 | 1.00 | 35.16 | Z |
| ATOM | 4075 | O2 | SO4 | Z | 1 | 17.425 | −0.473 | −16.787 | 1.00 | 32.29 | Z |
| ATOM | 4076 | O3 | SO4 | Z | 1 | 17.593 | −0.480 | −19.187 | 1.00 | 31.61 | Z |
| ATOM | 4077 | O4 | SO4 | Z | 1 | 16.139 | −2.038 | −18.069 | 1.00 | 33.87 | Z |
| ATOM | 4078 | O | HOH | W | 1 | 9.851 | −0.179 | 33.299 | 1.00 | 14.73 | W |
| ATOM | 4079 | O | HOH | W | 2 | 22.939 | −10.562 | −9.981 | 1.00 | 15.38 | W |
| ATOM | 4080 | O | HOH | W | 3 | 2.083 | 29.100 | 25.389 | 1.00 | 20.40 | W |
| ATOM | 4081 | O | HOH | W | 4 | 14.086 | −2.560 | 0.315 | 1.00 | 17.07 | W |
| ATOM | 4082 | O | HOH | W | 5 | 27.328 | −10.890 | 1.331 | 1.00 | 18.73 | W |
| ATOM | 4083 | O | HOH | W | 6 | 13.331 | 5.641 | 28.674 | 1.00 | 19.86 | W |
| ATOM | 4084 | O | HOH | W | 7 | 13.186 | 1.399 | 47.673 | 1.00 | 13.95 | W |
| ATOM | 4085 | O | HOH | W | 8 | 32.971 | −11.715 | 0.505 | 1.00 | 14.94 | W |
| ATOM | 4086 | O | HOH | W | 9 | 18.332 | −4.869 | 5.470 | 1.00 | 18.48 | W |
| ATOM | 4087 | O | HOH | W | 10 | 12.895 | −0.329 | 56.919 | 1.00 | 18.21 | W |
| ATOM | 4088 | O | HOH | W | 11 | 39.458 | −17.312 | 7.769 | 1.00 | 30.23 | W |
| ATOM | 4089 | O | HOH | W | 12 | 26.010 | −12.904 | −3.995 | 1.00 | 34.91 | W |
| ATOM | 4090 | O | HOH | W | 13 | 10.307 | 23.211 | 14.451 | 1.00 | 24.90 | W |
| ATOM | 4091 | O | HOH | W | 14 | 33.794 | −3.491 | −3.298 | 1.00 | 24.71 | W |
| ATOM | 4092 | O | HOH | W | 15 | −7.542 | −1.149 | 46.176 | 1.00 | 17.56 | W |
| ATOM | 4093 | O | HOH | W | 16 | 10.481 | 5.430 | 28.973 | 1.00 | 16.76 | W |
| ATOM | 4094 | O | HOH | W | 17 | 9.010 | 1.461 | 31.392 | 1.00 | 20.19 | W |
| ATOM | 4095 | O | HOH | W | 18 | 0.442 | −1.822 | 32.126 | 1.00 | 27.35 | W |
| ATOM | 4096 | O | HOH | W | 19 | 20.106 | −2.758 | 6.202 | 1.00 | 22.10 | W |
| ATOM | 4097 | O | HOH | W | 20 | 6.858 | 5.226 | −11.172 | 1.00 | 19.86 | W |
| ATOM | 4098 | O | HOH | W | 21 | 3.112 | 31.643 | 22.889 | 1.00 | 22.74 | W |
| ATOM | 4099 | O | HOH | W | 22 | 10.057 | 15.524 | 34.676 | 1.00 | 20.39 | W |
| ATOM | 4100 | O | HOH | W | 23 | 28.343 | −13.760 | −2.951 | 1.00 | 27.79 | W |
| ATOM | 4101 | O | HOH | W | 24 | 5.302 | 8.903 | 42.508 | 1.00 | 17.97 | W |
| ATOM | 4102 | O | HOH | W | 25 | 12.929 | 28.598 | 20.593 | 1.00 | 23.80 | W |
| ATOM | 4103 | O | HOH | W | 26 | −4.534 | 17.192 | 43.743 | 1.00 | 28.92 | W |
| ATOM | 4104 | O | HOH | W | 27 | 9.676 | 3.409 | 22.849 | 1.00 | 14.96 | W |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 4105 | O | HOH | W | 28 | 13.824 | −6.363 | 9.101 | 1.00 | 24.33 | W |
| ATOM | 4106 | O | HOH | W | 29 | 19.783 | −1.498 | 23.163 | 1.00 | 21.54 | W |
| ATOM | 4107 | O | HOH | W | 30 | 7.516 | 21.308 | 40.840 | 1.00 | 39.46 | W |
| ATOM | 4108 | O | HOH | W | 31 | 20.250 | −8.806 | 18.170 | 1.00 | 22.74 | W |
| ATOM | 4109 | O | HOH | W | 32 | 20.825 | −10.938 | −8.107 | 1.00 | 23.11 | W |
| ATOM | 4110 | O | HOH | W | 33 | −1.545 | −0.716 | 48.089 | 1.00 | 19.38 | W |
| ATOM | 4111 | O | HOH | W | 34 | 3.305 | −1.599 | 49.132 | 1.00 | 34.02 | W |
| ATOM | 4112 | O | HOH | W | 35 | 40.480 | −6.360 | 12.399 | 1.00 | 27.56 | W |
| ATOM | 4113 | O | HOH | W | 36 | 11.493 | 20.832 | 38.950 | 1.00 | 38.71 | W |
| ATOM | 4114 | O | HOH | W | 37 | 9.120 | 1.197 | 21.414 | 1.00 | 23.98 | W |
| ATOM | 4115 | O | HOH | W | 38 | −1.682 | 3.281 | 52.013 | 1.00 | 22.24 | W |
| ATOM | 4116 | O | HOH | W | 39 | −11.086 | 22.915 | 35.681 | 1.00 | 32.42 | W |
| ATOM | 4117 | O | HOH | W | 40 | 12.002 | 7.533 | −1.688 | 1.00 | 30.69 | W |
| ATOM | 4118 | O | HOH | W | 41 | 14.518 | −13.452 | −19.077 | 1.00 | 26.25 | W |
| ATOM | 4119 | O | HOH | W | 42 | 18.500 | 30.309 | 24.738 | 1.00 | 37.66 | W |
| ATOM | 4120 | O | HOH | W | 43 | 14.005 | −7.837 | 26.712 | 1.00 | 24.93 | W |
| ATOM | 4121 | O | HOH | W | 44 | 2.873 | −1.026 | 35.419 | 1.00 | 35.46 | W |
| ATOM | 4122 | O | HOH | W | 45 | 19.791 | −5.878 | 22.089 | 1.00 | 24.74 | W |
| ATOM | 4123 | O | HOH | W | 46 | 36.617 | −7.101 | −5.193 | 1.00 | 27.22 | W |
| ATOM | 4124 | O | HOH | W | 47 | 17.997 | 16.706 | 17.050 | 1.00 | 23.35 | W |
| ATOM | 4125 | O | HOH | W | 48 | 12.818 | 29.647 | 30.373 | 1.00 | 34.99 | W |
| ATOM | 4126 | O | HOH | W | 49 | 35.741 | 2.637 | 0.675 | 1.00 | 29.22 | W |
| ATOM | 4127 | O | HOH | W | 50 | −0.698 | −9.676 | 42.142 | 1.00 | 30.67 | W |
| ATOM | 4128 | O | HOH | W | 51 | −0.525 | 29.866 | 21.575 | 1.00 | 19.53 | W |
| ATOM | 4129 | O | HOH | W | 52 | 18.379 | −2.516 | 47.069 | 1.00 | 27.04 | W |
| ATOM | 4130 | O | HOH | W | 53 | 8.722 | 0.737 | 27.146 | 1.00 | 31.04 | W |
| ATOM | 4131 | O | HOH | W | 54 | 20.510 | 8.743 | 13.356 | 1.00 | 23.93 | W |
| ATOM | 4132 | O | HOH | W | 55 | 12.649 | 20.284 | 36.357 | 1.00 | 16.97 | W |
| ATOM | 4133 | O | HOH | W | 56 | −8.042 | 11.472 | 43.548 | 1.00 | 24.46 | W |
| ATOM | 4134 | O | HOH | W | 57 | −11.476 | 3.549 | 43.258 | 1.00 | 25.26 | W |
| ATOM | 4135 | O | HOH | W | 58 | 7.056 | −16.459 | −15.106 | 1.00 | 23.80 | W |
| ATOM | 4136 | O | HOH | W | 59 | 21.350 | −22.318 | 13.143 | 1.00 | 34.05 | W |
| ATOM | 4137 | O | HOH | W | 60 | 28.062 | 12.099 | 16.977 | 1.00 | 26.29 | W |
| ATOM | 4138 | O | HOH | W | 61 | −22.171 | 4.158 | 40.700 | 1.00 | 28.15 | W |
| ATOM | 4139 | O | HOH | W | 62 | 22.437 | 24.881 | 26.553 | 1.00 | 20.93 | W |
| ATOM | 4140 | O | HOH | W | 63 | 28.474 | 13.733 | 32.727 | 1.00 | 30.22 | W |
| ATOM | 4141 | O | HOH | W | 64 | 1.626 | −6.963 | 38.739 | 1.00 | 22.58 | W |
| ATOM | 4142 | O | HOH | W | 65 | 5.955 | 33.007 | 28.845 | 1.00 | 42.67 | W |
| ATOM | 4143 | O | HOH | W | 66 | 7.548 | 3.514 | 24.485 | 1.00 | 25.19 | W |
| ATOM | 4144 | O | HOH | W | 67 | 28.084 | 10.733 | 25.158 | 1.00 | 32.12 | W |
| ATOM | 4145 | O | HOH | W | 68 | 14.819 | −4.756 | 10.909 | 1.00 | 22.88 | W |
| ATOM | 4146 | O | HOH | W | 69 | 12.512 | −3.850 | 11.912 | 1.00 | 30.27 | W |
| ATOM | 4147 | O | HOH | W | 70 | 23.580 | −16.334 | 5.829 | 1.00 | 22.52 | W |
| ATOM | 4148 | O | HOH | W | 71 | 10.565 | −11.166 | −16.058 | 1.00 | 23.71 | W |
| ATOM | 4149 | O | HOH | W | 72 | 2.064 | 13.163 | 18.256 | 1.00 | 38.01 | W |
| ATOM | 4150 | O | HOH | W | 73 | 24.352 | 27.565 | 20.778 | 1.00 | 29.09 | W |
| ATOM | 4151 | O | HOH | W | 74 | 13.534 | 11.655 | 46.723 | 1.00 | 29.05 | W |
| ATOM | 4152 | O | HOH | W | 75 | −3.751 | 1.854 | 53.213 | 1.00 | 24.50 | W |
| ATOM | 4153 | O | HOH | W | 76 | 14.249 | −6.307 | 6.318 | 1.00 | 33.71 | W |
| ATOM | 4154 | O | HOH | W | 77 | 8.346 | 20.512 | 13.638 | 1.00 | 29.91 | W |
| ATOM | 4155 | O | HOH | W | 78 | 10.659 | −27.801 | −3.102 | 1.00 | 25.66 | W |
| ATOM | 4156 | O | HOH | W | 79 | 29.300 | −5.213 | −7.941 | 1.00 | 27.88 | W |
| ATOM | 4157 | O | HOH | W | 80 | 23.744 | 15.309 | 11.455 | 1.00 | 36.84 | W |
| ATOM | 4158 | O | HOH | W | 81 | 26.341 | −4.131 | −16.979 | 1.00 | 37.38 | W |
| ATOM | 4159 | O | HOH | W | 82 | −5.101 | −2.239 | 21.176 | 1.00 | 49.05 | W |
| ATOM | 4160 | O | HOH | W | 83 | 8.948 | −10.743 | 1.764 | 1.00 | 25.57 | W |
| ATOM | 4161 | O | HOH | W | 84 | 22.426 | 8.856 | 3.497 | 1.00 | 30.12 | W |
| ATOM | 4162 | O | HOH | W | 85 | 15.590 | −6.464 | 2.357 | 1.00 | 20.20 | W |
| ATOM | 4163 | O | HOH | W | 86 | 22.984 | −28.399 | 7.053 | 1.00 | 43.09 | W |
| ATOM | 4164 | O | HOH | W | 87 | 35.903 | −1.727 | 10.279 | 1.00 | 24.30 | W |
| ATOM | 4165 | O | HOH | W | 88 | 7.456 | 3.549 | 31.583 | 1.00 | 22.42 | W |
| ATOM | 4166 | O | HOH | W | 89 | 7.855 | −6.471 | 46.303 | 1.00 | 30.69 | W |
| ATOM | 4167 | O | HOH | W | 90 | 43.114 | −4.754 | 5.804 | 1.00 | 31.47 | W |
| ATOM | 4168 | O | HOH | W | 91 | 23.688 | 18.339 | 28.249 | 1.00 | 35.33 | W |
| ATOM | 4169 | O | HOH | W | 92 | 8.671 | 30.830 | 26.750 | 1.00 | 25.23 | W |
| ATOM | 4170 | O | HOH | W | 93 | 21.069 | 9.806 | 42.796 | 1.00 | 22.22 | W |
| ATOM | 4171 | O | HOH | W | 94 | 34.235 | 3.943 | 13.825 | 1.00 | 29.92 | W |
| ATOM | 4172 | O | HOH | W | 95 | 4.325 | −12.649 | 42.865 | 1.00 | 33.49 | W |
| ATOM | 4173 | O | HOH | W | 96 | 4.905 | −14.665 | 5.831 | 1.00 | 30.26 | W |
| ATOM | 4174 | O | HOH | W | 97 | 17.850 | 0.612 | 51.901 | 1.00 | 26.30 | W |
| ATOM | 4175 | O | HOH | W | 98 | 29.845 | −26.714 | −0.530 | 1.00 | 32.22 | W |
| ATOM | 4176 | O | HOH | W | 99 | 21.826 | 3.590 | 34.558 | 1.00 | 30.54 | W |
| ATOM | 4177 | O | HOH | W | 100 | 8.730 | 5.195 | 6.121 | 1.00 | 31.99 | W |
| ATOM | 4178 | O | HOH | W | 101 | −12.510 | −0.569 | 35.114 | 1.00 | 39.35 | W |
| ATOM | 4179 | O | HOH | W | 102 | 9.974 | 18.335 | 15.716 | 1.00 | 30.38 | W |

TABLE 2-continued

Structure coordinates (Table dicloses SEQ ID NO: 6 twice)

| | # | Name | Res. | Chain | Res # | X | Y | Z | occ | B | SegID |
|---|---|---|---|---|---|---|---|---|---|---|---|
| ATOM | 4180 | O | HOH | W | 103 | −20.727 | 6.780 | 40.198 | 1.00 | 31.21 | W |
| ATOM | 4181 | O | HOH | W | 104 | 17.245 | 3.775 | 27.753 | 1.00 | 23.95 | W |
| ATOM | 4182 | O | HOH | W | 105 | 12.204 | 31.282 | 32.900 | 1.00 | 47.25 | W |
| ATOM | 4183 | O | HOH | W | 106 | 30.849 | −13.455 | −10.120 | 1.00 | 44.05 | W |
| ATOM | 4184 | O | HOH | W | 107 | 31.232 | −11.424 | −3.737 | 1.00 | 34.09 | W |
| ATOM | 4185 | O | HOH | W | 108 | 0.616 | 0.645 | 30.187 | 1.00 | 19.02 | W |
| ATOM | 4186 | O | HOH | W | 109 | 9.969 | 10.406 | 39.896 | 1.00 | 41.21 | W |
| ATOM | 4187 | O | HOH | W | 110 | 4.951 | −13.348 | 36.812 | 1.00 | 25.64 | W |
| ATOM | 4188 | O | HOH | W | 111 | 24.217 | 0.126 | 32.380 | 1.00 | 42.27 | W |
| ATOM | 4189 | O | HOH | W | 112 | 7.760 | 3.239 | 27.484 | 1.00 | 31.56 | W |
| ATOM | 4190 | O | HOH | W | 113 | −13.150 | 10.929 | 35.305 | 1.00 | 37.37 | W |
| ATOM | 4191 | O | HOH | W | 114 | 14.414 | 10.760 | 49.023 | 1.00 | 25.40 | W |
| ATOM | 4192 | O | HOH | W | 115 | 9.753 | 12.679 | 37.102 | 1.00 | 37.47 | W |
| ATOM | 4193 | O | HOH | W | 116 | −4.457 | 0.109 | 25.639 | 1.00 | 31.43 | W |
| ATOM | 4194 | O | HOH | W | 117 | 31.098 | 5.122 | 20.729 | 1.00 | 32.11 | W |
| ATOM | 4195 | O | HOH | W | 118 | 9.748 | 22.778 | 39.579 | 1.00 | 29.38 | W |
| ATOM | 4196 | O | HOH | W | 119 | 15.530 | −4.123 | 52.634 | 1.00 | 29.51 | W |
| ATOM | 4197 | O | HOH | W | 120 | 14.408 | −3.786 | 6.247 | 1.00 | 35.75 | W |
| ATOM | 4198 | O | HOH | W | 121 | 3.061 | 16.521 | 16.785 | 1.00 | 25.91 | W |
| ATOM | 4199 | O | HOH | W | 122 | 39.801 | −19.133 | 1.482 | 1.00 | 26.72 | W |
| ATOM | 4200 | O | HOH | W | 123 | 37.378 | −1.402 | 24.102 | 1.00 | 39.79 | W |
| ATOM | 4201 | O | HOH | W | 124 | 14.576 | 12.610 | 44.487 | 1.00 | 30.08 | W |
| ATOM | 4202 | O | HOH | W | 125 | 4.145 | 16.097 | 43.565 | 1.00 | 34.79 | W |
| ATOM | 4203 | O | HOH | W | 126 | 7.682 | 25.781 | 13.009 | 1.00 | 45.48 | W |
| ATOM | 4204 | O | HOH | W | 127 | 9.845 | −12.141 | 9.020 | 1.00 | 29.42 | W |
| ATOM | 4205 | O | HOH | W | 128 | 15.739 | 10.997 | −9.996 | 1.00 | 27.09 | W |
| ATOM | 4206 | O | HOH | W | 129 | 6.716 | 10.052 | 44.773 | 1.00 | 20.65 | W |
| ATOM | 4207 | O | HOH | W | 130 | 14.744 | −8.445 | 4.732 | 1.00 | 23.00 | W |
| ATOM | 4208 | O | HOH | W | 131 | 21.909 | 24.767 | 16.946 | 1.00 | 31.22 | W |
| ATOM | 4209 | O | HOH | W | 132 | 33.120 | −12.601 | −1.941 | 1.00 | 27.91 | W |
| ATOM | 4210 | O | HOH | W | 133 | 23.283 | 3.901 | −16.585 | 1.00 | 40.81 | W |
| ATOM | 4211 | O | HOH | W | 134 | 27.581 | 13.334 | 14.368 | 1.00 | 31.58 | W |
| ATOM | 4212 | O | HOH | W | 135 | 23.546 | −8.108 | −4.594 | 1.00 | 38.50 | W |
| ATOM | 4213 | O | HOH | W | 136 | 3.316 | −6.614 | 1.955 | 1.00 | 31.34 | W |
| ATOM | 4214 | O | HOH | W | 137 | 17.363 | 1.926 | 49.485 | 1.00 | 28.70 | W |
| ATOM | 4215 | O | HOH | W | 138 | 38.393 | −7.509 | −2.153 | 1.00 | 31.36 | W |
| ATOM | 4216 | O | HOH | W | 139 | 14.920 | −4.060 | 2.471 | 1.00 | 31.77 | W |
| ATOM | 4217 | O | HOH | W | 140 | 38.118 | −0.901 | 8.667 | 1.00 | 31.86 | W |
| ATOM | 4218 | O | HOH | W | 141 | 26.383 | 5.332 | 2.546 | 1.00 | 34.89 | W |
| ATOM | 4219 | O | HOH | W | 142 | 35.405 | 3.798 | 3.233 | 1.00 | 34.38 | W |
| ATOM | 4220 | O | HOH | W | 143 | 11.409 | −21.800 | −16.697 | 1.00 | 35.84 | W |
| ATOM | 4221 | O | HOH | W | 144 | 39.725 | −6.596 | 7.646 | 1.00 | 38.73 | W |
| ATOM | 4222 | O | HOH | W | 145 | 17.070 | 6.806 | 11.706 | 1.00 | 34.49 | W |
| ATOM | 4223 | O | HOH | W | 146 | 3.371 | 3.664 | 29.494 | 1.00 | 39.22 | W |
| ATOM | 4224 | O | HOH | W | 147 | 13.400 | 6.010 | 35.121 | 1.00 | 36.31 | W |
| ATOM | 4225 | O | HOH | W | 148 | 11.012 | 18.450 | 40.465 | 1.00 | 37.80 | W |
| ATOM | 4226 | O | HOH | W | 149 | 35.666 | −17.196 | −3.005 | 1.00 | 33.54 | W |
| ATOM | 4227 | O | HOH | W | 150 | 27.587 | −15.335 | −11.411 | 1.00 | 32.63 | W |
| ATOM | 4228 | O | HOH | W | 151 | 24.903 | −9.920 | −1.819 | 1.00 | 37.55 | W |
| ATOM | 4229 | O | HOH | W | 152 | 15.833 | 8.081 | −12.357 | 1.00 | 42.37 | W |
| ATOM | 4230 | O | HOH | W | 153 | 28.438 | 16.821 | 21.396 | 1.00 | 44.90 | W |
| ATOM | 4231 | O | HOH | W | 154 | 21.332 | 29.602 | 23.542 | 1.00 | 39.67 | W |
| ATOM | 4232 | O | HOH | W | 155 | 12.772 | −9.868 | 3.678 | 1.00 | 36.84 | W |
| ATOM | 4233 | O | HOH | W | 156 | 16.961 | −7.689 | 35.260 | 1.00 | 44.42 | W |
| ATOM | 4234 | O | HOH | W | 157 | 10.499 | 10.751 | 16.433 | 1.00 | 34.39 | W |
| ATOM | 4235 | O | HOH | W | 158 | 28.327 | −5.237 | −10.882 | 1.00 | 45.84 | W |
| ATOM | 4236 | O | HOH | W | 159 | 36.087 | 4.558 | 6.039 | 1.00 | 28.34 | W |
| ATOM | 4237 | O | HOH | W | 160 | −0.994 | 29.266 | 35.756 | 1.00 | 35.83 | W |
| ATOM | 4238 | O | HOH | W | 161 | 0.695 | −6.498 | 29.582 | 1.00 | 33.46 | W |
| ATOM | 4239 | O | HOH | W | 162 | 26.373 | 21.757 | 15.011 | 1.00 | 43.14 | W |
| ATOM | 4240 | O | HOH | W | 163 | 15.148 | 32.436 | 21.985 | 1.00 | 36.34 | W |
| ATOM | 4241 | O | HOH | W | 164 | −3.288 | −2.573 | 49.020 | 1.00 | 37.67 | W |
| ATOM | 4242 | O | HOH | W | 165 | −1.628 | 26.470 | 37.063 | 1.00 | 33.28 | W |
| ATOM | 4243 | O | HOH | W | 166 | 27.897 | 14.312 | 24.143 | 1.00 | 35.59 | W |
| ATOM | 4244 | O | HOH | W | 167 | 7.738 | 17.438 | 39.142 | 1.00 | 46.82 | W |
| ATOM | 4245 | O | HOH | W | 168 | 10.899 | 4.880 | 52.240 | 1.00 | 32.86 | W |
| ATOM | 4246 | O | HOH | W | 169 | 10.635 | −22.038 | 3.450 | 1.00 | 43.02 | W |
| ATOM | 4247 | O | HOH | W | 170 | 25.343 | 2.041 | 28.575 | 1.00 | 43.36 | W |
| ATOM | 4248 | O | HOH | W | 171 | 4.243 | 6.461 | −2.841 | 1.00 | 33.86 | W |
| ATOM | 4249 | O | HOH | W | 172 | 4.073 | 6.130 | −9.321 | 1.00 | 37.81 | W |
| ATOM | 4250 | O | HOH | W | 173 | 7.805 | −22.135 | −12.033 | 1.00 | 33.34 | W |
| ATOM | 4251 | O | HOH | W | 174 | 13.170 | −15.783 | 10.760 | 1.00 | 40.16 | W |
| ATOM | 4252 | O | HOH | W | 175 | 15.268 | −15.546 | 12.623 | 1.00 | 39.35 | W |
| ATOM | 4253 | O | HOH | W | 176 | 8.067 | −4.029 | 50.607 | 1.00 | 41.24 | W |
| ATOM | 4254 | O | HOH | W | 177 | −2.564 | 26.998 | 20.110 | 1.00 | 40.38 | W |

TABLE 2-continued

Structure coordinates (Table discloses SEQ ID NO: 6 twice)

| | # | Name | Res. | Chain | Res # | X | Y | Z | occ | B | SegID |
|---|---|---|---|---|---|---|---|---|---|---|---|
| ATOM | 4255 | O | HOH | W | 178 | 20.599 | −7.598 | 44.029 | 1.00 | 35.32 | W |
| ATOM | 4256 | O | HOH | W | 179 | 7.493 | −14.259 | 8.323 | 1.00 | 45.07 | W |
| ATOM | 4257 | N1 | 989 | C | 701 | 12.950 | 16.155 | 29.632 | 1.00 | 25.58 | C |
| ATOM | 4258 | C2 | 989 | C | 701 | 12.751 | 15.346 | 28.400 | 1.00 | 26.75 | C |
| ATOM | 4259 | C3 | 989 | C | 701 | 11.423 | 15.061 | 28.357 | 1.00 | 25.91 | C |
| ATOM | 4260 | C4 | 989 | C | 701 | 10.740 | 15.698 | 29.489 | 1.00 | 26.53 | C |
| ATOM | 4261 | C5 | 989 | C | 701 | 11.639 | 16.305 | 30.277 | 1.00 | 24.85 | C |
| ATOM | 4262 | C6 | 989 | C | 701 | 11.345 | 17.031 | 31.471 | 1.00 | 25.38 | C |
| ATOM | 4263 | N7 | 989 | C | 701 | 11.135 | 17.620 | 32.434 | 1.00 | 28.13 | C |
| ATOM | 4264 | C8 | 989 | C | 701 | 14.187 | 16.785 | 30.127 | 1.00 | 23.90 | C |
| ATOM | 4265 | C12 | 989 | C | 701 | 13.748 | 15.000 | 27.362 | 1.00 | 26.02 | C |
| ATOM | 4266 | C13 | 989 | C | 701 | 15.088 | 14.717 | 27.732 | 1.00 | 26.27 | C |
| ATOM | 4267 | C14 | 989 | C | 701 | 16.102 | 14.633 | 26.756 | 1.00 | 27.92 | C |
| ATOM | 4268 | C15 | 989 | C | 701 | 15.772 | 14.704 | 25.388 | 1.00 | 28.20 | C |
| ATOM | 4269 | C16 | 989 | C | 701 | 14.419 | 14.901 | 24.980 | 1.00 | 26.87 | C |
| ATOM | 4270 | C17 | 989 | C | 701 | 13.419 | 15.084 | 25.984 | 1.00 | 27.22 | C |
| ATOM | 4271 | N18 | 989 | C | 701 | 16.760 | 14.547 | 24.458 | 1.00 | 30.23 | C |
| ATOM | 4272 | C19 | 989 | C | 701 | 16.515 | 14.415 | 23.126 | 1.00 | 31.26 | C |
| ATOM | 4273 | O20 | 989 | C | 701 | 15.208 | 14.452 | 22.722 | 1.00 | 31.21 | C |
| ATOM | 4274 | C21 | 989 | C | 701 | 14.108 | 14.960 | 23.483 | 1.00 | 29.70 | C |
| ATOM | 4275 | C22 | 989 | C | 701 | 12.917 | 14.062 | 23.101 | 1.00 | 28.20 | C |
| ATOM | 4276 | C26 | 989 | C | 701 | 13.888 | 16.419 | 23.039 | 1.00 | 27.96 | C |
| ATOM | 4277 | S30 | 989 | C | 701 | 17.846 | 14.580 | 22.146 | 1.00 | 28.30 | C |
| ATOM | 4278 | N1 | 989 | D | 701 | 28.639 | −9.086 | 6.656 | 1.00 | 28.57 | D |
| ATOM | 4279 | C2 | 989 | D | 701 | 27.632 | −8.815 | 7.706 | 1.00 | 29.39 | D |
| ATOM | 4280 | C3 | 989 | D | 701 | 26.668 | −9.755 | 7.546 | 1.00 | 27.96 | D |
| ATOM | 4281 | C4 | 989 | D | 701 | 26.974 | −10.590 | 6.385 | 1.00 | 28.44 | D |
| ATOM | 4282 | C5 | 989 | D | 701 | 28.128 | −10.194 | 5.838 | 1.00 | 28.00 | D |
| ATOM | 4283 | C6 | 989 | D | 701 | 28.775 | −10.812 | 4.721 | 1.00 | 29.08 | D |
| ATOM | 4284 | N7 | 989 | D | 701 | 29.314 | −11.293 | 3.826 | 1.00 | 32.15 | D |
| ATOM | 4285 | C8 | 989 | D | 701 | 30.021 | −8.594 | 6.590 | 1.00 | 27.50 | D |
| ATOM | 4286 | C12 | 989 | D | 701 | 27.714 | −7.844 | 8.821 | 1.00 | 29.66 | D |
| ATOM | 4287 | C13 | 989 | D | 701 | 28.293 | −6.561 | 8.626 | 1.00 | 30.33 | D |
| ATOM | 4288 | C14 | 989 | D | 701 | 28.500 | −5.693 | 9.723 | 1.00 | 32.12 | D |
| ATOM | 4289 | C15 | 989 | D | 701 | 28.076 | −6.071 | 11.018 | 1.00 | 31.15 | D |
| ATOM | 4290 | C16 | 989 | D | 701 | 27.461 | −7.340 | 11.226 | 1.00 | 31.11 | D |
| ATOM | 4291 | C17 | 989 | D | 701 | 27.287 | −8.212 | 10.117 | 1.00 | 30.39 | D |
| ATOM | 4292 | N18 | 989 | D | 701 | 28.293 | −5.221 | 12.072 | 1.00 | 33.73 | D |
| ATOM | 4293 | C19 | 989 | D | 701 | 27.907 | −5.501 | 13.348 | 1.00 | 34.14 | D |
| ATOM | 4294 | O20 | 989 | D | 701 | 27.191 | −6.652 | 13.554 | 1.00 | 33.18 | D |
| ATOM | 4295 | C21 | 989 | D | 701 | 26.998 | −7.721 | 12.626 | 1.00 | 32.21 | D |
| ATOM | 4296 | C22 | 989 | D | 701 | 25.485 | −8.011 | 12.650 | 1.00 | 32.12 | D |
| ATOM | 4297 | C26 | 989 | D | 701 | 27.816 | −8.917 | 13.151 | 1.00 | 34.10 | D |
| ATOM | 4298 | S30 | 989 | D | 701 | 28.475 | −4.462 | 14.528 | 1.00 | 34.00 | D |

OTHER EMBODIMENTS

A number of embodiments of the invention have been described. Nevertheless, it will be understood that various modifications may be made. For example, a structure of progesterone receptor can be determined where progesterone receptor is bound to a non-steroidal agent other than tanaproget. Accordingly, other embodiments are within the scope of the following claims.

What is claimed is:

1. A method of designing or selecting a non-steroidal candidate agent that interacts with a progesterone receptor, comprising:

(a) utilizing the three-dimensional structural coordinates of the progesterone receptor ligand binding domain:non-steroidal ligand complex of Table 2 ± a root mean square deviation for alpha carbon atoms of not more than 1.5 Å, to generate a three-dimensional model wherein said non-steroidal ligand from Table 2 forms a favorable hydrogen bond, hydrophobic and/or electrostatic interaction between said non-steroid ligand and Asn719 and Gln725, and between one or more of Leu797, Arg766, Thr894 or Cys891;

(b) identifying the amino acid residues forming a non-steroidal ligand binding pocket of the progesterone receptor ligand binding domain from the three-dimensional model in step (a) in order to generate a three-dimensional representation of the non-steroidal ligand binding pocket, wherein the non-steroidal ligand binding pocket comprises amino acids Ile699, Ala701, Leu714, Leu715, Leu718, Asn719, Leu721, Gln725, Trp755, Met756, Met759, Val760, Leu763, Arg766, Ser767, Tyr777, Phe778, Ala779, Leu782, Phe794, Leu797, Cys798, Met801, Ile804, Leu887, His888, Tyr890, Cys891, Asn893, Thr894, Phe895, Ser898, Leu901, Val903, Phe905, Met909, Ile913, and Leu917 according to Table 2, ± a root mean square deviation for alpha carbon atoms of not more than 1.5 Å, and wherein said three-dimensional representation of the non-steroidal ligand binding pocket optionally has the non-steroidal ligand from step (a) present or absent;

(c) employing said three dimensional representation from step (b) to design or select said candidate agent such that the favorable interactions from step (a) are maintained between the candidate non-steroidal ligand and the progesterone receptor ligand binding pocket;

(d) synthesizing said candidate agent; and (e) contacting said candidate agent with said progesterone receptor ligand binding domain to determine the ability of said candidate agent to interact or bind said progesterone receptor ligand binding domain;

whereby the detection of the ability of said candidate agent to interact or bind said progesterone receptor ligand binding domain thereby identifies said candidate agent as an agent that interacts with the progesterone receptor.

2. A method of designing or selecting a non-steroidal candidate agent that interacts with a progesterone receptor, comprising:

(a) utilizing the three-dimensional structural coordinates of the progesterone receptor ligand binding domain:non-steroidal ligand complex of Table 2± a root mean square deviation for alpha carbon atoms of not more than 1.5 Å, to generate a three-dimensional model wherein said non-steroidal ligand from Table 2 forms a favorable hydrogen bond, hydrophobic and/or electrostatic interaction between said non-steroid ligand and Asn719 and Gln725, and between one or more of Leu797, Arg766, Thr894 or Cys891;

(b) identifying the amino acid residues forming a non-steroidal ligand binding pocket of the progesterone receptor ligand binding domain from the three-dimensional model in step (a) in order to generate a three-dimensional representation of the non-steroidal ligand binding pocket, wherein the non-steroidal ligand binding pocket comprises amino acids Ile699, Ala701, Leu714, Leu715, Leu718, Asn719, Leu721, Gln725, Trp755, Met756, Met759, Val760, Leu763, Arg766, Ser767, Tyr777, Phe778, Ala779, Leu782, Phe794, Leu797, Cys798, Met801, Ile804, Leu887, His888, Tyr890, Cys891, Asn893, Thr894, Phe895, Ser898, Leu901, Val903, Phe905, Met909, Ile913, and Leu917, according to Table 2, ± a root mean square deviation for alpha carbon atoms of not more than 1.5 Å and wherein said three-dimensional representation of the non-steroidal ligand binding pocket optionally has the non-steroidal ligand from step(a) present or absent;

(c) employing said three dimensional representation from step (b) to design or select said candidate agent such that the favorable interactions from step (a) are maintained between the candidate non-steroidal ligand and the progesterone receptor ligand binding pocket;

(d) obtaining said candidate agent; and (e) contacting in vitro or in vivo said candidate agent with a polypeptide comprising said progesterone receptor ligand binding domain to determine the ability of said candidate agent to interact or bind said progesterone receptor ligand binding domain;

whereby the detection of the ability of said candidate agent to interact or bind said progesterone receptor ligand binding domain thereby identifies said candidate agent as an agent that interacts with the progesterone receptor.

3. The method of claim 1 or 2, wherein the progesterone receptor ligand binding domain comprises amino acids Gln682 to Lys932 of SEQ ID NO:4.

4. The method of claim 1 or 2, wherein the non-steroidal ligand is tanaproget.

5. The method of claim 1 or 2, wherein the three dimensional model of step (a) comprises structural coordinates of atoms of the candidate agent.

6. The method of claim 1 or 2, wherein the structural coordinates of the progesterone receptor ligand binding domain: non-steroidal ligand complex are according to Table 2, ± a root mean square deviation for alpha carbon atoms of not more than 1.0 Å.

7. The method of claim 1 or 2, wherein the structural coordinates of the progesterone receptor ligand binding domain:non-steroidal ligand complex are according to Table 2, ± a root mean square deviation for alpha carbon atoms of not more than 0.5 Å.

8. The method of claim 1 or 2, further comprising altering a computer-displayed representation of the non-steroidal ligand in the three dimensional model of step (a) or (b).

9. The method of claim 8, wherein altering the computer-displayed representation of the non-steroidal ligand comprises changing the structural coordinates of the non-steroidal ligand.

10. The method of claim 8, wherein altering the computer-displayed representation of the non-steroidal ligand comprises changing the chemical structure of the non-steroidal ligand.

11. The method of claim 8, wherein altering the computer-displayed representation of the non-steroidal ligand comprises superimposing a three dimensional structure of the candidate agent over the computer-displayed representation of the non-steroidal ligand.

12. The method of claim 1 or 2, further comprising determining a fit between the structural coordinates of the amino acids of the non-steroidal ligand binding pocket and a three-dimensional structure of the candidate agent.

13. The method of claim 12, wherein determining the fit comprises calculating a distance between an atom of the non-steroidal binding pocket and an atom of the candidate agent.

14. The method of claim 1, further comprising comparing a predicted interaction between the candidate agent and the non-steroidal ligand binding pocket progesterone receptor with the interaction between the non-steroidal ligand and the non-steroidal ligand binding pocket progesterone receptor.

15. The method of claim 12, wherein determining the fit comprises docking a three-dimensional model of the candidate agent to the three-dimensional model of the ligand binding domain of the progesterone receptor.

16. The method of claim 14, further comprising comparing the interaction of the candidate agent with the progesterone receptor to an interaction of a second agent with the progesterone receptor.

17. The method of claim 2, wherein the step of obtaining the agent comprises synthesizing the agent.

18. A method of designing or selecting an agent that interacts with a progesterone receptor, comprising:

(a) providing a three-dimensional structure of a complex comprising a human progesterone receptor ligand binding domain (hPR-LBD) and tanoproget, said three-dimensional structure being obtained by subjecting a co-crystal comprising the hPR-LBD in complex with tanoproget, wherein said hPR-LBD consists of SEQ ID NO:2 and said co-crystal is characterized by space group $P2_1$, with dimensions a=57.52 Å, b=64.50 Å, c=70.41 Å and β3=95.76, to X- ray diffraction and collecting data sufficient to determine the three-dimensional structure of said complex;

(b) generating a three-dimensional model from the three-dimensional structure of said complex;

(c) identifying the amino acid residues forming a non-steroidal ligand binding pocket of the progesterone receptor ligand binding domain from the three-dimensional model in step (b) in order to generate a three-dimensional representation of the non-steroidal ligand binding pocket, wherein the non-steroidal ligand binding pocket comprises amino acids Ile699, Ala701, Leu714, Leu715, Leu718, Asn719, Leu721, Gln725, Trp755, Met756, Met759, Val76O, Leu763, Arg766, Ser767, Tyr777, Phe778, Ala779, Leu782, Phe794, Leu797, Cys798, Met801, Ile804, Leu887, His888, Tyr890, Cys891, Asn893, Thr894, Phe895, Ser898, Leu901, Val903, Phe905, Met909, Ile913, and Leu917 of SEQ ID NO:4, according to Table 2, ± a root mean square deviation for alpha carbon atoms of not more than 1.5 Å and wherein said three-dimensional representation of the non-steroidal ligand binding pocket optionally has the non-steroidal ligand from step(b) present or absent;

(d) employing said three dimensional representation from step (c) to design or select said candidate agent;

(e) synthesizing said candidate agent; and (f) contacting said candidate agent with said progesterone receptor ligand binding domain to determine the ability of said candidate agent to interact or bind said progesterone receptor ligand binding domain;

whereby the detection of the ability of said candidate agent to interact or bind said progesterone receptor ligand binding domain thereby identifies said candidate agent as an agent that interacts with the progesterone receptor.

* * * * *

SEQUENCE LISTING

<160> NUMBER OF SEQ ID NOS: 4

<210> SEQ ID NO 1
<211> LENGTH: 483
<212> TYPE: PRT
<213> ORGANISM: Artificial Sequence
<220> FEATURE:
<223> OTHER INFORMATION: Synthetically generated peptide

<400> SEQUENCE: 1

Met Ser Pro Ile Leu Gly Tyr Trp Lys Ile Lys Gly Leu Val Gln Pro
 1               5                  10                  15

-continued

```
Thr Arg Leu Leu Leu Glu Tyr Leu Glu Glu Lys Tyr Glu Glu His Leu
            20                  25                  30
Tyr Glu Arg Asp Glu Gly Asp Lys Trp Arg Asn Lys Lys Phe Glu Leu
        35                  40                  45
Gly Leu Glu Phe Pro Asn Leu Pro Tyr Tyr Ile Asp Gly Asp Val Lys
    50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
        115                 120                 125
Met Leu Lys Met Phe Glu Asp Arg Leu Cys His Lys Thr Tyr Leu Asn
    130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Leu Val Pro Arg
    210                 215                 220
Gly Ser Pro Gly Gln Asp Ile Gln Leu Ile Pro Pro Leu Ile Asn Leu
225                 230                 235                 240
Leu Met Ser Ile Glu Pro Asp Val Ile Tyr Ala Gly His Asp Asn Thr
                245                 250                 255
Lys Pro Asp Thr Ser Ser Ser Leu Leu Thr Ser Leu Asn Gln Leu Gly
            260                 265                 270
Glu Arg Gln Leu Leu Ser Val Val Lys Trp Ser Lys Ser Leu Pro Gly
        275                 280                 285
Phe Arg Asn Leu His Ile Asp Asp Gln Ile Thr Leu Ile Gln Tyr Ser
    290                 295                 300
Trp Met Ser Leu Met Val Phe Gly Leu Gly Trp Arg Ser Tyr Lys His
305                 310                 315                 320
Val Ser Gly Gln Met Leu Tyr Phe Ala Pro Asp Leu Ile Leu Asn Glu
                325                 330                 335
Gln Arg Met Lys Glu Ser Ser Phe Tyr Ser Leu Cys Leu Thr Met Trp
            340                 345                 350
Gln Ile Pro Gln Glu Phe Val Lys Leu Gln Val Ser Gln Glu Glu Phe
        355                 360                 365
Leu Cys Met Lys Val Leu Leu Leu Asn Thr Ile Pro Leu Glu Gly
    370                 375                 380
Leu Arg Ser Gln Thr Gln Phe Glu Glu Met Arg Ser Ser Tyr Ile Arg
385                 390                 395                 400
Glu Leu Ile Lys Ala Ile Gly Leu Arg Gln Lys Gly Val Val Ser Ser
                405                 410                 415
Ser Gln Arg Phe Tyr Gln Leu Thr Lys Leu Leu Asp Asn Leu His Asp
            420                 425                 430
Leu Val Lys Gln Leu His Leu Tyr Cys Leu Asn Thr Phe Ile Gln Ser
```

```
                435                 440                 445
Arg Ala Leu Ser Val Glu Phe Pro Glu Met Met Ser Glu Val Ile Ala
    450                 455                 460
Ala Gln Leu Pro Lys Ile Leu Ala Gly Met Val Lys Pro Leu Leu Phe
465                 470                 475                 480
His Lys Lys

<210> SEQ ID NO 2
<211> LENGTH: 259
<212> TYPE: PRT
<213> ORGANISM: Homo sapiens

<400> SEQUENCE: 2

Gly Ser Pro Gly Gln Asp Ile Gln Leu Ile Pro Pro Leu Ile Asn Leu
1               5                   10                  15

Leu Met Ser Ile Glu Pro Asp Val Ile Tyr Ala Gly His Asp Asn Thr
                20                  25                  30

Lys Pro Asp Thr Ser Ser Leu Leu Thr Ser Leu Asn Gln Leu Gly
            35                  40                  45

Glu Arg Gln Leu Leu Ser Val Val Lys Trp Ser Lys Ser Leu Pro Gly
    50                  55                  60

Phe Arg Asn Leu His Ile Asp Asp Gln Ile Thr Leu Ile Gln Tyr Ser
65                  70                  75                  80

Trp Met Ser Leu Met Val Phe Gly Leu Gly Trp Arg Ser Tyr Lys His
                85                  90                  95

Val Ser Gly Gln Met Leu Tyr Phe Ala Pro Asp Leu Ile Leu Asn Glu
                100                 105                 110

Gln Arg Met Lys Glu Ser Ser Phe Tyr Ser Leu Cys Leu Thr Met Trp
            115                 120                 125

Gln Ile Pro Gln Glu Phe Val Lys Leu Gln Val Ser Gln Glu Glu Phe
130                 135                 140

Leu Cys Met Lys Val Leu Leu Leu Asn Thr Ile Pro Leu Glu Gly
145                 150                 155                 160

Leu Arg Ser Gln Thr Gln Phe Glu Glu Met Arg Ser Ser Tyr Ile Arg
                165                 170                 175

Glu Leu Ile Lys Ala Ile Gly Leu Arg Gln Lys Gly Val Val Ser Ser
            180                 185                 190

Ser Gln Arg Phe Tyr Gln Leu Thr Lys Leu Leu Asp Asn Leu His Asp
        195                 200                 205

Leu Val Lys Gln Leu His Leu Tyr Cys Leu Asn Thr Phe Ile Gln Ser
210                 215                 220

Arg Ala Leu Ser Val Glu Phe Pro Glu Met Met Ser Glu Val Ile Ala
225                 230                 235                 240

Ala Gln Leu Pro Lys Ile Leu Ala Gly Met Val Lys Pro Leu Leu Phe
                245                 250                 255

His Lys Lys

<210> SEQ ID NO 3
<211> LENGTH: 5
<212> TYPE: PRT
<213> ORGANISM: Homo sapiens

<400> SEQUENCE: 3

Leu Val Pro Arg Gly
1               5
```

```
<210> SEQ ID NO 4
<211> LENGTH: 933
<212> TYPE: PRT
<213> ORGANISM: Homo sapiens

<400> SEQUENCE: 4

Met Thr Glu Leu Lys Ala Lys Gly Pro Arg Ala Pro His Val Ala Gly
  1               5                  10                  15

Gly Pro Pro Ser Pro Glu Val Gly Ser Pro Leu Leu Cys Arg Pro Ala
             20                  25                  30

Ala Gly Pro Phe Pro Gly Ser Gln Thr Ser Asp Thr Leu Pro Glu Val
         35                  40                  45

Ser Ala Ile Pro Ile Ser Leu Asp Gly Leu Leu Phe Pro Arg Pro Cys
 50                  55                  60

Gln Gly Gln Asp Pro Ser Asp Glu Lys Thr Gln Asp Gln Gln Ser Leu
 65                  70                  75                  80

Ser Asp Val Glu Gly Ala Tyr Ser Arg Ala Glu Ala Thr Arg Gly Ala
                 85                  90                  95

Gly Gly Ser Ser Ser Pro Pro Glu Lys Asp Ser Gly Leu Leu Asp
            100                 105                 110

Ser Val Leu Asp Thr Leu Leu Ala Pro Ser Gly Pro Gly Gln Ser Gln
        115                 120                 125

Pro Ser Pro Pro Ala Cys Glu Val Thr Ser Ser Trp Cys Leu Phe Gly
130                 135                 140

Pro Glu Leu Pro Glu Asp Pro Pro Ala Ala Pro Ala Thr Gln Arg Val
145                 150                 155                 160

Leu Ser Pro Leu Met Ser Arg Ser Gly Cys Lys Val Gly Asp Ser Ser
                165                 170                 175

Gly Thr Ala Ala Ala His Lys Val Leu Pro Arg Gly Leu Ser Pro Ala
            180                 185                 190

Arg Gln Leu Leu Leu Pro Ala Ser Glu Ser Pro His Trp Ser Gly Ala
        195                 200                 205

Pro Val Lys Pro Ser Pro Gln Ala Ala Ala Val Glu Val Glu Glu Glu
210                 215                 220

Asp Ser Ser Glu Ser Glu Glu Ser Ala Gly Pro Leu Leu Lys Gly Lys
225                 230                 235                 240

Pro Arg Ala Leu Gly Gly Ala Ala Ala Gly Gly Gly Ala Ala Ala Cys
                245                 250                 255

Pro Pro Gly Ala Ala Ala Gly Gly Val Ala Leu Val Pro Lys Glu Asp
            260                 265                 270

Ser Arg Phe Ser Ala Pro Arg Val Ala Leu Val Glu Gln Asp Ala Pro
        275                 280                 285

Met Ala Pro Gly Arg Ser Pro Leu Ala Thr Thr Val Met Asp Phe Ile
290                 295                 300

His Val Pro Ile Leu Pro Leu Asn His Ala Leu Leu Ala Ala Arg Thr
305                 310                 315                 320

Arg Gln Leu Leu Glu Asp Glu Ser Tyr Asp Gly Gly Ala Gly Ala Ala
                325                 330                 335

Ser Ala Phe Ala Pro Pro Arg Thr Ser Pro Cys Ala Ser Ser Thr Pro
            340                 345                 350

Val Ala Val Gly Asp Phe Pro Asp Cys Ala Tyr Pro Pro Asp Ala Glu
        355                 360                 365

Pro Lys Asp Asp Ala Tyr Pro Leu Tyr Ser Asp Phe Gln Pro Pro Ala
370                 375                 380
```

```
Leu Lys Ile Lys Glu Glu Glu Gly Ala Glu Ala Ser Ala Arg Ser
385                 390                 395                 400

Pro Arg Ser Tyr Leu Val Ala Gly Ala Asn Pro Ala Ala Phe Pro Asp
            405                 410                 415

Phe Pro Leu Gly Pro Pro Pro Leu Pro Pro Arg Ala Thr Pro Ser
            420             425                 430

Arg Pro Gly Glu Ala Ala Val Thr Ala Ala Pro Ala Ser Ala Ser Val
            435                 440                 445

Ser Ser Ala Ser Ser Ser Gly Ser Thr Leu Glu Cys Ile Leu Tyr Lys
450                 455                 460

Ala Glu Gly Ala Pro Pro Gln Gln Gly Pro Phe Ala Pro Pro Pro Cys
465             470                 475                 480

Lys Ala Pro Gly Ala Ser Gly Cys Leu Leu Pro Arg Asp Gly Leu Pro
                485                 490                 495

Ser Thr Ser Ala Ser Ala Ala Ala Gly Ala Ala Pro Ala Leu Tyr
            500                 505                 510

Pro Ala Leu Gly Leu Asn Gly Leu Pro Gln Leu Gly Tyr Gln Ala Ala
            515                 520                 525

Val Leu Lys Glu Gly Leu Pro Gln Val Tyr Pro Pro Tyr Leu Asn Tyr
530                 535                 540

Leu Arg Pro Asp Ser Glu Ala Ser Gln Ser Pro Gln Tyr Ser Phe Glu
545                 550                 555                 560

Ser Leu Pro Gln Lys Ile Cys Leu Ile Cys Gly Asp Glu Ala Ser Gly
                565                 570                 575

Cys His Tyr Gly Val Leu Thr Cys Gly Ser Cys Lys Val Phe Phe Lys
            580                 585                 590

Arg Ala Met Glu Gly Gln His Asn Tyr Leu Cys Ala Gly Arg Asn Asp
            595                 600                 605

Cys Ile Val Asp Lys Ile Arg Arg Lys Asn Cys Pro Ala Cys Arg Leu
610                 615                 620

Arg Lys Cys Cys Gln Ala Gly Met Val Leu Gly Gly Arg Lys Phe Lys
625             630                 635                 640

Lys Phe Asn Lys Val Arg Val Arg Ala Leu Asp Ala Val Ala Leu
            645                 650                 655

Pro Gln Pro Leu Gly Val Pro Asn Glu Ser Gln Ala Leu Ser Gln Arg
            660                 665                 670

Phe Thr Phe Ser Pro Gly Gln Asp Ile Gln Leu Ile Pro Pro Leu Ile
            675                 680                 685

Asn Leu Leu Met Ser Ile Glu Pro Asp Val Ile Tyr Ala Gly His Asp
690                 695                 700

Asn Thr Lys Pro Asp Thr Ser Ser Leu Leu Thr Ser Leu Asn Gln
705                 710                 715                 720

Leu Gly Glu Arg Gln Leu Leu Ser Val Val Lys Trp Ser Lys Ser Leu
            725                 730                 735

Pro Gly Phe Arg Asn Leu His Ile Asp Asp Gln Ile Thr Leu Ile Gln
            740                 745                 750

Tyr Ser Trp Met Ser Leu Met Val Phe Gly Leu Gly Trp Arg Ser Tyr
            755                 760                 765

Lys His Val Ser Gly Gln Met Leu Tyr Phe Ala Pro Asp Leu Ile Leu
            770                 775                 780

Asn Glu Gln Arg Met Lys Glu Ser Ser Phe Tyr Ser Leu Cys Leu Thr
785                 790                 795                 800
```

```
-continued

Met Trp Gln Ile Pro Gln Glu Phe Val Lys Leu Gln Val Ser Gln Glu
            805                 810                 815

Glu Phe Leu Cys Met Lys Val Leu Leu Leu Leu Asn Thr Ile Pro Leu
            820                 825                 830

Glu Gly Leu Arg Ser Gln Thr Gln Phe Glu Glu Met Arg Ser Ser Tyr
            835                 840                 845

Ile Arg Glu Leu Ile Lys Ala Ile Gly Leu Arg Gln Lys Gly Val Val
        850                 855                 860

Ser Ser Ser Gln Arg Phe Tyr Gln Leu Thr Lys Leu Leu Asp Asn Leu
865                     870                 875                 880

His Asp Leu Val Lys Gln Leu His Leu Tyr Cys Leu Asn Thr Phe Ile
                885                 890                 895

Gln Ser Arg Ala Leu Ser Val Glu Phe Pro Glu Met Met Ser Glu Val
                900                 905                 910

Ile Ala Ala Gln Leu Pro Lys Ile Leu Ala Gly Met Val Lys Pro Leu
            915                 920                 925

Leu Phe His Lys Lys
    930
```